US008871468B2

(12) United States Patent
Kieliszewski

(10) Patent No.: US 8,871,468 B2
(45) Date of Patent: Oct. 28, 2014

(54) SYNTHETIC GENES FOR PLANT GUMS AND OTHER HYDROXYPROLINE-RICH GLYCOPROTEINS

(75) Inventor: Marcia J. Kieliszewski, Albany, OH (US)

(73) Assignee: Ohio University, Athens, OH (US)

( * ) Notice: Subject to any disclaimer, the term of this patent is extended or adjusted under 35 U.S.C. 154(b) by 308 days.

(21) Appl. No.: 13/149,016

(22) Filed: May 31, 2011

(65) Prior Publication Data

US 2012/0077226 A1 Mar. 29, 2012
US 2014/0287457 A9 Sep. 25, 2014

Related U.S. Application Data

(60) Continuation of application No. 12/781,490, filed on May 17, 2010, now abandoned, which is a continuation of application No. 10/437,708, filed on May 14, 2003, now abandoned, which is a division of application No. 09/547,693, filed on Apr. 12, 2000, now Pat. No. 6,639,050, which is a continuation-in-part of application No. 09/119,507, filed on Jul. 20, 1998, now Pat. No. 6,548,642, which is a continuation-in-part of application No. 08/897,556, filed on Jul. 21, 1997, now Pat. No. 6,570,062.

(51) Int. Cl.
| | | |
|---|---|---|
| C07K 14/415 | (2006.01) | |
| C12P 21/02 | (2006.01) | |
| C07H 21/04 | (2006.01) | |
| C12N 15/11 | (2006.01) | |
| C12N 15/82 | (2006.01) | |

(52) U.S. Cl.
CPC .......... *C07K 14/415* (2013.01); *C12N 15/8241* (2013.01); *C12N 15/8242* (2013.01); *C07K 2319/00* (2013.01)
USPC ..... 435/69.7; 435/69.1; 435/320.1; 536/23.1; 530/300

(58) Field of Classification Search
CPC ............ C07K 14/415; C07K 2319/00; C12N 15/8241; C12N 15/00
USPC ............... 435/69.1, 320.1; 536/23.1; 530/300
See application file for complete search history.

(56) References Cited

U.S. PATENT DOCUMENTS

| | | |
|---|---|---|
| 3,664,925 A | 5/1972 | Sonenberg et al. |
| 4,056,520 A | 11/1977 | Sonenberg et al. |
| 4,374,829 A | 2/1983 | Harris et al. |
| 4,478,827 A | 10/1984 | Haber et al. |
| 4,683,195 A | 7/1987 | Mullis et al. |
| 4,683,202 A | 7/1987 | Mullis |
| 4,940,838 A | 7/1990 | Schilperoort et al. |
| 4,956,282 A | 9/1990 | Goodman et al. |
| 4,965,188 A | 10/1990 | Mullis et al. |
| 5,034,322 A | 7/1991 | Rogers et al. |
| 5,350,836 A | 9/1994 | Kopchick et al. |
| 5,352,596 A | 10/1994 | Cheung et al. |
| 5,352,605 A | 10/1994 | Fraley et al. |
| 5,474,925 A | 12/1995 | Maliyakal et al. |
| 5,501,967 A | 3/1996 | Offringa et al. |
| 5,506,107 A | 4/1996 | Cunningham et al. |
| 5,534,617 A | 7/1996 | Cunningham et al. |
| 5,550,038 A | 8/1996 | Goodman et al. |
| 5,584,807 A | 12/1996 | McCabe |
| 5,629,175 A | 5/1997 | Goodman et al. |
| 5,637,686 A | 6/1997 | Tjian et al. |
| 5,641,670 A | 6/1997 | Treco et al. |
| 5,646,029 A | 7/1997 | Chen et al. |
| 5,650,307 A | 7/1997 | Sijmons et al. |
| 5,681,809 A | 10/1997 | Kopchick et al. |
| 5,695,971 A | 12/1997 | Kadokami et al. |
| 5,723,755 A | 3/1998 | Fortin |
| 5,728,810 A | 3/1998 | Lewis et al. |
| 5,733,771 A | 3/1998 | Lewis et al. |
| 5,756,677 A | 5/1998 | Lewis et al. |
| 5,763,394 A | 6/1998 | O'Connor et al. |
| 5,780,279 A | 7/1998 | Matthews et al. |
| 5,821,089 A | 10/1998 | Gruskin et al. |
| 5,830,747 A | 11/1998 | Chen et al. |
| 5,849,535 A | 12/1998 | Cunningham et al. |
| 5,958,879 A | 9/1999 | Kopchick et al. |
| 5,989,894 A | 11/1999 | Lewis et al. |
| 5,994,099 A | 11/1999 | Lewis et al. |
| 6,020,169 A | 2/2000 | Lee et al. |

(Continued)

FOREIGN PATENT DOCUMENTS

| | | |
|---|---|---|
| CA | 2296813 | 5/2011 |
| EP | 1156060 A1 | 11/2001 |

(Continued)

OTHER PUBLICATIONS

Charpentier et al., "Analysis of dipeptides in urine by gas chromatography/mass spectometry: implications for collagen breakdown in iminodipeptiduria following a study of the dipeptides by electron impact and chemical ionization", Clinica Chimica Acta, (1984), vol. 138, pp. 299-308.

Chen et al., "Functional antagonism between endogenous mouse growth hormone (GH) and a GH analog results in dwarf transgenic mice", Endocrinolgy, (1991) vol. 129, pp. 1402-1408.

Chen et al., "Glycine 119 of bovine growth hormone is critical for growth-promoting activity", Mol. Endocrinolgy, (1991) vol. 5, pp. 1845-1852.

Chen et al., "In Vitro and In Vivo Studies of Antagonistic Effect of Human Growth Hormone Analogs", The Journal of Biological Chemistry, (1994), vol. 269, No. 22, pp. 15892-15897.

Chen et al., "Mutations in the third α-helix of bovine growth hormone dramatically affect its intracellular distribution in vitro and growth enhancement in transgenic mice", J. Biol. Chem., (1991), vol. 266, pp. 2252-2258.

(Continued)

*Primary Examiner* — Chih-Min Kam
(74) *Attorney, Agent, or Firm* — Dinsmore & Shohl LLP

(57) ABSTRACT

A new approach in the field of plant gums is described which presents a new solution to the production of hydroxyproline (Hyp)-rich glycoproteins (HRGPs), repetitive proline-rich proteins (RPRPs) and arabinogalactan-proteins (AGPs). The expression of synthetic genes designed from repetitive peptide sequences of such glycoproteins, including the peptide sequences of gum arabic glycoprotein (GAGP), is taught in host cells, including plant host cells.

14 Claims, 19 Drawing Sheets

(56) References Cited

U.S. PATENT DOCUMENTS

| | | | |
|---|---|---|---|
| 6,033,895 A | 3/2000 | Garger et al. |
| 6,080,560 A | 6/2000 | Russell et al. |
| 6,096,547 A | 8/2000 | Goodman |
| 6,210,950 B1 | 4/2001 | Johnson et al. |
| 6,225,080 B1 | 5/2001 | Uhl et al. |
| 6,355,776 B1 | 3/2002 | Ferrari et al. |
| 6,486,382 B1 | 11/2002 | Gordan-Kamm et al. |
| 6,548,642 B1 | 4/2003 | Kieliszewski |
| 6,570,062 B1 | 5/2003 | Kielszewski |
| 6,583,115 B1 | 6/2003 | Kopchick et al. |
| 6,639,050 B1 | 10/2003 | Kieliszewski |
| 6,680,426 B2 | 1/2004 | Daniell et al. |
| 6,774,283 B1 | 8/2004 | Goodman et al. |
| 6,787,336 B1 | 9/2004 | Kopchick et al. |
| 7,378,506 B2 | 5/2008 | Kieliszewski |
| 7,388,081 B2 | 6/2008 | Seki et al. |
| 8,563,687 B2 | 10/2013 | Kieliszewski |
| 8,623,812 B2 | 1/2014 | Kieliszewski |
| 2002/0127652 A1 | 9/2002 | Schambye |
| 2002/0160944 A1 | 10/2002 | Boime et al. |
| 2002/0162135 A1 | 10/2002 | Daniell et al. |
| 2002/0174453 A1 | 11/2002 | Daniell et al. |
| 2003/0009783 A1 | 1/2003 | Daniell et al. |
| 2003/0036181 A1 | 2/2003 | Okkels et al. |
| 2003/0041353 A1 | 2/2003 | Daniell et al. |
| 2003/0167531 A1 | 9/2003 | Russell et al. |
| 2003/0204864 A1 | 10/2003 | Daniell |
| 2004/0009555 A1 | 1/2004 | Kieliszewski |
| 2004/0009557 A1 | 1/2004 | Kieliszewski |
| 2004/0230032 A1 | 11/2004 | Kieliszewski |
| 2005/0074838 A1 | 4/2005 | Kieliszewski |
| 2006/0026719 A1 | 2/2006 | Kieliszewski |
| 2006/0148680 A1 | 7/2006 | Kieliszewski |
| 2006/0252120 A1 | 11/2006 | Kieliszewski |
| 2007/0039073 A1 | 2/2007 | Kieliszewski |
| 2008/0242834 A1 | 10/2008 | Kieliszewski |
| 2008/0262198 A1 | 10/2008 | Kieliszewski |
| 2009/0030185 A1 | 1/2009 | Kieliszewski |
| 2010/0028993 A1 | 2/2010 | Kieliszewski |
| 2010/0029548 A1 | 2/2010 | Kieliszewski |
| 2010/0261874 A1 | 10/2010 | Kieliszewski |
| 2011/0003340 A1 | 1/2011 | Kieliszewski |
| 2011/0217766 A1 | 9/2011 | Kieliszewski |
| 2011/0230404 A1 | 9/2011 | Kieliszewski |

FOREIGN PATENT DOCUMENTS

| | | |
|---|---|---|
| EP | 1156060 B1 | 6/2007 |
| EP | 2133427 A1 | 12/2009 |
| EP | 1711533 B1 | 12/2013 |
| EP | 2133427 B1 | 12/2013 |
| JP | 2005-087172 | 4/2005 |
| NZ | 548513 | 9/2010 |
| WO | 9004788 | 5/1990 |
| WO | 9203478 | 3/1992 |
| WO | 9209690 | 6/1992 |
| WO | 9220713 | 11/1992 |
| WO | 9300109 | 1/1993 |
| WO | 9515377 | 6/1995 |
| WO | 9711178 | 3/1997 |
| WO | 9903978 | 1/1999 |
| WO | 0026354 | 5/2000 |
| WO | 0116339 | 3/2001 |
| WO | 0149830 | 7/2001 |
| WO | 0178503 | 10/2001 |
| WO | 01075132 | 10/2001 |
| WO | 02037313 | 5/2002 |
| WO | 03064619 | 8/2003 |
| WO | 2004094590 | 11/2004 |
| WO | 2004103275 | 12/2004 |
| WO | 2005069845 | 8/2005 |
| WO | 2005110015 | 11/2005 |
| WO | 2006035442 | 4/2006 |
| WO | 2007008708 | 1/2007 |
| WO | 2008008766 | 1/2008 |

OTHER PUBLICATIONS

Chen et al., "Specific Expression of an Extensin-Like Gene in the Style of *Nicotiana alata*", The Plant Cell, (1992), vol. 4, pp. 1053-1062.

Chen et al., "Conformation studies of biologically active fragments of bovine growth hormone", Biochemistry, (1977), vol. 16, No. 10, pp. 2110-2118.

Chiu et al., "Engineered GFP as a vital reporter in plants", Current Biology, (1996), vol. 6, No. 3, pp. 325-330.

Chou et al., "Predication of protein conformation", Biochemistry, (1974), vol. 13, No. 2, pp. 222-245.

Churms et al., "Some New Aspects of the Molecular Structure of *Acacia senegal* GUM (Gum Arabic)", Carbohydrate Research (1983), vol. 123, No. 267-279.

Clarke et al., "Form and Function of Arabinogalactans and arabinogalactan-Proteins", Phytochem., (1979), vol. 18, pp. 521-540.

Colbere-Garapin et al., "A New Dominant Hybrid Selective Market for Higher Eukaryotic Calls", J. Mol. Biol., (1981), vol. 150, pp. 1-14.

Connolly et al., "Effect of a Proteinase on the Macromolecular Distrubution of *Acacia senegal* Gum", Carbohydrate Polymers, (1998), vol. 8, pp. 23-32.

Crimmins et al., "Increasing the Sensitivity of 6-Aminoquinolyl-N-hydroxysuccinimidyl Carbamate Amino Acid Analysis: A Simple Solution", Analytical Biochemistry, (1997), vol. 244, pp. 407-410.

Cunningham et al., "Engineering human prolactin to bind the human growth hormone receptor", Science, (1990), vol. 247, pp. 1461-1465.

Cunningham et al., "High resolution epitope mapping of hGH-receptor interactions by alanine-scanning mutagenesis", Science, (1989), vol. 284, No. 4908, pp. 1081-1085.

Cunningham et al., "Receptor and antidoby epitopes in human grwoth hormone identified by homolog-scanning mutagenesis", Science, (1989), vol. 243, No. 4896, pp. 1330-1336.

De Blank et al., "Characterization of the soybean early nodulin cDNA clone GmENOD55", Plant Mol. Biol., (1993), vol. 22, pp. 1167-1171.

De Carvalho et al., "Suppression of β-1,3-glucanase transgene expression in homozygous plants", The EMBO J., (1992), vol. 11, pp. 2595-2602.

De Kock et al., "Administration of bovine, porcine and equine growth hormone to the horse: effect on insulin-like growth factor-I and selected IGF binding proteins" J. Endocrinol., (2001), vol. 171, No. 1, 163-171.

De Loose et al., "The extensin signal peptide allows secretion of a heterologous protein from protoplasts", Gene, (1991), vol. 99, pp. 95-100.

De Vos et al., "Human Growth Hormone and Extracellular Domain of its Receptor: Crystal Structure of the Complex", Science, (1992), vol. 255, pp. 306-312.

Defaye et al., "Structural Studies of Gum Arabic, the Exudate Polysaccharide from *Acacia senegal*", Carbohydrate Research, (1986), vol. 150, pp. 221-231.

Delonnay, "Determination of the Protein Constitutent of Gum Arabic", Master of Science Thesis, (1993).

Dziezak, "A focus on gums", Food Technology, (Mar. 1991), pp. 116-132.

Evans et al., "The extensin gene family in oilseed rape (*Brassica napus* L.): characterisation of sequences of representative members of the family", Mol Gen Genet. (Sep. 1990), vol. 223, No. 2, pp. 273-287.

Fares et al., "Design of a long-acting follitropin agonist by fusing the C-terminal sequence of the chorionic gonadotropin B subunit to the follitropin B subunit," Proc. Natl. Acad. Sci., vol. 89, pp. 4304-4308 (May 1992).

Fong et al., "A Gymnosperm Extensin Contains the Serine-Tetrahydroxyproline Motif", Plant Physiology, (1992), vol. 99, No. 2, pp. 548-552.

(56) References Cited

OTHER PUBLICATIONS

Forreiter, et al., "Stable transformation of an *Arabidopsis* cell suspension culture with firefly luciferase providing a cellular system for analysis of chaperone activity in vivo", Plant Cell, (1997), vol. 9, No. 12, pp. 2171-2181.
Forsyth, "Comparative aspects of placental lactogens: structure and function", Exp. Clin. Endocrinol. (1994), vol. 102, No. 3, pp. 244-251.
Fraley et al., "Liposome-mediated delivery tobacco mosaic virus RNA into tobacco protoplasts: A sensitive assay for monitoring liposome-protoplast interactions", Proc. Natl. Acad. Sci. USA, (1982), vol. 79, pp. 1859-1863.
Freemark et al., "Purification of a distinct platental lactogen receptor, a new member of the growth hormone/prolactin receptor family", J. Clin. Investig., (1989), vol. 83, pp. 883-889.
Fuh et al., "Prolactin receptor antagonists that inhibit the growth of breast cancer cell lines", J. Biol. Chem., (1995), vol. 270, No. 22, pp. 13133-13137.
Gao et al., "Isolation, characterization and immunolocalization of a novel, modular tomato arabinogalactan-protein corresponding to the LeAGP-1 gene," The Plant Journal (1999), 18(1), 43-55.
Gardiner et al., "Inovlvement of the Golgi Apparatus in the Synthesis and Secretion of Hydroxyproline-rich Cell Wall Glycoproteins", Plant Physiol., (1975), vol. 5, pp. 536-541.
Gastinel, "Galactosyltransferases: A Structural Overview of Their Funtion and Reaaction Mechanisms", Trends in Clycoscience and Glycotechnology, (2001), vol. 13, No. 70, pp. 131-145.
Gerken et al., "Determination of the Site-Specific O-Glycosylation Pattern of the Procine Submaxillary mucin Tandem Repeat Glycopeptide", J. Bio. Chem., (1997) vol. 272, pp. 9709-9719.
Gill et al., "Recombinant Chicken and Bovine Growth Hormones Accelerate Growth in Aquacultured Juvenile Pacific Salmon *Oncorhynchus kisutch*", Biotechnology, (1985), vol. 3, pp. 643-646.
Goffin et al., "Sequence-Function Relationships Within the Expanding Famliy of Prolactin, Growth Hormone, Placental Lactogen and Related Proteins in Mammals", Endocrine Revs., (1986), vol. 17, No. 4, pp. 385-410.
Goodenough et al., "Crystals of the *Chlamydomonas reinhardtii* Cell Wall: Polymerization, Depolymerization, and Purification of Glycoprotein Monomers", J. Cell. Biol., (1986), vol. 103, pp. 405-417.
Goodrum et al., "Gum arabic glycoprotein contains glycomodules of both extensisn and arabinogalactan-glycoprotiens", Phytochemistry, (2000), vol. 54, pp. 99-106.
Griesbach, "Incorporation of the GUS Gene into Orchids via Embryo Electrophoresis", HortScience, (1992), vol. 27, pp. 620.
Griesbach, et al., "Incorporation of the GUS Gene into Orchids through Embryo Electrophoresis", ISHS Acta Horticulturae 336: II International Symposium on In Vitro Culture and Horticultural Breeding (1993).
Guilley et al., "Nucleotide Sequence of Cucurbit Aphid-Borne Yellows Luteovirus", Virology, (1994), vol. 202, No. 2, pp. 1012-1017.
Gunther et al., "UDP-L-arabinose-hydroxyproline-O-glycosyltransferases in Volvox carted", FEBS, (1987), vol. 221, No. 2, pp. 293-298.
Haseloff et al., "Removal of a cryptic intron and subcellular localization of green fluorescent protein are required to mark transgenic *Arabidosis* plants brightly", Proc. Natl. Acad. Sci., (1997) vol. 94, pp. 2122-2127.
Hirsinger et al., "Characterization of a tobacco extensin gene and regulation of its gene family in healthy plants and under various stress conditions", Plant Mol Biol. (Jan. 1997), vol. 33, No. 2, pp. 279-289.
Holsters et al., "Transfection and Transformation of *Agrobacterium tumefaciens*", Molec. Gen. Genet., (1978), vol. 163, pp. 181-187.
Horsch et al., "A simple and General Method for Transferring Genes into Plants", Science, (1985), vol. 227, pp. 1229-1231.
Office Action in U.S. Appl. No. 12/820,943 mailed Oct. 15, 2012 (6 pages).
Notice of Allowance in U.S. Appl. No. 12/820,943 mailed May 30, 2013 (8 pages).
Office Action in U.S. Appl. No. 13/005,715 mailed Oct. 3, 2012 (12 pages).
Office Action in U.S. Appl. No. 13/019,819 mailed Nov. 13, 2012 (15 pages).
Office Action in U.S. Appl. No. 13/019,819 mailed Jun. 19, 2013 (15 pages).
Office Action in CA 2,573,918, dated Jan. 25, 2013 (2 pages).
Office Action in CA 2,553,257, dated Mar. 25, 2013 (2 pages).
Examination Report in EP 98 944 431.0, dated Aug. 7, 2012 (4 pages).
Examination Report in EP 98 944 431.0, dated Aug. 28, 2012 (4 pages).
Examination Report in EP 98 944 431.0, dated Apr. 2, 2013 (4 pages).
Summons to Attend Oral Proceedings in EP 05 726 258.6, mailed Nov. 19, 2012 (5 pages).
Notice of Grant in EP 05 726 258.6, mailed Jul. 17, 2013 (5 pages).
Examination Report in EP 05 779 913.2, mailed Feb. 21, 2013 (3 pages).
Summons to Attend Oral Proceedings in EP 09 004 742.4, mailed Nov. 16, 2012 (6 pages).
Notice of Grant in EP 09 004 742.4, mailed Jul. 25, 2013 (7 pages).
Office Action in IL 176781, mailed Aug. 5, 2013 (6 pages).
Furuhashi et al., "Fusing the Carboxy-Terminal Peptide of the Chorionic Gonadotropin (CG) Beta-Subunit to the Common Alpha-Subunit: Retention of O-Linked Glycosylation and Enhanced In Vivo Bioactivity of Chimeric Human CG," Mol. Endocrinology (1995), vol. 9, No. 1, pp. 54-63.
Office Action in JP 2006-549613, mailed Nov. 28, 2012 (2 pages).
Nishi, Tatsumari., "Qualitative Improvements of Therapeutic Glycoproteins by Glycotechnology", (1992), vol. 4 No. 16, pp. 336-344.
Notice of Allowance in U.S. Appl. No. 11/568,102 mailed Jul. 29, 2013 (3 pages).
Leonard, Renaud, et al., "Two Novel Types of O-Glycans on the Mugwort Pollen Allergen Art v 1 and Their Role in Antibody Binding," J. Biol. Chem., vol. 280, No. 9, pp. 7932-7940 (2005).
Tsumuraya, Yoichi et al., "Arabinogalactan-Proteins from Primary and Mature Roots of Radish (*Raphanus sativus* L.)," Plant Physiol. (1988) 86, 0155-0160.
Wilson, Iain BH, "Glycosylation of Proteins in Plants and Invertebrates," Curr Opin Struct Biol. Oct. 2002;12 (5):569-77.
Notice of Allowance in U.S. Appl. No. 12/820,943 mailed Sep. 6, 2013 (8 pages).
Office Action in U.S. Appl. No. 10/418,032, mailed Feb. 8, 2005 (5 pages).
Office Action in U.S. Appl. No. 10/418,032, mailed May 12, 2005 (13 pages).
Office Action in U.S. Appl. No. 10/418,032, mailed Apr. 13, 2006 (8 pages).
Office Action in U.S. Appl. No. 10/418,032, mailed Sep. 14, 2006 (8 pages).
Notice of Allowance in U.S. Appl. No. 10/418,032, mailed Jan. 12, 2007 (7 pages).
Notice of Allowance in U.S. Appl. No. 10/418,032, mailed Nov. 8, 2007 (6 pages).
Notice of Allowance in U.S. Appl. No. 10/418,032, mailed Feb. 13, 2008 (1 page).
Notice of Allowance in U.S. Appl. No. 10/418,032, mailed Mar. 17, 2008 (7 pages).
Issue Notice in U.S. Appl. No. 10/418,032, mailed May 27, 2008 (1 page).
Office Action in U.S. Appl. No. 10/437,708, mailed Aug. 11, 2004 (6 pages).
Office Action in U.S. Appl. No. 10/437,708, mailed Nov. 26, 2004 (10 pages).
Office Action in U.S. Appl. No. 10/437,708, mailed May 5, 2005 (8 pages).
Office Action in U.S. Appl. No. 10/437,708, mailed Oct. 3, 2005 (7 pages).
Office Action in U.S. Appl. No. 10/437,708, mailed Jun. 8, 2006 (6 pages).
Office Action in U.S. Appl. No. 10/437,708, mailed Feb. 28, 2007 (5 pages).

(56) References Cited

OTHER PUBLICATIONS

Office Action in U.S. Appl. No. 10/437,708, mailed Nov. 8, 2007 (7 pages).
Office Action in U.S. Appl. No. 10/437,708, mailed Feb. 1, 2008 (3 pages).
Office Action in U.S. Appl. No. 10/437,708, mailed May 9, 2008 (7 pages).
Office Action in U.S. Appl. No. 10/437,708, mailed Mar. 9, 2009 (7 pages).
Office Action in U.S. Appl. No. 10/437,708, mailed Dec. 16, 2009 (11 pages).
Office Action in U.S. Appl. No. 11/036,256, mailed Jul. 26, 2006 (11 pages).
Office Action in U.S. Appl. No. 11/036,256, mailed Oct. 4, 2006 (13 pages).
Office Action in U.S. Appl. No. 11/036,256, mailed Jul. 5, 2007 (10 pages).
Office Action in U.S. Appl. No. 11/036,256, mailed Dec. 17, 2007 (21 pages).
Office Action in U.S. Appl. No. 11/036,257, mailed Oct. 4, 2006 (13 pages).
Office Action in U.S. Appl. No. 11/036,257, mailed Feb. 26, 2007 (7 pages).
Office Action in U.S. Appl. No. 11/036,257, mailed Nov. 8, 2007 (7 pages).
Office Action in U.S. Appl. No. 11/173,811, mailed Jun. 12, 2007 (13 pages).
Office Action in U.S. Appl. No. 11/173,811, mailed Dec. 27, 2007 (13 pages).
Office Action in U.S. Appl. No. 11/173,811, mailed May 12, 2008 (16 pages).
Notice of Allowance in U.S. Appl. No. 11/173,811, mailed Oct. 8, 2008 (7 pages).
Office Action in U.S. Appl. No. 11/995,063 mailed Jul. 6, 2010 (10 pages).
Office Action in U.S. Appl. No. 12/117,692, mailed Jan. 26, 2010 (10 pages).
Office Action in U.S. Appl. No. 12/117,692, mailed Jul. 13, 2010 (7 pages).
Office Action in U.S. Appl. No. 12/121,140 mailed Dec. 22, 2009 (9 pages).
Office Action in U.S. Appl. No. 12/121,140 mailed Aug. 13, 2009 (5 pages).
Office Action in U.S. Appl. No. 12/122,606 mailed Jan. 26, 2010 (9 pages).
Office Action in U.S. Appl. No. 12/122,606 mailed Aug. 5, 2010 (18 pages).
Office Action in U.S. Appl. No. 12/781,490 mailed Dec. 2, 2010 (11 pages).
Office Action in U.S. Appl. No. 13/005,715 mailed Mar. 6, 2012 (10 pages).
PCT/US07/73137—International Preliminary Report on Patentability issued Jan. 13, 2009 (5 pages).
PCT/US07/73137—International Search Report, mailed Sep. 18, 2008 (5 pages).
PCT/US07/73137—Written Opinion, mailed Sep. 18, 2008 (4 pages).
PCT/US06/26594—International Search Report, mailed Jul. 31, 2008 (4 pages).
PCT/US06/26594—Written Opinion, mailed Jul. 31, 2008 (4 pages).
PCT/US05/13252—International Search Report, mailed Oct. 2, 2006 (3 pages).
PCT/US05/13252—Written Opinion, mailed Oct. 2, 2006 (3 pages).
PCT/US05/13252—International Preliminary Report on Patentability, issued Nov. 7, 2006 (4 pages).
PCT/US05/01160—International Search Report, mailed May 24, 2006 (5 pages).
PCT/US05/01160—Written Opinion, mailed May 24, 2006 (5 pages).
PCT/US05/01160—International Preliminary Report on Patentability, issued Aug. 7, 2006 (6 pages).
PCT/US04/11174—International Search Report and Written Opinion, mailed Feb. 15, 2005 (9 pages).
PCT/US04/11174—International Preliminary Report on Patentability, issued Oct. 21, 2005 (6 pages).
PCT/US01/12336—International Search Report, mailed Jan. 27, 2003 (4 pages).
PCT/US01/12336—International Preliminary Examination Report, issued Jan. 16, 2004 (5 pages).
PCT/US98/15083—International Search Report, mailed Dec. 8, 1998 (3 pages).
PCT/US98/15083—International Preliminary Examination Report, mailed May 17, 1999 (4 pages).
AU 2005206885—Notice of Allowance, dated Jan. 13, 2012 (3 pages).
Au 2005206885—Examination Report, dated Apr. 13, 2010 (5 pages).
CA 2,296,813—Office Action, dated Mar. 4, 2008 (1 page).
CA 2,296,813—Notice of Allowance, dated Jul. 22, 2009 (1 page).
CA 2,573,918—Office Action, dated Jan. 24, 2012 (3 pages).
CA 2,553,257—Office Action, dated Jan. 12, 2012 (4 pages).
CN 200580007911.6—Office Action dated Feb. 27, 2009 (with available partial translation).
EP 01 927 057.8—Supplementary European Search Report, dated May 26, 2004 (5 pages).
EP 01 927 057.8—Examination Report, dated Jul. 31, 2006 (6 pages).
EP 98 944 431.0—Supplementary European Search Report, dated Oct. 15, 2004 (4 pages).
EP 98 944 431.0—Examination Report, dated Nov. 20, 2008 (5 pages).
EP 98 944 431.0—Examination Report, dated Aug. 26, 2011 (6 pages).
EP 04 759 826.3—Supplementary European Search Report, dated Dec. 27, 2007 (6 pages).
EP 04 759 826.3—Examination Report, dated Jun. 9, 2008 (6 pages).
EP 05 726 258.6—Supplementary European Search Report, dated Jan. 25, 2008 (9 pages).
EP 05 726 258.6—Examination Report dated Jun. 11, 2008 (8 pages).
EP 05 726 258.6—Examination Report mailed Apr. 20, 2009 (3 pages).
EP 05 726 258.6—Examination Report, mailed Apr. 23, 2010 (4 pages).
EP 05 726 258.6—Examination Report, mailed Aug. 2, 2010 (5 pages).
EP 05 726 258.6—Examination Report, mailed Nov. 25, 2011 (6 pages).
EP 05 779 913.2—Supplementary European Search Report, mailed Jun. 6, 2008 (3 pages).
EP 05 779 913.2—Examination Report, mailed Feb. 27, 2009 (5 pages).
EP 05 779 913.2—Examination Report, mailed Sep. 6, 2010 (5 pages).
Idris et al., "Characterisation of gum from *Acacia senegal* trees of different age and location using multidetectiono gel permeation chromatography", Food Hydrocolloids, (1998), vol. 12, pp. 379-388.
Islam et al., "A review of recent developments on the regulatory, structural and funcitonal aspects of gum arabic", Food Hydrocolloids, (1997), vol. 11, pp. 493-505.
Ivan et al., "Biochemical purification and pharmacological inhibition of a mammalian prolyl hydroxylase acting on hypoxia-inducible factor," PNAS, (2002), vol. 99, pp. 13459-13464.
Keeler et al., "The Tertiary Structure and Bakcbone Dynamics of Human Prolactin", J. Molec. Biol., (2003), vol. 328, pp. 1105-1221.
Kieliszewski et al., "Extensin: repetitive motifs, function sites, post-translational codes, and phylogeny", The Plant Journal, (1994), vol. 5, No. 2, pp. 157-172.
Kieliszewski et al., "Cross-reactivities of polyclonal antibodies against extensin precursors determined via ELISA techniques", Phytochem., (1986), vol. 25, No. 3, pp. 673-677.

(56) References Cited

OTHER PUBLICATIONS

Kieliszewski et al., "A Repetitive Prolin-Rich Protein from the Gymnosperm Douglas Fir Is a Hydroxyproline-Rich Glycoprotein", Plant Physiol, (1992), vol. 98, pp. 919-926.
Kieliszewski et al., "Tandem mass spectrometry and structural elucidation of glycopeptidases from a hydroxyproline-rich plant cell wall glycoprotein indicate that continguous hydroxyprotien residues are the major sites of hydroxyproline O-arabinosylation", J. Biol. Chem., (1995), vol. 270, No. 6, pp. 2541-2549.
Kieliszewski et al., "Gum arabic glycoprotein: a new model", FASEB, (1997), vol. 11, No. 9, Abastract #3286.
Kieliszewski et al., "A Histidine-Rich Extensin from *Zea mays* is an Arabinogalactan Protein", Plant Physiology, (1992), vol. 9, pp. 538-547.
Kieliszewski et al., "Potato lectin: modular protein sharing sequence similarities with the extensisn family, the hevein lectin family, and snake venom disintegrins (platelet aggregation inhibitors)", The Plant Journal, (1994), vol. 5, No. 6, pp. 849-861.
Kieliszewski et al., "Synthetic Genes for the Elucidation of Glycosylation Codes for Arabinogalactan-proteins and Other Hydroxyproline-rich Glycoproteins", Cell & Molecular Life Science, (2001), vol. 58, pp. 1386-1398.
Kieliszewski et al., "Structure of the Threonine-Rich Extensin from *Zea mays*", Plant Physiology, (1990), vol. 92, pp. 316-326.
Kieliszewski et al., "Synthetic Genes for the Elucidation of Glycosylation Codes of Hydroxyproline-Rich Glycoproteins," Abstract published/presented at the XVI International Botanical Congress, St. Louis, MO, Jul. 31 to Aug. 3, 1999.
Kivirikko et al., "A colorimetric Method for Determination of Hydroxyproline in Tissue Hydrolysates", Scand J. Clin. Lab. Invest., (1959), vol. 11, pp. 128-131.
Klee et al., "Agrobacterium-mediated plant trasnformation and its further applications to plant biology", Ann. Rev. Plant Phys., (1987), vol. 38, pp. 467-486.
Kopchick et al., "Growth Hormone Receptor Antagonists: Discovery, Development, and Use in Patients with Acromegaly", Endocrine Reviews, (2002), vol. 23, No. 5, pp. 623-646.
Krens et al., "In vitro transformation of plant protoplasts with Ti-plasmid DNA", Nature, (1982), vol. 296, pp. 72-74.
Lamport, "Hydroxyproline-O-glycosidic Linkage of the Plant Cell Wall Glycoprotein Extensin", Nature, (1967), vol. 216, pp. 1322-1324.
Lamport et al., "Galactosylserine in Extensin", Biochem. J., (1973), vol. 133, pp. 125-131.
Lamport et al., "Hydroxyproline Arabinosides in the Plant Kingdom", Plant Physiology, (1971), vol. 48, pp. 454-456.
Lamport et al., "Hydroxyproline in Primary Cell Walls of Niger Plants", Nature, (1960), vol. 188, pp. 665-666.
Leonard et al., "Two novel types of O-glycans on the mugwort pollen allergen Art v 1 and their role in antibody binding", JBC Papers in Press, Published Dec. 10, 2004 as Manuscript M410407200.
Leung et al., "Growth Hormone receptor and serum binding protein: purification, cloning and expression", Nature, (1987), vol. 330, No. 6148, pp. 537-543.
Lewis et al., "Expression and Purification of a silk spider protein: A new Strategy for Producing Repetitive Proteins", Protein Express. Purif, (1996), vol. 7, pp. 400-406.
Lewis et al., "Structure and Properties of Members of the High Family: A Review", Endocrine Journal, (2000), vol. 47, No. Suppl., pp. S1-S8.
Li et al., "A Chenopod Extensisn Lacks Repetitive Tetrahydroxyproline Blocks", Plant Physiol, (1990), vol. 92, pp. 327-333.
Li et al., "Cloning and developmental/stress-regulated expression of a gene encoding a tomato arabinogalactan protein", Plant Mol. Biol., (1996), vol. 32, No. 4, pp. 641-652.
Li et al., "Purification and characterization of four β-expansisns (*Zea m 1* isoforms) from maize pollen", Plant Physiol., (2003), vol. 132 No. 4, pp. 2073-2085.

Liu et al., "Epidsodic Evoluation of Growth Hormone in Primates and Emergence of the Species Specificity of Human Growth Hormone Receptor", Mol. Biology & Evolution, (2001), vol. 18, No. 6., pp. 945-953.
Ma, et al., "The production of recombinant pharmaceutical proteins in plants", Nature Reviews Genetics, (2003) vol. 4, No. 10, pp. 153-157.
Mann et al., "The amino acid sequence of a type I copper protein with an unusual serine- and hydroxyproline-rich C-terminal domain isolated from cucumber peelings", FEBS, (1992), vol. 314, No. 3, pp. 220-223.
Marusina et al., "Novel peptide-binding proteins and peptide transport in normal and TAP-deficient microsomes", Biochemistry (Jan. 1997), vol. 36, No. 4, pp. 856-863.
McCormick et al., "Leaf disc transformation of cultivated tomato (*L. esculentum*) using *Agrobacterium tumefaciens*", Plant Cell Reports, (1986), vol. 5, pp. 81-84.
McGrath et al., "Chemical and Biosynthetic Approaches to the Production of Novel Polypeptide Materials", Biotechnol. Prog., (1990), vol. 6, pp. 188-192.
Memelink et al., "Structure and regulation of tobacco extensin", The Plant Journal, (1993), vol. 4, No. 6, pp. 1011-1022.
Merle et al., Hydroxylated human homotrimeric collagen I in *Agrobacterium tumefaciens*—mediated transient expression and in transgenic tobacco plant, Febs letters 515 (2002) pp. 114-115.
Merlke et al., "Carbohydrate Composition Analysis of Glycoconjugates by Gas-Liquid Chromatography/Mass Spectrometry", in Methods in Enzymology (Lennarz & Hart, Ed., Academic Press, NY, 1994), vol. 230, pp. 1-15.
Miller et al., "Hydroxyproline Heterooligosaccharides in *Chlamydomonas*", Science, (1972), vol. 176, pp. 918-920.
Miller et al., "Molecular cloning of DNA complementary to bovine growth hormone mRNA", J. Biol. Chem., (1980), vol. 255, pp. 7521-7524.
Mollard et al., "Acacia senegal cells cultured in suspension secrete a hydroxyproline-deficint rabinogalactan-protein", Plant Physiol. Biochem., (1994), vol. 32, pp. 703-709.
Nacka et al., "Induction of new physicochemical and functional properties by the glycosylation of whey proteins", Journal of Protein Chemistry, (1998), vol. 17, No. 5, pp. 495-503.
Nan et al., "Genetic Transformation in *Dendrobium* (orchid)" in Biotechnology in Agriculture and Forestly, (Y.P.S. Bajaj, Ed., Springer-Verlag, Berling, Heidelberg, 1995), vol. 34, pp. 145-155.
Napoli et al., "Introduction of a Chimeric Chalcone Synthase Gene into Petunia Results in Reversible Co-Suppression of Homologous Gene in trans", The Plant Cell, (1990), vol. 2, pp. 279-289.
Nicoll et al., "Structural Features of Prolactins and Growth Hormones that Can Be related to Their Biological Properties", Endocrine Revs., (1986), vol. 7, No. 2, pp. 169-203.
Nothnagel, "Proteoglycans and Related Components in Plant Cells", International Review of Cytology, (1997), vol. 174, pp. 195-291.
Osman et al., "Characterization of Gum Arabic Fractions Obtained by Anion-Exchange Chromatography", Phytochemistry, (1995), vol. 38, pp. 409-417.
Pagny et al., "Structural requirements for *Arabidopsis* (β1, 2-xylosyltransferase activity and targeting to the Golgi", The Plant Journal, (2003), vol. 33, pp. 189-203.
Pearce et al., "Emulsifying Properties of Proteins: Evaluation of a Turbidimetric Technique", J. Agric. Food Chem., (1978), vol. 26, No. 3, pp. 716-723.
Notice of Allowance in U.S. Appl. No. 11/173,811, mailed Aug. 14, 2009 (7 pages).
Office Action in U.S. Appl. No. 11/243,295, mailed Nov. 15, 2006 (6 pages).
Office Action in U.S. Appl. No. 11/243,295, mailed Jul. 25, 2007 (8 pages).
Office Action in U.S. Appl. No. 11/243,295, mailed Jan. 3, 2008 (8 pages).
Notice of Allowance in U.S. Appl. No. 11/243,295, mailed Apr. 23, 2008 (7 pages).
Office Action in U.S. Appl. No. 11/243,295, mailed Oct. 10, 2008 (6 pages).

(56) References Cited

OTHER PUBLICATIONS

Notice of Allowance in U.S. Appl. No. 11/243,295, mailed May 1, 2009 (12 pages).
Notice of Allowance in U.S. Appl. No. 11/243,295, mailed Sep. 10, 2009 (10 pages).
Office Action in U.S. Appl. No. 11/568,102 mailed May 25, 2011 (11 pages).
Office Action in U.S. Appl. No. 11/568,102 mailed Apr. 13, 2010 (4 pages).
Office Action in U.S. Appl. No. 11/568,102 mailed Sep. 14, 2010 (11 pages).
Office Action in U.S. Appl. No. 11/995,063 mailed Dec. 16, 2009 (5 pages).
Office Action in U.S. Appl. No. 12/820,943 mailed Feb. 2, 2011 (5 pages).
Office Action in U.S. Appl. No. 12/820,943 mailed Aug. 25, 2011 (9 pages).
Office Action in U.S. Appl. No. 12/820,943 mailed Feb. 22, 2012 (8 pages).
Office Action in U.S. Appl. No. 13/019,819 mailed Mar. 8, 2012 (20 pages).
Gleeson et al., "Characterization of the hydroxyproline-rich protein core of an arabinogalactan-protein secreted from suspension-cultured *Lolium muliflorum* (Italian ryegrass) endosperm cells," Biochem. J. (1989) 264, 857-862.
Menassa et al., "A Self-contained system for the field production of plant recombinant interleukin-10", Molecular Breeding (2001), vol. 8, pp. 177-185.
Shpak et al., "Synthetic Genes for glycoprotein design and the eludication of hydroxyproline-O-glycosylation codes", Proc. Natl. Aca, Sci., (1999), vol. 96, pp. 14736-14741.
Notice of Allowance in U.S. Appl. No. 11/173,811, mailed Mar. 6, 2009 (14 pages).
EP 05 779 913.2—Examination Report, mailed Jun. 1, 2012 (4 pages).
EP 07 799 434.1—Extended European Search Report, mailed Dec. 14, 2009 (6 pages).
EP 09 004 742.4—Extended European Search Report, mailed Oct. 27, 2009 (9 pages).
EP 09 004 742.4—Examination Report, mailed Jul. 19, 2010 (5 pages).
EP 09 004 742.4—Examination Report, mailed Nov. 25, 2011 (8 pages).
IL 176781—Official Action, mailed Jul. 16, 2009 (3 pages).
IL 176781—Official Action, mailed Aug. 19, 2010 (2 pages).
JP 2000-503184—Office Action, mailed Feb. 19, 2008 (4 pages).
JP 2000-503184—Office Action, mailed Jun. 12, 2009 (4 pages).
JP 2001-575817—Office Action, mailed Mar. 2, 2011 (12 pages).
JP 2006-549613—Office Action, mailed Nov. 21, 2011 (3 pages).
JP 2006-549613—Office Action, mailed Aug. 31, 2010 (4 pages).
MX 2006/008126—Office Action, mailed Jan. 26, 2010 (3 pages).
NZ 548,513—Examination Report, mailed Mar. 10, 2008 (2 pages).
NZ 548,513—Examination Report, mailed Oct. 5, 2009 (2 pages).
NZ 579,586—Examination Report, mailed Sep. 15, 2009 (3 pages).
Abstract No. XP-002295046 for Accession No. P41479, created Nov. 1, 1995.
Genbank Accession No. AF227194, dated Feb. 21, 2003.
Genbank Accession No. D41504, dated Nov. 15, 1994.
Genbank Accession No. P41479, dated Nov. 1, 1995.
Genbank Accession No. S50755, dated May 8, 1993.
Genbank Accession No. X69156, dated Nov. 14, 2006.
Abdel-Meduid et al., "Three Dimensional Structure of a genetically engineered variate of porcine growth hormone", Proc. Nat. Acad. Sci. USA, (1987), vol. 64, pp. 6434-6437.
Akiyama et al., "Gum Arabic is a Kind of Arabinogalactan-Protein", Agric. Biol. Chem., (1984) vol. 48, pp. 235-237.
Alexandrou et al., "Inhibition of Anglotensisn Converting Enzyme by L-ALANYL-4 or 5 Substituted-L-Prolines and Their N-Phosphoryl-Derivatives", Biochemicstry International, (1990), vol. 21, No. 1, pp. 271-278.

Allan et al., "Identification of novel sites in the ovine growth hormone receptor involved in binding hormone and conferring species specificity", Eur. J. Biochem., (1999), vol. 261, No. 2, pp. 555-561.
Altschul et al., "Basic Local Assignment Search Took", J. Mol. Biol., (1990), vol. 215, pp. 403-410.
Amado et al., "Identification and characterization of large galactosyltransferase gene families galactosyltransferases for all functions", Biochimica et Biophysica Acta, (1999), vol. 1473, pp. 35-53.
An, et al., "Binary Vectors", Plant Molecular Biology Manual, (1988) vol. A3, pp. 1-19.
An, "High Efficiency Transformation of Cultured Tobacco Cells", Plant Physiol, (1985), vol. 79, pp. 568-570.
Anderson, et al., "The Chemcial characterization of the gum exudates from eight Australian *Acacia* species of the series Phyllodineae", Food Hydrocolloids, (1988), vol. 2, pp. 329-336.
Aspinall, "Plant gums", in the Carbohydrates, (Ed. Pigman & Horton, Academic Press, NY, 1970), vol. 2B, pp. 522-536.
Aspinall, et al., "The location of a β-D-galactopyranose residues in gum arabic", Carbohyd. Res., (1986), vol. 157, pp. 257-260.
Ausubel, "Chapter 3: Enzymatic Manipulation of DNA and RNA", in Current Protocols in Molecular Biology, (John Wiley & Sons, Inc., Ny, 1995), pp. 3.2.1-3.3.2 and 3.16.1-3.16.11.
Averyhart-Fullard et al., "A hydroxproline-rich protein in the soybean cell wall", Proc. Nat. Acad. Sci. USA, (1988), vol. 85, pp. 1082-1085.
Ayres, Martin D. et al., "The Complete DNA Sequence of *Autographa californica* Nuclear Polyhedrosis Virus," Virology (1994), vol. 202, pp. 586-605.
Bacic et al., "Fine Structure of the Arabinogalactan-Protein from *Lollium multiflorum*", Carbohyd. Res., (1987), vol. 162, pp. 85-93.
Bailon, et al., "Rational Design of a Potent, Long-Lasting Form of Interferon: A 40 kDa Branched Polyethylene Glyco-Conjugated Interferon α-2a for the Treatment of Hepatitis C", Bioconjugate Chem., (2001) vol. 12, No. 2, pp. 195-202.
Baldwin et al., "The ptl1 gene expressed in the transmitting tissue of Antirrhinum encodes an extensin-like protein", The Plant Journal, (1992), vol. 2, No. 5, pp. 733-739.
Bell et al., "Crystallization and Preliminary X-ray Characterization of Bovine Growth Hormone", J. Biol. Chem., (1985), vol. 260, No. 14, pp. 8520-8525.
Benfey et al., "Sequence Requirements of the 5-Enolpyruvylshikimate-3-phosphate Synthase 5'—Upstream Region for the Tissue-Specific Expression in Flowers and Seedlings", Plant Cell, (1990), vol. 2, pp. 849-856.
Bergman et al., "Amino Acid Analysis by High Performance Liquid Chromatography of Phenylthiocarbamyl Derivatives", in Advanced Methods in Protein Microsequence Analysis (Ed. Wittmann-Liebold, Springer-Vertag, Berlin, 1986), pp. 45-55.
Berra et al., "The hypoxia—inducible-factor hydroxylases bring fresh air into hypoxia signalling," EMBO Reports, vol. 7, No. 1, pp. 41-45 (2006).
Bidney et al., "Micrprojectile bombardment of plant tissues increases transformation frequency by *Agrobacteruim tumefaciens*", Plant Molec. Biol., (1992), vol. 18, pp. 301-313.
Borner et al., "Identification of Glycosylphosphatidylinositol-Anchored Proteins in *Arabidopsis*. A Proteomic and Genomic Analysis", Plant Physiology, (2003), vol. 132, pp. 568-577.
Boutin et al., "Cloning and expression of the rat prolactin receptor, a member of the growth hormone/prolactin receptor gene family", Cell, (1998), vol. 53, No. 1, pp. 69-77.
Brady et al., "Di-isodityrosine, a novel tetrameric derivative of tyrosine in plant cell wall proteins: a new potential cross-link," Biochem. J. (1996) 315, 323-327.
Brady et al., "Formation of Di-Isodityrosine and Loss of Isodityrosine in the Cell Walls of Tomato Cell-Suspension Cultures Treated with Fungal Elicitors of H2O2," Plant Physiol. (1997) 115: 87-92.
Breton et al., "Sequence-Function Relationships of Prokaryotic and Eukaryotic Galactosyltransferases", J. Biochem, (Tokyo) (1998), vol. 123, pp. 1000-1009.

(56) References Cited

OTHER PUBLICATIONS

Cabanes-Macheteau et al., "N-glycosylation of a mouse IgG expressed in transgenic tobacc plants", Glycobiology, (1999), vol. 9, pp. 365-372.
Perlman et al., "Glycosylation of an N-Terminal extension prolongs the half-life and increases the in vivo activity of follicle stimulating hormone," J. Clin. Endocrinol. Metab., 2003, 88: 3227-3235.
Pope, "Relationships between Hydroxyproline-containing Proteins Secreted into the Cell Wall and Medium by Suspension-cultured *Acer pseudoplantanus* Cells", Plant Physiology, (1977), vol. 59, pp. 894-900.
Prakash, et al., "The effects of added proteins on the functionality of gum arabic in soft drink emulsion systems" Food Hydrocolloids, (1990), vol. 4, No. 3, pp. 177-184.
Putney et al., "Improving Protein Therapeutics with Sustained-Release Formulations", Nature Biotechnology, (1998), vol. 16, pp. 153-157.
Qi et al., "Gum Arabic Clycoprotein Is a Twisted Hairy Rope", Plant Physiol., (1991), vol. 96, pp. 848-855.
Raz et al., "The sequence of a hydroxyproline-rich glycoprotein gene from *Sorghum vulgare*", Plant Molecular Biology, (1991), vol. 16, pp. 365-367.
Rhodes et al., "Transformation of Maize by Electroporation of Embryos," Methods Mol Biol (1995), vol. 55, pp. 121-131.
Rogers, KK, "The Potential of Plant-Made Pharmaceuticals," published online (2003).
Ross et al., "Binding and functional studies with the growth hormone receptor antagonist, B2036-PEG (pegvisomant), reveal effects of pegylation and evidence that it binds to a receptor dimer", J Clin Endocrinol Metab, (2001), vol. 86, No. 4, pp. 1716-1723.
Sambrook et al., Molecular Cloning Laboratory Manual, (Roe, Ed., Cold Spring Harbor Laboratory Press, NY, 1989), pp. 13.7-13.9 and 16.33-16.36.
Schenk et al., "Medium and Techniques for Induction and Growth of Monocotyledonous and Dicotyledonous Plant Cell Cultures", Can. J. Bot., (1972), vol. 50, pp. 199-204.
Schnabelrauch et al., "Isolation of pI4.6 extensisn peroxidase from tomato cell suspension cultures and identification of Val-Tyr-Lys as putative intermolecular cross-link site", The Plant J., (1996), vol. 9, No. 4, pp. 477-489.
Service, "Unnatural Amino Acid Could Prove Boon for Protein Therapeutics", Science, (2005), vol. 308, pp. 44.
Shaper et al., "The Galactosyltransferases", in Carbohydrates in Chemistry and Biology, (Ernst, Ed., Weinheim, NY, 2000), vol. 3, Ch. 10, pp. 175-196.
Sheikholeslam et al., "Acetosyringone promotes high efficiency transformation of *Arabidopsis thaliana* explants by *Agrobacterium tumefaciens*", Plant Molec. Biol., (1987), vol. 8, pp. 291-298.
Shirsat et al., "Expression of a *Brassica napus* extensin gene in the vascular system of transgenic tobacco and rape plants", Plant Mol Biol. (Oct. 1991), vol. 17, No. 4, pp. 701-709.
Shimizu et al., "Experimental determination of proline hydroxylation and hydroxyproline araginoglactosylation motifs in secretory proteins," The Plant Journal, (2005), vol. 42, pp. 877-889.
Shpak et al., "Contiguous Hydroxyproline Residues Direct Hydroxyproline Arabinosylation in *Nicotiana tabacum*", The Journal of Biological Chemistry, (2001), vol. 276, No. 14, pp. 11272-11276.
Smith et al., "Tomato Extensin Precursors P1 and P2 are highly periodic structures", Phytochem., (1986), vol. 25, No. 5, pp. 1021-1030.
Sommer-Knudsen et al., "Hydroxyproline-rich plant glycoproteins", Phytochemistry (1998), vol. 47, pp. 483-497.
Stephen et al., "Exudate Gums", Methods Plant Biochem., (1990), vol. 2, pp. 483-522.
Sticher et al., "Posttranslational Processing of a New Class of Hydroxyproline-Containing Proteins", Plant Physiol., (1993), vol. 101, pp. 1239-1247.
Sticher et al., "Vacuolar Chitinases of Tobacco: A new Class of Hydroxyproline-Containing Proteins", Science, (1992), vol. 257, No. 5070j, pp. 665-657.
Stiefel et al., "Molecular cloning of cDNAs encoding a putative cell wall protein from *Zea mays* and immunological identification of related polypeptides", Plant Molecular Biology, (1988), vol. 11, pp. 483-493.
Strahl-Bolsinger et al., "Protein O-mannosylation", Biochimica et Biophysica Acta, (1999), vol. 1426, pp. 297-307.
Stryer, Biochemistry, W.H. Freeman & Co., San Francisco, CA, (1975), pp. 16-17, 208-209.
Takahashi et al., "Brief report: Short stature caused by a mutant growth hormone", New England Journal of Medicine, (1996), vol. 334, No. 7, pp. 432-436.
Tan, "O-Glycosylation Motifs in Arabinogalactan-Proteins", Dotoral Dissertation, Ohio University, presented Jun. 2003.
Tan, et al., "Glycosylation Motifs that direct arabingogalactan addition to arabinogalactan-proteins", Plant Physiol., (2003), vol. 132, pp. 1362-1369.
Tan, et al., "Structure of a hydroxyproline (Hyp)-arabinogalactan polysaccharide from repetitive Ala-Hyp expressed in transgenic *Nicotiana tabacum*", J. Biol. Chem, (Mar. 26, 2004), vol. 279, No. 13 pp. 13156-13165.
Tsien, "The Green Fluroescent Protein", Annu. Rev. Biochem., (1998), vol. 67, pp. 509-544.
Twyman et al., "Transgenic plants in the biopharmaceutical market," Expert Opin. Emerging Drugs (Feb. 2005) 10 (1):185-218.
Van Wandelen, et al., "Using quaternary high-performance liquid chromatography eluent systems for separating 6-aminoquinolyl-N-hydroxysuccinimidyl carbamate-derivatized amino acid mixtures", J. Chromatography A, (1997), vol. 763, pp. 11-22.
Watahiki et al., "Conserved and unique amino acid residues in the domains of the growth hormones. Flounder growth hormone deduced from the cDNA sequence has the minimal size in the growth hormone prolactin gene family", J. Biol. Chem. (1989), vol. 264, pp. 312-316.
Watanabe et al., "Cloning and expression of two genes encoding auxin-binding proteins from tobacco", PMB, (1998), vol. 36, pp. 63-74.
Wells et al., "Structure and Function of Human Growth Hormone: Implications for the Hematopoietins", Ann. Rev. Biophys. Biomol. Struct., (1993), vol. 22, pp. 329-351.
Wigler, et al., "Transformation of mammalian cells with an amplifiable dominant-acting gene", Pro. Nai. Acad. Sci, (1980), vol. 7, pp. 3567-3570.
Wileman, Thomas E., "Properties of asparaginase-dextran conjugates". Adv. Drug Delivery Revs., (1991), vol. 6, pp. 167-180.
Woessner et al., "Domain conservation in several volvocalean cell wall proteins", Plant Molec. Biol., (1994), vol. 26, pp. 947-960.
Xu, et al., "Production of recombinant plant gum with tobacco cell culture in bioreactor and gum characterization", Biotechnol Bioeng., (Jun. 5, 2005), vol. 90, No. 5, pp. 578-588.
York, et al., "Isolation and Characterization of Plant Cell Walls and Cell Wall Components", Methods in Enzymology, (1985), vol. 118, p. 3.
Zhang et al., "Expression of an environmentally friendly synthetic protein-based polymer gene in transgenic tobacco plants", Plant Cell Reports, (1996), vol. 16, pp. 174-179.
Zhang et al., "Expression of Eukaryotic Proteins in Soluble Form in *Escherichia coli*", Protein Expression and Purification, (1998), vol. 12, No. 2, pp. 159-165.
Zhao et al., "Tomato LeAGP-1 arabinogalactan-protein pruified from transgenic tobacco corroborates the Hyp contiguity hypothesis", Plant J., (2002), vol. 31, No. 4, pp. 431-444.
Zhou et al., "Molecular cloning of a human UDP-galactose:GlcNAcβ1, 3GalNAcβ1, 3 galactosyltransferase gene enciding an O-linked core3-elongation enzyme", Eur. J. Biochem., (1999), Vol. 263, pp. 571-576.
Du et al., "Isolation of the Protein Backbone of an Arabinogalactan-Protein from the Styles of *Nicotiana alata* and Characterization of a Corresponding cDNA", Plant Cell, (1994), vol. 6, pp. 1643-1653.

(56) References Cited

OTHER PUBLICATIONS

Xu, et al., "High-Yields and Extended Serum Half-Life of Human Interferon alpha2b Expressed in Tobacco Cells as Arabinogalactan-Protein Fusions", Biotechnol Bioeng., (Feb. 27, 2007), vol. 97, No. 5, pp. 997-1008.

Sundstrom et al., "Crystal Structure of an Antagonist Mutant of Human Growth Hormone, G120R, in Complex with Its Receptor at 2.9 A Resolution," J. Biol. Chem., 271, 32197-32203 (1996).

Official Communication dated Jul. 23, 2014 pertaining to Israeli Patent Application Serial No. 176781 filed Jan. 14, 2005.

Notice of Reasons for Rejection dated Aug. 28, 2014 pertaining to Japanese Patent Application Serial No. 2013-065541 filed Mar. 27, 2013.

```
 BamHI    XmaI                                                                                                              AgeI        EcoRI
|_        |_                                                                                                                |_          |_
GCT GGA TCC TCA ACC CGG GCC TCA CCA CCA CCT TCA CCT CCA CCC CCA TCT CCA CCA CCT TCA CCT CCA CCC CCA TCT CCA CCA CCT TCA CCG GTC GCC CGG AAT TCA CCA CCC
CGA CCT AGG AGT TGG GCC CGG AGT GGT GGT GGA AGT GGA GGT GGG GGT AGA GGT GGA AGT GGA GGT GGG GGT AGA GGT GGA AGT GGA GGT GGG GGT AGA GGT GGA AGT GGA GGT GGG GGT AGA GGT GGC CAG CGG GCC TTA AGT GGT GGG
 A   G   S   S   T   R   A   S   P   P   P   S   P   P   P   P   S   P   P   P   S   P   P   P   P   S   P   P   P   S   P   V   A   R   N   S   P   P
```

FIG. 1

SER-PRO INTERNAL REPEAT
5'-TCA CCC TCA CCA TCT CCT TCG CCA TCA CCC-3' (SEQ ID NO:112)
        3'-GGT AGA GGA AGC GGT AGT GGG AGT GGG AGT-5' (SEQ ID NO:113)
     S   P   S   P   S   P   S   P   S   P  (SEQ ID NO:114)

GAGP INTERNAL REPEAT
5'-TCA CCC TCA CCA ACT CCT ACC GCA CCA CCT GGT CGT GGT GGA CCA GGT GTG AGT GGT GGT TGT AAC AGT GGG
AGT-5' (SEQ ID NO:116)
          3'-GGT TGA GGA TGG AGG ATG CGT GGT GGA CCA GCA CCA CCT GGT CCA CAC TCA CCA CCA ACA TTG-3' (SEQ ID NO:115)
     S   P   S   P   T   P   T   A   P   P   G   P   H   S   P   P   P   T   L  (SEQ ID NO:117)

SIGNAL SEQUENCE
5'-GCTGCCGGATCCGCAATGGGAAAAATGCTTCTCTATTGCCACATTTTA GTGGTTTTAGTGTCACTTAGCTTAGCAC
AAACAACC-3' (SEQ ID NO:118)
3'-CACCAAAATCACAGTGAATCGAATGTGTTTGTTGGGCCCATCATGGCGACCGACAGTCTGCCCCC-5' (SEQ ID NO:119)

5'-LINKER
5'-GCT GCC GGA TCC TCA ACC CGG GCC-3'(SEQ ID NO:120)
3'-CGA CGG CCT AGG AGT TGG GCC CGG AGT GGG AGT-5' (SEQ ID NO:121)
     A   A   G   S   S   T   R   A  (SEQ ID NO:122)

3'-LINKER
5'-TCA CCC TCA CCG GTC GCC CGG AAT TCA CCA CCC-3' (SEQ ID NO:123)
        3'-GGC CAG CGG GCC TTA AGT GGT GGG-5' (SEQ ID NO:124)
     S   P   S   P   V   A   T   N   S   P   P   P (SEQ ID NO:125)

FIG. 11

A. S P S X S X S X S X S (SEQ ID NO:126)
   S S O S O S O S O S O S O S O S O (SEQ ID NO:127)

B. D S O* S P T O* T A O O G P H S O O O (SEQ ID NO:128)
   D S S O T O T A O O G P H S O P O T L S O S O T (SEQ ID NO:129)

FIG. 14

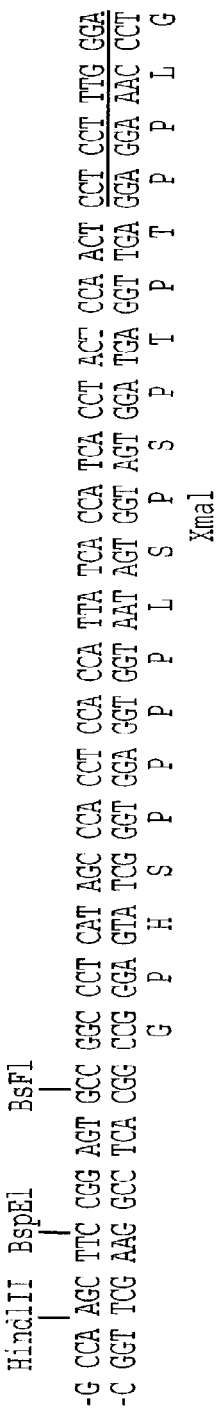
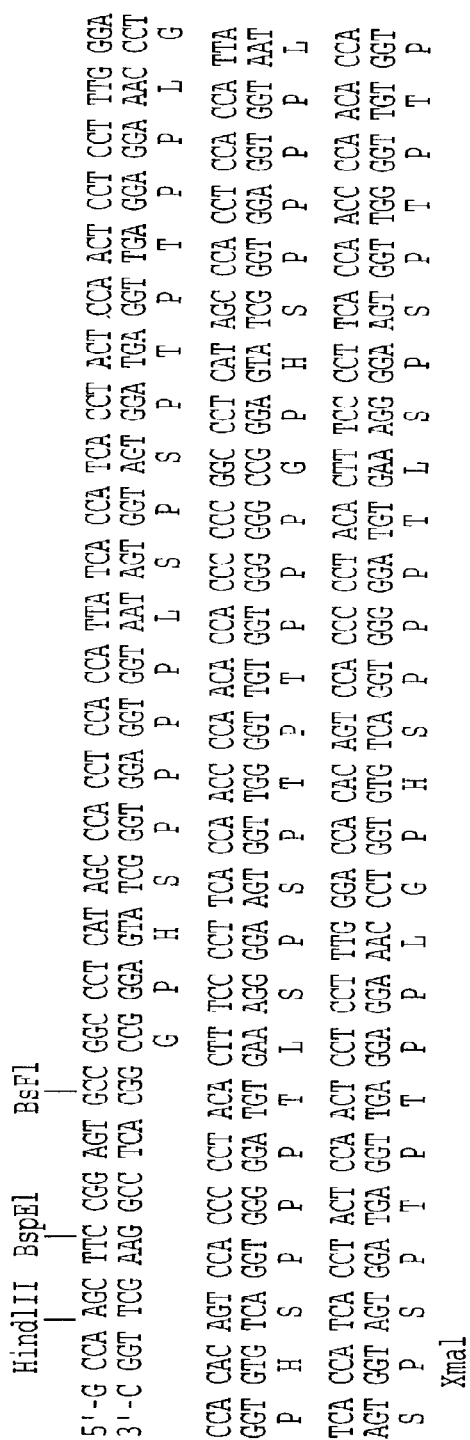
FIG. 16A
FIG. 16B

SYNTHETIC GENES FOR PLANT GUMS AND OTHER HYDROXYPROLINE-RICH GLYCOPROTEINS

CROSS-REFERENCE TO RELATED APPLICATIONS

This application is filed under 35 U.S.C. §111(a) as a continuation of U.S. application Ser. No. 12/781,490, filed on May 17, 2010, now abandoned, which is a continuation of U.S. application Ser. No. 10/437,708, filed on May 14, 2003, now abandoned, which is a divisional of U.S. application Ser. No. 09/547,693, filed on Apr. 12, 2000, now U.S. Pat. No. 6,639,050, which is a continuation-in-part of U.S. application Ser. No. 09/119,507, filed on Jul. 20, 1998, now U.S. Pat. No. 6,548,642, which is a continuation-in-part of U.S. application Ser. No. 08/897,556, filed on Jul. 21, 1997, now U.S. Pat. No. 6,570,062.

FIELD OF THE INVENTION

The present invention relates generally to the field of plant gums and other hydroxyproline-rich glycoproteins, and in particular, to the expression of synthetic genes designed from repetitive peptide sequences.

BACKGROUND

Gummosis is a common wound response that results in the exudation of a gum sealant at the site of cracks in bark. A. M. Stephen et al., "Exudate Gums", *Methods Plant Biochem.* (1990). Generally the exudate is a composite of polysaccharides and glycoproteins structurally related to cell wall components such as galactans [G. O. Aspinall, "Plant Gums", *The Carbohydrates* 2B:522536 (1970)] and hydroxyproline-rich glycoproteins [Anderson and McDougall, "The chemical characterization of the gum exudates from eight Australian *Acacia* species of the series Phyllodineae." *Food Hydrocolloids*, 2: 329 (1988)].

Gum arabic is probably the best characterized of these exudates (although it has been largely refractory to chemical analysis). It is a natural plant exudate secreted by various species of *Acacia* trees. *Acacia senegal* accounts for approximately 80% of the production of gum arabic with *Acacia seyal*, *Acacia laeta*, *Acacia camplylacantha*, and *Acacia drepanolobium* supplying the remaining 20%. The gum is gathered by hand in Africa. It is a tedious process involving piercing and stripping the bark of the trees, then returning later to gather the dried tear drop shaped, spherical balls that form in response to mechanical wounding.

The exact chemical nature of gum arabic has not been elucidated. It is believed to consist of two major components, a microheterogeneous glucurono-arabinorhamnogalactan polysaccharide and a higher molecular weight hydroxyproline-rich glycoprotein. Osman et al., "Cliaracterization of Gum Arabic Fractions Obtained By Anion-Exchange Chromatography" *Phytochemistry* 38:409 (1984) and Qi et al., "Gum Arabic Glycoprotein Is A Twisted Hairy Rope" *Plant Physiol.* 96:848 (1991). While the amino composition of the protein portion has been examined, little is known with regard to the precise amino acid sequence.

While the precise chemical nature of gum arabic is elusive, the gum is nonetheless particularly useful due to its high solubility and low viscosity compared to other gums. The FDA declared the gum to be a GRAS food additive. Consequently, it is widely used in the food industry as a thickener, emulsifier, stabilizer, surfactant, protective colloid, and flavor fixative or preservative. J. Dziezak, "A Focus on Gums" *Food Technology* (March 1991). It is also used extensively in the cosmetics industry.

Normally, the world production of gum arabic is over 100,000 tons per year. However, this production depends on the environmental and political stability of the region producing the gum. In the early 1970s, for example, a severe drought reduced gum production to 30.00 tons. Again in 1985, drought brought about shortages of the gum, resulting in a 600% price increase.

Three approaches have been used to deal with the somewhat precarious supply problem of gum arabic. First, other gums have been sought out in other regions of the world. Second, additives have been investigated to supplement inferior gum arabic. Third, production has been investigated in cultured cells.

The effort to find other gums in other regions of the world has met with some limited success. However, the solubility of gum arabic from *Acacia* is superior to other gums because it dissolves well in either hot or cold water. Moreover, while other exudates are limited to a 5% solution because of their excessive viscosity, gum arabic can be dissolved readily to make 55% solutions.

Some additives have been identified to supplement gum arabic. For example, whey proteins can be used to increase the functionality of gum arabic. A. Prakash et al., "The effects of added proteins on the functionality of gum arabic in soft drink emulsion systems," *Food Hydrocolloids* 4:177 (1990). However, this approach has limitations. Only low concentrations of such additives can be used without producing off-flavors in the final food product.

Attempts to produce gum arabic in cultured *Acacia senegal* cells has been explored. Unfortunately, conditions have not been found which lead to the expression of gum arabic in culture. A. Mollard and J-P. Joseleau, "*Acacia senegal* cells cultured in suspension secrete a hydroxyproline-deficient arabinogalactan-protein" *Plant Physiol. Biochem.* 32:703 (1994).

Clearly, new approaches to improve gum arabic production are needed. Such approaches should not be dependent on environmental or political factors. Ideally, such approaches should simplify production and be relatively inexpensive.

SUMMARY OF THE INVENTION

The present invention involves a new approach in the field of plant gums and presents a new solution to the production of hydroxyproline(Hyp)-rich glycoproteins (HRGPs), repetitive proline-rich proteins (RPRPs) and arabinogalactan-proteins (AGPs). The present invention contemplates the expression of synthetic genes designed from repetitive peptide sequences of such glycoproteins, including the peptide sequences of gum arabic glycoprotein (GAGP).

With respect to GAGP, the present invention contemplates a substantially purified polypeptide comprising at least a portion of the amino acid sequence Ser-Hyp-Hyp-Hyp-[Hyp/Thr]-Leu-Ser-Hyp-Ser-Hyp-Thr-Hyp-Thr-Hyp-Hyp-Hyp-Gly-Pro-His (SEQ ID NO:1 and SEQ ID NO:2) or variants thereof. By "variants" it is meant that the sequence need not comprise the exact sequence; up to five (5) amino acid substitutions are contemplated. For example, a Leu or Hyp may be substituted for the Gly; Leu may also be substituted for Ser and one or more Hyp. By "variants" it is also meant that the sequence need not be the entire nineteen (19) amino acids. Illustrative variants are shown in Table 3. In one preferred embodiment, variants contain one or more of the following three motifs: Ser-Hyp$_4$, Ser-Hyp$_3$-Thr, and Xaa-Hyp-Xaa-Hyp, where Xaa is any amino acid other than hydroxyproline.

Indeed, it is not intended that the present invention be limited by the precise length of the purified polypeptide. In one embodiment, the peptide comprises more than twelve (12) amino acids from the nineteen (19) amino acids of the sequence. In another embodiment, a portion of the nineteen (19) amino acids (see SEQ ID NO:1 and SEQ ID NO:2) is utilized as a repetitive sequence. In yet another embodiment, all nineteen (19) amino acids (see SEQ ID NO:1 and SEQ ID NO:2) with or without amino acid substitutions) are utilized as a repetitive sequence.

It is not intended that the present invention be limited by the precise number of repeats. The sequence (i.e. SEQ ID NO:1 and SEQ ID NO:2) or variants thereof may be used as a repeating sequence between one (1) and up to fifty (50) times, more preferably between ten (10) and up to thirty (30) times, and most preferably approximately twenty (20) times. The sequence (i.e. SEQ ID NO:1 and SEQ ID NO:2) or variants thereof may be used as contiguous repeats or may be used as non-contiguous repeats (with other amino acids, or amino acid analogues, placed between the repeating sequences).

The present invention specifically contemplates fusion proteins comprising a non-gum arabic protein or glycoprotein sequence and a portion of the gum arabic glycoprotein sequence (SEQ ID NO:1 and SEQ ID NO:2). It is not intended that the present invention be limited by the nature of the non-gum arabic glycoprotein sequence. In one embodiment, the non-gum arabic glycoprotein sequence is a green fluorescent protein.

As noted above, the present invention contemplates synthetic genes encoding such peptides. By "synthetic genes" it is meant that the nucleic acid sequence is derived using the peptide sequence of interest (in contrast to using the nucleic acid sequence from cDNA). In one embodiment, the present invention contemplates an isolated polynucleotide sequence encoding a polypeptide comprising at least a portion of the polypeptide of SEQ ID NO:1 and SEQ ID NO:2 or variants thereof. The present invention specifically contemplates a polynucleotide sequence comprising a nucleotide sequence encoding a polypeptide comprising one or more repeats of SEQ ID NO:1 and SEQ ID NO:2 or variants thereof. Importantly, it is not intended that the present invention be limited to the precise nucleic acid sequence encoding the polypeptide of interest.

The present invention contemplates synthetic genes encoding portions of HRGPs, wherein the encoded peptides contain one or more of the highly conserved Ser-Hyp$_4$ (SEQ ID NO:3) motif(s). The present invention also contemplates synthetic genes encoding portions of RPRPs, wherein the encoded peptides contain one or more of the pentapeptide motif: Pro-Hyp-Val-Tyr-Lys (SEQ ID NO:4) and variants of this sequence such as X-Hyp-Val-Tyr-Lys (SEQ ID NO:5) and Pro-Hyp-Val-X-Lys (SEQ ID NO:6) and Pro-Pro-X-Tyr-Lys and Pro-Pro-X-Tyr-X (SEQ ID NO:8), where "X" can be Thr, Glu, Hyp, Pro, His and Ile. The present invention also contemplates synthetic genes encoding portions of AGPs, wherein the encoded peptides contain one or more Xaa-Hyp-Xaa-Hyp (SEQ ID NO:9) repeats. Such peptides can be expressed in a variety of forms, including but not limited to fusion proteins.

With regard to motifs for HRGPs, the present invention contemplates a polynucleotide sequence comprising the sequence: 5'-CCA CCA CCT TCA CCT CCA CCC CCA TCT CCA-3' (SEQ ID NO:10). With regard to motifs for AGPs, the invention contemplates a polynucleotide sequence comprising the sequence: 5'-TCA CCA TCA CCA TCT CCT TCG CCA TCA CCC-3' (SEQ ID NO:11). Of course, it is not intended that the present invention be limited by the particular sequence. Indeed, the present invention specifically contemplates sequences that are not identical but are nonetheless homologous to the sequences of SEQ ID NOS: 10 and 11. The present invention also contemplates sequences that are complementary (including sequences that are only partially complementary) sequences to the sequences of SEQ ID NOS: 10 and 11. Such complementary sequences include sequences that will hybridize to the sequences of SEQ ID NOS: 10 and 11 under low stringency conditions as well as high stringency conditions (see Definitions below).

The present invention also contemplates the mixing of motifs (i.e. modules) which are not found in wild-type sequences. For example, one might add GAGP modules to extensin and RPRP crosslinking modules to AGP-like molecules.

The present invention contemplates using the polynucleotides of the present invention for expression of the polypeptides in vitro and in vivo. Therefore, the present invention contemplates polynucleotide sequences encoding two or more repeats of the sequence of SEQ ID NO:1 and SEQ ID NO:2 or variants thereof, wherein said polynucleotide sequence is contained on a recombinant expression vector. It is also contemplated that such vectors will be introduced into a variety of host cells, both eukaryotic and prokaryotic (e.g. bacteria such as E. coli).

In one embodiment, the vector further comprises a promoter. It is not intended that the present invention be limited to a particular promoter. Any promoter sequence which is capable of directing expression of an operably linked nucleic acid sequence encoding a portion of a plant gum polypeptide (or other hydroxyproline-rich polypeptide of interest as described above) is contemplated to be within the scope of the invention. Promoters include, but are not limited to, promoter sequences of bacterial, viral and plant origins. Promoters of bacterial origin include, but are not limited to, the octopine synthase promoter, the nopaline synthase promoter and other promoters derived from native Ti plasmids. Viral promoters include, but are not limited to, the 35S and 19S RNA promoters of cauliflower mosaic virus (CaMV), and T-DNA promoters from *Agrobacterium*. Plant promoters include, but are not limited to, the ribulose-1,3-bisphosphate carboxylase small subunit promoter, maize ubiquitin promoters, the phaseolin promoter, the E8 promoter, and the Tob7 promoter.

The invention is not limited to the number of promoters used to control expression of a nucleic acid sequence of interest. Any number of promoters may be used so long as expression of the nucleic acid sequence of interest is controlled in a desired manner. Furthermore, the selection of a promoter may be governed by the desirability that expression be over the whole plant, or localized to selected tissues of the plant, e.g., root, leaves, fruit, etc. For example, promoters active in flowers are known (Benfy et al. (1990) Plant Cell 2:849-856).

The promoter activity of any nucleic acid sequence in host cells may be determined (i.e., measured or assessed) using methods well known in the art and exemplified herein. For example, a candidate promoter sequence may be tested by ligating it in-frame to a reporter gene sequence to generate a reporter construct, introducing the reporter construct into host cells (e.g. tomato or potato cells) using methods described herein, and detecting the expression of the reporter gene (e.g., detecting the presence of encoded mRNA or encoded protein, or the activity of a protein encoded by the reporter gene). The reporter gene may confer antibiotic or herbicide resistance. Examples of reporter genes include, but are not limited to, dhfr which confers resistance to methotrexate [Wigler M et al., (1980) *Proc Natl Acad Sci* 77:3567-70]; npt, which confers resistance to the aminoglycosides neomycin and G-418 [Colbere-Garapin F et al., (1981) *J. Mol. Biol.* 150:1-14] and als or pat, which confer resistance to chlorsulfuron and phosphinothricin acetyl transferase, respectively. Recently, the use of a reporter gene system which expresses visible markers has gained popularity with such markers as β-glucuronidase and its substrate (X-Gluc), luciferase and its substrate (luciferin), and β-galactosidase and its substrate (X-Gal) being widely used not only to identify transformants, but also to quantify the amount of transient or stable protein expression attributable to a specific vector system [Rhodes C A et al. (1995) Methods Mol Biol 55:121-131].

In addition to a promoter sequence, the expression construct preferably contains a transcription termination sequence downstream of the nucleic acid sequence of interest to provide for efficient termination. In one embodiment, the termination sequence is the nopaline synthase (NOS) sequence. In another embodiment the termination region comprises different fragments of sugarcane ribulose-1,5-biphosphate carboxylase/oxygenase (rubisco) small subunit (scrbcs) gene. The termination sequences of the expression constructs are not critical to the invention. The termination sequence may be obtained from the same gene as the promoter sequence or may be obtained form different genes.

If the mRNA encoded by the nucleic acid sequence of interest is to be efficiently translated, polyadenylation sequences are also commonly added to the expression construct. Examples of the polyadenylation sequences include, but are not limited to, the *Agrobacterium* octopine synthase signal, or the nopaline synthase signal.

The invention is not limited to constructs which express a single nucleic acid sequence of interest. Constructs which contain a plurality of (i.e., two or more) nucleic acid sequences under the transcriptional control of the same promoter sequence are expressly contemplated to be within the scope of the invention. Also included within the scope of this invention are constructs which contain the same or different nucleic acid sequences under the transcriptional control of different promoters. Such constructs may be desirable to, for example, target expression of the same or different nucleic acid sequences of interest to selected plant tissues.

As noted above, the present invention contemplates using the polynucleotides of the present invention for expression of a portion of plant gum polypeptides in vitro and in vivo. Where expression takes place in vivo, the present invention contemplates transgenic plants. The transgenic plants of the invention are not limited to plants in which each and every cell expresses the nucleic acid sequence of interest. Included within the scope of this invention is any plant (e.g. tobacco, tomato, maize, algae, etc.) which contains at least one cell which expresses the nucleic acid sequence of interest. It is preferred, though not necessary, that the transgenic plant express the nucleic acid sequence of interest in more than one cell, and more preferably in one or more tissue. It is particularly preferred that expression be followed by proper glycosylation of the plant gum polypeptide fragment or variant thereof, such that the host cell produces functional (e.g. in terms of use in the food or cosmetic industry) plant gum polypeptide.

The fact that transformation of plant cells has taken place with the nucleic acid sequence of interest may be determined using any number of methods known in the art. Such methods include, but are not limited to, restriction mapping of genomic DNA, PCR analysis, DNA-DNA hybridization, DNA-RNA hybridization, and DNA sequence analysis.

Expressed polypeptides (or fragments thereof) can be immobilized (covalently or non-covalently) on solid supports or resins for use in isolating HRGP-binding molecules from a variety of sources (e.g. algae, plants, animals, microorganisms). Such polypeptides can also be used to make antibodies.

The invention further provides a substantially purified polypeptide comprising at least a portion of the gum arabic consensus sequence. In particular, the invention provides a substantially purified polypeptide comprising at least a portion of amino acid sequence A-Hyp-B-C-D-E-F-Hyp-G-H-I-Hyp-J-Hyp-Hyp-K-L-Pro-M (SEQ ID NO:136), wherein A is selected from Ser, Thr, and Ala; B is selected from Hyp, Pro, Leu, and Ile; C is selected from Pro and Hyp; D is selected from Hyp, Pro, Ser, Thr, and Ala; E is selected from Leu and Ile; F is selected from Ser, Thr, and Ala; G is selected from Ser, Leu, Hyp, Thr, Ala, and Ile; H is selected from Hyp, Pro, Leu, and Ile; I is selected from Thr, Ala, and Ser; J is selected from Thr, Ser, and Ala; K is selected from Thr, Leu, Hyp, Ser, Ala, and Ile; L is selected from Gly, Leu, Ala, and Ile; and M is selected from His and Pro; and wherein the portion is greater than twelve contiguous amino acids of the amino acid sequence. In a preferred embodiment, the portion occurs in the polypeptide as a repeating sequence. In a more preferred embodiment, the repeating sequence repeats from 1 to 64 times. In an alternative preferred embodiment, A is Ser; B is selected from Hyp, and Leu; D is selected from Hyp, Ser, and Thr; E is Leu; F is Ser; G is selected from Ser, Leu, and Hyp; H is selected from Hyp, Pro, and Leu; I is selected from Thr and Ala; J is Thr; K is selected from Thr, Leu, and Hyp; L is selected from Gly and Leu; and M is selected from His and Pro. In another alternative embodiment, the amino acid sequence is selected from Ser-Hyp-Hyp-Hyp-Hyp-Leu-Ser-Hyp-Ser-Hyp-Thr-Hyp-Thr-Hyp-Hyp-Leu-Gly-Pro-His (SEQ ID NO:143), Ser-Hyp-Hyp-Hyp-Thr-Leu-Ser-Hyp-Ser-Hyp-Thr-Hyp-Thr-Hyp-Hyp-Hyp-Gly-Pro-His (SEQ ID NO:144), Ser-Hyp-Hyp-Hyp-Ser-Leu-Ser-Hyp-Ser-Hyp-Thr-Hyp-Thr-Hyp-Hyp-Thr-Gly-Pro-His (SEQ ID NO:145), Ser-Hyp-Hyp-Hyp-Hyp-Leu-Ser-Hyp-Ser-Hyp-Thr-Hyp-Thr-Hyp-Hyp-Hyp-Gly-Pro-Hyp (SEQ ID NO:146), Ser-Hyp-Leu-Pro-Thr-Leu-Ser-Hyp-Leu-Pro-Thr-Hyp-Thr-Hyp-Hyp-Hyp-Gly-Pro-His (SEQ ID NO:147), Ser-Hyp-Leu-Pro-Thr-Leu-Ser-Hyp-Leu-Pro-Ala-Hyp-Thr-Hyp-Hyp-Hyp-Gly-Pro-His (SEQ ID NO:148), Ser-Hyp-Hyp-Hyp-Hyp-Leu-Ser-Hyp-Ser-Leu-Thr-Hyp-Thr-Hyp-Hyp-Leu-Gly-Pro-Hyp (SEQ ID NO:149), Ser-Hyp-Hyp-Hyp-Hyp-Leu-Ser-Hyp-Ser-Hyp-Thr-Hyp-Thr-Hyp-Hyp-Hyp-Gly-Pro-His (SEQ ID NO:150), Ser-Hyp-Hyp-Hyp-Thr-Leu-Ser-Hyp-Ser-Hyp-Thr-Hyp-Thr-Hyp-Hyp-Hyp-Gly-Pro-His (SEQ ID NO:151), Ser-Hyp-Hyp-Hyp-Hyp-Leu-Ser-Hyp-Ser-Hyp-Ala-Hyp-Thr-Hyp-Hyp-Hyp-Gly-Pro-His (SEQ ID NO:152), Ser-Hyp-Hyp-Hyp-Hyp-Leu-Ser-Hyp-Leu-Pro-Thr-Hyp-Thr-Hyp-Hyp-Leu-Gly-Pro-His (SEQ ID NO:153), Ser-Hyp-Hyp-Hyp-Ser-Leu-Ser-Hyp-Leu-Pro-Thr-Hyp-Thr-Hyp-Hyp-Leu-Gly-Pro-His (SEQ ID NO:154), Ser-Hyp-Hyp-Hyp-Thr-Leu-Ser-Hyp-Hyp-Leu-Thr-Hyp-Thr-Hyp-Hyp-Leu-Leu-Pro-His (SEQ ID NO:155), Hyp-Hyp-Thr-Leu-Ser-Hyp-Hyp-Leu-Thr-Hyp-Thr-Hyp-Hyp-Leu-Leu-Pro (SEQ ID NO:156), Ser-Hyp-Hyp-Hyp-Ser-Leu-Ser-Hyp-Leu-Pro-Thr-Hyp-Thr-Hyp-Hyp-Leu (SEQ ID NO:157), Hyp-Hyp-Leu-Ser-Hyp-Leu-Pro-Thr-Hyp-Thr-Hyp-Hyp-Leu-Gly-Pro-His (SEQ ID NO:158), Ser-Hyp-Hyp-Hyp-Thr-Leu-Ser-Hyp-Ser-Hyp-Thr-Hyp-Thr-Hyp (SEQ ID NO:159), Leu-Ser-Hyp-Ser-Leu-Thr-Hyp-Thr-Hyp-Hyp-Leu-Gly-Pro-Hyp (SEQ ID NO:160), Hyp-Thr-Leu-Ser-Hyp-Leu-Pro-Ala-Hyp-Thr- Hyp-Hyp-Hyp-Gly (SEQ ID NO:161), Ser-Hyp-Hyp-Hyp-Hyp-Leu-Ser-Hyp-Ser-Hyp-Thr-Hyp (SEQ ID NO:162), Ser-Leu-Ser-Hyp-Ser-Hyp-Thr-Hyp-Thr-Hyp-Hyp-Thr (SEQ ID NO:163), Hyp-Hyp-Thr-Leu-Ser-Hyp-Ser-Hyp-Thr-Hyp-Thr-Hyp (SEQ ID NO:164), Hyp-Thr-Hyp-Thr-Hyp-Hyp-Leu-Gly-Pro-His (SEQ ID NO:165), Hyp-Hyp-Thr-Leu-Ser-Hyp-Hyp-Leu-Thr-Hyp (SEQ ID NO:166), Ser-Hyp-Hyp-Hyp-Ser-Leu-Ser-Hyp-Leu-Pro (SEQ ID NO:167), Hyp-Thr-Hyp-Hyp-Leu-Gly-Pro-His (SEQ ID NO:168), Hyp-Leu-Ser-Hyp-Ser-Hyp-Ala-Hyp (SEQ ID NO:169), Hyp-Hyp-Hyp-Thr-Leu-Ser-Hyp-Ser (SEQ ID NO:170), Thr-Hyp-Hyp-Hyp-Gly-Pro (SEQ ID NO:171), Hyp-Hyp-Leu-Ser-Hyp-Ser (SEQ ID NO:172), Ser-Hyp-Leu-Pro-Ala-Hyp (SEQ ID NO:173), Leu-Pro-Thr-Leu-Ser-Hyp (SEQ ID NO:174), Ser-Hyp-Ser-Hyp (SEQ ID NO:175), Ser-Hyp-Thr-Hyp (SEQ ID NO:176), Thr-Hyp-Thr-Hyp (SEQ ID NO:177), Thr-Hyp-Hyp-Hyp (SEQ ID NO:178), Ser-Hyp-Pro-Pro-Pro-Leu-Ser-Hyp-Ser-Hyp-Thr-Hyp-Thr-Hyp-Hyp-Leu-Gly-Pro-His (SEQ ID NO:217), Ser-Hyp-Hyp-Pro-Pro-Leu-Ser-Hyp-Ser-Hyp-Thr-Hyp-Thr-Hyp-Hyp-Leu-Gly-Pro-His (SEQ ID NO:218), Ser-Hyp-Pro-Hyp-Pro-Leu-Ser-Hyp-Ser-Hyp-Thr-Hyp-Thr-Hyp-Hyp-Leu-Gly-Pro-His (SEQ ID NO:219), Ser-Hyp-Pro-Pro-Hyp-Leu-Ser-Hyp-Ser-Hyp-Thr-Hyp-Thr-Hyp-Hyp-Leu-Gly-Pro-His (SEQ ID NO:220), Ser-Hyp-Hyp-Hyp-Pro-Leu-Ser-Hyp-Ser-Hyp-Thr-Hyp-Thr-Hyp-Hyp-Leu-Gly-Pro-His (SEQ ID NO:221), Ser-Hyp-Hyp-Pro-Hyp-Leu-Ser-Hyp-Ser-Hyp-Thr-Hyp-Thr-Hyp-Hyp-Leu-Gly-Pro-His (SEQ ID NO:222), Ser-Hyp-Pro-Hyp-Hyp-Leu-Ser-Hyp-Ser-Hyp-Thr-Hyp-Thr-Hyp-Hyp-Leu-Gly-Pro-His (SEQ ID NO:223), Ser-Hyp-Hyp-Hyp-Hyp-Leu-Ser-Hyp-Ser-Pro-Thr-Hyp-Thr-Hyp-Hyp-Leu-Gly-Pro-His (SEQ ID NO:224), Ser-Hyp-Hyp-Hyp-Hyp-Leu-Ser-Hyp-Ser-Leu-Thr-Hyp-Thr-Hyp-Hyp-Leu-Gly-Pro-His (SEQ ID NO:225), Ser-Hyp-Hyp-Hyp-Thr-Leu-Ser-Hyp-Ser-Hyp-Thr-Hyp-Thr-Hyp-Hyp-Hyp-Gly-Pro-His-Ser-Hyp-Hyp-Hyp-(Hyp) (SEQ ID NO:18), Ser-Hyp-Ser-Hyp-Thr-Hyp-Thr-Hyp-Hyp-Leu-Gly-Pro-His (SEQ ID NO:23), Ser-Hyp-Hyp-Hyp-A-Leu-Ser-Hyp-Ser-Hyp-Thr-Hyp-Thr-Hyp-Hyp-B-Gly-Pro-His (SEQ ID NO:179), where A is selected from Hyp, Thr, and Ser, and B is selected from Hyp and Lys, SEQ ID NO:131, and SEQ ID NO:133. In yet another alternative embodiment, the portion comprises a motif selected from (Xaa-Hyp)$_x$ (SEQ ID NO:182) and Xaa-Hyp-Xaa-Xaa-Hyp-Xaa (SEQ ID NO:183), wherein Xaa is any amino acid other than hydroxyproline, and wherein x is from 2 to 1000. In a preferred embodiment, the portion comprises the sequence Xaa-Hyp-Xaa-Hyp (SEQ ID NO:9), and wherein Xaa is selected from Ser, Thr, and Ala. In a further alternative embodiment, the portion comprises a motif selected from Xaa-Hyp-Hyp. (SEQ ID NO:209) and Xaa-Pro-Hyp. (SEQ ID NO:210), wherein n is from 1 to 100, and wherein Xaa is any amino acid other than hydroxyproline. In a preferred embodiment, the portion comprises a peptide sequence selected from Ser-Hyp$_2$ (SEQ ID NO:211), Ser-Hyp$_3$ (SEQ ID NO:212), Ser-Hyp$_o$ (SEQ ID NO:3), Thr-Hyp$_2$ (SEQ ID NO:213), and Thr-Hyp$_3$ (SEQ ID NO:214). In an additional alternative embodiment, the portion comprises a peptide sequence selected from Ser-Hyp$_2$-Pro (SEQ ID NO:215) and Ser-Hyp$_2$-Pro-Hyp (SEQ ID NO:216).

The invention further provides a substantially purified polypeptide comprising a non-contiguous hydroxyproline motif. In particular, the invention provides a substantially purified polypeptide comprising a first motif selected from (Xaa-Hyp)$_x$ (SEQ ID NO:182) and Xaa-Hyp-Xaa-Xaa-Hyp-Xaa (SEQ ID NO:183), wherein Xaa is any amino acid other than hydroxyproline, and wherein x is from 2 to 1000. In one embodiment, the sequence is Xaa-Hyp-Xaa-Hyp (SEQ ID NO:9), wherein Xaa is selected from Ser, Thr, and Ala. In an alternative embodiment, the polypeptide further comprises a contiguous hydroxyproline motif (i.e., a second motif) selected from Xaa-Hyp-Hyp$_n$ (SEQ ID NO:209) and Xaa-Pro-Hyp$_n$ (SEQ ID NO:210), wherein n is from 1 to 100, and wherein Xaa is any amino acid other than hydroxyproline. In a preferred embodiment, the first and second motifs alternate in the polypeptide. In a more preferred embodiment, the alternating first and second motifs repeat from 1 to 500 times.

Also provided herein is a substantially purified polypeptide comprising a motif selected from Xaa-Hyp-Hyp$_n$ (SEQ ID NO:209) and Xaa-Pro-Hyp$_n$ (SEQ ID NO:210), wherein n is from 1 to 100, and wherein Xaa is any amino acid other than hydroxyproline. In one embodiment, the portion comprises a peptide sequence selected from Ser-Hyp$_2$ (SEQ ID NO:211), Ser-Hyp$_3$ (SEQ ID NO:212), Ser-Hyp$_o$ (SEQ ID NO:3), Thr-Hyp$_2$ (SEQ ID NO:213), and Thr-Hyp$_3$ (SEQ ID NO:214).

The invention also provides a fusion protein comprising a first sequence selected from a non-gum arabic protein sequence and a non-gum arabic glycoprotein sequence operably linked to at least a portion of an amino acid sequence selected from (a) A-Hyp-B-C-D-E-F-Hyp-G-H-I-Hyp-J-Hyp-Hyp-K-L-Pro-M (SEQ ID NO:136), wherein A is selected from Ser, Thr, and Ala; B is selected from Hyp, Pro, Leu, and Ile; C is selected from Pro and Hyp; D is selected from Hyp, Pro, Ser, Thr, and Ala; E is selected from Leu and Ile; F is selected from Ser, Thr, and Ala; G is selected from Ser, Leu, Hyp, Thr, Ala, and Ile; H is selected from Hyp, Pro, Leu, and Ile; I is selected from Thr, Ala, and Ser; J is selected from Thr, Ser, and Ala; K is selected from Thr, Leu, Hyp, Ser, Ala, and Ile; L is selected from Gly, Leu, Ala, and Ile; and M is selected from His and Pro; and wherein the portion is greater than twelve contiguous amino acids of the amino acid sequence, (b) a polypeptide comprising a first motif selected from (Xaa-Hyp)$_x$ (SEQ ID NO:182) and Xaa-Hyp-Xaa-Xaa-Hyp-Xaa (SEQ ID NO:183), wherein x is from 2 to 1000, (c) a polypeptide comprising a second motif selected from Xaa-Hyp-Hyp$_n$ (SEQ ID NO:209) and Xaa-Pro-Hyp$_n$ (SEQ ID NO:210), wherein n is from 1 to 500, and (d) a polypeptide comprising the first motif and the second motif, wherein Xaa is any amino acid other than hydroxyproline. In one embodiment, the first sequence is a green fluorescent protein amino acid sequence.

Also provided by the invention is an isolated polynucleotide sequence encoding at least a portion of an amino acid sequence selected from (a) A-Hyp-B-C-D-E-F-Hyp-G-H-1-Hyp-J-Hyp-Hyp-K-L-Pro-M (SEQ ID NO:136), wherein A is selected from Ser, Thr, and Ala; B is selected from Hyp, Pro, Leu, and Ile; C is selected from Pro and Hyp; D is selected from Hyp, Pro, Ser, Thr, and Ala; E is selected from Leu and Ile; F is selected from Ser, Thr, and Ala; G is selected from Ser, Leu, Hyp, Thr, Ala, and Ile; H is selected from Hyp, Pro, Leu, and Ile; I is selected from Thr, Ala, and Ser; J is selected from Thr, Ser, and Ala; K is selected from Thr, Leu, Hyp, Ser, Ala, and Ile; L is selected from Gly, Leu, Ala, and Ile; and M is selected from His and Pro; and wherein the portion is greater than twelve contiguous amino acids of the amino acid sequence, (b) a polypeptide comprising a first motif selected from (Xaa-Hyp). (SEQ ID NO:182) and Xaa-Hyp-Xaa-Xaa-Hyp-Xaa (SEQ ID NO:183), wherein x is from 2 to 1000, (c) a polypeptide comprising a second motif selected from Xaa-Hyp-Hyp$_n$ (SEQ ID NO:209) and Xaa-Pro-Hyp$_n$ (SEQ ID NO:210), wherein n is from 1 to 500, and (d) a polypeptide comprising the first motif and the second motif, wherein Xaa is any amino acid other than hydroxyproline.

The invention further provides a recombinant expression vector comprising a polynucleotide sequence encoding a portion of an amino acid sequence selected from (a) A-Hyp-B-C-D-E-F-Hyp-G-H-I-Hyp-J-Hyp-Hyp-K-L-Pro-M (SEQ ID NO:136), wherein A is selected from Ser, Thr, and Ala; B is selected from Hyp, Pro, Leu, and Ile; C is selected from Pro and Hyp; D is selected from Hyp, Pro, Ser, Thr, and Ala; E is selected from Leu and Ile; F is selected from Ser, Thr, and Ala; G is selected from Ser, Leu, Hyp, Thr, Ala, and Ile; H is selected from Hyp, Pro, Leu, and Ile; I is selected from Thr, Ala, and Ser; J is selected from Thr, Ser, and Ala; K is selected from Thr, Leu, Hyp, Ser, Ala, and Ile; L is selected from Gly, Leu, Ala, and Ile; and M is selected from His and Pro; and wherein the portion is greater than twelve contiguous amino acids of the amino acid sequence, (b) a polypeptide comprising a first motif selected from (Xaa-Hyp)$_x$ (SEQ ID NO:182) and Xaa-Hyp-Xaa-Xaa-Hyp-Xaa (SEQ ID NO:183), wherein x is from 2 to 1000, (c) a polypeptide comprising a second motif selected from Xaa-Hyp-Hyp$_n$ (SEQ ID NO:209) and Xaa-Pro-Hyp$_n$ (SEQ ID NO:210), wherein n is from 1 to 500, and (d) a polypeptide comprising the first motif and the second motif, wherein Xaa is any amino acid other than hydroxyproline. In one embodiment, the expression vector further comprises a promoter operably linked to the polynucleotide sequence. In a preferred embodiment, the promoter is a viral promoter. In a more preferred embodiment, the viral promoter is selected from the group consisting of the 35S and 19S RNA promoters of cauliflower mosaic virus. In an alternative preferred embodiment, the expression vector further comprises a signal sequence selected from extensin signal sequence (SEQ ID NO:14), and tomato arabinogalactan-protein signal sequence (SEQ ID NO:215). In a more preferred embodiment, the expression vector further comprises a reporter gene. In a yet more preferred embodiment, the reporter gene is the green fluorescence protein gene. In another embodiment, the vector is contained within a host cell. In a preferred embodiment, the host cell is a plant cell. In a more preferred embodiment, the plant cell expresses a glycoprotein comprising the portion.

Also provided herein is a method for producing at least a portion of a glycoprotein, comprising: a) providing: i) a recombinant expression vector comprising a polynucleotide sequence encoding at least a portion of an amino acid sequence selected from (a) A-Hyp-B-C-D-E-F-Hyp-G-H-I-Hyp-J-Hyp-Hyp-K-L-Pro-M (SEQ ID NO:136), wherein A is selected from Ser, Thr, and Ala; B is selected from Hyp, Pro, Leu, and Ile; C is selected from Pro and Hyp; D is selected from Hyp, Pro, Ser, Thr, and Ala; E is selected from Leu and Ile; F is selected from Ser, Thr, and Ala; G is selected from Ser, Leu, Hyp, Thr, Ala, and Ile; H is selected from Hyp, Pro, Leu, and Ile; I is selected from Thr, Ala, and Ser; J is selected from Thr, Ser, and Ala; K is selected from Thr, Leu, Hyp, Ser, Ala, and Ile; L is selected from Gly, Leu, Ala, and Ile; and M is selected from His and Pro; and wherein the portion is greater than twelve contiguous amino acids of the amino acid sequence, (b) a polypeptide comprising a first motif selected from (Xaa-Hyp)$_x$ (SEQ ID NO:182) and Xaa-Hyp-Xaa-Xaa-Hyp-Xaa (SEQ ID NO:183), wherein x is from 2 to 1000, (c) a polypeptide comprising a second motif selected from Xaa-Hyp-Hyp$_n$ (SEQ ID NO:209) and Xaa-Pro-Hyp$_n$ (SEQ ID NO:210), wherein n is from 1 to 500, and (d) a polypeptide comprising the first motif and the second motif, wherein Xaa is any amino acid other than hydroxyproline; and ii) a host cell; and b) introducing the vector into the host cell under conditions such that the portion is expressed. In one embodiment, the host cell is growing in culture. In a preferred embodiment, the method further comprises the step of c) recovering the portion from the host cell culture. In an alternative embodiment, the host cell is a plant cell. In a more preferred embodiment, the plant cell is derived from a plant selected from the family Leguminoseae.

DESCRIPTION OF THE DRAWINGS

FIG. 1 shows the nucleic acid sequence (SEQ ID NO:12) of one embodiment of a synthetic gene of the present invention.

FIG. 11 shows the oligonucleotide sequence (SEQ ID NOs:112, 113, 115, 116, 118-121, 123 and 124) sets used to build the synthetic genes which encode the Ser-Pro internal repeat polypeptide (SEQ ID NO:114), the GAGP internal repeat polypeptide (SEQ ID NO:117), the 5'-linker (SEQ ID NO:122) and 3'-linker (SEQ ID NO:125).

FIG. 14 shows polypeptide sequences of (Ser-Hyp)$_{32}$-EGFP and (GAGP)$_3$-EGFP before and after deglycosylation. (A) N-terminal amino acid sequence of the glycoprotein, (Ser-Hyp)$_{32}$-EGFP, with partial sequence of both the glycoprotein (upper sequence) (SEQ ID NO:126) and its polypeptide after deglycosylation (lower sequence) (SEQ ID NO:127). X denotes blank cycles which correspond to glycosylated Hyp; glycoamino acids tend to produce blank cycles during Edman degradation, an exception being arabinosyl Hyp. (B) Polypeptide sequence of glycosylated (GAGP)$_3$-EGFP (upper sequence) (SEQ ID NO:128) and deglycosylated (GAGP)$_3$-EGFP (lower sequence) (SEQ ID NO:129). Residues marked with an asterisk (*) denote low molar yields of Hyp and likely sites of arabinogalactan polysaccharide attachment in glycosylated (GAGP)$_3$-EGFP. For example, yields were 480 pM Asp in the first cycle, 331 pM Scr in the second, 194 pM Hyp in the third, and 508 pM Ser in the fourth cycle.

FIG. 16 depicts the exemplary (A) nucleotide sequence (SEQ ID NO:130) and amino acid sequence (SEQ ID NO:131) of two GAGP repeats, and (B) nucleotide sequence (SEQ ID NO:132) and amino acid sequence (SEQ ID NO:133) of four GAGP repeats (SEQ ID NOs:133).

DEFINITIONS

Figure 2:
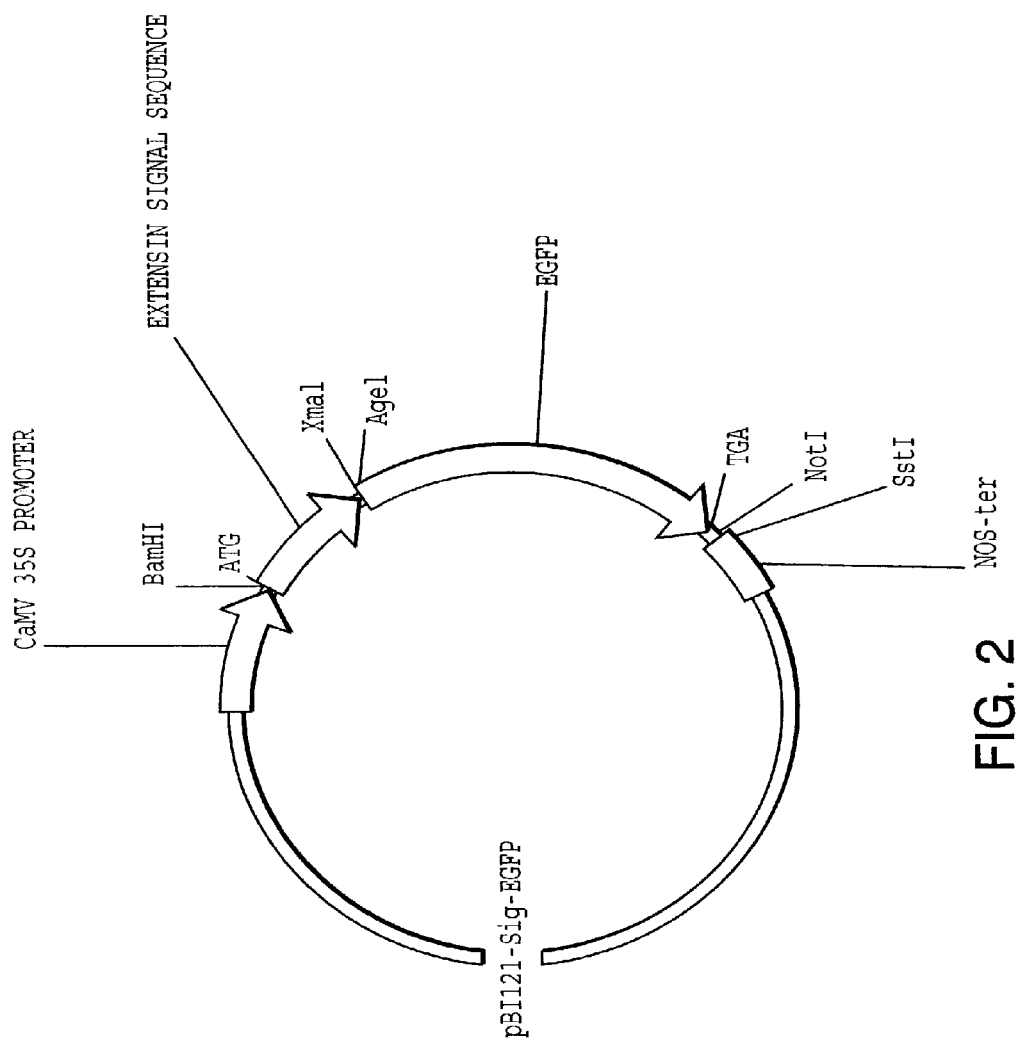
FIG. 2 shows one embodiment of a synthetic gene in one embodiment of an expression vector.

The term "gene" refers to a DNA sequence that comprises control and coding sequences necessary for the production of a polypeptide or its precursor. The polypeptide can be encoded by a full length coding sequence or by any portion of the coding sequence.

The term "nucleic acid sequence of interest" refers to any nucleic acid sequence the manipulation of which may be deemed desirable for any reason by one of ordinary skill in the art (e.g., confer improved qualities).

The term "wild-type" when made in reference to a gene refers to a gene which has the characteristics of a gene isolated from a naturally occurring source. The term "wild-type" when made in reference to a gene product refers to a gene product which has the characteristics of a gene product isolated from a naturally occurring source. A wild-type gene is that which is most frequently observed in a population and is thus arbitrarily designated the "normal" or "wild-type" form of the gene. In contrast, the term "modified" or "mutant" when made in reference to a gene or to a gene product refers, respectively, to a gene or to a gene product which displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "recombinant" when made in reference to a DNA molecule refers to a DNA molecule which is comprised of segments of DNA joined together by means of molecular biological techniques. The term "recombinant" when made in reference to a protein or a polypeptide refers to a protein molecule which is expressed using a recombinant DNA molecule.

As used herein, the terms "vector" and "vehicle" are used interchangeably in reference to nucleic acid molecules that transfer DNA segment(s) from one cell to another.

The term "expression vector" or "expression cassette" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "targeting vector" or "targeting construct" refer to oligonucleotide sequences comprising a gene of interest flanked on either side by a recognition sequence which is capable of homologous recombination of the DNA sequence located between the flanking recognition sequences.

The terms "in operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "transformation" as used herein refers to the introduction of foreign DNA into cells. Transformation of a plant cell may be accomplished by a variety of means known in the art including particle mediated gene transfer (see, e.g., U.S. Pat. No. 5,584,807 hereby incorporated by reference); infection with an *Agrobacterium* strain containing the foreign DNA for random integration (U.S. Pat. No. 4,940,838 hereby incorporated by reference) or targeted integration (U.S. Pat. No. 5,501,967 hereby incorporated by reference) of the foreign DNA into the plant cell genome; electroinjection (Nan et al. (1995) In "Biotechnology in Agriculture and Forestry," Ed. Y. P. S. Bajaj, Springer-Verlag Berlin Heidelberg, Vol 34:145-155; Griesbach (1992) HortScience 27:620); fusion with liposomes, lysosomes, cells, minicells or other fusible lipid-surfaced bodies (Fraley et al. (1982) *Proc. Natl. Acad. Sci. USA* 79:1859-1863; polyethylene glycol (Krens et al. (1982) *Nature* 296:72-74); chemicals that increase free DNA uptake; transformation using virus, and the like.

The terms "infecting" and "infection" with a bacterium refer to co-incubation of a target biological sample, (e.g., cell, tissue, etc.) with the bacterium under conditions such that nucleic acid sequences contained within the bacterium are introduced into one or more cells of the target biological sample.

The term "*Agrobacterium*" refers to a soil-borne, Gram-negative, rod-shaped phytopathogenic bacterium which causes crown gall. The term "*Agrobacterium*" includes, but is not limited to, the strains *Agrobacterium tumefaciens*, (which typically causes crown gall in infected plants), and *Agrobacterium rhizogens* (which causes hairy root disease in infected host plants). Infection of a plant cell with *Agrobacterium* generally results in the production of opines (e.g., nopaline, agropine, octopine etc.) by the infected cell. Thus, *Agrobacterium* strains which cause production of nopaline (e.g., strain LBA4301, C58, A208) are referred to as "nopaline-type" *Agrobacteria*; *Agrobacterium* strains which cause production of octopine (e.g., strain LBA4404, Ach5, B6) are referred to as "octopine-type" *Agrobacteria*; and *Agrobacterium* strains which cause production of agropine (e.g., strain EHA105, EHA101, A281) are referred to as "agropine-type" *Agrobacteria*.

The terms "bombarding, "bombardment," and "biolistic bombardment" refer to the process of accelerating particles towards a target biological sample (e.g., cell, tissue, etc.) to effect wounding of the cell membrane of a cell in the target biological sample and/or entry of the particles into the target biological sample. Methods for biolistic bombardment are known in the art (e.g., U.S. Pat. No. 5,584,807, the contents of which are herein incorporated by reference), and are commercially available (e.g., the helium gas-driven microprojectile accelerator (PDS-1000/He) (BioRad).

The term "microwounding" when made in reference to plant tissue refers to the introduction of microscopic wounds in that tissue. Microwounding may be achieved by, for example, particle or biolistic bombardment.

The term "transgenic" when used in reference to a plant cell refers to a plant cell which comprises a transgene, or whose genome has been altered by the introduction of a transgene. The term "transgenic" when used in reference to a plant refers to a plant which comprises one or more cells which contain a transgene, or whose genome has been altered by the introduction of a transgene. These transgenic cells and transgenic plants may be produced by several methods including the introduction of a "transgene" comprising nucleic acid (usually DNA) into a target cell or integration into a chromosome of a target cell by way of human intervention, such as by the methods described herein.

The term "transgene" as used herein refers to any nucleic acid sequence which is introduced into the genome of a plant cell by experimental manipulations. A transgene may be an "endogenous DNA sequence," or a "heterologous DNA sequence" (i.e., "foreign DNA"). The term "endogenous DNA sequence" refers to a nucleotide sequence which is naturally found in the cell into which it is introduced so long as it does not contain some modification (e.g., a point mutation, the presence of a selectable marker gene, etc.) relative to the naturally-occurring sequence. The term "heterologous DNA sequence" refers to a nucleotide sequence which is ligated to, or is manipulated to become ligated to, a nucleic acid sequence to which it is not ligated in nature, or to which it is ligated at a different location in nature. Heterologous DNA is not endogenous to the cell into which it is introduced, but has been obtained from another cell. Heterologous DNA also includes an endogenous DNA sequence which contains some modification. Generally, although not necessarily, heterologous DNA encodes RNA and proteins that are not normally produced by the cell into which it is expressed. Examples of heterologous DNA include mutated wild-type genes (i.e., wild-type genes that have been modified such that they are no longer wild-type genes), reporter genes, transcriptional and translational regulatory sequences, selectable marker proteins (e.g., proteins which confer drug resistance), etc.

As used herein, the term "probe" when made in reference to an oligonucleotide (i.e., a sequence of nucleotides) refers to an oligonucleotide, whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. Oligonucleotide probes may be labelled with a "reporter molecule," so that the probe is detectable using a detection system. Detection systems include, but are not limited to, enzyme, fluorescent, radioactive, and luminescent systems.

The term "selectable marker" as used herein, refer to a gene which encodes an enzyme having an activity that confers resistance to an antibiotic or drug upon the cell in which the selectable marker is expressed. Selectable markers may be "positive" or "negative." Examples of positive selectable markers include the neomycin phosphotransferase (NPTII) gene which confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme.

The terms "promoter element," "promoter," or "promoter sequence" as used herein, refer to a DNA sequence that is located at the 5' end (i.e. precedes) the protein coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

The term "amplification" is defined as the production of additional copies of a nucleic acid sequence and is generally carried out using polymerase chain reaction technologies well known in the art [Dieffenbach C W and G S Dveksler (1995) *PCR Primer, a Laboratory Manual*, Cold Spring Harbor Press, Plainview N.Y.]. As used herein, the term "polymerase chain reaction" ("PCR") refers to the method disclosed in U.S. Pat. Nos. 4,683,195, 4,683,202 and 4,965,188, all of which are hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With modern methods of PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; and/or incorporation of $^{32}$P-labeled deoxyribonucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications. Amplified target sequences may be used to obtain segments of DNA (e.g., genes) for the construction of targeting vectors, transgenes, etc.

The present invention contemplates using amplification techniques such as PCR to obtain the cDNA (or portions thereof) of plant genes encoding plant gums and other hydroxyproline-rich polypeptides. In one embodiment, primers are designed using the synthetic gene sequences (e.g. containing sequences encoding particular motifs) described herein and PCR is carried out (using genomic DNA or other source of nucleic acid from any plant capable of producing a gum exudate) under conditions of low stringency. In another embodiment, PCR is carried out under high stringency. The amplified products can be run out on a gel and isolated from the gel.

The term "hybridization" as used herein refers to any process by which a strand of nucleic acid joins with a complementary strand through base pairing [Coombs J (1994) *Dictionary of Biotechnology*, Stockton Press, New York N.Y.].

As used herein, the terms "complementary" or "complementarity" when used in reference to polynucleotides refer to polynucleotides which are related by the base-pairing rules. For example, for the sequence 5'-AGT-3' is complementary to the sequence 5'-ACT-3'. Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" when used in relation to nucleic acids refers to a degree of complementarity. There may be partial homology or complete homology (i.e., identity). A partially complementary sequence is one that at least partially inhibits a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a sequence which is completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

Low stringency conditions when used in reference to nucleic acid hybridization comprise conditions equivalent to binding or hybridization at 68° C. in a solution consisting of 5×SSPE (43.8 g/l NaCl, 6.9 g/l NaH$_2$PO$_4$.H$_2$O and 1.85 g/l EDTA, pH adjusted to 7.4 with NaOH), 1% SDS, 5×Denhardt's reagent [50×Denhardt's contains the following per 500 ml: 5 g Ficoll (Type 400, Pharmacia), 5 g BSA (Fraction V; Sigma)] and 100 µg/ml denatured salmon sperm DNA followed by washing in a solution comprising 0.2×SSPE, and 0.1% SDS at room temperature when a DNA probe of about 100 to about 1000 nucleotides in length is employed.

High stringency conditions when used in reference to nucleic acid hybridization comprise conditions equivalent to binding or hybridization at 68° C. in a solution consisting of 5×SSPE, 1% SDS, 5×Denhardt's reagent and 100 µg/ml denatured salmon sperm DNA followed by washing in a solution comprising 0.1×SSPE, and 0.1% SDS at 68° C. when a probe of about 100 to about 1000 nucleotides in length is employed.

The term "equivalent" when made in reference to a hybridization condition as it relates to a hybridization condition of interest means that the hybridization condition and the hybridization condition of interest result in hybridization of nucleic acid sequences which have the same range of percent (%) homology. For example, if a hybridization condition of interest results in hybridization of a first nucleic acid sequence with other nucleic acid sequences that have from 50% to 70% homology to the first nucleic acid sequence, then another hybridization condition is said to be equivalent to the hybridization condition of interest if this other hybridization condition also results in hybridization of the first nucleic acid sequence with the other nucleic acid sequences that have from 50% to 70% homology to the first nucleic acid sequence.

When used in reference to nucleic acid hybridization the art knows well that numerous equivalent conditions may be employed to comprise either low or high stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of either low or high stringency hybridization different from, but equivalent to, the above listed conditions.

"Stringency" when used in reference to nucleic acid hybridization typically occurs in a range from about $T_m$-5° C. (5° C. below the $T_m$ of the probe) to about 20° C. to 25° C. below $T_m$. As will be understood by those of skill in the art, a stringent hybridization can be used to identify or detect identical polynucleotide sequences or to identify or detect similar or related polynucleotide sequences. Under "stringent conditions" a nucleic acid sequence of interest will hybridize to its exact complement and closely related sequences.

As used herein, the term "fusion protein" refers to a chimeric protein containing the protein of interest (i.e., GAGP and fragments thereof) joined to an exogenous protein fragment (the fusion partner which consists of a non-GAGP sequence). The fusion partner may provide a detectable moiety, may provide an affinity tag to allow purification of the recombinant fusion protein from the host cell, or both. If desired, the fusion protein may be removed from the protein of interest (i.e., GAGP protein or fragments thereof) by a variety of enzymatic or chemical means known to the art. In an alternative embodiment, the fusion proteins of the invention may be used as substrates for plant glycosyl transgresses. For example after deglycosylation, the exemplary (Ser-Hyp)$_{32}$-EGFP (see Example 23) may be used as an acceptor for galactose addition, with UDP-galactose as co-substrate, catalyzed by galactosyl transferase. The fusion partner EGFP allows facile isolation of the newly galactosylated polypeptide. Fusion proteins containing sequences of the invention may be isolated using methods known in the art, such as gel filtration (Example 22), hydrophobic interaction chromatograph (HIC), reverse phase chromatography, and anion exchange chromatography.

As used herein the term "non-gum arabic glycoprotein" or "non-gum arabic glycoprotein sequence" refers to that portion of a fusion protein which comprises a protein or protein sequence which is not derived from a gum arabic glycoprotein.

The term "protein of interest" as used herein refers to the protein whose expression is desired within the fusion protein. In a fusion protein the protein of interest (e.g., GAGP) will be joined or fused with another protein or protein domain (e.g., GFP), the fusion partner, to allow for enhanced stability of the protein of interest and/or ease of purification of the fusion protein.

As used herein, the term "purified" or "to purify" refers to the removal of contaminants from a sample. For example, recombinant HRGP polypeptides, including HRGP-GFP fusion proteins are purified by the removal of host cell components such as nucleic acids, lipopolysaccharide (e.g., endotoxin). "Substantially purified" molecules are at least 60% free, preferably at least 75% free, and more preferably at least 90% free from other components with which they are naturally associated.

The term "recombinant DNA molecule" as used herein refers to a DNA molecule which is comprised of segments of DNA joined together by means of molecular biological techniques.

The term "recombinant protein" or "recombinant polypeptide" as used herein refers to a protein molecule which is expressed from a recombinant DNA molecule.

As used herein the term "portion" when in reference to a protein (as in "a portion of a given protein") refers to fragments of that protein. The fragments may range in size from four (4) amino acid residues to the entire amino acid sequence minus one amino acid. Thus, a portion of an amino acid sequence which is 30 nucleotides long refers to any fragment of that sequence which ranges in size from 4 to 29 contiguous amino acids of that sequence. A polypeptide comprising "at least a portion of" an amino acid sequence comprises from four (4) contiguous amino acid residues of the amino acid sequence to the entire amino acid sequence. When made in reference to a nucleic acid sequence, the term "portion" means a fragment which ranges in size from twelve (12) nucleic acids to the entire nucleic acid sequence minus one nucleic acid. Thus, a nucleic acid sequence comprising "at least a portion of" a nucleotide sequence comprises from twelve (12) contiguous nucleotide residues of the nucleotide sequence to the entire nucleotide sequence.

The term "isolated" when used in relation to a nucleic acid, as in "an isolated nucleic acid sequence" refers to a nucleic acid sequence that is identified and separated from at least one contaminant nucleic acid with which it is ordinarily associated in its natural source.

The terms "motif" and "module" are equivalent terms when made in reference to an amino acid sequence, and refer to the particular type, number, and arrangement of amino acids in that sequence.

The term "glycomodule" refers to a glycopeptide in which the carbohydrate portion is covalently linked to an amino acid sequence motif.

The term "repeating sequence" when made in reference to a peptide sequence that is contained in a polypeptide sequence means that the peptide sequence is reiterated from 1 to 10 times, more preferably from 1 to 100 times, and most preferably from 1 to 1000 times, in the polypeptide sequence. The repeats of the peptide sequence may be non-contiguous or contiguous. The term "non-contiguous repeat" when made in reference to a repeating peptide sequence means that at least one amino acid (or amino acid analog) is placed between the repeating sequences. The term "contiguous repeat" when made in reference to a repeating peptide sequence means that there are no intervening amino acids (or amino acid analogs) between the repeating sequences.

GENERAL DESCRIPTION OF THE INVENTION

The present invention relates generally to the field of plant gums and other hydroxyproline-rich glycoproteins, and in particular, to the expression of synthetic genes designed from repetitive peptide sequences. The hydroxyproline-rich glycoprotein (HRGP) superfamily is ubiquitous in the primary cell wall or extracellular matrix throughout the plant kingdom. Family members are diverse in structure and implicated in all aspects of plant growth and development. This includes plant responses to stress imposed by pathogenesis and mechanical wounding.

Plant HRGPs have no known animal homologs. Furthermore, hydroxyproline residues are O-glycosylated in plant glycoproteins but never in animals. At the molecular level the function of these unique plant glycoproteins remains largely unexplored.

HRGPS are, to a lesser or greater extent, extended, repetitive, modular proteins. The modules are small (generally 4-6 amino acid residue motifs), usually glycosylated, with most HRGPs being made up of more than one of repetitive module. For purposes of constructing the synthetic genes of the present invention, it is useful to view the glycosylated polypeptide modules not merely as peptides or oligosaccharides but as small functional motifs.

The description of the invention involves A) the design of the polypeptide of interest, B) the production of synthetic genes encoding the polypeptide of interest, C) the construction of the expression vectors, D) selection of the host cells, E) introduction of the expression construct into a particular cell (whether in vitro or in vivo), F) preferred consensus sequences and portions thereof, and G) O-glycosylation codes.

A. Design of the Polypeptide of Interest

The present invention contemplates polypeptides that are fragments of hydroxyproline-rich glycoproteins (HRGPs), repetitive proline-rich proteins (RPRPs) and arabinogalactan-proteins (AGPs). The present invention contemplates portions of HRGPs comprising one or more of the highly conserved Ser-Hyp, (SEQ ID NO:3) motif(s). The present invention also contemplates portions of RPRPs comprising one or more of the pentapeptide motif: Pro-Hyp-Val-Tyr-Lys (SEQ ID NO:4). The present invention also contemplates portions of AGPs comprising one or more Xaa-Hyp-Xaa-Hyp (SEQ ID NO:9) repeats.

While an understanding of the natural mechanism of glycosylation is not required for the successful operation of the present invention, it is believed that in GAGP and other HRGPs, repetitive Xaa-Hyp motifs constitute a Hyp-glycosylation code where Hyp occurring in contiguous motifs (Xaa-Hyp-Hyp) and Hyp occurring in non-contiguous Hyp repeats is recognized by different enzymes: arabinosyltransferases and galactosyltransferases, respectively.

The RPRPs (and some nodulins) consist of short repetitive motifs (e.g. Soybean RPRP1: [POVYK]$_n$ where O=Hyp) containing the least amount of contiguous Hyp. They also exemplify the low end of the glycosylation range with relatively few Hyp residues arabinosylated and no arabinogalactan polysaccharide. For example, in soybean RPRP1, L-arabinofuranose is attached to perhaps only a single Hyp residue in the molecule.

The Extensins occupy an intermediate position in the glycosylation continuum, containing about 50% carbohydrate which occurs mainly as Hyp-arabinosides (1-4 Ara residues), but not as Hyp-arabinogalactan polysaccharide. Extensins contain the repetitive, highly arabinosylated, diagnostic Ser-Hyp$_4$ (SEQ ID NO:3) glycopeptide module. The precise function of this module is unknown, but earlier work indicates that these motifs of arabinosylated Hyp help stabilize the extended polyproline-II helix of the extensins. Monogalactose also occurs on the Ser residues.

The classical Ser-Hyp$_4$ (SEQ ID NO:3) glycopeptide module is of special interest. A tetra-L-arabinofuranosyl oligosaccharide is attached to each Hyp residue in the motif. Three uniquely b-linked arabinofuranosyl residues and an a-linked nonreducing terminus comprise the tetraarabinooligosaccharide. While an understanding of the natural mechanism of glycosylation is not required for the successful operation of the present invention, it is believed that the arabinosylated Hyp residues together with the single galactosyl-serine residue undoubtedly form a unique molecular surface topography which interacts with and is recognized by other wall components, possibly including itself. Shorter motifs of Hyp, namely $Hyp_3$ and $Hyp_2$, lack the fourth (a-linked) arabinose residue, again suggesting that the fourth Ara unique to the $Hyp_4$ motif, has a special role and is presented for recognition or cleavage.

Tetra-arabinose and tri-arabinose are attached to known tetra-Hyp motifs. Those Ser-$Hyp_4$ isolated from native extensins have every Hyp residue arabinosylated. However, the Ser-$Hyp_4$ repeats fused to EGFP as disclosed herein showed that some Hyp residues were nonglycosylated, while some were mono- and di-arabinosylated. Mainly, the Hyp residues were tri-arabinosylated and tetra-arabinosylated. For example, Hyp-$Ara_4$ was 31% of total Hyp, Hyp-$Ara_3$ was 52% of total Hyp, Hyp-$Ara_2$ was 8% of total Hyp, and Hyp-Ara was 2% of total Hyp. 7% of the total Hyp was not glycosylated. Most of the serine residues in the invention's exemplary Ser-$Hyp_o$ repeats fused to EGFP were not galactosylated. This is in contrast to naturally occurring Ser-$Hyp_4$ in which Ser is often mono-galactosylated. Importantly, Hyp-polysaccharide were never detected by the inventors in the Ser-$Hyp_4$ repeats fused to EGFP.

At the high end of the glycosylation range (~90% sugar), the arabinogalactan-proteins (AGPs) and the related gum arabic glycoprotein (GAGP) are uniquely glycosylated with arabinogalactan polysaccharides. GAGP and all AGPs so far characterized by Hyp-glycoside profiles contain Hyp-linked arabinosides assigned to contiguous Hyp residues by the Hyp contiguity hypothesis. However these glycoproteins also uniquely contain Xaa-Hyp-Xaa-Hyp (SEQ ID NO:9) repeats. These repeats are putative polysaccharide attachment sites.

The present invention contemplates in particular fragments of gum arabic glycoprotein (GAGP). As noted above, GAGP has been largely refractory to chemical analysis. Prior to the inventors' discovery of the sequences disclosed herein, the largest peptide obtained and sequenced from gum arabic was a peptide of twelve (12) amino acids having the sequence Ser-Hyp-Ser-Hyp-Thr-Hyp-Thr-Hyp-Hyp-Hyp-Gly-Pro (SEQ ID NO:13). C. L. Delonnay, "Determination of the Protein Constituent Of Gum Arabic" Master of Science Thesis (1993). The present invention contemplates using this Dclonnay sequence as well as (heretofore undescribed) larger peptide fragments of GAGP (and variants thereof) for the design of synthetic genes. In this manner, "designer plant gums" can be produced ("designer extensins" are also contemplated).

In one embodiment, the present invention contemplates a substantially purified polypeptide comprising at least a portion of the amino acid consensus sequence Ser-Hyp-Hyp-Hyp-[Hyp/Thr]-Leu-Ser-Hyp-Ser-Hyp-Thr-Hyp-Thr-Hyp-Hyp-Hyp-Gly-Pro-His (SEQ ID NO:1 and SEQ ID NO:2) or variants thereof. While an understanding of the natural mechanism of glycosylation is not required for the successful operation of the present invention, it is believed that this GAGP 19-amino acid consensus repeat (which contains both contiguous Hyp and non-contiguous Hyp repeats) is glycosylated in native GAGP with both Hyp-arabinosides and Hyp-polysaccharide in molar ratios. It is further believed that the high molecular weight protein component of gum arabic (i.e. GAGP) is responsible for the remarkable (and advantageous) emulsifying and stabilizing activity exploited by the food and soft drink industries.

The sequences of the invention may be used to isolate hydroxyproline rich glycoprotein-binding molecules. For example, polypeptides encoded by the invention's polynucleotide sequences may be immobilized (covalently or non-covalently) on solid supports or resins for use in isolating HRGP-binding molecules from a variety of sources (e.g. algae, plants, animals, microorganisms). Generic methods for immobilizing polypeptides are known in the art using commercially available kits. For example, the desired polypeptide sequence may be expressed as a fusion protein with heterologous protein A which allows immobilization of the fusion protein on immobilized immunoglobulin. Additionally, pGEX vectors (Promega, Madison Wis.) may be used to express the desired polypeptides as a fusion protein with glutathione S-transferase (GST) which may be adsorbed to glutathione-agarose beads.

The invention's sequences may also be used to make polyclonal and monoclonal antibodies. Generic methods for generating polyclonal and monoclonal antibodies are known in the art. For example, monoclonal antibodies may be generated using the methods of Kohler and Milstein (1976) Eur. J. Immunol. 6:511-519 (Exhibit B) and of J. Goding (1986) In "Monoclonal Antibodies: Principles and Practice," Academic Press, pp 59-103.

B. Production of Synthetic Genes

The present invention contemplates the use of synthetic genes engineered for the expression of repetitive glycopeptide modules in cells, including but not limited to callus and suspension cultures. It is not intended that the present invention be limited by the precise number of repeats.

In one embodiment, the present invention contemplates the nucleic acid sequences encoding the consensus sequence for GAGP (i.e. SEQ ID NO: 1 and SEQ ID NO:2) or variants thereof may be used as a repeating sequence between two (2) and up to fifty (50) times, more preferably between ten (10) and up to thirty (30) times, and most preferably approximately twenty (20) times. The nucleic acid sequence encoding the consensus sequence (i.e. SEQ ID NO:1 and SEQ ID NO:2) or variants thereof may be used as contiguous repeats or may be used as non-contiguous repeats.

In designing any HRGP gene cassette the following guidelines are employed:

1) Minimization of the repetitive nature of the coding sequence while still taking into account the HRGP codon bias of the host plant (e.g., when tomato is the host plant, the codon usage bias of the tomato which favors CCA and CCT [but not CCG] for Pro residues, and TCA and TCC for Ser residues is employed). Zea mays (such as corn) and perhaps other gramineous monocotyledons (e.g. rice barley, wheat and all grasses) prefer CCG and CCC for proline; GTC and CTT for valine; and AAG for lysine. Dicotyledons (including legumes) prefer CCA and CCT for proline and TCA and TCT for serine.

2) Minimization of strict sequence periodicity.

3) Non-palindromic ends are used for the monomers and end linkers to assure proper "head-to-tail" polymerization.

4) The constructs contain no internal restriction enzyme recognition sites for the restriction enzymes employed for the insertion of these sequences into expression vectors or during subsequent manipulations of such vectors. Typically, the 5' linker contains a XmaI site downstream of the BamHI site used for cloning into the cloning vector (e.g., pBluescript). The XmaI site is used for insertion of the HRGP gene cassette into the expression vector pBI121-Sig-EGFP). Typically, the 3' linker contains a AgeI site upstream of the EcoRI site used for cloning into the cloning vector (e.g., pBluescript). The AgeI site is used for insertion of the HRGP gene cassette into the expression vector. [For plasmid pBI121-Sig—which does not contain GFP for the fusion protein—the same signal sequence (SS) is used, but the 3' linkers contain an Sst I restriction site for insertion as an Xma I/Sst I fragment behind the signal sequence and before the NOS terminator].

5) The oligonucleotides used are high quality (e.g., from GibcoBRL, Operon) and have been purified away from unwanted products of the synthesis.

6) The $T_M$ of correctly aligned oligomers is greater than the $T_M$ of possible dimers, hairpins or crossdimers.

One of skill in the art appreciates that the hydroxyproline (Hyp) residues in the sequences of the invention are produced as the result of post-translational modification of proline (Pro) residues in the polypeptide which is encoded by the gene. Thus, where a hydroxyproline residue is desired to be present in the sequences of the invention, the corresponding codon would be selected to encode proline. The Edman degradation may be used to identify which Pro residues had been hydroxylated to Hyp as described in Example 23, infra.

C. Construction of Expression Vectors

It is not intended that the present invention be limited by the nature of the expression vector. A variety of vectors are contemplated. In one embodiment, two plant transformation vectors are prepared, both derived from pBI121 (Clontech). Both contain an extensin signal sequence (SS) for transport of the constructs through the ER/Golgi for posttranslational modification. A first plasmid construct contained Green Fluorescent Protein (GFP) as a reporter protein instead of GUS. A second plasmid does not contain GFP.

pBI121 is the Jefferson vector in which the BamHI and SstI sites can be used to insert foreign DNA between the 35S CaMV promoter and the termination/polyadenylation signal from the nopaline synthase gene (NOS-ter) of the *Agrobacterium* Ti plasmid); it also contains an RK2 origin of replication, a kanamycin resistance gene, and the GUS reporter gene.

Signal Sequences. As noted above, the GUS sequence is replaced (via BamHI/SstI) with a synthetic DNA sequence encoding a peptide signal sequence based on the extensin signal sequences of *Nicotiana plumbaginifolia* and *N. tabacum*

MGKMASLFATFLVVLVSLSLAQTTRVVPVASSAP (SEQ ID NO: 14)

The DNA sequence also contains 15 bp of the 5' untranslated region, and restriction sites for Bam HI in its 5' terminus and Sst I in its extreme 3' terminus for insertion into pBI121 in place of GUS. An XmaI restriction site occurs 16 bp upstream from the Sst I site to allow subsequent insertion of EGFP into the plasmid as a Xma I/Sst I fragment.

The sequence underlined above targets *N. plumbaginifolia* extensin fusion proteins through the ER and Golgi for post-translational modifications, and finally to the wall. The signal sequence proposed also involves transport of extensins and extensin modules in the same plant family (Solanaceae). Alternatively, one can use the signal sequence from tomato P1 extensin itself.

TABLE 1

GFP MUTANTs

| MUTANT | Excitation | Emitting |
|---|---|---|
| mGFPX10; F99S, M153T, V163A | Excites at 395 | |
| mGFPX10-5 | Excites at 489 | Emits at 508 |
| GFPA2; I167T | Excites at 471 | |
| GFPB7; Y66H | Excites at 382 | Emits at 440 (blue fluorescence) |

TABLE 1-continued

GFP MUTANTs

| MUTANT | Excitation | Emitting |
|---|---|---|
| GFPX10-C7; F99S, M153T, V163A, I167T, S175G | Excites at 395 and 473 | |
| GFPX10-D3; F99S, M153T, V163A, Y66H | Excites at 382 | Emits at 440 |

In yet another alternative, the tomato arabinogalactan-protein (Le-AGP-1) signal sequence may be used. This sequence has previously been cloned [Li (1996) "Isolation and characterization of genes and complementary DNAs encoding a tomato arabinogalactan protein, PhD. Dissertation, Ohio University, Athens, Ohio] and encodes the protein sequence MDRKFVFLVSILCIVVASVTG (SEQ ID NO:215). This sequence has successfully been used by the inventors to target expression of the inventions's sequences to the extracellular medium of tobacco cell cultures and is being used to target (Ala-Pro)$_n$-EGFP and (Thr-Pro)$_n$-EGFP to the extracellular matrix of tobacco cell cultures.

Addition of GFP.

The repetitive HRGP-modules can be expressed as GFP fusion products rather than GUS fusions, and can also be expressed as modules without GFP. Fusion with a green fluorescent protein reporter gene appropriately red-shifted for plant use, e.g. EGFP (an S65T variant recommended for plants by Clontech) or other suitable mutants (see Table 1 above) allows the detection of <700 GFP molecules at the cell surface. GFP requires aerobic conditions for oxidative formation of the fluorophore. It works well at the lower temperatures used for plant cell cultures and normally it does not adversely affect protein function although it may allow the regeneration of plants only when targeted to the ER.

Promoters.

As noted above, it is not intended that the present invention be limited by the nature of the promoter(s) used in the expression constructs. The CaMV35S promoter is preferred, although it is not entirely constitutive and expression is "moderate". In some embodiments, higher expression of the constructs is desired to enhance the yield of HRGP modules; in such cases a plasmid with "double" CaMV35S promoters is employed.

D. Selection of Host Cells

A variety of host cells are contemplated (both eukaryotic and prokaryotic). It is not intended that the present invention be limited by the host cells used for expression of the synthetic genes of the present invention. Plant host cells are preferred, including but not limited to legumes (e.g. soy beans) and solanaceous plants (e.g. tobacco, tomato, etc.). Other cells contemplated to be within the scope of this invention are green algae [e.g., *Chlamydomonas*, Volvox, and duckweed (Lemna)].

The present invention is not limited by the nature of the plant cells. All sources of plant tissue are contemplated. In one embodiment, the plant tissue which is selected as a target for transformation with vectors which are capable of expressing the invention's sequences are capable of regenerating a plant. The term "regeneration" as used herein, means growing a whole plant from a plant cell, a group of plant cells, a plant part or a plant piece (e.g., from seed, a protoplast, callus, protocorm-like body, or tissue part). Such tissues include but are not limited to seeds. Seeds of flowering plants consist of an embryo, a seed coat, and stored food. When fully formed, the embryo consists basically of a hypocotyl-root axis bearing either one or two cotyledons and an apical meristem at the shoot apex and at the root apex. The cotyledons of most dicotyledons are fleshy and contain the stored food of the seed. In other dicotyledons and most monocotyledons, food is stored in the endosperm and the cotyledons function to absorb the simpler compounds resulting from the digestion of the food.

Species from the following examples of genera of plants may be regenerated from transformed protoplasts: *Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Hyoscyamus, Lycopersicon, Nicotiana, Solanum, Petunia, Digitalis, Majorana, Ciohorium, Helianthus, Lactuca, Bromus, Asparagus, Antirrhinum, Hererocallis, Nemesia, Pelargonium, Panicum, Pennisetum, Ranunculus, Senecio, Salpiglossis, Cucumis, Browaalia, Glycine, Lolium, Zea, Triticum, Sorghum*, and *Datura*.

For regeneration of transgenic plants from transgenic protoplasts, a suspension of transformed protoplasts or a petri plate containing transformed explants is first provided. Callus tissue is formed and shoots may be induced from callus and subsequently rooted. Alternatively, somatic embryo formation can be induced in the callus tissue. These somatic embryos germinate as natural embryos to form plants. The culture media will generally contain various amino acids and plant hormones, such as auxin and cytokinins. It is also advantageous to add glutamic acid and proline to the medium, especially for such species as corn and alfalfa. Efficient regeneration will depend on the medium, on the genotype, and on the history of the culture. These three variables may be empirically controlled to result in reproducible regeneration.

Plants may also be regenerated from cultured cells or tissues. Dicotyledonous plants which have been shown capable of regeneration from transformed individual cells to obtain transgenic whole plants include, for example, apple (*Malus pumila*), blackberry (*Rubus*), Blackberry/raspberry hybrid (*Rubus*), red raspberry (*Rubus*), carrot (*Daucus carota*), cauliflower (*Brassica oleracea*), celery (*Apium graveolens*), cucumber (*Cucumis sativus*), eggplant (*Solanum melongena*), lettuce (*Lactuca sativa*), potato (*Solanum tuberosum*), rape (*Brassica napus*), wild soybean (*Glycine canescens*), strawberry (*Fragaria x ananassa*), tomato (*Lycopersicon esculentum*), walnut (*Juglans regia*), melon (*Cucumis melo*), grape (*Vitis vinifera*), and mango (*Mangifera indica*). Monocotyledonous plants which have been shown capable of regeneration from transformed individual cells to obtain transgenic whole plants include, for example, rice (*Oryza sativa*), rye (*Secale cereale*), and maize.

In addition, regeneration of whole plants from cells (not necessarily transformed) has also been observed in: apricot (*Prunus armeniaca*), asparagus (*Asparagus officinalis*), banana (hybrid *Musa*), bean (*Phaseolus vulgaris*), cherry (hybrid *Prunus*), grape (*Vitis vinifera*), mango (*Mangifera indica*), melon (*Cucumis melo*), ochra (*Abelmoschus esculentus*), onion (hybrid *Allium*), orange (*Citrus sinensis*), papaya (*Carrica papaya*), peach (*Prunus persica*), plum (*Prunus domestica*), pear (*Pyrus communis*), pineapple (*Ananas comosus*), watermelon (*Citrullus vulgaris*), and wheat (*Triticum acstivum*).

The regenerated plants are transferred to standard soil conditions and cultivated in a conventional manner. After the expression vector is stably incorporated into regenerated transgenic plants, it can be transferred to other plants by vegetative propagation or by sexual crossing. For example, in vegetatively propagated crops, the mature transgenic plants are propagated by the taking of cuttings or by tissue culture techniques to produce multiple identical plants. In seed propagated crops, the mature transgenic plants are self crossed to produce a homozygous inbred plant which is capable of passing the transgene to its progeny by Mendelian inheritance. The inbred plant produces seed containing the nucleic acid sequence of interest. These seeds can be grown to produce plants that would produce the desired polypeptides. The inbred plants can also be used to develop new hybrids by crossing the inbred plant with another inbred plant to produce a hybrid.

It is not intended that the present invention be limited to only certain types of plants. Both monocotyledons and dicotyledons are contemplated. Monocotyledons include grasses, lilies, irises, orchids, cattails, palms, *Zea mays* (such as corn), rice barley, wheat and all grasses. Dicotyledons include almost all the familiar trees and shrubs (other than confers) and many of the herbs (non-woody plants).

Tomato cultures are the ideal recipients for repetitive HRGP modules to be hydroxylated and glycosylated: Tomato is readily transformed. The cultures produce cell surface HRGPs in high yields easily eluted from the cell surface of intact cells and they possess the required posttranslational enzymes unique to plants—HRGP prolyl hydroxylases, hydroxyproline O-glycosyltransferases and other specific glycosyltransferases for building complex polysaccharide side chains. Furthermore, tomato genetics, and tomato leaf disc transformation/plantlet regeneration are well worked out.

Other preferred recipients for the invention's sequences include tobacco cultured cells and plants.

E. Introduction of Nucleic Acid

Expression constructs of the present invention may be introduced into host cells (e.g. plant cells) using methods known in the art. In one embodiment, the expression constructs are introduced into plant cells by particle mediated gene transfer. Particle mediated gene transfer methods are known in the art, are commercially available, and include, but are not limited to, the gas driven gene delivery instrument descried in McCabe, U.S. Pat. No. 5,584,807, the entire contents of which are herein incorporated by reference. This method involves coating the nucleic acid sequence of interest onto heavy metal particles, and accelerating the coated particles under the pressure of compressed gas for delivery to the target tissue.

Other particle bombardment methods are also available for the introduction of heterologous nucleic acid sequences into plant cells. Generally, these methods involve depositing the nucleic acid sequence of interest upon the surface of small, dense particles of a material such as gold, platinum, or tungsten. The coated particles are themselves then coated onto either a rigid surface, such as a metal plate, or onto a carrier sheet made of a fragile material such as mylar. The coated sheet is then accelerated toward the target biological tissue. The use of the flat sheet generates a uniform spread of accelerated particles which maximizes the number of cells receiving particles under uniform conditions, resulting in the introduction of the nucleic acid sample into the target tissue.

Alternatively, an expression construct may be inserted into the genome of plant cells by infecting them with a bacterium, including but not limited to an *Agrobacterium* strain previously transformed with the nucleic acid sequence of interest. Generally, disarmed *Agrobacterium* cells are transformed with recombinant Ti plasmids of *Agrobacterium tumefaciens* or Ri plasmids of *Agrobacterium rhizogenes* (such as those described in U.S. Pat. No. 4,940,838, the entire contents of which are herein incorporated by reference) which are constructed to contain the nucleic acid sequence of interest using methods well known in the art (Sambrook, J. et al., (1989) supra). The nucleic acid sequence of interest is then stably integrated into the plant genome by infection with the transformed *Agrobacterium* strain. For example, heterologous nucleic acid sequences have been introduced into plant tissues using the natural DNA transfer system of *Agrobacterium tumefaciens* and *Agrobacterium rhizogenes* bacteria (for review, see Klee et al. (1987) Ann. Rev. Plant Phys. 38:467-486).

One of skill in the art knows that the efficiency of transformation by *Agrobacterium* may be enhanced by using a number of methods known in the art. For example, the inclusion of a natural wound response molecule such as acetosyringone (AS) to the *Agrobacterium* culture has been shown to enhance transformation efficiency with *Agrobacterium tumefaciens* [Shahla et al. (1987) Plant Molec. Biol. 8:291-298]. Alternatively, transformation efficiency may be enhanced by wounding the target tissue to be transformed. Wounding of plant tissue may be achieved, for example, by punching, maceration, bombardment with microprojectiles, etc. [see, e.g., Bidney et al. (1992) Plant Molec. Biol. 18:301-313].

It may be desirable to target the nucleic acid sequence of interest to a particular locus on the plant genome. Site-directed integration of the nucleic acid sequence of interest into the plant cell genome may be achieved by, for example, homologous recombination using *Agrobacterium*-derived sequences. Generally, plant cells are incubated with a strain of *Agrobacterium* which contains a targeting vector in which sequences that are homologous to a DNA sequence inside the target locus are flanked by *Agrobacterium* transfer-DNA (T-DNA) sequences, as previously described (Offring a et al., (1996), U.S. Pat. No. 5,501,967, the entire contents of which are herein incorporated by reference). One of skill in the art knows that homologous recombination may be achieved using targeting vectors which contain sequences that are homologous to any part of the targeted plant gene, whether belonging to the regulatory elements of the gene, or the coding regions of the gene. Homologous recombination may be achieved at any region of a plant gene so long as the nucleic acid sequence of regions flanking the site to be targeted is known.

Where homologous recombination is desired, the targeting vector used may be of the replacement- or insertion-type (Offring a et al. (1996), supra). Replacement-type vectors generally contain two regions which are homologous with the targeted genomic sequence and which flank a heterologous nucleic acid sequence, e.g., a selectable marker gene sequence. Replacement type vectors result in the insertion of the selectable marker gene which thereby disrupts the targeted gene. Insertion-type vectors contain a single region of homology with the targeted gene and result in the insertion of the entire targeting vector into the targeted gene.

Other methods are also available for the introduction of expression constructs into plant tissue, e.g., electroinjection (Nan et al. (1995) In "Biotechnology in Agriculture and Forestry," Ed. Y. P. S. Bajaj, Springer-Verlag Berlin Heidelberg, Vol 34:145-155; Griesbach (1992) HortScience 27:620); fusion with liposomes, lysosomes, cells, minicells or other fusible lipid-surfaced bodies (Fraley et al. (1982) *Proc. Natl. Acad. Sci. USA* 79:1859-1863; polyethylene glycol (Keens et al. (1982) *Nature* 296:72-74); chemicals that increase free DNA uptake; transformation using virus, and the like.

In one embodiment, the present invention contemplates introducing nucleic acid via the leaf disc transformation method. Horsch et al. *Science* 227:1229-1231 (1985). Briefly, disks are punched from the surface of sterilized leaves and submerged with gentle shaking into a culture of *A. tumefaciens* that had been grown overnight in Luria Broth (LB) at 28° C. The disks are then blotted dry and placed upside-down onto nurse culture plates to induce the regeneration of shoots. Following 2-3 days, the leaf disks are transferred to petri plates containing the same media without feeder cells or filter papers, but in the presence of carbenicillin (500 µg/ml) and kanamycin (300 µg/ml) to select for antibiotic resistance. 2-4 weeks later, the shoots that developed are removed from calli and placed into root-inducing media with the appropriate antibiotic. These shoots were then further transplanted into soil following the presence of root formation.

Cells and tissues which are transformed with a heterologous nucleic acid sequence of interest are readily detected using methods known in the art including, but not limited to, restriction mapping of the genomic DNA, PCR-analysis, DNA-DNA hybridization, DNA-RNA hybridization, DNA sequence analysis and the like.

Additionally, selection of transformed cells may be accomplished using a selection marker gene. It is preferred, though not necessary, that a selection marker gene be used to select transformed plant cells. A selection marker gene may confer positive or negative selection.

A positive selection marker gene may be used in constructs for random integration and site-directed integration. Positive selection marker genes include antibiotic resistance genes, and herbicide resistance genes and the like. In one embodiment, the positive selection marker gene is the NPTII gene which confers resistance to geneticin (G418) or kanamycin. In another embodiment the positive selection marker gene is the HPT gene which confers resistance to hygromycin. The choice of the positive selection marker gene is not critical to the invention as long as it encodes a functional polypeptide product. Positive selection genes known in the art include, but are not limited to, the ALS gene (chlorsulphuron resistance), and the DHFR-gene (methotrexate resistance).

A negative selection marker gene may also be included in the constructs. The use of one or more negative selection marker genes in combination with a positive selection marker gene is preferred in constructs used for homologous recombination. Negative selection marker genes are generally placed outside the regions involved in the homologous recombination event. The negative selection marker gene serves to provide a disadvantage (preferably lethality) to cells that have integrated these genes into their genome in an expressible manner. Cells in which the targeting vectors for homologous recombination are randomly integrated in the genome will be harmed or killed due to the presence of the negative selection marker gene. Where a positive selection marker gene is included in the construct, only those cells having the positive selection marker gene integrated in their genome will survive.

The choice of the negative selection marker gene is not critical to the invention as long as it encodes a functional polypeptide in the transformed plant cell. The negative selection gene may for instance be chosen from the aux-2 gene from the Ti-plasmid of *Agrobacterium*, the tk-gene from SV40, cytochrome P450 from *Streptomyces griseolus*, the Adh-gene from Maize or *Arabidopsis*, etc. Any gene encoding an enzyme capable of converting a substance which is otherwise harmless to plant cells into a substance which is harmful to plant cells may be used.

It is not intended that the host cells which are transformed with the invention's sequences or with expression constructs containing these sequences be limited to cells which display any particular phenotype. All that is necessary is that the transformed cells express a polypeptide encoded by the invention's sequences. Such host cells may be used to purify the expressed polypeptides for subsequent use, (e.g., in the food or cosmetic industry, for isolating HRGP-binding molecules, and for making antibodies).

Nor is the invention intended to be limited to transformed cells which express the invention's nucleotide sequences at a particular level, a particular time during the cell's life cycle, or a particular part of a transformed plant. Rather, the invention expressly contemplates cells which express relatively low and relatively high levels of expression of the desired proteins, regardless of whether such expression occurs in some or all parts of the transformed plant, and whether it changes or is unchanged in level during cell growth or plant development.

F. Preferred Consensus Sequences and Portions Thereof

The present invention provides GAGP sequences, and in particular the consensus sequence of SEQ ID NO:134. Gum arabic glycoprotein (GAGP) is a large molecular weight, hydroxyproline-rich arabinogalactan-protein (AGP) component of gum arabic. GAGP has a simple, highly biased amino acid composition indicating a repetitive polypeptide backbone. It has been suggested that the repetitive polypeptide backbone contains repetitive small (~10 amino acid residues) repetitive peptide motifs each with three Hyp-arabinoside attachment sites and a single Hyp-arabinogalactan polysaccharide attachment site [Qi et al. (1991) supra]. The inventors have tested this hypothesis by generating and sequencing peptides of GAGP, and determining the glycosyl and linkage analysis of an isolated Hyp-polysaccharide. Surprisingly, the inventors discovered a 19-amino acid consensus sequence, which is roughly twice the size of that previously postulated by Qi et al. (1991). In addition to the difference in size of the repeating motif, the inventors also surprisingly discovered that the peptides in the invention's 19-amino acid consensus sequence lacked some of the amino acids present in Qi et al.'s the empirical formula [i.e., $Hyp_4$ $Ser_2$ Thr Pro Gly Leu His (SEQ ID NO:135)] of the repeat motif suggested by Qi et. al. [Qi et al. (1991) supra], most notably His (Table 6, peptide PH3G2.) The inventors also surprisingly discovered that the invention's 19-amino acid GAGP consensus motif contains approximately nine Hyp residues, with only a single polysaccharide attachment site. Judging from the Hyp-glycoside profile of GAGP, the invention's consensus motif contained six Hyp-arabinosides rather than Qi et al.'s three, and two Hyp-polysaccharides rather than Qi et al.'s one.

The invention provides the consensus sequence (SEQ ID NO:136): A-Hyp-B-C-D-E-F-Hyp-G-H-I-Hyp-J-Hyp-Hyp-K-L-Pro-M, wherein A is selected from Ser, Thr, and Ala; B is selected from Hyp, Pro, Leu, and Ile; C is selected from Pro and Hyp; D is selected from Hyp, Pro, Ser, Thr, and Ala; E is selected from Leu and Ile; F is selected from Ser, Thr, and Ala; G is selected from Ser, Leu, Hyp, Thr, Ala, and Ile; H is selected from Hyp, Pro, Leu, and Ile; I is selected from Thr, Ala, and Ser; J is selected from Thr, Ser, and Ala; K is selected from Thr, Leu, Hyp, Ser, Ala, and Ile; L is selected from Gly, Leu, Ala, and Ile; and M is selected from His, and Pro (Example 18, e.g., Tables 3 and 6). Also included within the scope of the invention are portions of the consensus sequence, having from 4 to 19 contiguous amino acid residues of the consensus sequence.

Figure 9:
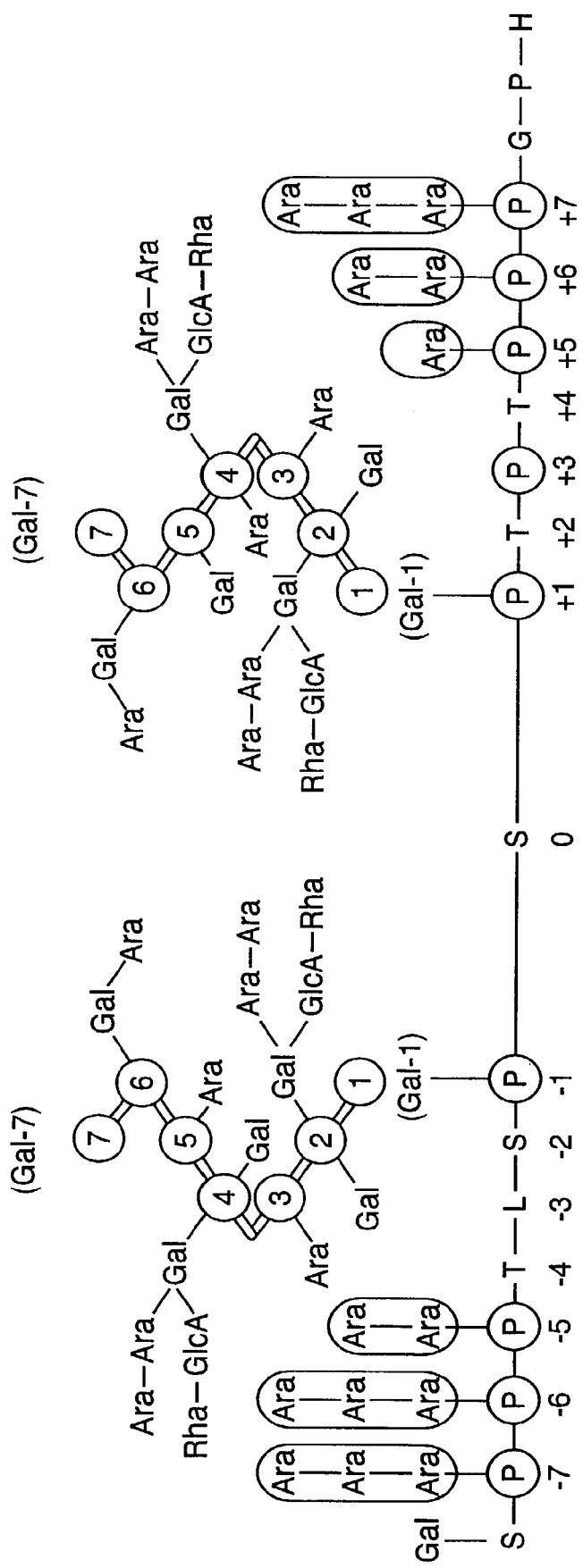
FIG. 9 shows a proposed model for an exemplary glycopeptide containing an exemplary consensus sequence.

In a preferred embodiment, the invention's GAGP consensus sequence contains 19 amino acids, of which approximately nine are Hyp residues. Judging from the Hyp-glycoside profile of GAGP (Table 7) about one in every five Hyp residues is polysaccharide-substituted. Thus, in one preferred embodiment, there are approximately two Hyp-polysaccharide sites in the consensus sequence and portions thereof. Without limiting the invention to any particular mechanism, the inventors predicted arabinosylation of contiguous Hyp residues and arabinogalactan-polysaccharide addition to clustered non-contiguous Hyp residues, such as the X-Hyp-X-Hyp modules common in AGPs [Nothnagel (1997) International Review of Cytology 174:195]. Also without limiting the invention to a particular theory, the inventors are of the view that the inventions's 19-amino acid consensus motif preferably contains approximately two polysaccharide attachment sites in the clustered non-contiguous Hyp motif [F-Hyp-G-H-1-Hyp (SEQ ID NO:137), where F is selected from Ser, Thr, and Ala; G is selected from Ser, Leu, Hyp, Thr, Ala, and Ile; H is selected from Hyp, Pro, Leu, and Ile; and I is selected from Thr, Ala, and Ser] which is exemplified by Ser-Hyp-Ser-Hyp-Thr-Hyp (SEQ ID NO:138)], and which is flanked by arabinosylated contiguous Hyp residues such as A-Hyp-B-C-D-E (SEQ ID NO:139) where A is selected from Ser, Thr, and Ala; B is selected from Hyp, Leu, and Ile; C is selected from Pro and Hyp; D is selected from Hyp, Ser, Thr, and Ala; E is selected from Leu and Ile; and more preferably Ser-Hyp-Hyp-Hyp-(Hyp/Thr/Ser)-Leu (SEQ ID NO:140), and such as J-Hyp-Hyp-K-L-Pro-M (SEQ ID NO:141) where J is selected from Thr, Ser, and Ala; K is selected from Thr, Leu, Hyp, Ser, Ala, and Ile; L is selected from Gly, Leu, Ala, and Ile; and M is selected from His, and Pro; and more preferably Hyp-Ser-Hyp-Thr-Hyp-Thr-Hyp-Hyp-(Hyp/Leu)-Gly-Pro-His (SEQ ID NOs:142) (FIG. 9). The following Table 2 shows 45 illustrative sequences which have from 4 to 19 amino acids and which are encompassed by the inventions' SEQ ID NO:136.

TABLE 2

Exemplary Sequences*

| Motif Number | Motif Sequence |
|---|---|
| 1 | Ser-Hyp-Hyp-Hyp-Hyp-Leu-Ser-Hyp-Ser-Hyp-Thr-Hyp-Thr-Hyp-Hyp-Leu-Gly-Pro-His (SEQ ID NO: 143) |
| 2 | Ser-Hyp-Hyp-Hyp-Thr-Leu-Ser-Hyp-Ser-Hyp-Thr-Hyp-Thr-Hyp-Hyp-Hyp-Gly-Pro-His (SEQ ID NO: 144) |
| 3 | Ser-Hyp-Hyp-Hyp-Ser-Leu-Ser-Hyp-Ser-Hyp-Thr-Hyp-Thr-Hyp-Hyp-Thr-Gly-Pro-His (SEQ ID NO: 145) |
| 4 | Ser-Hyp-Hyp-Hyp-Hyp-Leu-Ser-Hyp-Ser-Hyp-Thr-Hyp-Thr-Hyp-Hyp-Hyp-Gly-Pro-Hyp (SEQ ID NO: 146) |

TABLE 2-continued

Exemplary Sequences*

| Motif Number | Motif Sequence |
|---|---|
| 5 | Ser-Hyp-Leu-Pro-Thr-Leu-Ser-Hyp-Leu-Pro-Thr-Hyp-Thr-Hyp-Hyp-Hyp-Gly-Pro-His (SEQ ID NO: 147) |
| 6 | Ser-Hyp-Leu-Pro-Thr-Leu-Ser-Hyp-Leu-Pro-Ala-Hyp-Thr-Hyp-Hyp-Hyp-Gly-Pro-His (SEQ ID NO: 148) |
| 7 | Ser-Hyp-Hyp-Hyp-Hyp-Leu-Ser-Hyp-Ser-Leu-Thr-Hyp-Thr-Hyp-Hyp-Leu-Gly-Pro-Hyp (SEQ ID NO: 149) |
| 8 | Ser-Hyp-Hyp-Hyp-Hyp-Leu-Ser-Hyp-Ser-Hyp-Thr-Hyp-Thr-Hyp-Hyp-Hyp-Gly-Pro-His (SEQ ID NO: 150) |
| 9 | Ser-Hyp-Hyp-Hyp-Thr-Leu-Ser-Hyp-Ser-Hyp-Thr-Hyp-Thr-Hyp-Hyp-Hyp-Gly-Pro-His (SEQ ID NO: 151) |
| 10 | Ser-Hyp-Hyp-Hyp-Hyp-Leu-Ser-Hyp-Ser-Hyp-Ala-Hyp-Thr-Hyp-Hyp-Hyp-Gly-Pro-His (SEQ ID NO: 152) |
| 11 | Ser-Hyp-Hyp-Hyp-Hyp-Leu-Ser-Hyp-Leu-Pro-Thr-Hyp-Thr-Hyp-Hyp-Leu-Gly-Pro-His (SEQ ID NO: 153) |
| 12 | Ser-Hyp-Hyp-Hyp-Ser-Leu-Ser-Hyp-Leu-Pro-Thr-Hyp-Thr-Hyp-Hyp-Leu-Gly-Pro-His (SEQ ID NO: 154) |
| 13 | Ser-Hyp-Hyp-Hyp-Thr-Leu-Ser-Hyp-Hyp-Leu-Thr-Hyp-Thr-Hyp-Hyp-Leu-Leu-Pro-His (SEQ ID NO: 155) |
| 14 | Hyp-Hyp-Thr-Leu-Ser-Hyp-Hyp-Leu-Thr-Hyp-Thr-Hyp-Hyp-Leu-Leu-Pro (SEQ ID NO: 156) |
| 15 | Ser-Hyp-Hyp-Hyp-Ser-Leu-Ser-Hyp-Leu-Pro-Thr-Hyp-Thr-Hyp-Hyp-Leu (SEQ ID NO: 157) |
| 16 | Hyp-Hyp-Leu-Ser-Hyp-Leu-Pro-Thr-Hyp-Thr-Hyp-Hyp-Leu-Gly-Pro-His (SEQ ID NO: 158) |
| 17 | Ser-Hyp-Hyp-Hyp-Thr-Leu-Ser-Hyp-Ser-Hyp-Thr-Hyp-Thr-Hyp (SEQ ID NO: 159) |
| 18 | Leu-Ser-Hyp-Ser-Leu-Thr-Hyp-Thr-Hyp-Hyp-Leu-Gly-Pro-Hyp (SEQ ID NO: 160) |
| 19 | Hyp-Thr-Leu-Ser-Hyp-Leu-Pro-Ala-Hyp-Thr-Hyp-Hyp-Hyp-Gly (SEQ LD NO: 161) |
| 20 | Ser-Hyp-Hyp-Hyp-Hyp-Leu-Ser-Hyp-Ser-Hyp-Thr-Hyp (SEQ ID NO: 162) |
| 21 | Ser-Leu-Ser-Hyp-Ser-Hyp-Thr-Hyp-Thr-Hyp-Hyp-Thr (SEQ ID NO: 163) |
| 22 | Hyp-Hyp-Thr-Leu-Ser-Hyp-Ser-Hyp-Thr-Hyp-Thr-Hyp (SEQ ID NO: 164) |
| 23 | Hyp-Thr-Hyp-Thr-Hyp-Hyp-Leu-Gly-Pro-His (SEQ ID NO: 165) |
| 24 | Hyp-Hyp-Thr-Leu-Ser-Hyp-Hyp-Leu-Thr-Hyp (SEQ ID NO: 166) |
| 25 | Ser-Hyp-Hyp-Hyp-Ser-Leu-Ser-Hyp-Leu-Pro (SEQ ID NO: 167) |
| 26 | Hyp-Thr-Hyp-Hyp-Leu-Gly-Pro-His (SEQ ID NO: 168) |
| 27 | Hyp-Leu-Ser-Hyp-Ser-Hyp-Ala-Hyp (SEQ ID NO: 169) |
| 28 | Hyp-Hyp-Hyp-Thr-Leu-Ser-Hyp-Ser (SEQ ID NO: 170) |
| 29 | Thr-Hyp-Hyp-Hyp-Gly-Pro (SEQ ID NO: 171) |
| 30 | Hyp-Hyp-Leu-Ser-Hyp-Ser (SEQ ID NO: 172) |
| 31 | Ser-Hyp-Leu-Pro-Ala-Hyp (SEQ ID NO: 173) |
| 32 | Leu-Pro-Thr-Leu-Ser-Hyp (SEQ ID NO: 174) |
| 33 | Ser-Hyp-Ser-Hyp (SEQ ID NO: 175) |
| 34 | Ser-Hyp-Thr-Hyp (SEQ ID NO: 176) |
| 35 | Thr-Hyp-Thr-Hyp (SEQ ID NO: 177) |

TABLE 2-continued

Exemplary Sequences*

Motif
Number  Motif Sequence

36      Thr-Hyp-Hyp-Hyp (SEQ ID NO: 178)

37      Ser-Hyp-Pro-Pro-Pro-Leu-Ser-Hyp-Ser-Hyp-Thr-Hyp-Thr-Hyp-Hyp-Leu-Gly-Pro-
        His (SEQ ID NO: 217)

38      Ser-Hyp-Hyp-Pro-Pro-Leu-Ser-Hyp-Ser-Hyp-Thr-Hyp-Thr-Hyp-Hyp-Leu-Gly-Pro-
        His (SEQ ID NO: 218)

39      Ser-Hyp-Pro-Hyp-Pro-Leu-Ser-Hyp-Ser-Hyp-Thr-Hyp-Thr-Hyp-Hyp-Leu-Gly-Pro-
        His (SEQ ID NO: 219)

40      Ser-Hyp-Pro-Pro-Hyp-Leu-Ser-Hyp-Ser-Hyp-Thr-Hyp-Thr-Hyp-Hyp-Leu-Gly-Pro-
        His (SEQ ID NO: 220)

41      Ser-Hyp-Hyp-Hyp-Pro-Leu-Ser-Hyp-Ser-Hyp-Thr-Hyp-Thr-Hyp-Hyp-Leu-Gly-Pro-
        His (SEQ ID NO: 221)

42      Ser-Hyp-Hyp-Pro-Hyp-Leu-Ser-Hyp-Ser-Hyp-Thr-Hyp-Thr-Hyp-Hyp-Leu-Gly-Pro-
        His (SEQ ID NO: 222)

43      Ser-Hyp-Pro-Hyp-Hyp-Leu-Ser-Hyp-Ser-Hyp-Thr-Hyp-Thr-Hyp-Hyp-Leu-Gly-Pro-
        His (SEQ ID NO: 223)

44      Ser-Hyp-Hyp-Hyp-Hyp-Leu-Ser-Hyp-Ser-Pro-Thr-Hyp-Thr-Hyp-Hyp-Leu-Gly-Pro-
        His (SEQ ID NO: 224)

45      Ser-Hyp-Hyp-Hyp-Hyp-Leu-Ser-Hyp-Ser-Leu-Thr-Hyp-Thr-Hyp-Hyp-Leu-Gly-Pro-
        His (SEQ ID NO: 225)

*It is preferred, for gene design, that the last three amino acid sequences (e.g., Gly-Pro-Xaa) be moved from the end to the front of the DNA sequence. Most of the Pro residues will be post-translationally modified to Hyp and glycosylated when expressed in plants-Hyp glycosylation is crucial for function. This table does not list every variation that can be derived from the consensus sequence.

In one preferred embodiment, the consensus sequence and portions thereof is selected from Ser-Hyp-Hyp-Hyp-A-Leu-Ser-Hyp-Ser-Hyp-Thr-Hyp-Thr-Hyp-Hyp-B-Gly-Pro-His (SEQ ID NO:179), where A is selected from Hyp, Thr and Ser, and B is selected from Hyp and Leu (Table 6). Remarkably, fifteen amino acid residues of this sequence are "quasi-palindromic," i.e., the side chain sequence is almost the same whether read from the N-terminus or C-terminus. Without limiting the invention to a particular theory or mechanism, it is the inventors' consideration that such peptide symmetry, which occurs frequently in extensins and AGPs, may enhance molecular packing, recognition, and self-assembly. Indeed, palindromic symmetry rigidified by contiguous Hyp motifs in the motifs: Ser-Hyp-Hyp-Hyp-(Hyp) and Thr-Hyp-Hyp-(Hyp), may impart self-ordering properties in GAGP and other HRGPs. Thus, it is the inventor's consideration that GAGP properties are related to the polysaccharide substituents. In particular, the repeating glycopeptide symmetry of two central polysaccharides flanked by Hyp arabinosides may enhance gum arabic's remarkable properties which include: an anomalously low viscosity [Churms et al., (1983) Carbohydrate Research 123:267], the ability to act as a flavor emulsifier and stabilizer, and GAGP's biological role as a component, of a plastic sealant.

In one embodiment, the invention's sequences and portions thereof may be used as repeats. The repeats preferably range from 1 to 500, more preferably from 1 to 100 and most preferably from 1 to 10. Data disclosed herein demonstrates the production of 8, 16, 20, 32, and 64 repeats of gum arabic motifs (Example 19).

The repeats may be contiguous or noncontiguous. Contiguous repeats are those without intervening amino acids, or amino acid analogues, placed between the repeating sequences. The repeats may contain two or more sequences which are described by the consensus sequence (SEQ ID NO:136) and portions thereof. The two or more sequences may be the same or different. Examples of a single repeat in which the two 19-amino acid sequences are different are those of motif 1-motif 2 [motif 1 (SEQ ID NO:143)=Ser-Hyp-Hyp-Hyp-Hyp-Leu-Ser-Hyp-Ser-Hyp-Thr-Hyp-Thr-Hyp-Hyp-Leu-Gly-Pro-His; motif 2 (SEQ ID NO:144)=-Ser-Hyp-Hyp-Hyp-Thr-Leu-Ser-Hyp-Ser-Hyp-Thr-Hyp-Thr-Hyp-Hyp-Hyp-Gly-Pro-His], described below in Example 19. Another example of a single repeat in which the two 19-amino acid sequences are different are those of motif 7-motif 13 of Table 2, having the sequence (SEQ ID NO:180): Gly-Pro-Hyp-Ser-Hyp-Hyp-Hyp-Thr-Leu-Ser-Hyp-Hyp-Leu-Thr-Hyp-Thr-Hyp-Hyp-Leu-Leu-Pro-His-Ser-Hyp-Hyp-Hyp-Hyp-Leu-Ser-Hyp-Ser-Leu-Thr-Hyp-Thr-Hyp-Hyp-Leu, in which motif 13 is underlined, and is flanked by motif 7. Yet another example of a single repeat in which the two 19-amino acid sequences are different are those of Table 2's motif 10-motif 12 having the sequence (SEQ ID NO:181): Gly-Pro-His-Ser-Hyp-Hyp-Hyp-Hyp-Leu-Ser-Hyp-Ser-Hyp-Ala-Hyp-Thr-Hyp-Hyp-Hyp-Gly-Pro-His-Ser-Hyp-Hyp-Hyp-Ser-Leu-Ser-Hyp-Leu-Pro-Thr-Hyp-Thr-Hyp-Hyp-Leu, in which motif 10 is underlined and is flanked by motif 12. Examples of a single repeat in which the two 19-amino acid sequences are the same are those of (motif 1-motif 1), (motif 2-motif 2), (motif 3-motif 3), etc.

In an alternative embodiment, the invention's sequences and portions thereof are used as noncontiguous repeats, i.e., with from 1 to 1000, more preferably from 1 to 100, and even more preferably from 1 to 10, intervening amino acids, or amino acid analogues, placed between the repeating sequences. The term "amino acid analog" refers to an amino acid is a chemically modified amino acid. Illustrative of such modifications would be replacement of hydrogen by an alkyl, acyl, or amino group, or formation of covalent adducts with biotin or fluorescent groups. Amino acids include biological amino acids as well as non-biological amino acids. The term "biological amino acid" refers to any one of the known 20 coded amino acids that a cell is capable of introducing into a polypeptide translated from an mRNA. The term "non-biological amino acid" refers to an amino acid that is not a biological amino acid. Non-biological amino acids are useful, for example, because of their stereochemistry or their chemical properties. The non-biological amino acid norleucine, for example, has a side chain similar in shape to that of methionine. However, because it lacks a side chain sulfur atom, norleucine is less susceptible to oxidation than methionine. Other examples of non-biological amino acids include aminobutyric acids, norvaline and allo-isoleucine, that contain hydrophobic side chains with different steric properties as compared to biological amino acids. The term "derivative" when in reference to an amino acid sequence means that the amino acid sequence contains at least one amino acid analog.

The production of repeating sequences may be achieved using methods known in the art [for example, Lewis et al. (1996) Protein Expression & Purification 7:400-406] and the methods described herein (Example 19).

In a preferred embodiment, the consensus sequence and portions thereof contains at least one noncontiguous hydroxyproline sequence and/or at least one contiguous hydroxyproline sequence. In a more preferred embodiment, the consensus sequence and portions thereof contains at least one noncontiguous hydroxyproline sequence and at least one contiguous hydroxyproline sequence.

The term "noncontiguous hydroxyproline sequence" refers to a sequence selected from $(Xaa-Hyp)_x$ and Xaa-Hyp-Xaa-Xaa-Hyp-Xaa, wherein Xaa is any amino acid other than hydroxyproline, and wherein x is from 2 to 1000, more preferably from 2 to 100, and most preferably from 2 to 50. In a preferred embodiment, the noncontiguous hydroxyproline sequence is Xaa-Hyp-Xaa-Hyp (SEQ ID NO:9), wherein Xaa is selected from Ser, Thr, and Ala.

The term "contiguous hydroxyproline sequence" refers to a sequence selected from $Xaa-Hyp-Hyp_{en}$ (SEQ ID NO:209) and $Xaa-Pro-Hyp_n$ (SEQ ID NO:210), wherein n is from 1 to 100, and wherein Xaa is any amino acid other than hydroxyproline. In a preferred embodiment, the contiguous hydroxyproline sequence is selected from $Ser-Hyp_2$ (SEQ ID NO:211), $Ser-Hyp_3$ (SEQ ID NO:212), $Ser-Hyp_4$ (SEQ ID NO:3), $Thr-Hyp_2$ (SEQ ID NO:213), and $Thr-Hyp_3$ (SEQ ID NO:214).

Data presented herein demonstrates that noncontiguous hydroxyproline sequences [e.g., $(Xaa-Hyp)_x$ where x is preferably at least 2] are functional glycomodules which direct the exclusive addition of arabinogalactan polysaccharide to Hyp, while contiguous hydroxyproline sequences are functional glycomodules which direct arabinosylation (Example 23). The term "functional" when made in reference to a noncontiguous hydroxyproline sequence or to sequences containing a noncontiguous hydroxyproline sequence means that the sequence directs exclusive addition of arabinogalactan polysaccharide to Hyp residues in that sequence. The addition of arabinogalactan polysaccharide to Hyp residues may be determined using methods described herein (Example 23). The term "functional" when made in reference to a contiguous hydroxyproline sequence or to sequences containing a contiguous hydroxyproline sequence means that the sequence directs arabinosylation of Hyp residues in that sequence as determined by methods disclosed herein (Example 23).

The invention contemplates sequences that are complementary, and partially complementary to SEQ ID NO:136 and portions thereof, such as those which hybridize under low stringency conditions and high stringency conditions to these sequences.

The sequences of the invention may be used to isolate hydroxyproline rich glycoprotein-binding molecules and to make polyclonal and monoclonal antibodies as described supra. In addition, the invention's sequences may be used as emulsifying agents and/or to stabilize emulsions, both of which are properties which are highly valued by the food industry for GAGP. The emulsifying and emulsion stabilizing activities of the invention's proteins, glycoproteins, and portions thereof may be determined using generic methods known in the art [Kevin & John (1978) J. Agric. Food Chem 26(3):716-723; James & Patel, "Development of a standard oil-in-water emulsification test for proteins," Leatherhead Food RA Res. Rep. No. 631] which employ commercially available reagents.

For example, the following assay may be employed using orange oil (Sigma) following essentially the manufacturer's instructions. Freeze-dried glycoproteins are dissolved in 0.05 M phosphate buffer (pH 6.5) at a concentration of 0.5% (m/v). The aqueous solutions are combined with orange oil in a 60:40 (v/v) ratio. A 1 ml emulsion is prepared in a glass tube at 0° C. with a Sonic Dismembrator (Fisher Scientific) equipped with a Microtip probe. The amplitude value is set at 4 and mixing time is set to 1 min. For the determination of emulsifying ability (EA), the emulsion is diluted serially with a solution containing 0.1 M NaCl and 0.1% SDS to give a final dilution of 1/1500. The optical density of the diluted emulsion is then determined in a 1-cm pathlength cuvette at a wavelength of 50 nm and defined as EA. The emulsion is stored vertically in a glass tube for 3 h at room temperature, then the optical density of 1:1500 dilution of the low phase of the stored sample is measured. Emulsifying stability (ES) is defined as the percentage optical density remaining after 2 hour of storage. BSA is used as a positive control. This assay has been used to determine the activity of sequences within the scope of the invention, as described in Example 24.

G. O-Glycosylation Codes

The invention further provides sequences which signal O-glycosylation. The O-glycosylation sequences are the noncontiguous hydroxyproline sequences $(Xaa-Hyp)_x$ (SEQ ID NO:182) and Xaa-Hyp-Xaa-Xaa-Hyp-Xaa (SEQ ID NO:183), wherein Xaa is any amino acid other than hydroxyproline, and wherein x is a number from 1 to 1000, more preferably from 2 to 100, and yet more preferably from 2 to 50. In a more preferred embodiment, the sequence is Xaa-Hyp-Xaa-Hyp (SEQ ID NO:9), wherein Xaa is selected from Ser, Thr, and Ala.

The inventors' discovery of these sequences was based on their hypothesis that clustered, non-contiguous Hyp residues are sites for arabinogalactan polysaccharide attachment. In particular, the inventors predicted that Hyp galactosylation of clustered non-contiguous Hyp residues, such as the Xaa-Hyp-Xaa-Hyp repeats of AGPs, results in the addition of a galactan core with sidechains of arabinose and other sugars to form characteristic Hyp-arabinogalactan polysaccharides. Hitherto, these sites of arabinogalactan polysaccharide attachment have been poorly defined because AGPs resist proteases, and because degradation by partial alkaline hydrolysis yields arabinogalactan-glycopeptides that are difficult to purify.

The inventor's discovery of the O-glycosylation sequences relied on a new approach to HRGP glycosylation site mapping as disclosed herein. To test their hypothesis that noncontiguous Hyp residues are sites for arabinogalactan polysaccharide attachment, the inventors designed three synthetic genes: The first synthetic gene, dubbed Sig-(Ser-Pro)$_{32}$-EGFP, encoded a signal sequence (Sig) at the N-terminus followed by a repetitive Ser-Hyp motif [i.e., (Ser-Pro)$_{32}$] which encoded only clustered non-contiguous Hyp residues, which the inventors predicted would code as polysaccharide addition sites. The (Ser-Pro)$_{32}$ was followed by EGFP at the C-terminus (FIG. 11). The inventors predicted that polysaccharide addition to noncontiguous Hyp should yield an expression product containing Hyp-polysaccharide exclusively. The second synthetic gene, dubbed Sig-(GAGP)$_3$-EGFP, encoded three repeats of a slightly modified 19-amino acid residue GAGP consensus sequence (FIG. 14) and was used by the inventors to determine whether it yielded an expression product that contains Hyp arabinosides as well as Hyp-polysaccharide. The third synthetic gene was a control construct (Sig-EGFP) that encoded only the signal sequence and EGFP. The expression product was a control to test whether or not any Hyp glycosylation could be attributed to EGFP modification that encode putative AGP glycomodules. Data presented herein shows that, when expressed and targeted for secretion, the two experimental sequence modules behaved as simple endogenous substrates for HRGP glycosyl transferases. The first construct expressing noncontiguous Hyp showed exclusive polysaccharide addition with polysaccharide O-linked to all Hyp residues. In contrast, the second construct containing noncontiguous Hyp and additional contiguous Hyp showed both polysaccharide and arabinooligosaccharide. From this data, the inventors arrived at the invention's O-glycosylation sequences.

The invention's sequences find use as substrates for O-Hyp arabinosyl- and galactosyltransferases. These substrates may be used to isolate and unambiguously identify these enzymes as well as to determine the enzymes' substrate preferences.

Yet another use for the inventions' sequences is in the identification of potential sites of oligoarabinoside addition in HRGPs, which may be inferred from their genomic sequences. Furthermore, these sequences would permit the transfer of useful products like exudate gum glycoproteins [Breton et al. (1998) *J. Biochem.* (*Tokyo*) 123, 1000-1009; Islam et al. (1997) *Food Hydrocolloids* 11, 493-505] such as GAGP from thorny desert scrub like *Acacia* to other desirable crop plants.

A further use for the invention's sequences is that they facilitate the de novo design of new HRGPs and their manipulation to enhance desirable properties. For example, glycoproteins which contain the O-glycosylation sequences of the invention may be used as emulsifying agents and/or to stabilize emulsions, as described supra as well as in Example 24.

EXPERIMENTAL

The following examples serve to illustrate certain preferred embodiments and aspects of the present invention and are not to be construed as limiting the scope thereof.

In the experimental disclosure which follows, the following abbreviations apply: g (gram); mg (milligrams); μg (microgram); M (molar); mM (millimolar); μM (micromolar); nm (nanometers); L (liter); ml (milliliter); μl (microliters); ° C. (degrees Centigrade); m (meter); sec. (second); DNA (deoxyribonucleic acid); cDNA (complementary DNA); RNA (ribonucleic acid); mRNA (messenger ribonucleic acid); X-gal (5-bromo-4-chloro-3-indolyl-β-D-galactopyranoside); LB (Luria Broth), PAGE (polyacrylamide gel electrophoresis); NAA (α-naphtaleneacetic acid); BAP (6-benzyl aminopurine); Tris(tris(hydroxymethyl)-aminomethane); PBS (phosphate buffered saline); 2×SSC (0.3 M NaCl, 0.03 M Na$_3$citrate, pH 7.0); Agri-Bio Inc. (North Miami, Fla.); Analytical Scientific Instruments (Alameda, Calif.); BioRad (Richmond, Calif.); Clontech (Palo Alto Calif.); Delmonte Fresh Produce (Kunia, Hi.); Difco Laboratories (Detroit, Mich.); Dole Fresh Fruit (Wahiawa, Hi.); Dynatech Laboratory Inc. (Chantilly Va.); Gibco BRL (Gaithersburg, Md.); Gold Bio Technology, Inc. (St. Louis, Mo.); GTE Corp. (Danvers, Mass.); MSI Corp. (Micron Separations, Inc., Westboro, Mass.); Operon (Operon Technolies, Alameda, Calif.); Pioneer Hi-Bred International, Inc. (Johnston, Iowa); 5 Prime 3 Prime (Boulder, Colo.); Sigma (St. Louis, Mo.); Promega (Promega Corp., Madison, Wis.); Stratagene (Stratagene Cloning Systems, La Jolla, Calif.); USB (U.S. Biochemical, Cleveland, Ohio).

Example 1

Determination of the Peptide Sequence of *Acacia* Gum Arabic Glycoproteins

In this example, GAGP (SEQ ID NO:15) was isolated and (by using chymotrypsin) the deglycosylated polypeptide backbone was prepared. Although GAGP does not contain the usual chymotryptic cleavage sites, it does contain leucyl and histidyl residues which are occasionally cleaved. Chymotrypsin cleaved sufficient of these "occasionally cleaved" sites to produce a peptide map of closely related peptides.

Purification and Deglycosylation of GAGP (SEQ ID NO: 15).

GAGP was isolated via preparative Superose-6 gel filtration. Anhydrous hydrogen fluoride deglycosylated it (20 mg powder/mL HF at 4° C., repeating the procedure twice to ensure complete deglycosylation), yielding dGAGP which gave a single symmetrical peak (data not shown) after re-chromatography on Superose-6. Further purification of dGAGP by reverse phase chromatography also gave a single major peak, showing a highly biased but constant amino acid composition in fractions sampled across the peak. These data indicated that dGAGP was a single polypeptide component sufficiently pure for sequence analysis.

Sequence Analysis.

An incomplete pronase digest gave a large peptide PRP3 which yielded a partial sequence (Table 3) containing all the amino acids present in the suggested dGAGP repeat motif. In view of the limitations of pronase, for further peptide mapping and to obtain more definitive sequence information, dGAGP was digested with chymotrypsin, followed by a two-stage HPLC fractionation scheme. Initial separation of the chymotryptides on a PolySULFOETHYL A™ (designated PSA, PolyLC, Inc. Ellicott City, Md.) cation exchanger yielded three major fractions: S1 and S2 increased with digestion time while S3 showed a concomitant decrease. Further chromatography on PRP-1 resolved PSA fractions S and S2 into several peptides.

TABLE 3

AMINO ACID SEQUENCES OF THE GUM ARABIC GLYCOPROTEIN POLYPEPTIDE BACKBONE

| Peptide | Sequence | |
|---|---|---|
| SlP5 | Ser-Hyp-Hyp-Hyp-Leu-Ser-Hyp-Ser-Leu-Thr-Hyp-Thr-Hyp-Hyp-Leu-Gly-Pro-(Pro) | (SEQ ID NO: 16) |
| S1P3 | Ser-Hyp-Hyp-Hyp-Leu-Ser-Hyp-Ser-Hyp-Thr-Hyp-Thr-Hyp-Hyp-Leu-Gly-Pro-(Pro) | (SEQ ID NO: 17) |
| S3 | Ser-Hyp-Hyp-Hyp-Thr-Leu-Ser-Hyp-Ser-Hyp-Thr-Hyp-Thr-Hyp-Hyp-Hyp-Gly-Pro-His-Ser-Hyp-Hyp-Hyp-(Hyp) | (SEQ ID NO: 18) |
| S1P2 | Ser-Hyp-Hyp-Hyp-Ser-Leu-Ser-Hyp-Ser-Hyp-Thr-Hyp-Thr-Hyp-Hyp-Thr-Gly-Pro-His | (SEQ ID NO: 19) |
| S2P1 | Ser-Hyp-Ser-Hyp-Thr-Hyp-Thr-Hyp-Hyp-Hyp-Gly-Pro-His | (SEQ ID NO: 20) |
| S2P2a | Ser-Hyp-Ser-Hyp-Ala-Hyp-Thr-Hyp-Hyp-Hyp-Leu-Gly-Pro-His | (SEQ ID NO: 21) |
| S2P2b | Ser-Hyp-Leu-Pro-Thr-Hyp-Thr-Hyp-Hyp-Hyp-Leu-Gly-Pro-His | (SEQ ID NO: 22) |
| S2P3a | Ser-Hyp-Ser-Hyp-Thr-Hyp-Thr-Hyp-Hyp-Hyp-Leu-Gly-Pro-His | (SEQ ID NO: 23) |
| S2P4 | Ser-Hyp-Hyp-Leu-Thr-Hyp-Thr-Hyp-Hyp-Hyp-Leu-Leu-Pro-His | (SEQ ID NO: 24) |
| S1P4 | Ser-Hyp-Leu-Pro-Thr-Leu-Ser-Hyp-Leu-Pro-Ala/Thr-Hyp-Thr-Hyp-Hyp-Hyp-Gly-Pro-His | (SEQ ID NOS: 25 and 26) |

Consensus: Ser-Hyp-Hyp-Hyp-Thr/Hyp-Leu-Ser-Hyp-Ser-Hyp-Thr-Hyp-Thr-Hyp-Hyp-Leu-Gly-Pro-His (SEQ ID NOS: 27 and 28)

Substitutions indicated below consensus: (Leu) (Pro) (Ser) ... (Leu) (Leu) (Ala) ... (Hyp) ... (Pro); (Pro)

Edman degradation showed that these chymotryptides were closely related to each other, to the partial sequence of the large pronase peptide (Table 3), and to the major pronase peptide of GAGP isolated earlier by Delonnay (see above). Indeed, all can be related to a single 19-amino acid residue consensus sequence with minor variation in some positions (Table 3). These peptides also reflect the overall amino acid composition and are therefore evidence of a highly repetitive polypeptide backbone with minor variations in the repetitive motif; these include occasional substitution of Leu for Hyp and Ser. Remarkably, fifteen residues of the consensus sequence are "quasi-palindromic" i.e. the side chain sequence is almost the same whether read from the N-terminus or C-terminus.

Example 2

Construction of Synthetic HRGP Gene Cassettes

Synthetic gene cassettes encoding contiguous and noncontiguous Hyp modules are constructed using partially overlapping sets consisting of oligonucleotide pairs, "internal repeat pairs" and "external 3'- and 5'-linker pairs" respectively, all with complementary "sticky" ends. The design strategy for the repetitive HRGP modules combines proven approaches described earlier for the production in *E. coli* of novel repetitive polypeptide polymers (McGrath et al. [1990] Biotechnol. Prog. 6:188), of a repetitious synthetic analog of the bioadhesive precursor protein of the mussel *Mytilus edulis*, of a repetitive spider silk protein (Lewis et al. [1996] Protein Express. Punt: 7:400), and of a highly repetitive elastin-like polymer in tobacco [Zhang, X., Urry, D. W., and Daniell, H. "Expression of an environmentally friendly synthetic protein-based polymer gene in transgenic tobacco plants," *Plant Cell Reports,* 16: 174 (1996)].

The basic design strategy for synthetic HRGP gene cassettes is illustrated by the following illustrative constructs.

a) Ser-Hyp$_o$ (SEQ ID NO:3) Gene Cassette

A synthetic gene encoding the extensin-like Ser-Hyp$_4$ (SEQ ID NO:3) module is constructed using the following partially overlapping sets of oligonucleotide pairs.

```
5'-Linker:
Amino Acid (SEQ ID NO: 29):    A   G   S   S   T   R   A   S   P   (P
                               P   P)
              5'-GCT GGA TCC TCA ACC CGG GCC TCA CCA             (SEQ ID NO: 30)
                  CGA CCT AGG AGT TGG GCC CCG AGT GGT GGT GGT GGA-5'   (SEQ ID NO: 31)

3' Linker (for pBI121-Sig-EGFP):
Amino Acid (SEQ ID NO: 32):    P   P   P   S   P   V   A   R   N   S   P
                               P
              5'-CCA CCA CCT TCA CCG GTC GCC CGG AAT TCA CCA CCC         (SEQ ID NO: 33)
                  AGT GGT CAG CGG GCC TTA AGT GGT GGG-5'          (SEQ ID NO: 34)
```

-continued

```
3' Linker (for pBI121-Sig):
Amino Acid:
            5'-CCA CCA CCT TAA TAG AGC TCC CCC              (SEQ ID NO: 35)

ATT ATC TCG AGG GGG-5'              (SEQ ID NO: 36)

Internal Repeat
Amino Acid (SEQ ID NO: 37):   P   P   P   S   P   P   P   P   S   P
            5'-CCA CCA CCT TCA CCT CCA CCC CCA TCT CCA      (SEQ ID NO: 38)
               AGT GGA GGT GGG GGT AGA GGT GGT GGT GGA-5'   (SEQ ID NO: 39)
```

Conversion of the "internal" and 5' & 3' "external" gene cassettes to long duplex DNA is accomplished using the following steps:

1. Heat each pair of complementary oligonucleotides to 90° and then anneal by cooling slowly to 60° thereby forming short duplex internal and external DNAs.
2. Combine the 5' external linker duplex with the internal repeat duplexes in an approximately 1:20 molar ratio and anneal by further cooling to yield long duplex DNA capped by the 5' linker. The 5' linker is covalently joined to the internal repeat duplex by ligation using T4 DNA ligase. (Preferably up to 50, more preferably up to 30, repeats of the internal repeat duplex can be used).
3. In molar excess, combine the 3' external linker duplex with the above 5' linker-internal repeat duplex, anneal and ligate as described above.
4. Digest the 5' linker-internal repeat-3' linker duplex with BamHI (cuts within the 5'-linker) and EcoR1 (cuts within the 3'-linker).
5. Size fractionate the reaction products using Sephacryl gel permeation chromatography to select constructs greater than 90 bp.
6. Insert the sized, digested synthetic gene cassette into a plasmid having a polylinker containing BamHI and EcoRI sites (e.g., pBluescript SK+ or KS+ [Stratagene]).
7. Transform *E. coli* cells (e.g., by electroporation or the use of competent cells) with the plasmid into which the synthetic gene construct has been ligated.
8. Following *E. coli* transformation, the internal repeat oligonucleotides are used to screen and identify Ampicillin-resistant colonies carrying the synthetic gene construct.
9. The insert contained on the plasmids within the Ampicillin-resistant colonies are sequenced to confirm the fidelity of the synthetic gene construct.

b) GAGP (SEQ ID NO:15) Consensus Sequence Cassette

A synthetic gene cassette encoding the GAGP consensus sequence is generated as described above using the following 5' linker, internal repeat and 3' linker duplexes.

```
5'-Linker
Amino Acid (SEQ ID NO: 40):   A   A   G   S   S   T   R   A   (S   P
S)
            5'-GCT GCC GGA TCC TCA ACC CGG GCC-3'           (SEQ ID NO: 41)

3'-CGA CGG CCT AGG AGT TGG GCC CGG AGT GGC AGT-5'  (SEQ ID NO: 42)

3'-Linker (for pBI121-Sig-EGFP)
Amino Acid (SEQ ID NO: 43):   S   P   S   P   V   A   R   N   S
PP
            5'-TCA CCC TCA CCG GTC GCC CGG AAT TCA CCA CCC-3'  (SEQ ID NO: 44)

3'GGC CAG CGG GCC TTA AGT GGT GGG-5'   (SEQ ID NO: 45)

3'-Linker (for pBI121-Sig)
Amino Acid:
            5'-TCA CCC TCA TAA TAG AGC TCC CCC-3'           (SEQ ID NO: 46)

3'ATT ATC TCG AGG GGG-5'            (SEQ ID NO: 47)

Internal Repeat
Amino Acid (SEQ ID NO: 48):   S   P   S   P   T   P   T   P   P   P   G   P
H   S   P   P   P   T   L
            5'-TCA CCC TCA CCA ACT CCT ACC CCA CCA CCT GGT CCA CAC TCA CCA CCA

CCA ACA TTG-3'                                              (SEQ ID NO: 49)

3'-GGT TGA GGA TGG GGT GGT GGA CCA GGT GTG AGT GGT GGT

GGT TGT AAC AGT GGG AGT-5'                                  (SEQ ID NO: 50)
```

Conversion of the "internal" AGP-like motif and 5' & 3' "external" gene cassettes to long duplex DNA is accomplished using the steps described in section a) above. Up to fifty (50) repeats of the internal repeat duplex are desirable (more preferably up to thirty (30) repeats, and more preferably approximately twenty (20) repeats) (i.e., the wild-type protein contains 20 of these repeats).

Since the above GAGP internal repeat is a consensus sequence, it is also desirable to have repeats that comprise a repeat sequence that varies from the consensus sequence (see e.g. Table 3 above). In this regard, the variant sequences are likely to be glycosylated in a slightly different manner, which may confer different properties (e.g. more soluble etc.). Other constructs are shown for other illustrative modules in Table 4.

Example 3

Isolation of Tomato P1 Extensin cDNA Clones

In order to obtain the tomato P1 extensin signal sequence (i.e., signal peptide), P1 extensin cDNA clones were isolated using oligonucleotides designed after the P1-unique protein sequence (SEQ ID NO:51): Val-Lys-Pro-Tyr-His-Pro-Thr-Hyp-Val-Tyr-Lys. When present at the N-terminus of a protein sequence, the P1 extensin signal sequence directs the nascent peptide chain to the ER.

Example 4

Construction of One Embodiment of an Expression Vector pBI121 is an expression vector which permits the high level expression and secretion of inserted genes in plant cells (e.g., tomato, tobacco, members of the genus Solanaceae, members of the family Leguminoseae, non-graminaceous monocotyledons). pBI121 contains the 35S CaMV promoter, the tobacco (*Nicotiana plumbaginifolia*) extensin signal sequence, a EGFP gene, the termination/polyadenylation signal from the nopaline synthetase gene (NOS-ter), a kanamycin-resistance gene (nptII) and the right and left borders of T-DNA to permit transfer into plants by *Agrobacterium*-mediated transformation.

TABLE 4

ILLUSTRATIVE HRGP SYNTHETIC GENE MODULES

1. MODULES FOR AGP-LIKE SEQUENCES a. The [SP]$_n$ Module
   [SP]$_n$ Internal Repeat Oligo's:

5'-TCA CCC TCA CCA TCT CCT TCG CCA TCA CCC (SEQ ID NO: 52)
            GGT AGA GGA AGC GGT AGT GGG AGT GGG AGT-5' (SEQ ID NO: 53)

The [SP]$_n$ 3' & 5' External Linkers for both plasmids are the same as for the GAGP module.
b. The [AP]$_n$ Module
[AP]$_n$ Internal Repeat Oligo's:

5'-GCT CCA GCA CCT GCC CCA GCC CCT GCA CCA -3' (SEQ ID NO: 54)
            GGA CGG GGT CGG GGA CGT GGT -5' (SEQ ID NO: 55)

[AP]$_n$ External Linker Oligo's for plasmid pBI121-Sig-EGFP

5'-Linker: 5'-GCT GCC GGA TCC TCA ACC CGG (SEQ ID NO: 56)
          3'-CGA CGG CCT AGG AGT TGG GCC CGA GGT CGT-5' (SEQ ID NO: 57)

3'-Linker: 5'-GCT CCA GCA CCG GTC GCC CGG AAT TCA CCA CCC-3' (SEQ ID NO: 58)
          3'-           GGC CAG CGG GCC TTA AGT GGT GGG-5' (SEQ ID NO: 59)

[AP]$_n$ External 3' Linker Oligos for plasmid pBI121-Sig

5'-GCT CCA GCA TAA TAG AGC TCC CCC (SEQ ID NO: 60)
                    ATT ATC TCG AGG GGG-5' (SEQ ID NO: 61)

c. The [TP]$_n$ Module
   [TP]$_n$ Internal Repeat Oligo's:

5'-ACA CCA ACC CCT ACT CCC ACG CCA ACA CCT ACA CCC ACT CCA (SEQ ID NO: 62)
            GGA TGA GGG TGC GGT TGT GGA TCT GGG TGA GGT TGT GGT TGG-5' (SEQ ID NO: 63)

[TP]$_n$ External Linker Oligo's for pBI121-Sig-EGFP:

5'Linker: 5'-GCT GCC GGA TCC TCA ACC CGG (SEQ ID NO: 64)
         3'-CGA CGG CCT AGG AGT TGG GCC TGT GGT TGG-5' (SEQ ID NO: 65)

3'Linker: 5'-ACA CCA ACC CCG GTC GCC CGG AAT TCA CCA CCC-3' (SEQ ID NO: 66)
              GGC CAG CGG GCC TTA AGT GGT GGG-5' (SEQ ID NO: 67)

[TP]$_n$ External 3' Linker Oligos for pBI121-Sig

5'-ACA CCA ACC TAA TAG AGC TCC CCC (SEQ ID NO: 68)
              ATT ATC TCG AGG GGG-5' (SEQ ID NO: 69)

2. MODULES FOR EXTENSIN-LIKE SEQUENCES a. The [SPP]$_n$ Module
   [SPP]$_n$ Internal Repeat Oligo's:

5'-CCA CCA TCA CCA CCC TCT CCT CCA TCA CCC CCA TCC CCA CCA TCA (SEQ ID NO: 70)
            GGT GGG AGA GGA GGT AGT GGG GGT AGG GGT GGT AGT GGT GGT AGT-5' (SEQ ID NO: 71)

[SPP]$_n$ External Linkers for pBE121-Sig-EGFP:

5'Linker: 5'-GCT GCC GGA TCC TCA ACC CGG GCC (SEQ ID NO: 72)
         3'-CGA pGG CCT AGG AGT TOG GCC CGG GGT GGT AGT-5' (SEQ ID NO: 73)

TABLE 4-continued

ILLUSTRATIVE HRGP SYNTHETIC GENE MODULES

```
3'Linker: 5'-CCA,CCA TCA CCG GTC GCC CGG AAT TCA CCA CCC-3' (SEQ ID NO: 74)
                         GGC CAG CGG GCC TTA AGT GOT GGG-5' (SEQ ID NO: 75)

[SPP]n External 3' Linker for pBE121-Sig:

5'-CCA CCA TCA TAA TAG AGC TCC CCC (SEQ ID NO: 76)
                   ATT ATC TCG AGG GGG-5' (SEQ ID NO: 77)

b. The [SPPP]n Module
   [SPPP]n Internal Repeat Oligo's:

5'-CCA CCA CCT TCA CCA CCT CCA TCT CCC CCA CCT TCC CCT CCA CCA TCA (SEQ ID NO: 78)
            AGT GGT GGA GGT AGA GGG GGT GGA AGG GGA GGT GGT AGT GGT GGT GGA-5' (SEQ ID NO: 79)

[SPPP]n External Linker Oligo's for pBI121-Sig-EGFP:

5'-Linker: 5'-GCT GGA TCC TCA ACC CGG GCC TCA (SEQ ID NO: 80)
           3'-CGA CCT AGG AGT TGG GCC CGG AGT GGT GGT GGA-5' (SEQ ID NO: 81)

3'-Linker: 5'-CCA CCA CCT TCA CCG GTC GCC CGG AAT TCA CCA CCC-3' (SEQ ID NO: 82)
                      AGT GGC CAG CGG GCC TTA AGT GGT GGG-5' (SEQ ID NO: 83)

[SPPP]n External 3' Linker Oligos for pBI121-Sig:

5'-CCA CCA CCT TAA TAG AGC TCC CCC (SEQ ID NO: 84)
                  ATT ATC TCG AGG GGG-5' (SEQ ID NO: 85)

d. The P3-Type Extensin Palindromic. Module:
   P3-Type Extensin Palindromic Internal Repeat Oligo's:

5'-CCA CCA CCT TCA CCC TCT CCA CCT CCA CCA TCT CCG TCA CCA (SEQ ID NO: 86)
              AGT GGG AGA GGT GGA GGT GGT AGA GGC AGT GGT GGT GGT GGA-5' (SEQ ID NO: 87)

P3-Type Extensin Palindromic External Linker Oligo's: Use the [SPPP]n linkers (SEE ABOVE)
e. The Potato Lectin HRGP Palindromic Module:
Potato Lectin HRGP Palindromic External Linker Oligo's:

5'-CCA CCA CCT TCA CCC CCA TCT CCA CCT CCA CCA TCT CCA CCG TCA CCA (SEQ ID NO: 88)
              AGT GGG GGT AGA GGT GGA GGT GGT AGA GGT GGC AGT GGT GGT GGT GGA-5' (SEQ ID NO: 89)

Potato Lectin HRGP Palindromic External Linker Oligo's: Use the [SPPP]n linkers (SEE ABOVE)
f. P1-Extensin-Like Modules:
    i. The SPPPPTPVYK Module:
       SPPPPTPVYK Internal Repeat Oligo's:

5'-CCA CCA CCT ACT CCC GTT TAC AAA TCA CCA CCA CCA CCT ACT CCC GTT TAC AAA TCA CCA (SEQ ID NO: 90)
           TGA GGG CAA ATG TTT AGT GGT GGT GGT GGA TCA GGG CAA ATG TTT AGT GGT GGT GGT GGA-5'
(SEQ ID NO: 91)

SPPPPTPVYK External Linker Oligo's: Use the [SPPP]n linkers (SEE ABOVE)
    ii. The SPPPPVKPYHPTPVFL Module:
        SPPPPVKPYHPTPVFL Internal Repeat Oligo's:

5'-CCA CCA CCT GTC AAG CCT TAC CAC CCC ACT CCC GTT TTT CTT TCA CCA (SEQ ID NO: 92)
             CAG TTC GGA ATG GTG GGG TGA GGG CAA AAA GAA AGT GGT GGT GGT GGA-5' (SEQ ID NO: 93)

SPPPPVKPYHPTPVFL External Linker Oligo's: Use the [SPPP]n linkers (SEE ABOVE)
    iii. The SPPPPVLPFHPTPVYK Module:
         SPPPPVLPFHPTPVYK Internal Repeat Oligo's:

5'-CCA CCA CCT GTC TTA CCT TTC CAC CCC ACT CCC GTT TAC AAA TCA CCA (SEQ ID NO: 94)
             CAG AAT GGA AAG GTG GGG TGA GGG CAA ATG TTT AGT GGT GGT GGT GGA-5' (SEQ ID NO: 95)

SPPPPVLPFHPTPVYK External linker Oligo's: Use the [SPPP]n linkers (SEE ABOVE)
EGFP 3' Linker Oligo's needed to insert EGFP into pBI121-Sig-EGF 5'-GGC CGC GAG CTC CAG CAC GGG (SEQ ID NO: 96)
       CG CTC GAG GTC GTG CCC-5' (SEQ ID NO: 97)
```

The presence of the extensin signal sequence at the N-terminus of proteins encoded by genes inserted into the pBI121 expression vector (e.g., HRGPs encoded by synthetic gene constructs). The tobacco signal sequence was demonstrated to target extensin fusion proteins through the ER and Golgi for posttranslational modifications, and finally to the wall.

The targeted expression of recombinant HRGPs is not dependent upon the use of the tobacco extensin signal sequence. Signal sequences involved in the transport of extensins and extensin modules in the same plant family (Solanaceae) as tobacco may be employed; alternatively, the signal sequence from tomato P1 extensin may be employed.

The EGFP gene encodes a green fluorescent protein (GFP) appropriately red-shifted for plant use (the EGFP gene encodes a S65T variant optimized for use in plants and is available from Clontech). Other suitable mutants may be employed (see Table 1). These modified GFPs allow the detection of less than 700 GFP molecules at the cell surface. The use of a GFP gene provides a reporter gene and permits the formation of fusion proteins comprising repetitive HRGP modules. GFPs require aerobic conditions for oxidative formation of the fluorophore. It is functional at the lower temperatures used for plant cell cultures, normally it does not adversely affect protein function.

Plasmids pBI121-Sig and pBI121-Sig-EGFP are constructed as follows. For both plasmids, the GUS gene present in pBI121 (Clontech) is deleted by digestion with BamHI and SstI and a pair of partially complementary oligonucleotides encoding the tobacco extensin signal sequence is annealed to the BamHI and SstI ends. The oligonucleotides encoding the 21 amino acid extensin signal sequence have the following sequence: 5'-GA TCC GCA ATG GGA AAA ATG GCT TCT CTA TTT GCC ACA TTT TTA GTG GTT TTA GTG TCA CTT AGC TTA GCA CAA ACA ACC CGG GTA CCG GTC GCC ACC ATG GTG TAA AGC GGC CGC GAG CT-3' (SEQ ID NO:98) and 5'-C GCG GCC GCT TTA CAC CAT GGT GGC GAC CGG TAC CCG GGT TGT TTG TGC TAA GCT AAG TGA CAC TAA AAC CAC TAA AAA TGT GGC AAA TAG AGA AGC CAT TTT TCC CAT TGC G-3' (SEQ ID NO:99). In addition to encoding the extensin signal sequence, this pair of oligonucleotides, when inserted into the digested pBI121 vector, provides a BamHI site (5' end) and XmaI and SstI sites (3' end). The XmaI and SstI sites allow the insertion of the GFP gene. The modified pBI121 vector lacking the GUS gene and containing the synthetic extensin signal sequence is termed pBI121-Sig. Proper construction of pBI121 is confirmed by DNA sequencing.

The GFP gene (e.g., the EGFP gene) is inserted into pBI121-Sig to make pBI121-Sig-EGFP as follows. The EGFP gene is excised from pEGFP (Clontech) as a 1.48 kb XmaI/NotI fragment (base pairs 270 to 1010 in pEGFP). This 1.48 kb XmaI/NotI fragment is then annealed and ligated to a synthetic 3' linker (see above). The EGFP-3' linker is then digested with SstI to produce an XmaI/SstI EGFP fragment which in inserted into the XmaI/SstI site of pBI121-Sig to create pBI121-Sig-EGFP. The AgeI (discussed below), XmaI and SstI sites provide unique restriction enzyme sites. Proper construction of the plasmids is confirmed by DNA sequencing.

The EGFP sequences in pBI121-Sig-EGFP contain an AgeI site directly before the translation start codon (i.e., ATG) of EGFP. Synthetic HRGP gene cassettes are inserted into the plasmid between the signal sequence and the EGFP gene sequences as XmaI/AgeI fragments; the HRGP gene cassettes are excised as XmaI/AgeI fragments from the pBluescript constructs described in Ex. 2. Proper construction of HRGP-containing expression vectors is confirmed by DNA sequencing and/or restriction enzyme digestion.

Expression of the synthetic HRGP gene cassettes is not dependent upon the use of the pBI121-Sig and pBI121-Sig-EGFP gene cassette. Analogous expression vectors containing other promoter elements functional in plant cells may be employed (e.g., the CaMV region IV promoter, ribulose-1,6-biphosphate (RUBP) carboxylase small subunit (ssu) promoter, the nopaline promoter, octopine promoter, mannopine promoter, the β-conglycinin promoter, the ADH promoter, heat shock promoters, tissue-specific promoters, e.g., promoters associated with fruit ripening, promoters regulated during seed ripening (e.g., promoters from the napin, phaseo- lin and glycinin genes). For example, expression vectors containing a promoter that directs high level expression of inserted gene sequences in the seeds of plants (e.g., fruits, legumes and cereals, including but not limited to corn, wheat, rice, tomato, potato, yam, pepper, squash cucumbers, beans, peas, apple, cherry, peach, black locust, pine and maple trees) may be employed. Expression may also be carried out in green algae.

In addition, alternative reporter genes may be employed in place of the GFP gene. Suitable reporter genes include β-glucuronidase (GUS), neomycin phosphotransferase II gene (nptII), alkaline phosphatase, luciferase, CAT (Chloramphenicol acetyltransferase). Preferred reporter genes lack Hyp residues. Further, the proteins encoded by the synthetic HRGP genes need not be expressed as fusion proteins. This is readily accomplished using the pBI121-Sig vector.

Example 5

Expression of Recombinant HRGPs In Tomato Cell Suspension Cultures

The present invention contemplates recombinant HRGPs encoded by expression vectors comprising synthetic HRGP gene modules are expressed in tomato cell suspension cultures. The expression of recombinant HRGPs in tomato cell suspension cultures is illustrated by the discussion provided below for recombinant GAGP expression.

a) Expression of Recombinant GAGP

An expression vector containing the synthetic GAGP gene cassette (capable of being expressed as a fusion with GFP or without GFP sequences) is introduced into tomato cell suspension cultures. A variety of means are known to the art for the transfer of DNA into tomato cell suspension cultures, including *Agrobacterium*-mediated transfer and biolistic transformation.

*Agrobacterium*-Mediated Transformation:

The present invention contemplates transforming both suspension cultured cells (Bonnie Best cultures) and tomato leaf discs by mobilizing the above-described plasmid constructions (and others) from *E. coli* into *Agrobacterium tumefaciens* strain LBA4404 via triparental mating. Positive colonies are used to infect tomato cultures or leaf discs (*Lysopersicon esculentum*). Transformed cells/plants are selected on MSO medium containing 500 mg/mL carbenicillin and 100 mg/mL kanamycin. Expression of GFP fusion products are conveniently monitored by fluorescence microscopy using a high Q FITC filter set (Chroma Technology Corp.). FITC conjugates (e.g. FITC-BSA) can be used along with purified recombinant GFP as controls for microscopy set-up. Cultured tomato cells show only very weak autofluorescence. Thus, one can readily verify the spatiotemporal expression of GFP-Hyp module fusion products.

Transgenic cells/plants can be examined for transgene copy number and construct fidelity genomic Southern blotting and for the HRGP construct mRNA by northern blotting, using the internal repeat oligonucleotides as probes. Controls include tissue/plants which are untransformed, transformed with the pBI121 alone, pBI121 containing only GFP, and pBI121 having the signal sequence and GFP but no HRGP synthetic gene.

Microprojectile Bombardment:

1.6 M gold particles are coated with each appropriate plasmid construct DNA for use in a Biolistic particle delivery system to transform the tomato suspension cultures/callus or other tissue. Controls include: particles without DNA, particles which contain PBI121 only, and particles which contain PBI121 and GFP.

b) Expression of Other HRGPS of Interest

As noted above, the present invention contemplates expressing a variety of HRGPs, fragments and variants. Such HRGPs include, but are not limited to, RPRps, extensins, AGPs and other plant gums (e.g. gum Karaya, gum Tragacanth, gum Ghatti, etc.). HRGP chimeras include but are not limited to HRGP plant lectins, including the solanaceous lectins, plant chitinases, and proteins in which the HRGP portion serves as a spacer (such as in sunflower). The present invention specifically contemplates using the HRGP modules (described above) as spacers to link non-HRGP proteins (e.g. enzymes) together.

Example 6

Construction of a Synthetic HRGP Gene Cassette Incorporating A GAGP Construct

Synthetic gene cassettes encoding contiguous and noncontiguous Hyp modules were constructed using partially overlapping sets consisting of oligonucleotide pairs, "internal repeat pairs" and "external 3'- and 5'-linker pairs" respectively, all with complementary "sticky" ends. The following 5'-linker, internal repeat and 3'-linker duplexes were employed:

```
5'-Linker
    A   A   G   S   S   T   R   A   (S   P   S)                  (SEQ ID NO: 40)
5'-GCT GCC GGA TCC TCA ACC CGG GCC-3'                             (SEQ ID NO: 41)

3'-CGA CGG CCT AGG AGT TGG GCC CGG AGT GGG AGT-5'                 (SEQ ID NO: 42)

3'-Linker
    S   P   S   P   V   A   R   N   S   P   P                    (SEQ ID NO: 43)
5'-TCA CCC TCA CCG GTC GCC CGG AAT TCA CCA CCC-3'                 (SEQ ID NO: 44)

3'-GGC CAG CGG GCC TTA AGT GGT GGG-5'                      (SEQ ID NO: 45)

Internal Repeat
        S   P   S   P   T   P   T   A   P   P   G   P   H   S   P   P   P    (SEQ ID NO: 100)
    T   L
[5'-TCA CCC TCA CCA ACT CCT ACC GCA CCA CCT GGT CCA CAC TCT CCA CCA CCA       (SEQ ID NO: 101)

ACA TTG-3']

[3'-AGT GGG AGT GGT TGA GGA TGG CGT GGT GGA CCA GGT GTG AGA GGT GGT GGT      (SEQ ID NO: 102)

TGT AAC-5']₂
then:

S   P   S   P   T   P   T   A   P   P   G   P   H   S   P   P   P    (SEQ ID NO: 103)
    S   L
5'-TCA CCC TCA CCA ACT CCT ACC GCA CCA CCT GGT CCA CAC TCT CCA CCA CCA        (SEQ ID NO: 104)

TCA TTG-3'

3'-AGT GGG AGT GGT TGA GGA TGG CGT GGT GGA CCA GGT GTG AGA GGT GGT GGT       (SEQ ID NO: 105)

AGT AAC-5'
```

The following synthetic gene (SEQ ID NO:106) was eventually expressed in tobacco and tomato cell cultures and tobacco plants using the above constructs:

```
                M   G   K   M   A   S   L   F   A   T   F   L   V   V   L   V
5'-GGA TCC GCA ATG GGA AAA ATG GCT TCT CTA TTT GCC ACA TTT TTA GTC GTT TTA GTG
3'-CCT AGG CGT TAC CCT TTT TAC CGA AGA GAT AAA CGG TGT AAA AAT CAC CAA AAT CAC

S   L   S   L   A   Q   T   T   R   D   S   P   S   P   T   P   T   A   P
TCA CTT AGC TTA GCA CAA ACA ACC CGG GAC TCA CCC TCA CCA ACT CCT ACC GCA CCA

AGT GAA TCG AAT CGT GTT TGT TGG GCC CTG AGT GGG AGT GGT TGA GGA TGG CGT GGT

P   G   P   H   S   P   P   P   T   L   S   P   S   P   T   P   T   A   P
CCT GGT CCA CAC TCT CCA CCA CCA ACA TTG TCA CCC TCA CCA ACT CCT ACC GCA CCA

GGA CCA GGT GTG AGA GGT GGT GGT TGT AAC AGT GGG AGT GGT TGA GGA TGG CGT GGT
```

```
    P   G   P   H   S   P   P   P   T   L   S   P   S   P   T   P   T   A   P
    CCT GGT CCA CAC TCA CCA CCA CCA ACA TTG TCA CCC TCA CCA ACT CCT ACC GCA CCA

GGA CCA GGT GTG AGT GGT GGT GGT TGT AAC AGT GGG AGT GGT TGA GGA TGG CGT GGT

P   G   P   H   S   P   P   P   S   L   S   P   S   P   V
    CCT GGT CCA CAC TCA CCA CCA CCA TCA TTG TCA CCC TCA CCG GTC GCC ACC-gfp-3'

GGA CCA GGT GTG AGT GGT GGT GGT AGT AAC AGT GGG AGT GGC CAG CGG TGG-gfp-5'
```

This example involved: (A) Oligonucleotide pair preparation; (B) Oligonucleotide polymerization; (C) Construct precipitation; (D) Restriction of gene 3'-linker and 5'-linker capped ends; (E) Size-fractionation and removal of enzyme contaminants; (F) Gene insertion into SK plasmid vector. All SDS-PAGE purified oligonucleotides were synthesized by Gibco-BRL.

(A) Oligonucleotide Pair Preparation

In separate Eppendorf tubes were combined:
Tube 1) 5.5 µl GAGP internal repeat sense oligonucleotide (0.5 nmol/µl), 5.5 µl GAGP internal repeat antisense oligonucleotide (0.5 nmol/µl), 11 µl T4 ligase 10× ligation buffer (New England Biolabs);
Tube 2) 2 µl 5'-sense linker (0.05 nmol/µl), 2 µl 5'-antisense linker (0.05 nmol/µl), 1 µl H2O, 5 µl T4 ligase 10× ligation buffer (New England Biolabs);
Tube 3) 2 µl 3'-sense linker (1 nmol/µl), 2 µl 3-antisense linker (1 nmol/µl), 1 µl water, 5 µl T4 ligase 10× ligation buffer (New England Biolabs).
All tubes were heated to 90-95° C. for 5 minutes, then slowly cooled over the next 3 hours to 45° C. The tubes were then incubated at 45° C. for 2 hours.

(B) Oligonucleotide Polymerization

10 µl of solution from Tube 1 (internal repeat pair) was combined with 10 µl of solution from Tube 2 (5' linker pair), and incubated at 17° C. for 3 hours. To this mixture was added 80 µl water and 2 µl (4000 U) T4 DNA ligase (New England Biolabs), and again incubated at 12-15° C. for 36 hours. The degree of polymerization was verified on 2.2% agarose gel (Fisher).

The 3'-end of the polymer was then capped by adding 50 µl of the ligated GAGP 5'-linker mixture from above to 5 µl of solution from Tube 3 (3'-linker), heating to 30° C., and incubating at 17° C. for 3 hours. 20 µl water and 2 µl T4 DNA ligase (New England Biolabs) was then added, and the solution incubated at 12-15° C. for 36 hr. Finally, the solution was heated at 65° C. for 10 minutes to denature the ligase.

(C) Construct Precipitation

10 µl GAGP construct from (B) above was combined with 25 µl water and 5 µl 3 M NaAcetate. 150 µl EtOH was then added and the solution incubated at 4° C. for 30 minutes The solution was then centrifuged at 10,000 rpm for 30 minutes The resultant pellet was washed with 70% EtOH and dried.

(D) Restriction Of Gene 3'-Linker And 5'-Linker Capped Ends

The pellet from (C) above was dissolved in 14 µl water. 2 µl 10×EcoRI restriction buffer (New England Biolabs), 2 µl EcoRI 10 U/µl (New England Biolabs), and 2 µl BamHI 20 U/µl (New England Biolabs) was then added and the mixture incubated at 37° C. overnight.

(E) Size-Fractionation and Removal of Enzyme Contaminants

10 µl water was added to 20 µl of the restricted genes from Step (D) above. This mixture was then loaded onto a Sephacryl S-400 (Pharmacia Microspin™) minicolumn and spun to remove small (<90 bp) oligonucleotide fragments. The first effluent from the column (i.e. the large MW material) was collected. Finally, the enzymes were removed using a Qiaquick Nucleotide removal kit (Qiagen). The final volume of mixture was approximately 50 µl.

(F) Gene Insertion Into SK Plasmid Vector

SK plasmid vector (Strategene) was restricted with BamHI and EcoRI and restricted large plasmid fragments were isolated from agarose gel. To 2-3 µg restricted SK plasmid in 10 µl water was added 6 µl restricted GAGP gene construct from Step (E), 2 µl T4 DNA ligase buffer (New England Biolabs), and 1 µl T4 DNA ligase (New England Biolabs). The solution was then kept at 8° C. overnight for ligation. 100 µl competent XL1-Blue cells (Stratagene) were then transformed with 3 ligation mixture. Clones were selected via Blue/White assay (Promega Corporation), as described by Promega Protocols and Applications Guide, 2 ed. (1991), by hybridization with 32-labeled antisense internal oligonucleotide, and by restriction mapping.

Example 7

Construction of a Synthetic HRGP Gene Cassette Incorporating An SP Construct

Synthetic gene cassettes encoding contiguous and noncontiguous Hyp modules were constructed using partially overlapping sets consisting of oligonucleotide pairs, "internal repeat pairs" and "external 3'- and 5'-linker pairs" respectively, all with complementary "sticky" ends. The following 5'-linker, internal repeat and 3'-linker duplexes were employed:

```
5'-Linker
       A   A   G   S   S   T   R   A   (S   P   S)            (SEQ ID NO: 40)
    5'-GCT GCC GGA TCC TCA ACC CGG GCC-3'                     (SEQ ID NO: 41)

3'-CGA CGG CCT AGG AGT TGG GCC CGG AGT GGG AGT-5'         (SEQ ID NO: 42)

3'-Linker
       S   P   S   P   V   A   R   N   S   P   P             (SEQ ID NO: 43)
    5'-TCA CCC TCA CCG GTC GCC CGG AAT TCA CCA CCC-3'         (SEQ ID NO: 44)

3'-GGC CAG CGG GCC TTA AGT GGT GGG-5'                    (SEQ ID NO: 45)
```

```
                                      -continued
Internal Repeat
      S    P    S    P    S    P    S    P    S    P   (S    P    S)         (SEQ ID NO: 107)
5'- TCA  CCC  TCA  CCA  TCT  CCT  TCG  CCA  TCA  CCC                         (SEQ ID NO: 108)

3'- GGT  AGA  GGA  AGC  GGT  AGT  GGG  AGT  GGG  AGT -5'       (SEQ ID NO: 109)
```

The following synthetic gene (SEQ ID NO:110) was eventually expressed in tobacco and tomato cell cultures and tobacco plants using the above constructs:

```
        G    S    A    M    G    K    M    A    S    L    F    A    T    F    L    V    V    L    V
5'- GGA  TCC  GCA  ATG  GGA  AAA  ATG  GCT  TCT  CTA  TTT  GCC  ACA  TTT  TTA  GTG  GTT  TTA  GTG

3'- CCT  AGG  CGT  TAC  CCT  TTT  TAC  CGA  AGA  GAT  AAA  CGG  TGT  AAA  AAT  CAC  CAA  AAT  CAC

S    L    S    L    A    Q    T    T    R    A  [ S    P    S    P    S    P    S    P    S
   TCA  CTT  AGC  TTA  GCA  CAA  ACA  ACC  CGG  GCC [TCA  CCC  TCA  CCA  TCT  CCT  TCG  CCA  TCA

AGT  GAA  TCG  AAT  CGT  GTT  TGT  TGG  GCC  CGG [AGT  GGG  AGT  GGT  AGA  GGA  AGC  GGT  AGT

P ]       S    P    S    P    V    A    T
   CCC]₆     TCA  CCC  TCA  CCG  GTC  GCC  ACC -gfp-3'

GGG]₆     AGT  GGG  AGT  GGC  CAG  CGG  TGG -gfp-5'
```

This example involved: (A) Oligonucleotide pair preparation; (B) Oligonucleotide polymerization; (C) Construct precipitation; (D) Restriction of gene 3'-linker and 5'-linker capped ends; (E) Size-fractionation and removal of enzyme contaminants; (F) Gene insertion into SK plasmid vector. All SDS-PAGE purified oligonucleotides were synthesized by Gibco-BRL.

(A) Oligonucleotide Pair Preparation

In separate Eppendorf tubes were combined:

Tube 1) 5.5 µl SP internal repeat sense oligonucleotide (0.5 nmol/µl), 5.5 µl SP internal repeat antisense oligonucleotide (0.5 nmol/µl), 11 µl T4 ligase 10× ligation buffer (New England Biolabs);

Tube 2) 2 µl. 5'-sense linker (0.05 nmol/µl), 2 µl 5'-antisense linker (0.05 nmol/µl), 1 µl H2O, 5 µl T4 ligase 10× ligation buffet (New England Biolabs);

Tube 3) 2 µl 3'-sense linker (1 nmol/µl), 2 µl 3'-antisense linker (1 nmol/µl), 1 µl water, 5 µl T4 ligase 10× ligation buffer (New England Biolabs).

All tubes were heated to 90-95° C. for 5 minutes, then slowly cooled over the next 3 hours to 45° C. The tubes were then incubated at 45° C. for 2 hours.

(B) Oligonucleotide Polymerization

10 µl of solution from Tube 1 (internal repeat pair) was combined with 10 µl of solution from Tube 2 (5' linker pair), and incubated at 17° C. for 3 hours. To this mixture was added 80 µl water and 2 µl (4000 U) T4 DNA ligase (New England Biolabs), and again incubated at 12-15° C. for 36 hours. The degree of polymerization was verified on 2.2% agarose gel (Fisher).

The 3' end of the polymer was then capped by adding 50 µl of the ligated SP-5' linker mixture from above to 5 µl of solution from Tube 3 (3' linker), heating to 30° C., and incubating at 17° C. for 3 hours. 20 µl water and 2 µl T4 DNA ligase (New England Biolabs) was then added, and the solution was incubated at 12-15° C. for 36 hr. Finally, the solution was heated at 65° C. for 10 minutes to denature the ligase.

(C) Construct Precipitation

10 µl SP construct from (B) above was combined with 25 µl water and 5 µl 3 M NaAcetate. 150 µl EtOH was then added and the solution incubated at 4° C. for 30 minutes The solution was then centrifuged at 10,000 rpm for 30 minutes The resultant pellet was washed with 70% EtOH and dried.

(D) Restriction Of Gene 3'-Linker And 5'-Linker Capped Ends

The pellet from (C) above was dissolved in 14 µl water. 2 µl 10×EcoRI restriction buffer (New England Biolabs), 2 µl EcoRI 10 U/µl (New England Biolabs), and 2 µl BamHI 20 U/µl (New England Biolabs) was then added and the mixture incubated at 37° C. overnight.

(E) Size-Fractionation and Removal of Enzyme Contaminants

10 µl water was added to 20 µl of the restricted genes from Step (D) above. This mixture was then loaded onto a Sephacryl S-400 (Pharmacia Microspin™) minicolumn and spun to remove small (<90 bp) oligonucleotide fragments. The first effluent from the column (i.e. the high molecular weight material) was collected. Finally, the enzymes were removed using a Qiaquick Nucleotide removal kit (Qiagen). The final volume of mixture was approximately 50 µl.

(F) Gene Insertion Into SK Plasmid Vector

SK plasmid vector (Strategene) was restricted with BamHI and EcoRI and restricted large plasmid fragments were isolated from agarose gel. To 2-3 µg restricted SK plasmid in 10 µl water was added 6 µl restricted SP gene construct from Step (E), 2 µl T4 DNA ligase buffer (New England Biolabs), and 1 µl T4 DNA ligase (New England Biolabs). The solution was then kept at 8° C. overnight for ligation. 100 µl competent XL1-Blue cells (Stratagene) were then transformed with 3 µl ligation mixture. Clones were selected via Blue/White assay (Promega Corporation), as described by Promega Protocols and Applications Guide, 2 ed. (1991), by hybridization with 32P-labeled antisense internal oligonucleotide, and by restriction mapping.

Example 8

Gene Subcloning Into pEGP, pKS, pUC18

And pBI121 And Signal Sequence Synthesis

The methods of the following example were used to incorporate the synthetic genes of Examples 6 and 7 into the pBI121 plasmid. Restriction digests, ligations, subclonings, and E. Coli transformations were performed generally according to F. M. Ausubel, ed., "Current Protocols in Molecular Biology," (1995), Chapter 3: Enzymatic Manipulation of DNA and DNA Restriction Mapping, Subcloning of DNA Fragments. The restriction digests used were 1-2 µg of plasmid DNA, 5-10 U of restriction enzyme, and 1× recommended restriction buffer (starting with the 10× buffer provided by the company). Samples were run on 1-2.2% agarose gels in TBE buffers. Plasmid and DNA fragments were isolated from gels using QIAEX II gel extraction kits (Qiagen). The DNA ligase employed was 400 U T4 (New England Biolabs). Vector:fragment ratios employed were 1:2-1:6, and ligation volumes were 20 µl.

Transformation of *E. coli* was done in 5-10 µl ligation reaction volumes with XL-Blue competent cells (Stratagene). Cells were plated on LB plates containing 50 µg/ml ampicillin or 30 µg/ml kanamycin.

Plasmid isolation was performed by growing transformed XL-Blue cells in 3 mL LB-ampicillin or LB-kanamycin medium. The plasmids were then isolated using a Wizard Plus Miniprep DNA Purification System (Promega).

This example involved: (A) Insertion of the synthetic gene into pEGFP; (B) Insertion of GAGP-EGFP or SP-EGFP fragment into pKS; (C) Construction of the Signal Sequence and cloning into pUC18; (D) Insertion of GAGP-EGFP or SP-EGFP construct into pUC18; (E) Insertion of SS-GAGP-EGFP or SS-SP-EGFP genes into pBI121.

(A) Insert Synthetic Gene For GAGP Or SP Into pEGFP

This step was carried out to allow directional cloning of the gene at the 5' end of EGFP. First, the GAGP or SP gene was isolated from pSK [from Examples 6(F) and 7(F)] as a BamHI (New England Biolabs) and AgeI (New England Biolabs) fragment. The pEGFP (Clontech) was then restricted with BamHI and AgeI. Finally, the BamHI/AgeI-restricted gene was annealed with BamHI/AgeI-restricted pEGFP, and ligated to yield pEGFP containing the synthetic gene inserted at the 5' end of the EGFP.

(B) Insert GAGP-EGFP Or SP-EGFP Fragment Into pKS

This step was carried out to obtain an Sst I site at the 3' end of EGFP. The GAGP-EGFP or SP-EGFP construct from (A) above was isolated from pEGFP as an XmaI/NotI fragment. pKS (Strategene) was then restricted with XmaI and NotI (New England Biolabs). Finally, the GAGP-EGFP or SP-EGFP construct was annealed with cut pKS and ligated to yield pKS containing GAGP-EGFP or SP-EGFP.

(C) Construct Of The Signal Sequence And Cloning Into pUC18

In order to anneal the partially overlapping sense and anti-sense oligonucleotides encoding the extensin signal sequence, 2 µl signal sequence sense oligonucleotide (0.1 nmol/µl), 2 µl signal sequence antisense oligonucleotide (0.1 nmol/µl), 2 µl 10×DNA Polymerase Buffer (New England Biolabs), and 14 µl H$_2$O was combined and heated to 85° C. for 5 minutes The mixture was then slowly cooled to 40° C. over 1 hour.

The annealed oligonucleotides were then extended via primer extension. To the above mixture was added 2 µl dNTP 2.5 mM (New England Biolabs) and 1 µl DNA Polymerase 5 U/µl (New England Biolabs), and the resultant mixture incubated at 37° C. for 10 minutes The polymerase was then denatured by heating at 70° C. for 10 minutes Then 8 µl Buffer 4 (New England Biolabs), 66 µl H$_2$O, 2 µl BamHI 20 U/µl (New England Biolabs), and 2 µl SstI 14 U/µl (Sigma) was added and the mixture incubated at 37° C. overnight. The restriction enzymes were then denatured by heating at 70° C. for 10 minutes.

The mixture was then precipitated with EtOH/NaAcetate (6 µl NaAcetate/300 µl EtOH), and pelletized in a centrifuge. The pellet was washed with 70% EtOH and dried. The pellet was then dissolved in 20 µl H$_2$O and 4 µl was used for ligation into 2 µg pSK (Stratagene) as a BamHI/SstI fragment. Finally, the signal sequence was subcloned into pUC18 as a BamHI/SstI fragment.

(D) Insertion Of GAGP-EGFP Or SP-EGFP Construct Into pUC18

This step was carried out to insert the GAGP-EGFP or SP-EGFP construct "behind" the signal sequence. The GAGP-EGFP or SP-EGFP construct from (B) above was removed from pKS as an XmaI/SstI fragment. pUC18 containing the signal sequence (SS-pUC18) was restricted with XmaI/Sst. The GAGP-EGFP or SP-EGFP fragment was then annealed with cut SS-pUC18, and ligated. The SS-GAGP-EGFP or SS-SP-EGFP gene sequence was then confirmed through DNA sequencing using the pUC18 17-residue sequencing primer (Stratagene).

(E) Insertion Of SS-GAGP-EGFP Or SS-SP-EGFP Genes Into pBI121

The SS-GAGP-EGFP or SS-SP-EGFP gene from (D) above was removed from pUC18 as BamHI/SstI fragments. pBI121 (Clontech) was restricted with BamHI and SstI and the larger plasmid fragments recovered. The smaller fragments, containing the GUS reporter gene, were discarded. The SS-GAGP-EGFP or SS-SP-EGFP fragment was annealed with the restricted pBI121 fragment and ligated.

Example 9

*Agrobacterium* Transformation With pBI121-Derived Plasmids

2 µg of the pBI121 containing SS-GAGP-EGFP or SS-SP-EGFP from Example 8 above was used to transform *Agrobacterium tumefaciens* (Strain LB4404, from Dr. Ron Sederoff, North Carolina State University) according to An et al., Plant Molecular Biology Manual A3:1-19 (1988).

Example 10

Transformation of Tobacco Cultured Cells With pBI121-Derived Plasmids

All steps were carried out under sterile conditions. Tobacco cells were grown for 5-7 days in NT-1 medium (pH 5.2, per liter: 1 L packet of MS Salts (Sigma #S5524), 30 g sucrose, 3 ml 6% KH$_2$PO$_4$, 100 mg Myo-Inositol, 1 mL Thiamine.HCl (1 mg/ml stock), 20 µl 2,4-D (10 mg/ml stock)) containing 100 µg/ml kanamycin. The cells were grown in 1 L flasks containing 500 mL medium on a rotary shaker (94 rpm, 27° C.) to between 15-40% packed cell volume. *Agrobacterium* cells transformed with pBI121-derived plasmid (Example 9) were grown overnight in Luria Broth containing 30 µg/ml kanamycin. The *Agrobacterium* cell broth was pelletized for 1 minutes at 6000 rpm, and the pellet resuspended in 200 µl NT-1 medium.

Excess medium was removed from the tobacco cell broth until the broth had a consistency approximate to applesauce. The tobacco cells were placed in petri dish, and 200 µl of the *Agrobacterium* preparation was added. The mixture was then incubated at room temperature, no light, for 48 hours.

The mixture was then washed 4 times with 20 ml NT-1 to remove the *Agrobacterium* cells, and the plant cells were plate-washed on NT-1 plates containing 400 µg/ml timentin and 100 µg/ml kanamycin. Cells which grew on the antibiotics were selected and checked for green fluorescence through fluorescence microscopy, excitation wavelength 488 nm (see Example 16).

Example 11

Transformation of Tomato Cultured Cells With pBI2'-Derived Plasmids

All steps were carried out under sterile conditions. Tomato cells were grown for 5-7 days in Schenk-Hildebrand medium (pH 5.8, per liter: IL packet of S-H basal salt (Sigma #S6765), 34 g sucrose, 1 g Schenck-Hildebrandt vitamin powder (Sigma #S3766), 100 μl Kinetin 1 mg/ml stock (Sigma #K32532), 44 μl 2,4-D 10 mg/ml stock, 2.1 ml p-chlorophenoxy acetic acid 1 mg/ml stock (Sigma)) containing 200 μg/ml kanamycin. The cells were grown in 1 L flasks containing 500 mL medium on a rotary shaker (94 rpm, 27° C.) to between 15-40% packed cell volume. *Agrobacterium* cells transformed with pBI121-derived plasmid (Example 9) were grown overnight in Luria Broth containing 30 μg/ml kanamycin. The *Agrobacterium* cell broth was pelletized for 1 minutes at 6000 rpm, and the pellet resuspended in 200 μl NT-1 medium.

Excess medium was removed from the tomato cell broth until the broth had a consistency approximate to applesauce. The tomato cells were placed in petri dish, and 200 μl of the *Agrobacterium* preparation was added. The mixture was then incubated at room temperature, no light, for 48 hours.

The mixture was then washed 4 times with 20 ml NT-1 to remove the *Agrobacterium* cells, and then the plant cells were plate-washed on NT-1 plates containing 400 μg/ml timentin and 200 μg/ml kanamycin. Cells which grew on the antibiotics were selected and checked for green fluorescence through fluorescence microscopy, excitation wavelength 488 nm.

Example 12

Isolation Of GAGP-EGFP From Tobacco Cell Suspension Culture Medium

Figure 3:
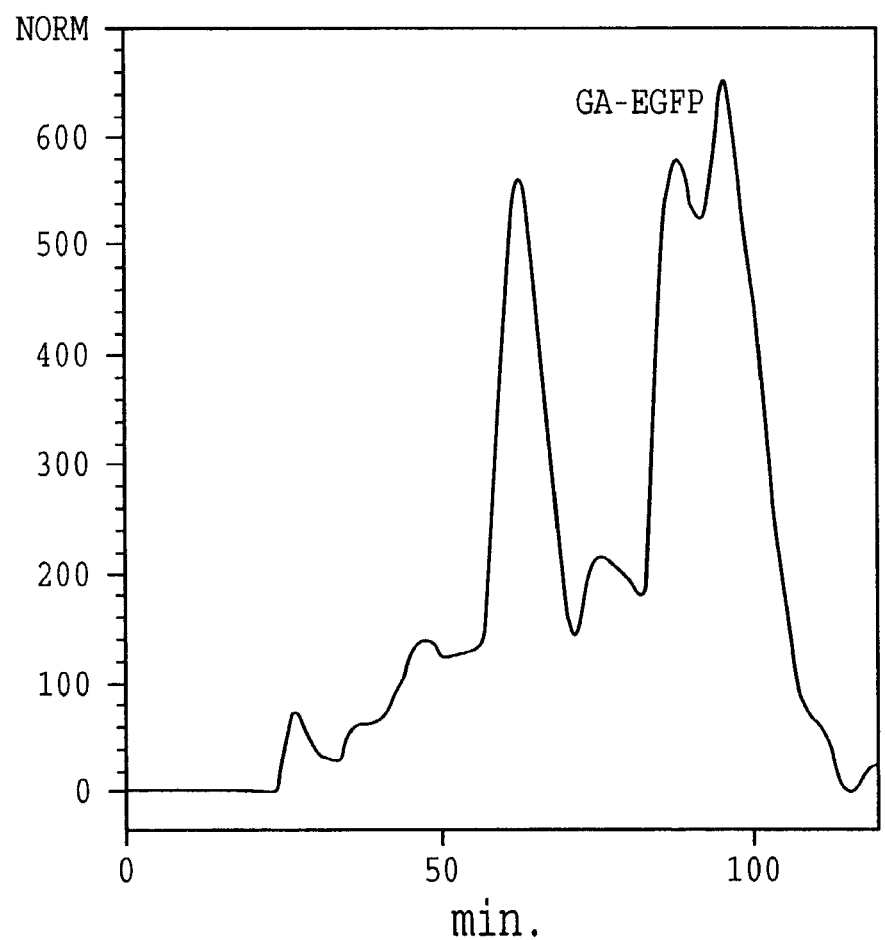
FIG. 3 is a graph showing size-fractionation of expressed protein from transformed tobacco cells.

Transformed tobacco cells were grown on rotary shaker as described in Example 11 above. The medium was separated from the cells by filtration on a glass sintered funnel (coarse grade), and the medium concentrated by freeze-drying. The medium was then resuspended in water (~50 ml/500 mL original volume before lyophilization), and dialyzed against cold water for 48 hours (water changed 6 times). The precipitated pectin contaminants were removed by centrifuge, the pellet discarded, and the supernatant freeze-dried. The dried supernatant was then dissolved in Superose Buffer 20 mg/ml (200 mM sodium phosphate buffer, pH 7, containing 0.05% sodium azide), and spun in a centrifuge to pelletize insolubles. 1.5 ml of this preparation (18-30 mg) was then injected into a semi-preparative Superose-12 gel filtration column (Pharmacia), equilibrated in Superose Buffer and eluted at 1 ml/minutes The UV absorbance was monitored at 220 nm. 2 ml fractions were collected throughout, with GAGP-EGFP expected to elute between 59 and 70 minutes (~2.5 Vo). GAGP-EGFP actually eluted at 65 minutes (see FIG. 3, Example 15 for method used to analyze peaks).

Figure 4:
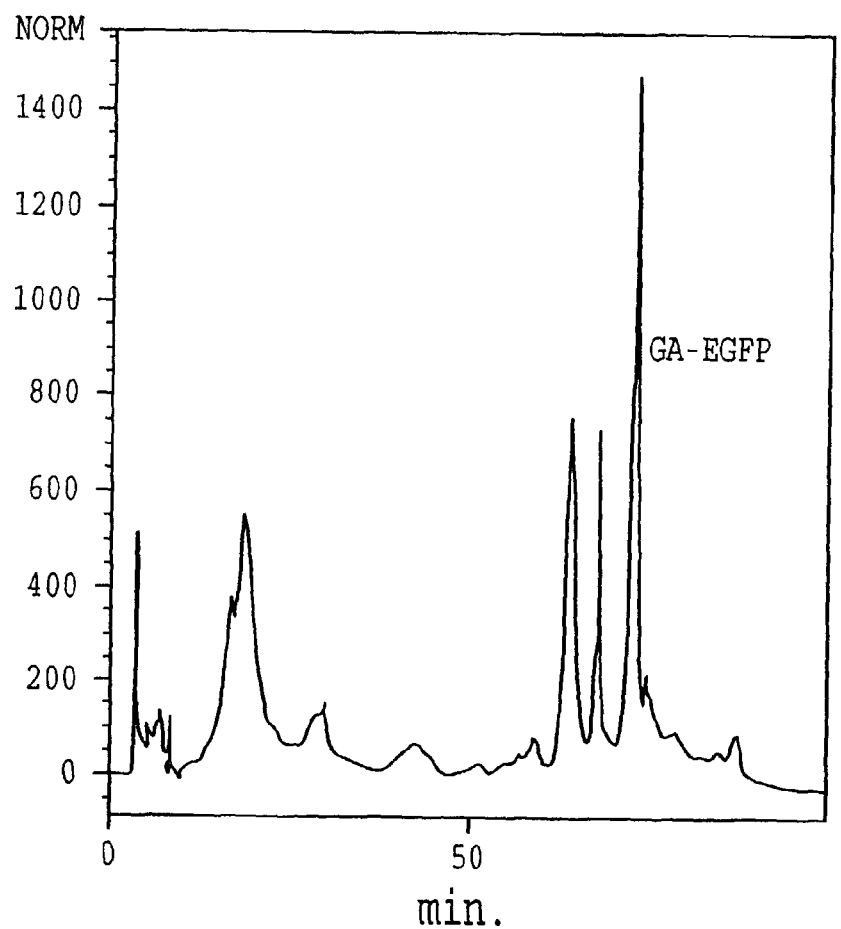
FIG. 4 is a graph showing the isolation of GA-EGFP by reverse phase chromatography.

The Superose peak containing GAGP-EGFP was dialyzed against cold water for 24 hours (4 water changes), and freeze-dried. The dried GAGP-EGFP peak was then dissolved in 250 μl 0.1% aqueous TFA (Pierce) and loaded onto a PRP-1 column (Polymeric Reverse Phase, Hamilton) equilibrated in Buffer A (0.1% aqueous TFA). The column was then eluted with Buffer B (0.1% TFA/80% acetonitrile in water; gradient=0-70% B/100 min) at a rate of 0.5 mL/minutes UV absorbance was monitored at 220 nm, and GAGP-EGFP eluted at 63 minutes (see FIG. 4, Example 15 for method used to analyze peaks). Finally, the TFA/acetonitrile was removed through $N_2$ (g) blowdown.

Example 13

Characterization Of GAGP-EGFP By Neutral Sugar Analysis

100 μg of GAGP-EGFP isolated from tobacco cells was aliquoted into a 1 ml glass microval and dried under $N_2$ (g). 200 μl 2N TFA was added and the vial capped. The vial was heated at 121° C. for 1 hour, then blown down under $N_2$ at 50° C. to rid the sample of acid. 25 μl of sodium borohydride solution (20 mg/ml in 3 M ammonium hydroxide) was added and the mixture kept at room temperature for 1 hour. 1-3 drops of concentrated acetic acid were added until fizzing stops, and the mixture blown down under $N_2$ at 40° C. 100 μl MeOH was added, the mixture vortexed, and blown down under $N_2$ at 40° C., then this step was repeated. A mixture of 100 μl MeOH and 100 μl $H_2O$ was added, vortexed, and blown down under $N_2$ at 40° C., then the procedure of adding 100 μl MeOH, vortexing, and $N_2$ treatment was repeated 3 times. The resultant mixture was then dried under vacuum overnight.

50 μl reagent grade acetic anhydride was added and the mixture heated at 121° C. for 0.5 hour. The sample was then analyzed by gas chromatography as described in Kieliszewski et al., Plant Physiol. 98:919 (1992). The sample was shown to contain hydroxyproline and sugar, accounting for ~50% of the fusion product on a dry weight basis. Galactose, arabinose, and rhamnose occur in 3:3:1 molar ratio similar to that of native GAGP's 3.5:4:1 molar ratio. This is consistent with the likely presence of both Hyp-arabinosides and Hyp-arabinogalactan polysaccharide in the expressed construct. The lower ratio of Ara in the GAGP-EGFP fusion glycoprotein is consistent with the Ala for Pro substitution (See Example 6), which removes one arabinosylation site in the peptide.

Example 14

Characterization Of GAGP-EGFP By Hydroxyproline Assay

100 μg purified GAGP-EGFP was hydrolyzed with 6N HCl (Pierce) at 110° C. for 18 hours. The excess acid was then removed by blowing down under $N_2$. Hydroxyproline was then determined following Kivirikko and Liesma, *Scand. J. Clin. Lab. Invest.* 11:128 (1959).

Example 15

Characterization of Tobacco and Tomato Expression Products By Enzyme-Linked Immunosorbant Assay GAGP-EGFP and SP-EGFP products from tomato and tobacco cell medium and column peaks (see Example 12) were detected by Enzyme-Linked Immunosorbant Assays (ELISA) using the method of Kieliszewski and Lamport, "Cross-reactivities of polyclonal antibodies against extension precursors determined via ELISA techniques," *Phytochemistry* 25:673-677 (1986). The GAGP-EGFP product was also assayed using anti-EGFP antibodies. Anti-EGFP antibodies (Clontech) were the primary antibody, diluted 1000-fold as recommended by the manufacturer. The secondary antibody was Peroxidase conjugated goat-anti-rabbit IGG diluted 5000-fold (Sigma). Recombinant EGFP (Clontech) was used as a control. This assay was used to generate FIGS. 3 and 4 from Example 12 above.

Example 16

Characterization of Tobacco and Tomato Expression Products by Fluorescence

Culture medium from both tobacco and tomato cells transformed with the GAGP-EGFP and the SP-EGFP genes was collected. The EGFP tag fluoresces when exposed to UV light; the excitation wavelength used here was 488 nm. These media were compared with media which included EGFP expressed behind the signal sequence and secreted into the medium, cells transformed with unaltered pBI121 and medium from untransformed cells. The unmistakable bright green fluorescence (data not shown) allowed visualization of the targeted products during their transit through the ER/Golgi membrane system. As *Agrobacterium* lacks the posttranslational machinery to make HRGPs, the fluorescing proteins must be of plant origin.

Example 17

Tobacco Leaf Disc Transformation

Sterile tobacco leaves were cut into small pieces and wounded with a needle. 4 ml NT-1 medium without hormones (NT-1 medium of Example 10, omitting 2-4 D) and 150 ul concentrated overnight culture of *Agrobacterium* (see Example 9) was added to the leaves, and the leaf discs incubated for 48 hours, no light. The leaf discs were then washed with NT-1 medium, no hormones. The discs were then put on NT-1 solid medium plates (NT-1 medium of Example 10 plus 7.5 g Bactoagar (Difco Laboratories)), 400 ul/ml timentin, and 100 ug/ml kanamycin.

After 3 weeks, shoots were transferred from NT-B solid medium without hormones [NT-1 Medium of Example 10, omitting 2-4 D, and adding 300 ul/L benzyl adenine, made from a 2 mg/ml stock made up in DMSO(N-benzyl-9-(tetrahydropyranyl) adenine (Sigma)] to root. Transformed plants have expressed SP-EGFP and GAGP-EGFP in leaf and root cells, as determined by the fluorescence assay of Example 16 (data not shown)

Example 18

Sequence Analysis of GAGP and Determination of a Consensus Sequence

This Example describes amino acid sequencing, glycosyl and linkage analysis of GAGP which yielded sequences (including preferred consensus sequences) within the scope of SEQ ID NO:136.
1. Experimental
The following experimental protocols were used to arrive at preferred embodiments of the invention's sequences.
A. Size Fractionation
GAGP was isolated via preparative Superose-6 gel filtration using the method of Qi et al. [Qi et al. (1991) supra] as follows. Nodules of gum arabic (Kordofan Province, Sudan) were a gift from Gary Wine of AEP Colloids (Ballston Spa, NY). Nodules were ground to a fine flour (ca. 2 min.) in a Tekmar A-10 mill. Samples of gum arabic (100 mg/ml) were dissolved in water then diluted to 50 mg/ml in 0.2 M sodium phosphate buffer (pH 7). Samples were spun to pellet insoluble material and 1 ml aliquots were injected onto a semi-preparative Superose-6 gel filtration column (1.6 cm i.d.×50 cm, Pharmacia), eluted isocratically as described previously [Qi et al. (1991) supra]. The protein peaks corresponding to GAGP were dialyzed against water to remove salt and then freeze-dried.
B. HF-Deglycosylation
For chymotryptic peptide mapping GAGP was HF-deglycosylated as follows. The Superose-6 fractionated GAGP (designated dGAGP) was deglycosylated in anhydrous hydrogen fluoride (HF) (20 mg powder/ml HF for 1 h at 4°) as described earlier [Qi et al. (1991) supra], repeating the procedure twice to ensure complete deglycosylation.
C Purification of Size-Fractionated GAGP and DGAGP by Reverse Phase HPLC
Superose-fractionated GAGP was purified for glycoside analyses, or dGAGP samples were used for peptide mapping on a Hamilton PRP-1 semi-preparative column (10 mm, 250× 4.1 mm) by equilibrating with Buffer A (0.1% TFA, aqueous) and eluting with Buffer B (0.1% TFA, 80% acetonitrile, aqueous) by gradient elution (0-100% B/80 min.; 0.5 mL/min flow rate). The eluate was monitored at 220 nm. The collected peaks were blown down to dryness with $N_2(g)$, redissolved in $ddH_2O$, then freeze-dried.
D. Proteolysis of Deglycosylated GAGP with Chymotrypsin or Pronase
2-9 mg samples of dGAGP were digested with pronase or chymotrypsin as detailed earlier [Kieliszewski et al. (1992) Plant Physiology 99:538]. The digests were then freeze-dried.
E. Fractionation of dGAGP Chymotryptic Peptides by Cation Exchange HPLC
dGAGP chymotryptic peptides (400 mg/injection) were fractionated on a PolySULFOETHYL A™ cation exchange column (9.4 mm i.d.×200 mm; PolyLC, Ellicot City, Md.) equilibrated with Buffer. A (5 mM potassium phosphate/phosphoric acid buffer, pH 3, containing 25% v/v acetonitrile) and eluted with Buffer B (Buffer A containing 1 M KCl) using programmed gradient elution. The elution gradient was 0-4% Buffer B in 45 min., 4-8% Buffer B from 45 to 50 min, and 8-30% Buffer B from 50-65 min. The flow rate was 0.4 mL/min and the absorbance was monitored at 220 nm. The collected peaks were pooled, blown down with $N_2$ (g), redissolved in $ddH_2O$, then freeze dried.
F. Peptide Isolation via Reverse Phase HPLC
The partial pronase digest of dGAGP and major peaks S1 and S2 PolySULFOETHYL Aspartamide column were dissolved in Buffer A (0.1% TFA, aqueous) and injected onto a Hamilton PRP-1 analytical reverse phase column (4.1 mm i.d.×150 mm) which was eluted at 0.5 mL/min with a Buffer B (0.1% TFA and 80% v/v acetonitrile) gradient of 0-50% in 100 min. The effluent was monitored at 220 nm and collected peaks were blown down with $N_2(g)$, re-dissolved in $ddH_2O$, and then freeze dried prior to sequencing. For increased resolution of pronase peptide P3 (FIG. 6), P3 was run through the PRP-1 column a second time, eluting with a 0-30% Buffer B gradient.
G. Automated Edman Degradation of dGAGP Chymotryptic Peptides
dGAGP peptides were sequenced at the Michigan State University Macromolecular Facility on a 477A Applied Biosystems (Foster City, Calif.) gas phase sequencer.
H. Amino Acid Analysis
Amino acid compositions were determined by precolumn derivatization of amino acids with 6-aminoquinolyl-N-hydroxysuccinimidyl carbamate followed by reverse-phase HPLC (Nova-Pak™ $C_{18}$ column) using the Waters AccQ-Tag Chemistry Package and the gradient recommended by Waters for analyzing collagen hydrolysates [Crimmins and Cheman (1997) Analytical Biochemistry 244:407; van Wandelen and Cohen (1997) Journal of Chromatography A 763:11].

Hydroxyproline Glycoside Profile. The distribution of GAGP hydroxyproline glycosides was determined after alkaline hydrolysis (105°, 18 h, 0.22 N Ba(OH)$_2$) and neutralization followed by chromatography on a 75×0.6 cm Technicon Chromobeads C2 cation exchange resin as described earlier [Lamport and Miller (1971) Plant Physiology 48:454].

I. Isolation of the Hyp-polysaccharide

Alkaline hydrolysates (see above) of Superose-6 and PRP-1 purified GAGP were loaded onto a G-50 Sephadex gel permeation column eluted isocratically with 100 mM ammonium acetate buffer, pH 6.8, at a flow rate of 0.3 ml/min. One ml fractions were collected and 40 ml aliquots of each fraction were assayed for Hyp as described earlier [Kivirikko and Liesmaa (1959) Scandinavian Journal of Clinical Laboratories 11:128; Kieliszewski et al. (1990) Plant Physiology 92:316]. The fractions were freeze-dried, then weighed, and the amounts of Hyp and sugar in the fractions were calculated from the recovered weights, Hyp assays, and monosaccharide composition analyses.

J. Partial Alkaline Hydrolysis of GAGP

Superose-fractionated GAGP (10 mg/ml) was dissolved in 0.2 N NaOH/NaBH$_4$ and heated it at 50° C. as described earlier [Akiyama and Kato (1984) Agricultural and Biological Chemistry 48:235]. A 200 ml aliquot was removed immediately (time zero control) and hourly for 6 h, cooled in ice, then 20 ml glacial acetic acid was added (final pH=5.8). Each sample was assayed for Hyp as described earlier [Kivirikko and Liesmaa (1959) Scandinavian Journal of Clinical Laboratories 11:128; Kieliszewski et al. (1990) Plant Physiology 92:316].

K. Saccharide Composition and Linkage Analysis

Monosaccharide compositions and linkage analyses were determined at the Complex Carbohydrate Research Center, University of Georgia following the methods of York et al [York et al. (1985) Methods in Enzymology 118:3] and Merkle and Poppe [Merkle and Poppe (1994) Methods Enzymology 230:1].

2. Determination of an Exemplary Consensus Sequence

Figure 5:
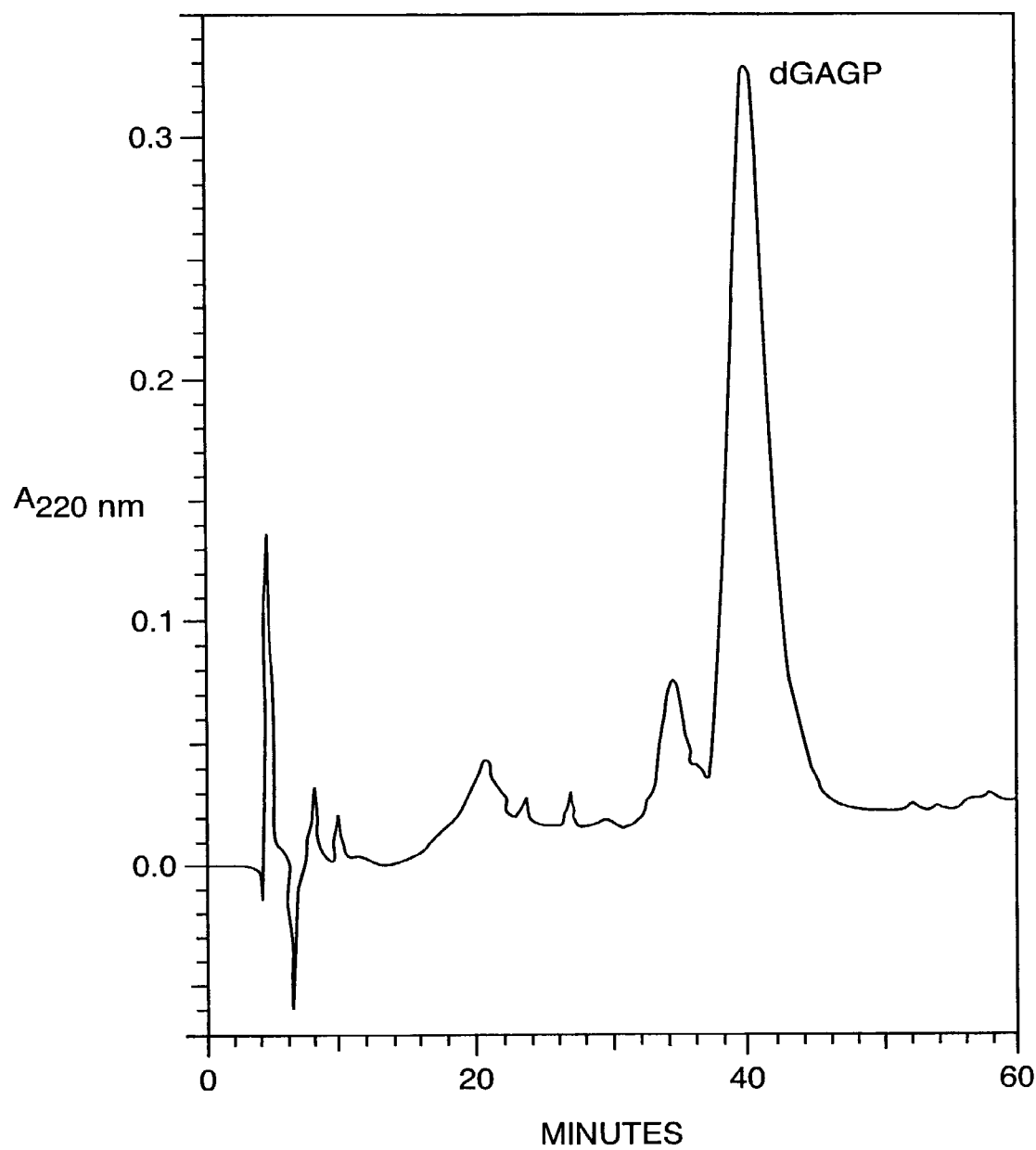
FIG. 5 is the elution profile for dGAGP by reverse phase chromatography on a Hamilton PRP-1 column and fractionation by gradient elution.

Using the method of Qi et al. [Qi et al. (1991) supra] the inventors isolated GAGP via preparative Superose-6 gel filtration. For chymotryptic peptide mapping HF-deglycosylated GAGP was used. This gave a major symmetrical peak (designated dGAGP) when further fractionated by reverse phase chromatography as shown in FIG. 5. FIG. 5 is the elution profile for dGAGP by reverse phase chromatography on a Hamilton PRP-1 column and fractionation by gradient elution. The component at 35 min. was a Hyp-poor contaminant.

Amino acid analysis showed dGAGP had a highly biased but constant amino acid composition in fractions sampled across the peak (Table 5), indicating that dGAGP was a single polypeptide component sufficiently pure for sequence analysis.

TABLE 5

Amino acid compositions of glycosylated GAGP (GAGP) and deglycosylated GAGP (dGAGP) fractions obtained by reverse phase HPLC compared to dGAGP isolated by Qi et. al. [Qi et al. (1991) Plant Physiology 96: 848] dGAGP Peak Fractions*

| Amino Acid[+] | GAGP | Ascending | Center | Descending | GAGP [Qi et al. (1991) supra] |
|---|---|---|---|---|---|
| Hyp | 40.0 | 38.4 | 36.7 | 36.3 | 36.9 |
| Asx | 0.0 | 0.0 | 0.0 | 0.0 | 1.6 |
| Ser | 22.2 | 21.6 | 21.6 | 22.5 | 19.4 |
| Glx | 0.0 | 0.0 | 0.0 | 0.0 | 1.9 |
| Gly | 4.5 | 4.8 | 4.4 | 4.3 | 6.4 |
| His | 6.6 | 8.7 | 8.2 | 8.4 | 7.1 |
| Arg | 0.0 | 0.0 | 0.0 | 0.0 | 0.0 |
| Thr | 10.2 | 10.6 | 12.2 | 11.4 | 8.8 |
| Ala | 1.2 | 0.7 | 0.8 | 1.0 | 1.3 |
| Pro | 8.0 | 7.6 | 8.3 | 8.1 | 6.8 |
| Tyr | 0.0 | 0.0 | 0.0 | 0.0 | 0.3 |
| Val | 0.0 | 0.0 | 0.0 | 0.0 | 0.8 |
| Met | n.d.[++] | n.d.[++] | n.d.[++] | n.d.[++] | n.d.[++] |
| Lys | 0.0 | 0.0 | 0.0 | 0.0 | 1.0 |
| Ile | 0.2 | 0.0 | 0.0 | 0.0 | 0.4 |
| Leu | 6.4 | 7.6 | 7.8 | 8.1 | 6.4 |
| Phe | 0.5 | 0.0 | 0.0 | 0.0 | 0.9 |
| Trp | n.d.[++] | n.d.[++] | n.d.[++] | n.d.[++] | n.d.[++] |
| Cys | 0.0 | 0.0 | 0.0 | 0.0 | 0.0 |

*To check peak homogeneity, three consecutive fractions across the dGAGP peak were analyzed (designated Ascending, Center, and Descending).
[+]represented as mole percent.
[++]not determined.

This was confirmed by the isolation of peptides (Table 6) similar in composition to one other and to the parent GAGP (Table 5).

TABLE 6

Pronase and chymotryptic peptide sequences from the dGAGP Polypeptide Backbone

| | Sequence |
|---|---|
| Pronase Peptide | |
| P1 (SEQ ID NOs: 184, 185) | SOOOTLSOSOTOTOOOGPHSOOO(O)- |
| P3 (SEQ ID NOs: 186, 187) | SOOO(T/S)LSOSOTOTXOO- |
| PH3G2+ (SEQ ID NO: 188) | SOSOTOTOOOGP |
| Chymotryptic Peptide | |
| S1P2 (SEQ ID NO: 189) | SOOOSLSOSOTOTOOTGPH |
| S1P3 (SEQ ID NO: 190) | SOOOOLSOSOTOTOOOGP- |
| S1P4 (SEQ ID NOs: 191, 192) | SOLPTLSOLP(A/T)OTOOOGPH |
| S1P5 (SEQ ID NO: 193) | SOOOOLSOSLTOTOOLGP- |
| S2P1 (SEQ ID NO: 194) | SOSOTOTOOOGPH |
| S2P2a (SEQ ID NO: 195) | SOSOAOTOOLGPH |
| S2P2b (SEQ ID NO: 196) | SOLPTOTOOLGPHS |

TABLE 6-continued

Pronase and chymotryptic peptide sequences from
the dGAGP Polypeptide Backbone

| | Sequence |
|---|---|
| S2P3 (SEQ ID NO: 197) | SOSOTOTOOLGPH |
| S2P4 (SEQ ID NO: 198) | SOOLTOTOOLLPH |
| Consensus++ (SEQ ID NO: 179) | SOOO(O/T/S)LSOSOTOTOO(O/L)GPH |

* denotes hydroxyproline in the peptide sequences; X denotes a blank cycle.
+From Delonnay et al. (1993)
++Derived from the major peptides P1, P3, S1P3, S1P5, S2P1, S2P3 and PH3G2.

Figure 6:
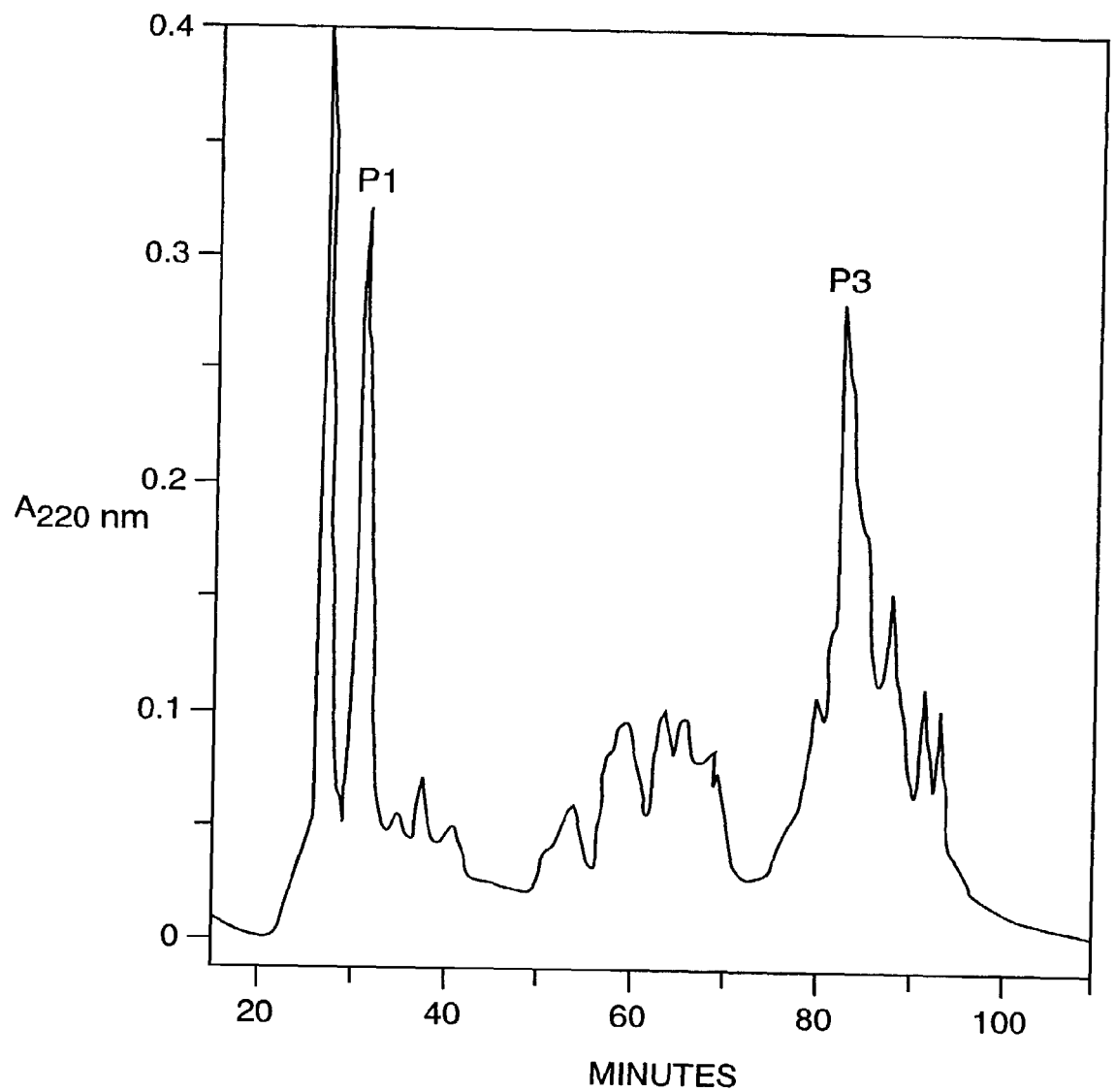
FIG. 6 is the elution profile for dGAGP incomplete pronase digest by reverse phase chromatography. An incomplete digest of dGAGP fractionated on the Hamilton PRP-1 reverse phase column yielded two major peptide fractions, designated P1 and P3.
Figure 7:
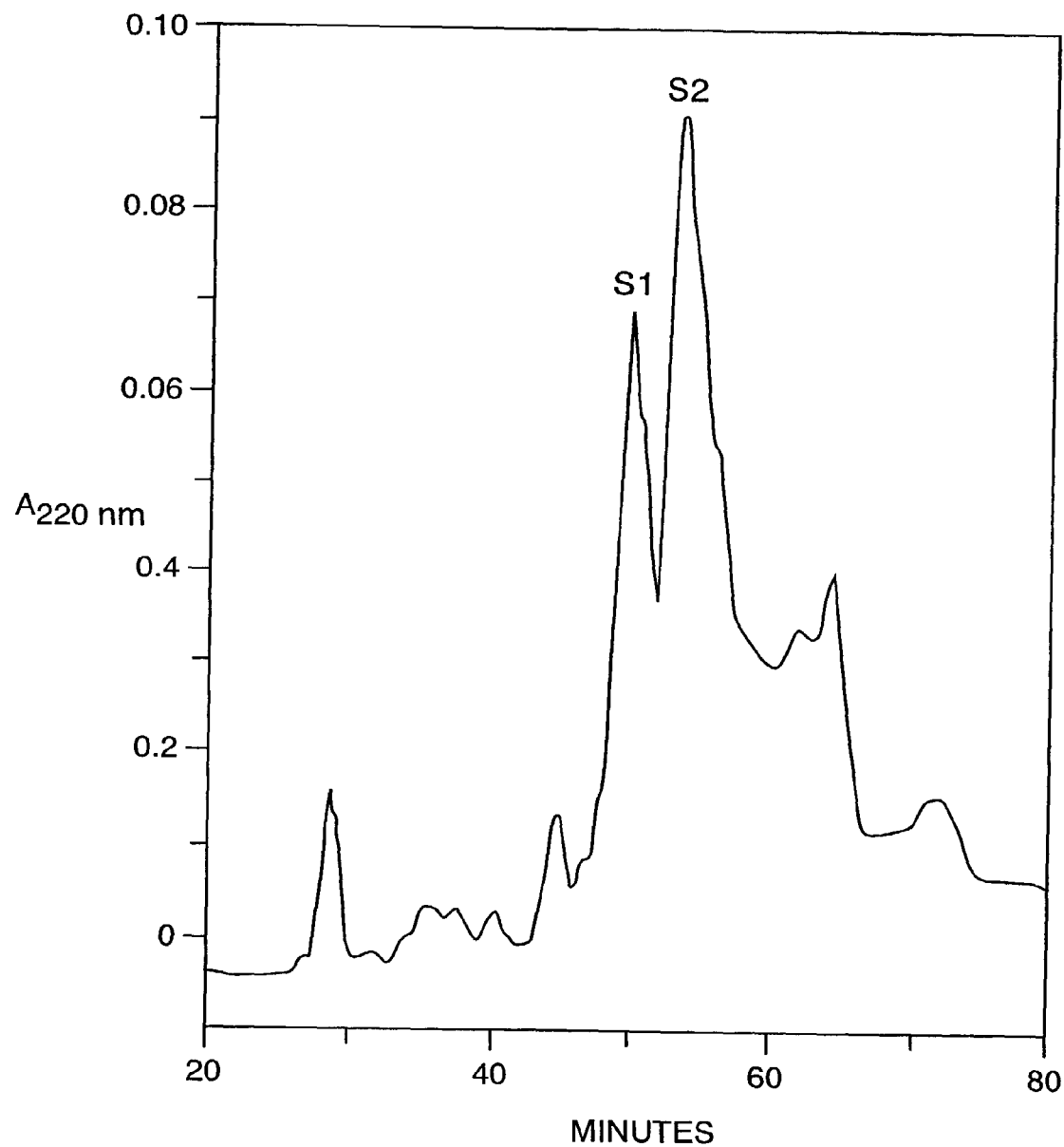
FIG. 7 is the elution profile for a chymotryptic digest of dGAGP fractionated on a Polysulfoethyl aspartamide cation exchange column.
Figure 8A:
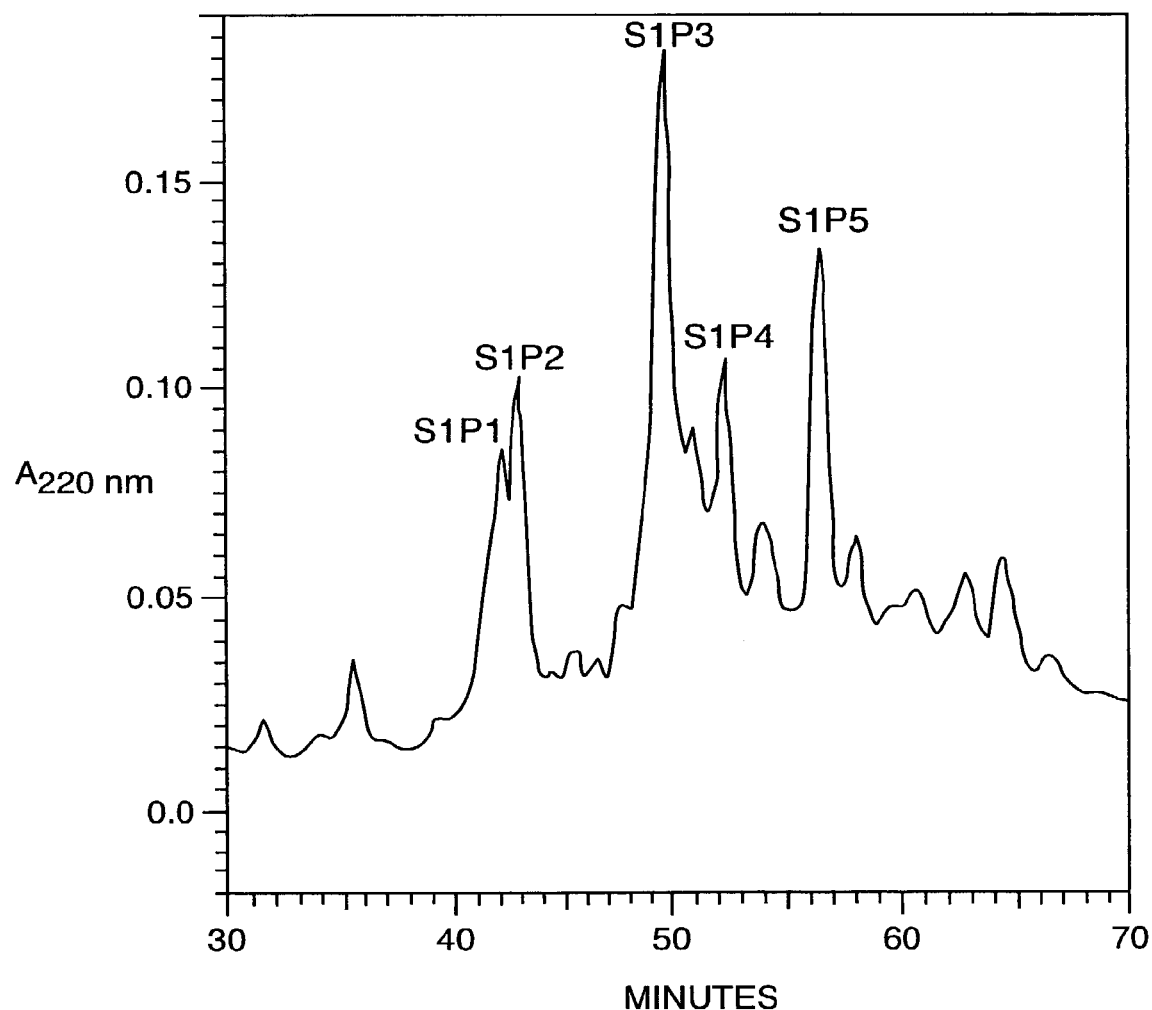
FIG. 8 is the elution profile of dGAGP chymotryptic peptides by reverse phase column chromatography of a) S1, and b) S2.
Figure 8B:
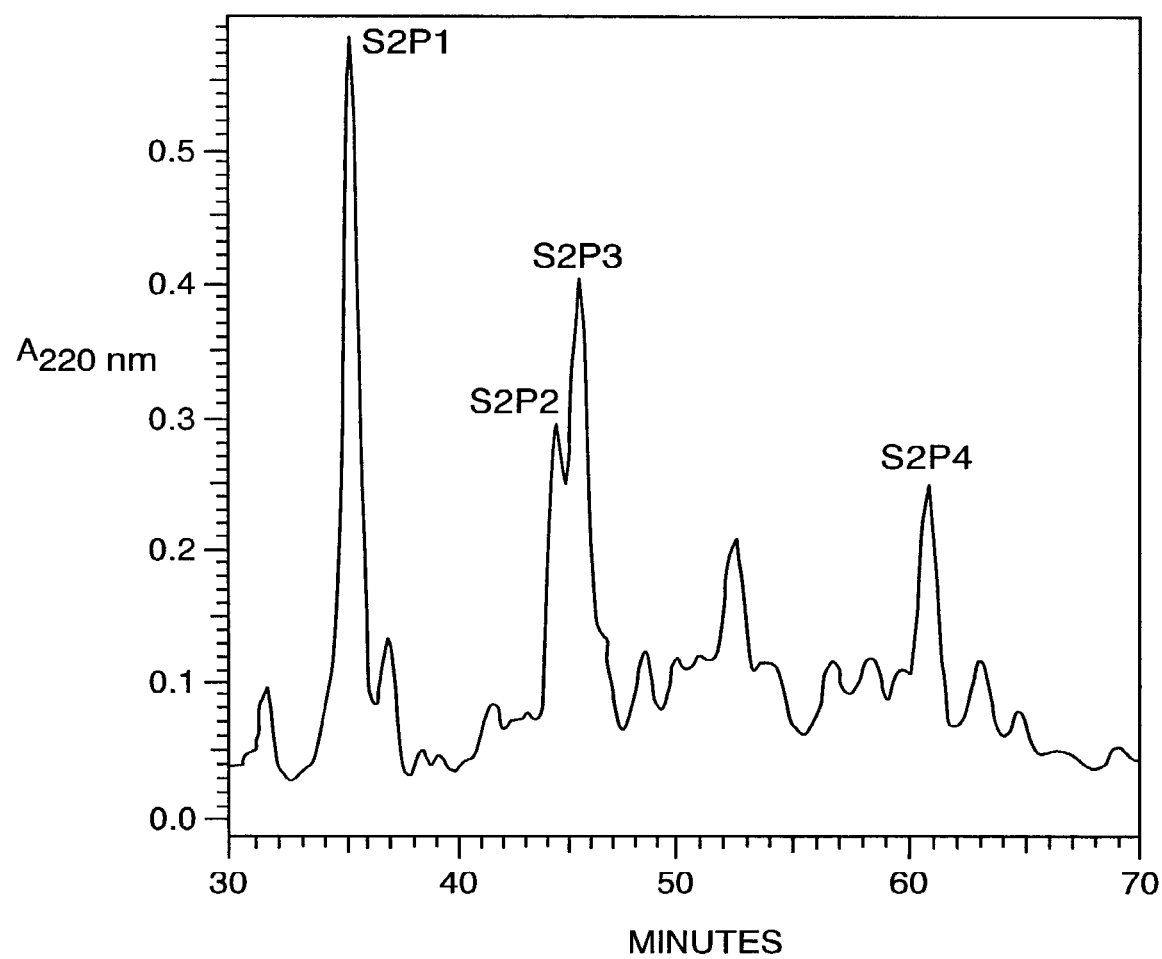

Although native GAGP resists pronase digestion [Akiyama and Kato (1984) Agricultural and Biological Chemistry 48:235; Chikamai et al. (1996) Food Hydrocolloids 10:309], which only generates large fragments of ~200 kDa [Connolly et al. (1988) Carbohydrate Polymers 8:23], preliminary work in Lamport's laboratory showed that exhaustive digestion with pronase effectively cleaved dGAGP to small peptides [Delonnay (1993) Masters Thesis, Michigan State University, MI]. However, the peptides lacked some of the amino acids present in Qi et al.'s empirical formula: $Hyp_4$ $Ser_2$ Thr Pro Gly Leu His (SEQ ID NO:199) of the repeat motif suggested by Qi et. al. [Qi et al. (1991) supra], most notably His (Table 6, peptide PH3G2.) Therefore, a partial pronase digestion of dGAGP was performed. This gave two large major peptides P1 and P3, as shown in FIG. 6, with partial sequences (Table 6) containing all of the amino acids in the empirical formula.

dGAGP was also digested with chymotrypsin, which slowly cleaved leucyl and histidyl bonds, followed by a two-stage HPLC fractionation scheme. Initial separation of the chymotryptides on a PolySULFOETHYL A™ (PolyLC, Inc. Ellicott City, Md.) cation exchanger yielded two major fractions designated S1 and S2 (FIG. 7). The major chymotryptic fractions, S1 and S2, were collected for further fractionation by reverse phase column chromatography. Further chromatography on a Hamilton PRP-1 reverse phase column resolved fraction S1 into five major peptides labeled S1P1-SIPS, while fractionation of S2 resolved four major peptides, designated S2P1-S2P4, which were sequenced (FIG. 8a & b). Edman degradation showed that these chymotryptides were closely related to each other and to the pronase peptides (Table 6). These peptides reflect the overall amino acid composition of GAGP and can be related to the 19-amino acid residue consensus sequence (SEQ ID NO:179) shown in Table 6.

From the above data, the inventors concluded that GAGP possesses a highly repetitive polypeptide, albeit with minor variations in the sequence. Based on a linear GAGP molecule of 150 nm [Qi et al. (1991) supra], and presuming the extended polyproline II helix present in both extensins and AGPs [Kieliszewski and Lamport (1994) Plant Journal 5:157; Nothnagel (1997) International Review of Cytology 174:195], the inventors estimate that GAGP contains about 20 peptide repeats with occasional partial repeats. Partial repeats of the consensus sequence may account for the somewhat higher serine content in native GAGP compared to that in the consensus sequence.

The exemplary 19-amino acid residue GAGP consensus sequence of Table 6 contains approximately nine Hyp residues and is roughly twice the size of that previously postulated to contain only a single polysaccharide attachment site [Qi et al. (1991) supra]. Judging from the Hyp-glycoside profile of GAGP (Table 7) [Qi et al. (1991) supra], about one in every five Hyp residues is polysaccharide-substituted.

TABLE 7

GAGP Hydroxyproline glycoside profile

| Hydroxyproline glycoside | Percent of total hydroxyproline |
|---|---|
| Hyp-polysaccharide | 20 |
| $Hyp-Ara_4$ (SEQ ID NO: 200) | 5 |
| $Hyp-Ara_3$ (SEQ ID NO: 201) | 27 |
| $Hyp-Ara_2$ (SEQ ID NO: 202) | 27 |
| Hyp-Ara (SEQ ID NO: 203) | 10 |
| Nonglycosylated Hyp | 11 |

Thus, there are approximately two Hyp-polysaccharide sites in the invention's exemplary consensus sequence. In order to determine which Hyp residues are involved in polysaccharide attachment, without limiting the invention to any particular mechanism, the inventors predict arabinosylation of contiguous Hyp residues and arabinogalactan-polysaccharide addition to clustered non-contiguous Hyp residues, such as the X-Hyp-X-Hyp modules common in AGPs [Nothnagel (1997) International Review of Cytology 174:195]. Based on this prediction, it is the inventor's view that the exemplary consensus sequence of Table 6 contains approximately two polysaccharide attachment sites in the clustered non-contiguous Hyp motif: Ser-Hyp-Ser-Hyp-Thr-Hyp which is flanked by arabinosylated contiguous Hyp residues as depicted in FIG. 9. FIG. 9 uses the standard single letter code for amino acids except for Hyp which is denoted by [Du et al. (1994) Plant Cell 6:1643], and the standard three letter code for sugars, except for glucuronic acid which is denoted as GlcA. This model depicts a symmetrical distribution of arabinosides and polysaccharide substituents which is directed by the palindrome-like arrangement of the Hyp residues in the peptide backbone; Ser-0 is the palindromic center. However degenerate variations occur (Table 6). The inventors base this structure on compositional and linkage analyses of the isolated Hyp-polysaccharide fraction (Tables 7 & 8) [Qi et al. (1991) supra] and on the pentasaccharide side-chain structure elucidated for crude gum arabic by Defaye and Wong [Defaye and Wong (1986) Carbohydrate Research 150:221] (corresponding to $Rha_f$, $Ara_f$, 3-Ara, 4-GlcA, and 2,3,6-Gal in Table 9).

Hydroxyproline-O-glycosidic linkages are stable in base [Lamport (1967) Nature 216:1322; Miller et al. (1972) Science 176:918; Pope (1977) Plant Physiology 59:894], in contrast to other O-glycosylated hydroxyamino acids such as serine and threonine, which undergo β-elimination [Lamport et al. (1973) Biochemical Journal 133:125]. Therefore, alkaline hydrolysis was used to isolate and characterize Hyp-arabinogalactan polysaccharides from GAGP as demonstrated earlier [Qi et al. (1991) supra].

Figure 10:
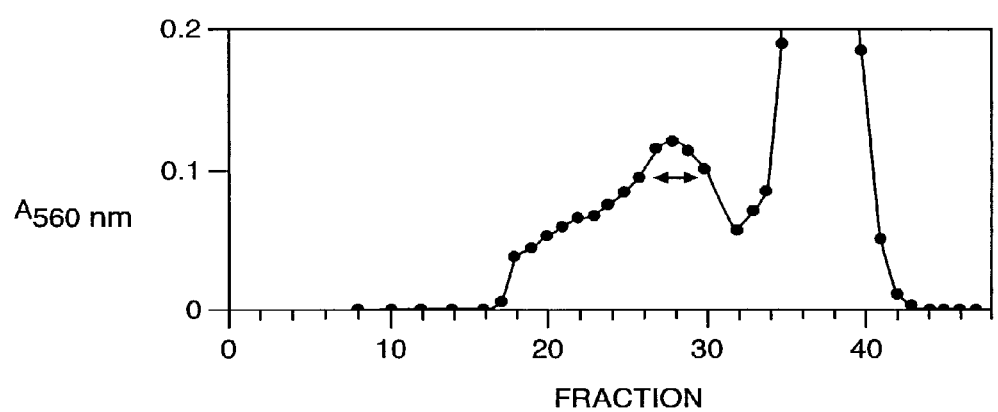
FIG. 10 is the elution profile of the GAGP base hydrolysate by Sephadex G-50 gel permeation chromatography.
Figure 12A:
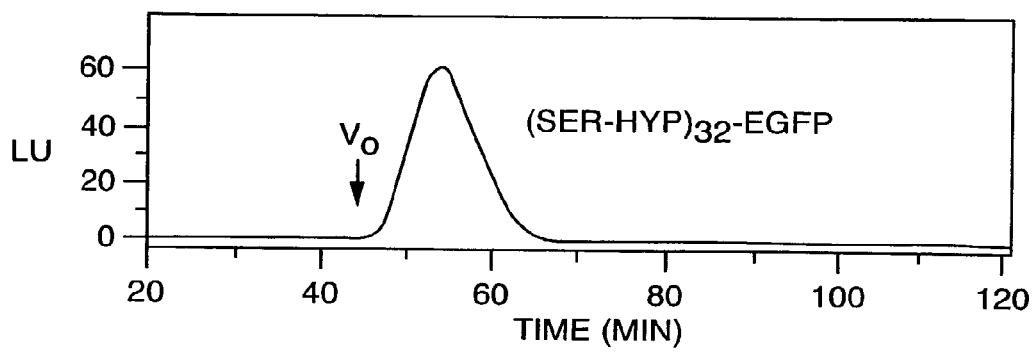
FIG. 12 shows Superose-12 gel permeation chromatography with fluorescence detection of (A) culture medium containing (Ser-Hyp)$_{32}$-EGFP, (B) (GAGP)$_3$-EGFP medium concentrated four-fold, (C) Medium of EGFP targeted to the extracellular matrix (concentrated ten-fold), and (D) 10 mg standard EGFP from Clontech.
Figure 12B:
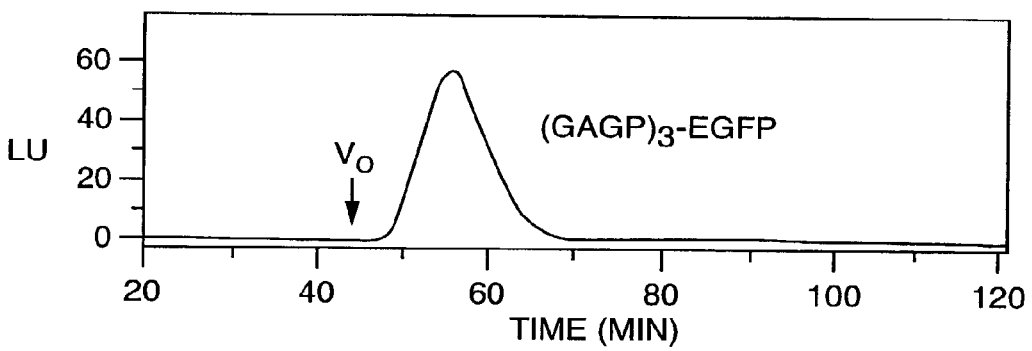
Figure 12C:
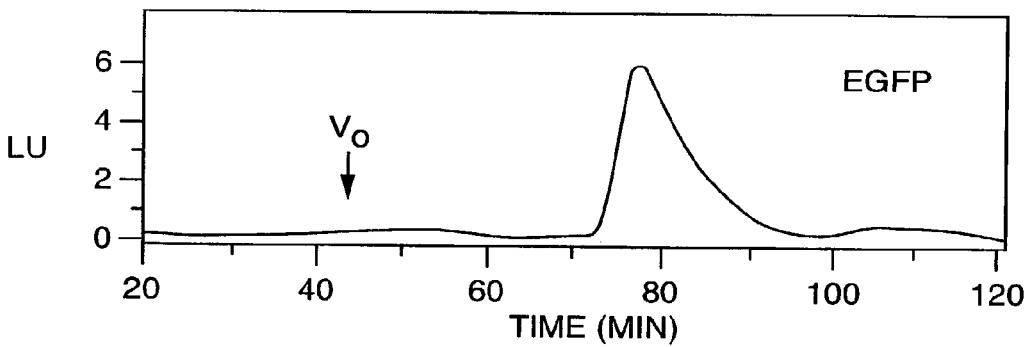
Figure 12D:
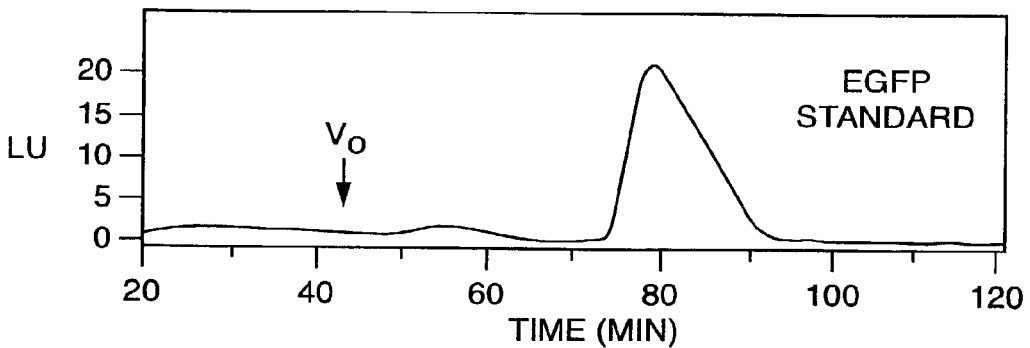

Compositional analysis of the small Hyp-polysaccharides isolated from GAGP after fractionation of the alkaline hydrolysate on Sephadex G-50 (FIG. 10; Table 8) indicated a content of 5158 nM sugar.

TABLE 8

Glycosyl compositions of intact GAGP and a GAGP Hyp-polysaccharide isolated from GAGP base hydrolysates

| Glycosyl Residue | GAGP[Qi et al. (1991) supra] | GAGP Hyp-polysaccharide Mol % |
|---|---|---|
| Ara | 36 | 38 |
| Gal | 46 | 34 |
| Rha | 10 | 13 |
| GlcUA | 9 | 15 |

In FIG. 10, assay of Hyp across the recovered fractions indicated a broad size range for the Hyp-polysaccharide (fractions 17-32). Fractions 27-30 were collected for linkage and composition analyses. Hyp arabinosides and non-glycosylated Hyp eluted in fractions 33-42. Corresponding quantitative Hyp assays showed a total of 220 nm Hyp in the peak isolated and analyzed (FIG. 10). The molar ratio of 220 nm Hyp: 5156 nm sugar indicated a ~23-residue rhamnoglucuronoarabinogalactan Hyp-polysaccharide substituent in this fraction. Methylation analysis of the polysaccharide (Table 9) showed linkages consistent with the model featured in FIG. 9, but containing 21-22 sugar residues rather than the 23 featured in FIG. 9.

TABLE 9

Glycosyl linkages of Intact GAGP and a GAGP Hyp-polysaccharide isolated from the GAGP base hydrolysate

| Glycosyl Linkage | GAGP | GAGP Hyp-Polysaccharide Mol % | |
|---|---|---|---|
| t-Rha | 6.7 | 10.4 | (2)* |
| 2,3,4-Rha | 3.3 | 0.0 | |
| t-Ara (f) | 13.3 | 16.2 | (4) |
| t-Ara (p) | 1.7 | 2.3 | (0-1) |
| 2-Ara (f) | 2.5 | 0.0 | |
| 3-Ara (f) | 8.3 | 11.0 | (2-3) |
| 4-Ara (p) or 5-Ara (f) | 1.7 | 0.0 | |
| 2,4-Ara or 2,5-Ara (f) | 0.8 | 0.0 | |
| 2,3,4-Ara or 2,3,5-Ara (f) | 2.5 | 0.0 | |
| t-Gal | 5.8 | 11.8 | (3) |
| 2-Gal | 0.8 | 0.0 | |
| 3-Gal | 2.7 | 4.5 | (1) |
| 4-Gal | 0.8 | 0.5 | |
| 6-Gal | 2.5 | 2.4 | (0-1) |
| 3,4-Gal | 2.5 | 7.7 | (2) |
| 3,6-Gal | 11.7 | 12.7 | (3) |
| 3,4,6-Gal | 10.0 | 9.4 | (2) |
| 2,3,6-Gal | 3.3 | 0.0 | |
| 2,3,4,6-Gal | 5.8 | 0.0 | |
| t-GlcUA | 1.7 | 0.9 | |
| 4-GlcUA | 7.5 | 10.2 | (2) |
| 3,4-GlcUA | 1.7 | 0.0 | |
| 2,4-GlcUA | 0.8 | 0.0 | |
| 2,3,4-GlcUA | 0.8 | 0.0 | |
| 4-Glc | 0.8 | 0.0 | |

*Estimated number of residues/polysaccharide.

Based on the above data, the inventors conclude that each small polysaccharide contains two pentasaccharide side chains (Gal, $Ara_2$, GlcA, Rha) arranged along a ~7-residue (1-3)β-D-galactan backbone helix which also contains monosaccharide side chains of Ara and Gal.

Data presented herein demonstrates that the linkage analyses of both Hyp-polysaccharide and GAGP (Table 9) are similar, thus providing evidence of similarity between GAGP and gum arabic polysaccharides. These results suggest that the larger Hyp-polysaccharides (FIG. 10) may be comprised of repeat units containing approximately 12 galactose residues/repeat. Hence, without limiting the invention to any particular theory or mechanism, the inventors estimate that as many as five side-chains (~40 sugars) occur in the larger arabinogalactan moieties which eluted in fractions 18-26 from the G-50 Sephadex column (FIG. 10). The inventors further believe that GAGP and other AGP sensitivity to alkaline degradation involves peptide bonds rather than glycosidic linkages.

Example 19

Construction of 8, 16, 20, 32, and 64 repeats of Gum Arabic Motifs and Expression In Plant Cells This Example discloses construction of synthetic genes for the expression of gum arabic glycoprotein repeats based on the invention's consensus sequences. The genes had 8, 20, 32, or 64 contiguous units of two motifs [motif 1 (SEQ ID NO:143)=Ser-Hyp-Hyp-Hyp-Hyp-Leu-Ser-Hyp-Ser-Hyp-Thr-Hyp-Thr-Hyp-Hyp-Lcu-Gly-Pro-His; motif 2 (SEQ ID NO:144)=Ser-Hyp-Hyp-Hyp-Thr-Leu-Ser-Hyp-Ser-Hyp-Thr-Hyp-Thr-Hyp-Hyp-Hyp-Gly-Pro-His], each of which is encompassed by the invention's consensus sequence. The 64 contiguous units [i.e., (motif 1-motif 2)$_{32}$] were constructed using a modification of the previously described [Lewis et al. (1996) Protein Expression & Purification 7:400-406] strategy involving compatible but nonregenerable restriction sites, which allowed construction of very large inserts with precise control over the number of DNA repeat number.

1. Site-Directed Mutagenesis of pUC18 to Eliminate BsrFI Restriction Site from the Amp$^r$ Gene Plasmid pUC18 has an endogenous BsrFI site in the Amp$^r$ gene. This site was eliminated by mutation to make the plasmid amenable to subcloning of the XmaI-BsrFI synthetic gene fragments, using the PCR core system I kit (Promega). The PCR Primer 1: (upstream primer) had the sequence (SEQ ID NO:204) GATACCGCGAGACCCACGCTC ACC<u>A</u>GCTCC; this primer was designed from nucleotides 1756 to 1785 of pUC18 except for 1 substitution (A for G) at position 1780 (bolded and underlined). This changes one Ala codon (GCC) for another (GCT), retaining the Amp$^r$ amino acid sequence while mutating the BsrFI site. PCR Primer 2: (downstream primer) had the sequence (SEQ ID NO:205) CTCGGTCGCCGCATACACTAT and was designed from nt 2220 to 2198 of pUC18. The PCR reaction conditions were 2 min @ 95° C., 30 sec @ 95° C., 1 min @ 48° C., 1 min @ 72° C. (30 cycles), 5 min @ 72° C. PCR products were separated on a 1.5% agarose gel. The 464 bp PCR fragment was extracted from the gel using the QIAEX II gel extraction kit. The isolated fragment was restricted and subcloned into pUC18 as a ScaI-BpmI fragment. The new plasmid was designated MpUC18 and has an active Amp$^r$ gene and no BsrFI site.

2. Synthesis of Gum Arabic Glycoproteins (GAGP) Repeats Using Mutually Priming Oligonucleotides DNA encoding gum arabic glycoprotein contiguous units of motif 1 linked to motif was constructed using previously described methods [Current Protocols in Molecular Biology section 8.2.8-8.2.10]. A DNA fragment encoding the two GAGP motifs was synthesized by primer extension of two partially overlapping synthetic oligonucleotides: First oligonucleotide (SEQ ID NO:206): 5'-G GCA AGC TTC CGG AGT GCC GGC CCT CAT AGC CCA CCT CCA CCA TTA TCA CCA TCA CCT ACT CCA ACT CCT CCTTTGGGACCACACAG-3'; second oligonucleotide (SEQ ID NO:207): 5'-GGT CCC GGG GGG TGG TGT TGG GGT TGG TGA AGG GGA AAG TGT AGG GGG TGG A CTGTGTGGTCCCAAAGGAGG-3'. The oligonucleotides (0.05 nm of each) were heated for 5 min @ 95° C., annealed for 5 min @ 48° C., then extended by DNA polymerase I Klenow fragment (Promega) for 30 min @ 37° C. The reaction was stopped by heating 10 min at 75° C. and the buffer was exchanged via a Sephacryl S-200 column (Pharmacia Microspin™). The plasmid was then subcloned into MpUC18 as a Hind I—XmaI fragment. The plasmid was sequenced with the pUC/M13 forward primer (17-mer).

Figure 15:
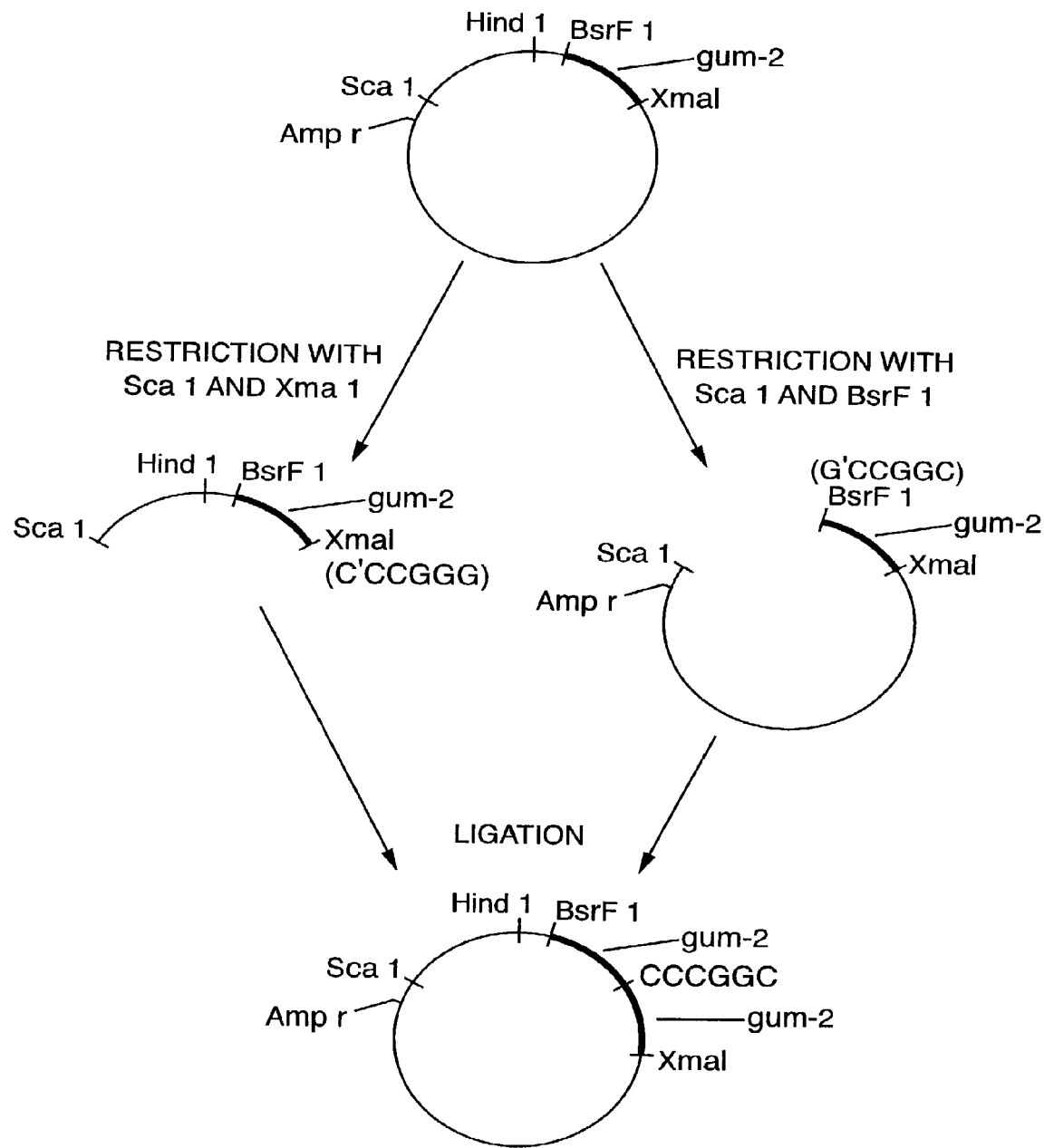
FIG. 15 is a diagram of the cloning strategy for generating repeats of GAGP sequences.

3. Multiplication of GAGP Internal Repeat Using Nonregenerable Restriction Sites Synthetic genes containing controlled numbers of GAGP repeats were synthesized as follows, and as illustrated in FIG. 15. MpUC18 containing the PCR product described above (two GAGP motifs as shown in FIG. 16A) (designated MpUC gum-2) was divided between two tubes. MpUC gum-2 in tube 1 was restricted with ScaI and BsrFI; MpUC gum-2 in tube 2 was restricted with ScaI and XmaI. The digests were separated on a 1% agarose gel. The 1884 kb band from tube 1 (ScaI/BsrFI digest) and the 1044 kb band from the tube 2 (ScaI/XmaI digest) were excised from the gel, combined and ligated together. The resulting plasmid (MpUC gum-4) contained 4 GAGP internal repeats [i.e., (motif 1-motif 2)$_2$] (FIG. 16B). This strategy was successfully used to build plasmids containing 8, 16, 20, 32, and 64 internal repeats of GAGP.

4. Subcloning of Synthetic Gum Repeats into pUC ss-EGFP Plasmid

The gum genes (gum-8, gum-20, and gum-32) were removed from MpUC18 plasmid as BspEI/SacI fragments and subcloned into pUC ss-EGFP plasmid behind the signal sequence. During this subcloning, EGFP was removed from pUC ss-EGFP as XmaI/SacI fragment. XmaI and BspEI restriction sites are compatible but nonregenerable.

The next subcloning was done to put the EGFP gene in frame behind the gum sequences. pUC ss-EGFP plasmid was cut with XmaI and treated with Mung Bean endonuclease (New England Biolabs). The enzymes were inactivated by phenol/chloroform extraction followed by ethanol precipitation. Then plasmid was cut with SacI. The EGFP fragment isolated after restriction was subcloned into pUC ss-gum plasmids which was cut with SmaI/SacI restriction enzymes. The signal sequence-synthetic gene-EGFP fragments were removed from MpUC18 plasmid as BamHI/SacI fragments and subcloned into pBI121, replacing the β-glucuronidase reporter gene. The MpUC ss-gum$_{20}$-EGFP and MpUC ss-gum$_{32}$-EGFP plasmids were sequenced with pUC/M13 forward (17 mer) primer and with GFP primer GAAGATG-GTGCGCTCCTGGACGT (SEQ ID NO:226) from nucleotide 566 to nucleotide 588 of pEGFP.

5. Transformation of Tobacco Cultured Cells, Tobacco Leaf Discs, and Tomato Cultured Cells, and Expression of Multiple GAGP Internal Repeats The expression vectors contained an extension signal sequence or a tomato signal sequence for transport of the constructs through the ER/Golgi for posttranslational modification, as well as Green Fluorescent Protein (GFP) as a reporter protein as described below.

A. Extensin Signal Sequence

Transformation vectors were derived from pBI121 (Clontech). These vectors contained an extensin signal sequence (SS) as well as Green Fluorescent Protein (GFP) as a reporter protein. 8, 20, 32, and 64 internal repeats of GAGP were inserted between the signal sequence and GFP to yield plasmids SS-GAGP$_8$-EGFP, SS-GAGP$_{20}$-EGFP, SS-GAGP$_{32}$-EGFP, and SS-GAGP$_{64}$-EGFP, respectively. Because preliminary data showed that the gene encoding the 64 repeats of GAGP was unstable in pBI12, plasmids SS-GAGP$_8$-EGFP, SS-GAGP$_{20}$-EGFP, and SS-GAGP$_{32}$-EGFP were used to transform *Agrobacterium tumefacienes* as described supra (Example 9).

B. Tomato LeAGP-1 Signal Sequence

As an alternative to the extensin signal sequence, the tomato LeAGP-1 signal sequence was used. Cloning of the LeAGP-1 signal sequence was as follows using the sense primer 5'-CTC TTT TTC TCT G↓GATCC GGt CTA TAT TTT CTT TTA GC-3' (SEQ ID NO:227) (Tm: 68° C.) with the arrow showing the BamHI restriction site, and the antisense primer 5'-CGG GTG CTG C↓CCGGG TTG TCT GAC CCG TGA CAC TTG C-3' (SEQ ID NO:228) (Tm: 80° C.) with the arrow showing the XmaI restriction site.

PCR was carried out using 52.8 pmol of sense primer and 47 pmol of antisense primer. The LeAGP-1 signal sequence template (0.01 µg) was added together with the PCR mixture. The reaction solution was covered with oil and the incubation was at 95° C. 5 min (circle one); 95° C. 45 sec, 58° C. 1 min, 74° C. 1 min (circle 2-30); 74° C. 5 min. 20 µl out of 50 µl total PCR solution was removed and purified using 2% agarose gel. The PCR product was 127-bp in size and was isolated by using QIAEXII kit. This fragment was digested as follows at 37° C. overnight:

| Purified PCR fragment | 100 ng | pUC-SS$^{Tob}$GFP | 200 ng |
|---|---|---|---|
| BamH1 | 5 u | BamH1 | 2 u |
| XmaI | 4 u | XmaI | 2 u |
| Buffer B | 3 µl | Buffer B | 3 µl |
| Add water to 30 µl | | Add water to 30 µl | |

The digested samples were run on an agarose gel. The vector and fragment were cut from the gel and were isolated with the QIAEXII kit. The ligation reaction [pUC-SS$^{Tob}$GFP (BX) 100 ng, PCR fragment(BX) 20 ng, Ligase Buffer (10×) 1 µl, Ligase 1 µl] was incubated at 10° C. overnight.

Transformation was carried out and 3 clones were cultured separately in LB media containing ampicillin overnight. Plasmids were isolated from the transformed cells and digested with BamH1 and XmaI to confirm that the fragments were 99 bp long. The plasmid containing the tomato signal sequence was named pUC-SS$^{Tom}$-GFP.

Plasmids containing the tomato signal sequence in tandem with repeating GAGP sequences and with EGFP as a reporter gene is used to transform *Agrobacterium tumefacienes* as described supra (Example 9).

The transformed *Agrobacterium* cells were used to transform tobacco cultured cells as described above (Example 10). Transformed cells were selected by detection of fluorescent cells which express GFP.

Transformed *Agrobacterium* cells will be used to transform tomato cultured cells and tobacco discs as described above (Examples 11 and 17, supra). Transformed cells will be selected by detection of fluorescent cells which express GFP. Successful expression of 8, 20, and 32, internal repeats of GAGP in tobacco cultured cells, tobacco leaf discs, and tomato cultured cells will be confirmed using the methods described in the above Examples.

Example 20

Construction of Genes and Vectors Containing Contiguous and Noncontiguous Hydroxyproline glycomodules (SP)$_{32}$, (GAGP)$_3$, (SPP)$_{24}$, (SPPP)$_{16}$, and (SPPPP)$_{18}$ This Example describes construction of three plasmids, each encoding a tobacco signal sequence and EGFP, as well as subcloning of (SP)$_{32}$, (GAGP)$_3$, EGFP, (SPP)$_{24}$, (SPPP)$_{16}$, (SPPPP)$_{18}$. In the three plasmids described here, the signal sequence was used to direct the products through the ER and Golgi, then out to the extracellular matrix [Goodenough et al. (1986) *J. Cell Biol.* 103, 403; Gardiner & Chrispeels (1975) *Plant Physiol.* 55, 536-541]. Two of the plasmids also contained a synthetic gene (SEQ ID NOs:112, 113, 115, 116) encoding either six (Ser-Pro) internal repeat units (SEQ ID NO:117) or three (GAGP) internal repeat units (SEQ ID NO:122) (FIG. 11) sandwiched between the signal sequence and gene-enhanced green fluorescent protein (EGFP). In FIG. 11, internal repeat oligonucleotide sets encoding Ser-Pro repeats or the GAGP sequence were polymerized head-to-tail in the presence of the 5'-linker set [SEQ ID NOs:120 and 121 which encode SEQ ID NO:122]. Following ligation, the 3'-linker [SEQ ID NOs:123 and 124 which encode SEQ ID NO:125] was added and the genes then restricted with BamHI and EcoRI and inserted into pBluescript II SK. The signal sequence (SEQ ID NOs:118 and 119) was built by primer extension of the overlapping oligonucleotides featured here. The overlap is underlined.

The conserved (Ser-Hyp)$_n$ motif was chosen because it occurs both in green algae (Chlamydomonas) and in higher plant AGPs. This noncontiguous Hyp motif is of particular interest because it also occurs together with a contiguous Hyp motif in the consensus sequence of GAGP which contains both oligoarabinoside and polysaccharide addition sites.

The signal sequence (FIG. 11) was modeled after an extensin signal sequence from *Nicotiana plumbaginifolia*; mutually priming oligonucleotides were extended by T7 DNA Polymerase and the duplex placed in pUC18 as a Bam HI-Sst I fragment. Construction of a given synthetic gene involved the polymerization of three sets of partially overlapping, complementary oligonucleotide pairs as described earlier (FIG. 11). The following subclonings were required to create DNA fragments/restriction sites which allowed facile transfer of the Signal Sequence-synthetic gene-enhanced green fluorescent protein (EGFP) unit to the plant transformation vector pBI121 (Clontech): The synthetic genes were placed in pBluescript II SK (Stratagene) as BamHI-EcoRI fragments and then subcloned the genes into pEGFP (Clontech) as BamHI-AgeI fragments preceding the EGFP gene (Tsien, R. Y. (1998) *Annu. Rev. Biochem.* 67, 509-544; Haseloff, J., Siemering, K. R., Prasher, D. C. & Hodge, S. (1997) *Proc. Natl. Acad. Sci.* 94, 2122-2127.22). The synthetic gene-EGFP fragments were then subcloned into pBluescript II KS (Stratagene) as XmaI/NotI fragments, removed as XmaI-SstI fragments and subcloned into pUC18 behind the signal sequence. DNA sequences were confirmed by sequence analysis before insertion into pBI121 as BamHI/SstI fragments, replacing the b-glucuronidase reporter gene. All constructs were under the control of the 35S cauliflower mosaic virus promoter. The oligonucleotides were synthesized by Lifesciences (Gibco/BRL). An Ala for Pro/Hyp substitution at residue 8 of the gum arabic glycoprotein (GAGP) internal repeat module (SEQ ID NO:208) (Ser-Pro-Ser-Pro-Thr-Pro-Thr-Pro-Pro-Pro-Gly-Pro-His-Ser-Pro-Pro-Pro-Thr-Leu) was inadvertently introduced during synthesis by a G for C base substitution in the sense strand.

The following is a more detailed description of the protocol used to subclone (SP)$_{32}$, (GAGP)$_3$, EGFP, (SPP)$_{24}$, (SPPP)$_{16}$, (SPPPP)$_{18}$. Briefly, Everything was first built and sequenced in pUC18, then transferred as a block (i.e., signal sequence-synthetic gene-EGFP) to pBI121. The constructs in pBI121 were not sequenced. The pBI121 plasmids were used to transform *Agrobacterium* and the transformed *Agrobacterium* was used to transform the plant cells, as described infra in Example 21.

1. Synthesis of the Signal Sequence

The signal sequence was assembled by using mutually priming oligonucleotides [Current Protocols in Molecular Biology," (1995) pages 8.2.8-8.2.10]. Oligonucleotides (0.2 nmol, 0.2 nmol) were annealed (5 min at 70° C. followed by 5 min at 40° C.) and extended by DNA polymerase I (Klenow) large fragment (Promega) (30 min at 37° C.). The reaction was stopped by heating 10 min at 75° C. The resulting DNA fragment was cut with BamHI and SstI enzymes and was placed in pUC18 plasmid. The plasmid was sequenced with pUC/M13 forward (17 mer)

2. Synthesis and Subcloning of Synthetic Genes

Oligonucleotides were synthesized and SDS-PAGE purified by Gibco-BRL or Integrated DNA Technologies Inc. They were dissolved in water at appropriate concentrations.

A. (SP)$_{32}$ and (GAGP)$_3$ Synthesis and Subcloning i. Annealing Reaction

Oligonucleotide-pairs were combined in eppendorf tubes as follows:

a) 5.5 µl internal repeat sense oligonucleotide (0.5 nmol/µl)
   5.5 µl internal repeat antisense oligonucleotide (0.5 nmol/µl)
   11 µl T4 ligase 10× ligation buffer
b) 2 µl 5'-end sense linker (0.05 nmol/µl)
   2 µl 5'-end antisense linker (0.05 nmol/µl)
   1 µl water
   5 µl T4 ligase 10× ligation buffer
c) 2 µl 3'-end sense linker (1 nmol/µl)
   2 µl 3'-end antisense linker (1 nmol/µl)
   1 µl water
   5 µl T4 ligase 10× ligation buffer All tubes were heated 5 min at 90-95° C. Then they were cooled to 45° C. over next 3 hours and kept at 45° C. for 2 more hours.

ii. Oligonucleotide Polymerization

10 µl of the internal repeat pair was combined with 10 µl of the 5'-end linker pair (15:1 molar ratio). This mixture was incubated 3 hour at 17° C. Then, 80 µl of water (to receive 1× concentration of ligation buffer) and 2 µl of T4 DNA ligase (4,000 U) were added. The ligation reaction was incubated 36 hours at 12-15° C. The extent of polymerization was checked on 2.2% agarose gel.

The 5'-end linker-internal repeat polymers were capped with the 3'-end linker. 5 µl of the 3'-end linker were added to 50 µl of ligation reaction from the step above. The mixture was heated to 30° C. (to destroy unspecific hybridization), and incubated at 17° C. for 3 hours. 20 µl of water and 2 µl T4 DNA ligase (4,000 U) were added and the ligation reaction was incubated at 12-15° C. for 36 hours. The reaction was stopped by heating at 65° C. for 10 min.

The constructs were ethanol precipitated, washed with 70% ethanol and air dried. The pellet was dissolved in 80 µl of water. 10 µl was used for restriction with EcoRI (10 Units) and BamHI (20 Units). The Sephacryl S-400 column (Pharmacia Microspin™) was used to remove salts and small oligonucleotide fragments. Qiaquick Nucleotide removal kit (Qiagen) was used to remove enzymes. The resultant fragments were inserted in pBluescript II SK plasmid (Stratagene) The selection of clones was done by white-blue assay. The structure of synthetic genes was checked by sequencing with pUC/M13 forward (17 mer) primer.

iii. Subcloning

The synthetic genes were first removed from pBluescript II SK (Stratagene) as BamHI/AgeI fragments and subcloned in pEGFP (Clontech). (This step allowed directional cloning). The synthetic gene—EGFP fragments were removed from pEGFP as XmaI/NotI fragments and subcloned in KS (Stratagene) (This step was done to obtain SstI site at the end of EGFP). The synthetic gene—EGFP fragments were removed from KS as XmaI/SstI fragments and subcloned in pUC-signal sequence plasmid behind the signal sequence. The structure of the synthetic genes was checked by sequencing with pUC/M13 forward (17 mer) primer. The signal sequence-synthetic gene-EGFP fragments were removed from pUC18 plasmid as BamHI/SstI fragments and subcloned in pBI121 (Clontech).

iv. EGFP Subcloning

The EGFP fragment was removed from pEGFP as XmaI/NotI fragments and subcloned in KS. (This step was done to obtain SstI site at the end of EGFP). The EGFP fragment was removed from KS as XmaI/SstI fragments and subcloned in pUC-signal sequence plasmid behind the signal sequence. The signal sequence-EGFP fragment was removed from pUC18 plasmid as BamHI/SstI fragments and subcloned in pBI121.

B. $(SPP)_{24}$, $(SPPP)_{16}$, $(SPPPP)_{18}$, Palindromic Repeat Synthesis and Subcloning i. Annealing Reaction Oligonucleotide-pairs were combined in eppendorf tubes as follows:

a) 2 µl internal repeat sense oligonucleotide (0.25 nmol/µl)
2 µl internal repeat antisense oligonucleotide (0.25 nmol/µl)
3 µl T4 ligase 10× ligation buffer
23 µl water b) 1 µl 5'-end sense linker (0.5 nmol/µl)
1 µl 5'-end antisense linker (0.5 mmol/µl)
4 µl T4 ligase 10× ligation buffer
34 µl water c) 2 µl 3'-end sense linker (0.25 nmol/µl)
2 µl 3'-end antisense linker (0.25 nmol/µl)
3 µl T4 ligase 10× ligation buffer
23 µl water All tubes were heated to 90-95° C. for 5 min. Then they were cooled to annealing temperature ( ) over next 30 min and kept at that temperature for 1 more hour.

ii. Oligonucleotides Polymerization

25 µl of internal repeat pair was combined with 20 µl of 5'-end linker pair (1.5:1 ratio). The mixture was heated to 35° C. to destroy circular structures formed by internal repeat pair. After cooling to 20° C. 0.5 µl of T4 DNA ligase (1.5 U) was added. The ligation reaction was incubated 3 hours at 20° C. 3 µl of ligation mixture was used to check the extent of polymerization on 2% agarose gel.

The 5'-end linker-internal repeat polymers were capped with 3'-end linker. I added 15 µl of the 3'-end linker to 40 µl of ligation reaction from step above and 0.5 µl of T4 DNA ligase (1.5 U). The ligation reaction was incubated 3 hours at 20° C. The reaction was stopped by heating at 65° C. for 10 min. 3 µl of ligation mixture was used to check the extent of polymerization on 2% agarose gel. The Sephacryl S-200 column (Pharmacia Microspin)™ was used to remove salts. 4-6 µl of solution was used for restriction with EcoRI (10 Units) and BamHI (20 units). After restriction, 150-bp to 500-bp fragments were cut out of 2% agarose gel. QIAEX II gel extraction kit was used to isolate fragments from the gel.

The resultant fragments were inserted in pUC18 plasmid. The selection of clones was done by white-blue assay. The structure of synthetic genes was checked by sequencing with pUC/M13 forward (17 mer) primer.

iii. Subcloning

The synthetic genes were removed from pUC18 as XmaI/NcoI fragments and subcloned behind the signal sequence and in front of EGFP in pUC-signal sequence-EGFP plasmid. The signal sequence-synthetic gene-EGFP fragments were removed from pUC18 plasmid as BamHI/SstI fragments and subcloned in pBI121.

The above protocols yielded pBI121 expression constructs in which genes encoding each of $(SP)_{32}$, $(GAGP)_3$, EGFP, $(SPP)_{24}$, $(SPPP)_{16}$, $(SPPPP)_{18}$ palindromic repeats were ligated to sequences encoding the signal sequence and EGFP.

Example 21

Transformation of Tobacco Cells And Selection of Transformed Cell Lines

This Example describes transformation of suspension cultured tobacco cells with the expression vectors of Example 20 and selection of transformants which express green fluorescent protein.

Suspension cultured tobacco cells (*Nicotiana tabacum*, BY2) were transformed with *Agrobacterium tumifaciens* strain LBA4404 containing the pBI121-derived plant transformation vector. Transformed cell lines were selected on solid Murashige-Skoog medium (Sigma #5524) containing 100 mg/mL kanamycin. Timentin was initially included at 400 mg/mL to kill *Agrobacterium*. Cells were later grown in 1 L flasks containing 500 mL Shenck-Hildebrand medium (Sigma #6765) and 100 mg/mL kanamycin, rotated at 100 rpm on a gyrotary shaker.

After transformation of tobacco cells with *Agrobacterium* harboring the plant transformation plasmid pBI121 outfitted with either Sig-$(GAGP)_3$-EGFP, Sig-$(Ser-Pro)_{32}$-EGFP, or Sig-EGFP (described in Example 20), selection on solid medium and subsequent growth in liquid culture yielded cells bathed in a green fluorescent medium. The fluorescence in these highly vacuolated, cultured cells surrounds the nuclei, but is not within judging by optical sections (not shown). The microscope was a Molecular Dynamics Sarastro 2000 confocal laser scanning microscope using a 488 nm laser wave length filter, 510 nm primary beam splitter and a 510 nm barrier filter.

Figure 13A:
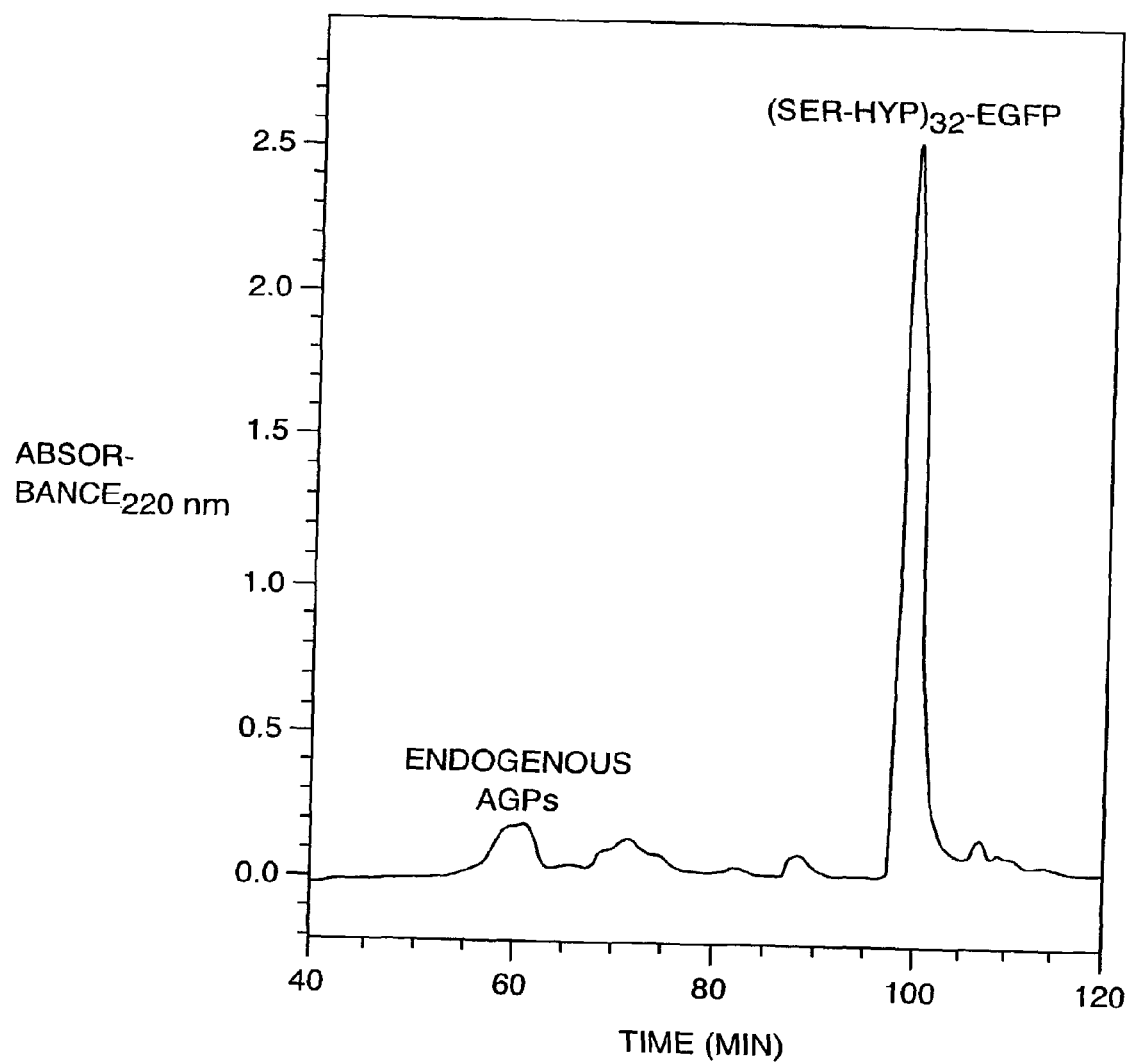
FIG. 13 shows PRP-1 reverse-phase fractionation of the Superose-12 peaks containing (A) (Ser-Hyp)$_{32}$-EGFP, (B) (GAGP)$_3$-EGFP, and (C) (Glyco)proteins in the medium of non-transformed tobacco cells.
Figure 13B:
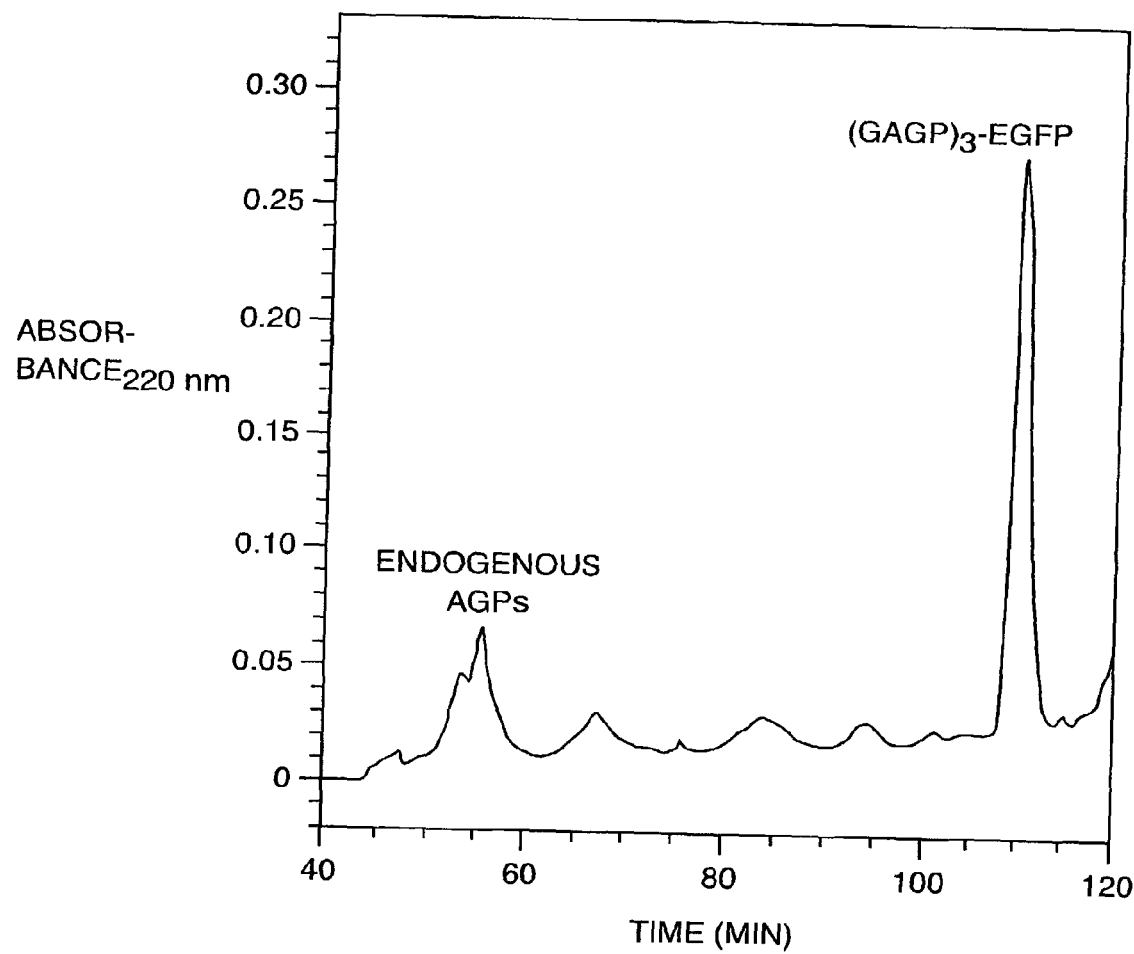
Figure 13C:
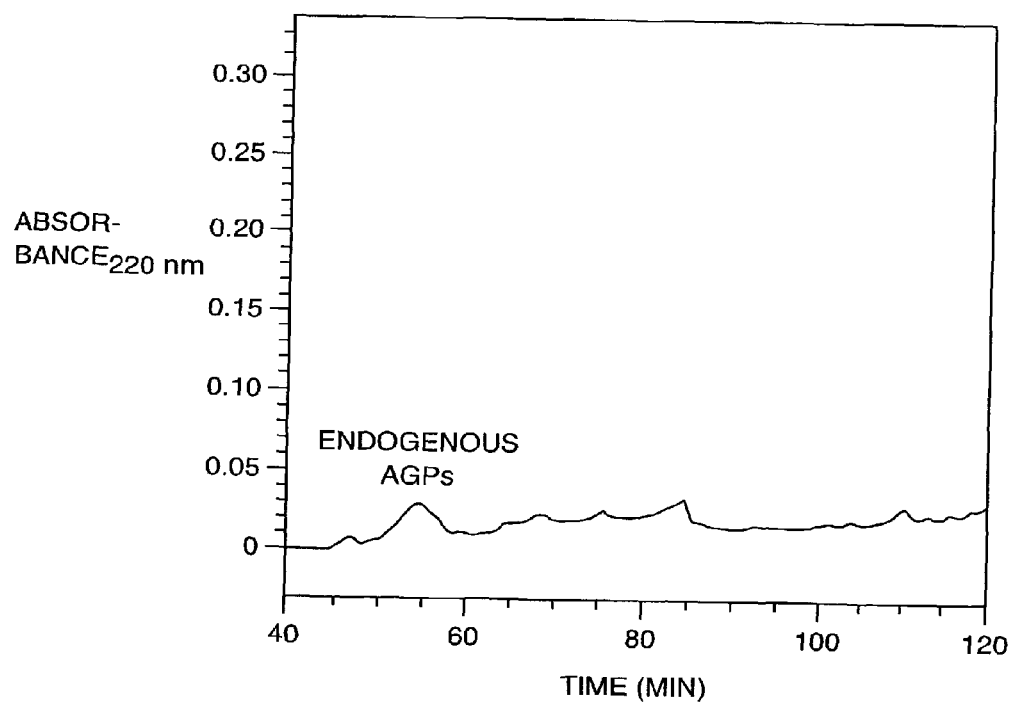

This Example demonstrates that inclusion of the EGFP reporter protein facilitated the selection of transformed cells and subsequent detection of the expression products during isolation (FIGS. 13 & 14). EGFP fluorescence in the growth medium was also a visual demonstration of Sig efficacy in directing secretion. The absence of any obvious cell lysis in the cultures and excellent product yields of the glycosylated expression products confirmed that the green fluorescence represented bona fide secretory products. Interestingly, EGFP without a glycomodule was secreted at very low levels, perhaps due to lower solubility.

Example 22

Isolation of $(Ser-Hyp)_{32}$-EGFP, $(GAGP)_3$-EGFP, $(SPP)_{24}$-EGFP, $(SPPP)_{16}$-EGFP, and $(SPPPP)_{18}$-EGFP From Transformed Cells This Example describes the isolation of sequences containing contiguous and noncontiguous Hyp residues from the growth medium of tobacco cells transformed with expression vectors which express these polypeptides.

Culture medium of cells described in Example 21, supra, was harvested 7 to 21 days after subculture, and the gene products were purified by gel permeation and reverse-phase chromatography (FIGS. 13 and 14) as follows. Culture medium was concentrated ten fold via rotovapping, then injected onto a Superose-12 gel filtration column (Pharmacia)

equilibrated in 200 mM sodium phosphate buffer, pH 7, and eluted at a flow rate of 1 mL/min. EGFP fluorescence was monitored by a Hewlett-Packard 1100 Series flow-through fluorimeter (Excitation=488 nm; Emission=520 nm). The Superose-12 column was calibrated with molecular weight standards (BSA, insulin, catalase, and sodium azide). Fluorescent Superose-12 fractions were injected directly onto a Hamilton PRP-1 reverse phase column and gradient eluted at a flow rate of 0.5 mL/min. Start buffer consisted of 0.1% TFA (aq) and elution buffer was 0.1% TFA/80% acetonitrile (aq). The sample was repeatedly injected (0.5 mL/minute) onto the column over 35 min, then eluted with a gradient of elution buffer (0-70%/135 min). Native GAGP was isolated from gum arabic nodules as described by Qi et. al. Endogenous tobacco AGPs were isolated as by PRP-1 reverse-phase and the results are shown in FIG. 13. FIG. 13 shows PRP-1 reverse-phase fractionation of the Superose-12 peaks containing (A) (Ser-Hyp)$_{32}$-EGFP, (B) (GAGP)$_3$-EGFP, and (C) Glycoproteins in the medium of non-transformed tobacco cells. Endogenous tobacco AGPs eluted between 47 and 63 minutes; extensins eluted at ~67 min. (C) Control medium collected from non-transformed tobacco cells was first fractionated on Superose-12 and the fractions eluting between 47 and 63 min collected for further separation on PRP-1 to determine if any endogenous AGPs/HRGPs co-chromatographed with (Ser-Hyp)$_{32}$-EGFP or with (GAGP)$_3$-EGFP, which they did not.

Six cell lines examined [three each of (Ser-Hyp)$_{32}$-EGFP and (GAGP)$_3$-EGFP] synthesized fluorescent glycoproteins of comparable sizes, although product yields between lines differed as much as ten-fold. For product characterization high-yielding lines were chosen which typically produced 23 mg/L of (Ser-Hyp)$_{32}$-EGFP and 8 mg/L of (GAGP)$_3$-EGFP after isolation.

FIG. 12 shows Superose-12 gel permeation chromatography with fluorescence detection of (A) culture medium containing (Ser-Hyp)$_{32}$-EGFP, (B) (GAGP)$_3$-EGFP medium concentrated four-fold, (C) Medium of EGFP targeted to the extracellular matrix (concentrated ten-fold), and (D) 10 mg standard EGFP from Clontech. Not shown is the fractionation of medium from non-transformed tobacco cells, which gave no fluorescent peaks consistent with the results discussed above. Superose-12 fractionation of the two fusion glycoproteins (FIG. 12) compared to molecular weight standards (not shown) indicated mass ranges of ~95-115 kD for (Ser-Hyp)$_{32}$-EGFP and ~70-100 kD for (GAGP)$_3$-EGFP. The above data demonstrates successful isolation of GAGP sequences from cells which had been transformed with vectors that are capable of expressing these sequences.

The recombinant (SPP)$_{24}$-EGFP, (SPPP)$_{16}$-EGFP, and (SPPPP)$_{18}$-EGFP were isolated from transformed cells as described supra in this Example with respect to (SP)$_{32}$-EGFP and (GAGP)$_3$-EGFP.

Example 23

Characterization of Glycoproteins Isolated from Transformed Cells

The glycoproteins isolated from transformed tobacco cells as described in Example 22 were characterized as follows, and were shown to be new arabinogalactan-proteins (AGPs).

1. Co-Precipitation with Yariv Reagent (Ser-Hyp)$_{32}$-EGFP, (GAGP)$_3$-EGFP, tobacco AGPs, and native GAGP were co-precipitated with the Yariv reagent as described earlier. Both (Ser-Hyp)$_{32}$-EGFP and (GAGP)$_3$-EGFP precipitated with Yariv reagent (Table 10), which is a specific property of b-1,3-linked arabinogalactan-proteins.

TABLE 10

Yariv Assay of (Ser-Hyp)$_{32}$ - EGFP and (GAGP)$_3$ - EGFP

| | Absorbencies at 420 nm | | | |
|---|---|---|---|---|
| | | | Standards | |
| Sample Weight (µg) | (Ser-Hyp)$_{32}$ - EGFP | (GAGP)$_3$ - EGFP | GAGP | Tobacco AGP |
| 20 | 0.16 | 0.27 | 0.51 | 0.16 |
| 50 | 0.45 | 0.56 | 1.22 | 0.38 |
| 100 | 1.00 | 1.21 | 2.69 | 0.85 |

2. Hydroxyproline Glycoside Profiles

Hyp-glycoside profiles were determined as described by Lamport and Miller. We hydrolyzed 5.8-12.2 mg (Ser-Hyp)$_{32}$-EGFP or (GAGP)$_3$-EGFP in 0.44 N NaOH and neutralized the hydrolysate with 0.3 M HCl before injection onto a C2 cation exchange column. Each Hyp residue in (Ser-Hyp)$_{32}$-EGFP contained an arabinogalactan-polysaccharide substituent; (GAGP)$_3$-EGFP Hyp residues contained arabinooligosaccharide substituents in addition to arabinogalactan-polysaccharide (Table 11).

TABLE 11

Hyp-Glycoside Profiles of (Ser-Hyp)$_{32}$ - EGFP and (GAGP)$_3$ - EGFP and Native Crude GAGP

| | % of Total Hyp | | |
|---|---|---|---|
| Hyp-Glycoside | (Ser-Hyp)$_{32}$ - EGFP | GAGP$_3$ - EGFP | Native GAGP |
| Hyp-polysaccharide | 100 | 62 | 25 |
| Hyp-Ara | 0 | 4 | 10 |
| Hyp-Ara$_2$ | 0 | 12 | 17 |
| Hyp-Ara$_3$ | 0 | 7 | 31 |
| Hyp-Ara$_4$ | 0 | 4 | 5 |
| Non-glycosylated Hyp | 0 | 11 | 12 |

The Hyp-glycoside profile of (Ser-Hyp)$_{32}$-EGFP gave a single peak of Hyp corresponding to Hyp-polysaccharide. Significantly, peaks corresponding to Hyp-arabinosides and non-glycosylated Hyp were absent. Importantly, this indicates that all of the Hyp residues in the glycomodule were linked to a polysaccharide.

In contrast, (GAGP)$_3$-EGFP yielded peaks corresponding to Hyp-arabinosides, non-glycosylated Hyp, and Hyp-polysaccharide. However, (GAGP)$_3$-EGFP (FIGS. 11 & 15) was designed with fewer contiguous Hyp residues than the consensus sequence of native GAGP and yielded fewer Hyp arabinosides consistent with fewer contiguous Hyp arabinosylation sites [Kieliszewski & Lamport (1994) Plant J. 5, 157-172; Kieliszewski et al. (1992) Plant Physiol. 98, 919-926. Kieliszewski et al. (1995) J. Biol. Chem. 270, 2541-2549]. In addition, occasional incomplete hydroxylation of the middle proline residue in the Pro-Pro-Pro motif (FIG. 14B) converted a region of contiguous Hyp (putative arabinosylation site) to noncontiguous Hyp (polysaccharide addition sites). Control EGFP targeted to the extracellular matrix contained no Hyp, hence no glycosylated Hyp, judging by manual Hyp assays.

The following describes the sequences of the genes and the expressed proteins as well as the Hyp-glycoside glycoprotein profile which were obtained using the SPP, and SPPP modules described in Table 4, as well as the SPPPP module.

A. Ser-Pro-Pro Gene

The [SPP]$_n$ module described in Table 4, item 2.a. was expressed using the following sequence:

```
GGA TCC GCA ATG GGA AAA ATG GCT TCT CTA TTT GCC ACA TTT TTA GTG GTT TTA   (SEQ ID No: 229)
 G   S   A   M   G   K   M   A   S   L   F   A   T   F   L   V   V   L   (SEQ ID No: 230)

GTG TCA CTT AGC TTA GCA CAA ACA ACC CGG GCC [CCA CCT TCA CCC CCA TCT CCA
 V   S   L   V   L   A   Q   T   T   R   A  [ P   P   S   P   P   S   P

CCG AGT CCA CCA TCC]₆ CCA CCT TCA TCC ATG GCA TAA TAG AGC TCG
 P   S   P   P   S ]₆  P   S   S   M   A  Stop Stop.
```

The Ser-Pro-Pro gene expressed the protein sequence [Pro-Hyp-Ser-Hyp-Hyp-Ser-Hyp-Hyp-Ser-Hyp-Hyp-Ser]$_6$ (SEQ ID NO:231) which had the following Hyp-glycoside profile: Hyp (51% of total Hyp), Hyp-Ara (0% of total Hyp), Hyp-Ara$_2$ (0% of total Hyp), Hyp-Ara$_3$ (49% of total Hyp), Hyp-Ara$_4$ (0% of total Hyp), Hyp-Polysaccharide (0% of total Hyp).

B. Ser-Pro-Pro-Pro Gene

The [SPPP]$_n$ module described in Table 4, item b. was expressed using the following sequence:

```
GGA TCC TCA ACC CGG GCC TCA CCA [CCA CCA CCT TCT CCA CCT CCA TCA CCC CCA   (SEQ ID NO: 232)
 G   S   S   T   R   A   S   P  [ P   P   P   S   P   P   P   S   P   P   (SEQ ID NO: 233)

CCT TCG CCT CCA CCA TCC]₄ CCT TCC ATG GCA TAA TAG AGC TCG AAT TCG
 P   S   P   P   P   S ]₄  P   S   M   A  STOP STOP
```

The expressed the protein sequence had the following Hyp-glycoside profile: Hyp (0% of total Hyp), Hyp-Ara (0% of total Hyp), Hyp-Ara$_2$ (21% of total Hyp), Hyp-Ara$_3$ (39% of total Hyp), Hyp-Ara$_4$ (3% of total Hyp), Hyp-Polysaccharide (37% of total Hyp).

C. The Ser-Pro-Pro-Pro-Pro Gene

The [SPPPP]$_n$ module was expressed using the following sequence:

```
GGA TCC TCA ACC CGG GCC TCA CCA [CCA CCA CCT TCA CCT CCA CCC CCA TCT  (SEQ ID NO: 234)
 G   S   S   T   R   A   S   P  [ P   P   P   S   P   P   P   P   S   (SEQ ID NO: 235)

CCA]₉ CCA CCA CCT TCC ATG GCA TTA TAG AGC TCG
 P ]₉  P   P   P   S   M   A  Stop Stop
```

The expressed the protein sequence had the following Hyp-glycoside profile: Hyp (7% of total Hyp), Hyp-Ara (2% of total Hyp), Hyp-Ara$_2$ (8% of total Hyp), Hyp-Ara$_3$ (52% of total Hyp), Hyp-Ara$_4$ (31% of total Hyp), Hyp-Polysaccharide (0% of total Hyp).

3. Monosaccharide and Glycosyl Linkage Analysis

Monosaccharide compositions and linkage analyses were determined at the Complex Carbohydrate Research Center, University of Georgia as described earlier. The results are shown in Table 12.

TABLE 12

Glycosyl Compositions of (Ser-Hyp)$_{32}$ - EGFP (GAGP)$_3$-EGFP, Native GAGP and Crude Gum Arabic Mol %

| Glycosyl Residue | (Ser-Hyp)$_{32}$- EGFP | (GAGP)$_3$- EGFP[a] | Native GAGP | Crude Gum Arabic |
|---|---|---|---|---|
| Ara | 28 | 23 | 36 | 28 |
| Gal | 45 | 49 | 46 | 37 |
| Rha | 8 | 8 | 10 | 13 |
| Xyl | 0 | 2 | 0 | 0 |

TABLE 12-continued

Glycosyl Compositions of (Ser-Hyp)$_{32}$ - EGFP (GAGP)$_3$-EGFP, Native GAGP and Crude Gum Arabic Mol %

| Glycosyl Residue | (Ser-Hyp)$_{32}$- EGFP | (GAGP)$_3$- EGFP[a] | Native GAGP | Crude Gum Arabic |
|---|---|---|---|---|
| GlcUA | 19 | 16 | 9 | 17 |
| Mann | 1 | 1 | 0 | 0 |

[a]values corrected for a small amount of glucose contamination.

Gal and Ara accounted for the bulk of the saccharides in both fusion proteins, with lesser amounts of Rha and GlcUA (Table 12); saccharide accounted for 58% (dw) of (Ser-Hyp)$_{32}$-EGFP and 48% (dw) of (GAGP)$_3$-EGFP. Methylation analyses indicated that 3- and 3,6-linked galactose species accounted for 50 mole % of the sugars in (Ser-Hyp)$_{32}$-EGFP and 46 mole % of (GAGP)$_3$-EGFP; 2-linked arabinofuranose (Ara (f) accounted for 1.6 and 3.1 mole % respectively; terminal Ara(f) accounted for 20 and 21 mole % respectively; 4-arabinopyranose or 5-Ara(f) accounted for 6 and 8% respectively; all rhamnose was terminal; and all GlcUA was 4-linked.

The sugar analysis data in Table 12 shows that both fusion glycoproteins had sugar compositions typical of AGPs: a galactose:arabinose molar ratio of ~2:1 with lesser amounts of glucuronic acid and rhamnose. The predominantly 3- and 3,6-linked galactose and terminal arabinofuranose determined by methylation analysis, was in keeping with a (-1,3-linked galactan backbone having sidechains of arabinose, glucuronic acid and rhamnose [Nothnagel, E. A. (1997) Int. Rev. Cytol. 174, 195-291]. The very low amount of 1,2-linked arabinose in (Ser-Hyp)$_{32}$-EGFP agreed with the absence of Hyp arabinosides while the presence of 1,2-linked arabinose in (GAGP)$_3$-EGFP agreed with the presence of Hyp arabinosides in its Hyp glycoside profile as they are known to be largely 1,2-linked [Sticher et al. (1993) Plant Physiol. 101, 1239-1247; Akiyama et al. (1980) Agric. Biol. Chem. 44, 2487-2489]. Thus, (GAGP)$_3$-EGFP contained both types of Hyp glycosylation consistent with the presence of a polypeptide having contiguous and non-contiguous Hyp as putative arabinosylation and polysaccharide addition sites, respectively.

With respect to the size of attached polysaccharide, Hyp glycoside profiles showed the molar ratio of Hyp-polysaccharide in each fusion glycoprotein (Table 11). This gives the number of (polysaccharide)-Hyp residues in each glycoprotein molecule. (e.g. Hyp-polysaccharide accounted for 100% of the Hyp glycosides in (Ser-Hyp)$_{32}$ i.e. 31-32 Hyp-polysaccharide). Glycoprotein size before and after deglycosylation gave an approximate size for the attached polysaccharide. The size of each fusion protein before and after deglycosylation was ~95-115 kDa and 34 kDa respectively for (Ser-Hyp)$_{32}$-EGFP (~71 kDa carbohydrate), and ~70-100 kDa and 34 kDa respectively for (GAGP)$_3$-EGFP (~51 kDa carbohydrate). Judging by the gene sequence (not shown) and FIG. 14, (Ser-Hyp)$_{32}$-EGFP contains ~31-32 Hyp residues, all noncontiguous, hence with an average polysaccharide size of 71 kDa/31=2.2-2.3 kDa which corresponds to 14-15 sugar residues (average sugar residue weight of 155 calculated from the sugar composition in Table 12) and is consistent with the empirical formula Gal$_6$ Ara$_3$ GlcA$_2$ Rha based on compositional data in Table 12. Similarly, (GAGP)$_3$-EGFP contains ~23-25 Hyp residues of which 62% (Table 11), or ~15 occur with polysaccharide attached. Hence the polysaccharide approximates 51 kDa/15=3.4 kDa corresponding to about 22 sugar residues, a modest overestimate as it includes arabinose from the Hyp arabinooligosaccharides.

The similarity of these fusion glycoproteins to native GAGP (Table 12) suggests a model for the Hyp-polysaccharide based on the general arabinogalactan structure [Akiyama et al. (1980) *Agric. Biol. Chem.* 44, 2487-2489; Aspinall & Knebl (1986) *Carbohyd. Res.* 157, 257-260; Defaye & Wong (1986) *Carbohydr. Res.* 150, 221-231] of a galactan core with small sidechains containing rhamnose, arabinose and glucuronic acid. Possibly larger arabinogalactan polysaccharide can be built up by repeated addition [Clarke et al. (1979) *Phytochem.* 18, 521-540; Bacic et al. (1987) *Carbohyd. Res.* 162, 85-93] of small ~12 residue motifs represented by the above empirical formula.

4. Hydroxyproline Assay of Secreted EGFP

Secreted EGFP, the product of the Sig-EGFP gene, was isolated by the Superose-12 fractionation. We removed EGFP from the fusion glycoproteins by overnight pronase digestion (1% ammonium bicarbonate, 5 mM CaCl$_2$; 27° C. 1:100 enzyme:substrate ratio) followed by isolation of EGFP by gel permeation chromatography as described above. After dialysis and freeze-drying, we assayed Hyp on 0.5 mg EGFP as described earlier. There was no Hyp in secreted EGFP or in EGFP removed from the fusion glycoproteins by pronase.

5. Anhydrous Hydrogen Fluoride (HF) Deglycosylation

We deglycosylated 4.5 mg each of (Ser-Hyp)$_{32}$-EGFP and (GAGP)$_3$-EGFP in anhydrous HF containing 10% dry methanol for 1 hr at 0° C. then quenched the reactions in ddH$_2$O. After deglycosylation of 4.5 mg of each fusion glycoprotein, we recovered 1 mg of deglycosylated (Ser-Hyp)$_{32}$-EGFP (i.e. ~23% weight recovery) and 2.2 mg deglycosylated (GAGP)$_3$-EGFP (i.e. ~50% recovery).

6. Protein and DNA Sequence Analysis

Protein sequence analysis was performed at the Michigan State University Macromolecular Facility on a 477-A Applied Biosystems Inc. gas phase sequencer. DNA sequencing was performed at the Guelph Molecular Supercentre, University of Guelph, Ontario, Canada. Edman degradation confirmed the gene sequences and identified which Pro residues had been hydroxylated to Hyp. In particular, N-terminal sequencing of both (Ser-Hyp)$_{32}$-EGFP and (GAGP)$_3$-EGFP (FIG. 14) verified the synthetic gene sequences and identified hydroxyproline residues. Occasional incomplete proline hydroxylation has been observed elsewhere [de Blanket al. (1993) *Plant Mol. Biol.* 22, 1167-1171] and may simply signify a prolyl hydroxylase with less than 100% fidelity.

The above data demonstrates that the repetitive Ser-Hyp motif directed the exclusive addition of arabinogalactan polysaccharide to Hyp in (Ser-Hyp)$_{32}$-EGFP while Hyp arabinosylation was correlated with the presence of contiguous Hyp motifs in (GAGP)$_3$-EGFP. Thus the O-Hyp glycosyltransferases of plants seem to resemble the O-Ser and O-Thr glycosyltransferases of animals in their multiplicity and ability to discriminate based on primary sequence and site clustering [Bacic et al. (1987) supra; Gerken et al. (1997) *J. Biol. Chem.* 272, 9709-9719].

Example 24

Assay of Emulsifying Activity and Emulsion Stabilizing Activity of GAGPs

This Example analyzes the emulsifying activity (EA) and emulsion stabilizing activity (ES) of recombinant (GAGP)$_3$-EGFP which was expressed in the medium of transformed tobacco cell cultures as described above (Example 23). These activities were compared with those for bovine serum albumin (BSA), crude gum arabic glycoprotein (crude GAGP) which was isolated from *Acacia senegal*, dialyzed gum arabic glycoprotein, and tobacco arabinogalactan-protein (AGP) which contains a mixture of at least four different arabinogalactan-proteins. In addition, this Example describes the emulsifying activity and emulsion stabilizing activity of (GAGP)$_3$-EGFP protein fractions which were fractionated on Superose-6 and reverse-phase columns (Example 23), as well as the effect of size and glycosylation of (GAGP)$_3$-EGFP on emulsifying activity and emulsion stabilizing activity: All GAGP emulsions used in Tables 14-17, infra, were prepared at a concentration of 0.5% (w/v).

The emulsifying activity and emulsion stabilizing activity were determined using orange oil (Sigma) following essentially the manufacturer's instructions. Freeze-dried glycoproteins were dissolved in 0.05 M phosphate buffer (pH 6.5) at a concentration of 0.5% (m/v). The aqueous solutions were combined with orange oil in a 60:40 (v/v) ratio. A 1 ml emulsion was prepared in a glass tube at 0° C. with a Sonic Dismembrator (Fisher Scientific) equipped with a Microtip probe. The amplitude value was set at 4 and mixing time was set to 1 min.

For the determination of emulsifying ability (EA), the emulsion was diluted serially with a solution containing 0.1 M NaCl and 0.1% SDS to give a final dilution of 1/1500. The optical density of the diluted emulsion was then determined in a 1-cm pathlength cuvette at a wavelength of 50 nm and defined as the emulsifying activity (EA). BSA was used as a positive control. Test samples which showed an emulsifying activity which was at least 10%, more preferably at least 50%, and most preferably at least 75% of the emulsifying activity of a BSA control are said to be "characterized by having emulsifying activity."

For emulsifying stability, the emulsion was stored vertically in a glass tube for 3 h at room temperature, then the optical density of 1:1500 dilution of the low phase of the stored sample was measured. Emulsifying stability (ES) was defined as the percentage optical density remaining after 2 hour of storage. BSA was used as a positive control. Test samples which showed an emulsion stabilizing activity which was at least 10%, more preferably at least 50%, and most preferably at least 75% of the emulsion stabilizing activity of a BSA control are said to be "characterized by having emulsion stabilizing activity."

To determine whether (GAGP)$_3$-EGFP had emulsifying activity and/or emulsion stabilizing activity, this glycoprotein was assayed as described above and its activities were compared with those for bovine serum albumin (BSA), crude gum arabic, dialyzed gum arabic, and tobacco AGP. The results are shown in Table 13, which demonstrates the emulsifying properties of native gum arabic when compared to BSA, the synthetic GAGP$_3$-EGFP, and native tobacco AGPs.

TABLE 13

Emulsions properties of crude Gum Arabic and other Materials[a]

| Materials | BSA (0.5%) | Crude GAGP (0.5%) | Crude GAGP (1.0%) | Dialyzed GAGP (0.5%) | Synthetic GAGP[b] (0.5%) | Tobacco AGP (0.5%) |
|---|---|---|---|---|---|---|
| EA | 0.801 | 0.102 | 0.472 | 0.146 | 0.007 | 0.035 |
| ES | 90.6% | 39.7% | 83.0% | 57.5% | 20.2% | 20.0% |

[a]Values in parentheses are of the concentration (wt %)
[b]Synthetic GAGP (i.e., GAGP$_3$-EGFP) was isolated from the medium of the recombinant tobacco cell culture. The fused GFP was knocked off by pronase digestion before emulsion property measurement.

In addition, different (GAGP)$_3$-EGFP fractions which were obtained from Superose-6 column fractionation were also assayed and the results are shown in Table 14 which demonstrates that fraction F-2, which contained native GAGP showed the highest emulsifying activity and emulsion stabilizing activity of all fractions tested. These results establish GAGP as the emulsifying component of gum arabic.

TABLE 14

Emulsion Properties of GAGP Protein Fractions separated by Superose-6 column

| Fractions | F-1 | F-2 | F-3 | F-4 | F-5 |
|---|---|---|---|---|---|
| EA | 0.442 | 0.558 | 0.299 | 0.081 | 0.019 |
| ES | 74.1% | 84.2% | 48.5% | 32.2% | 22.4% |

The F-2 fraction was further separated on Hydrophobic Interaction column (HIC). The F-2 fraction was dissolved in 4.2 M NaCl and injected onto the HIC column. The column was eluted, starting by 4.2 M NaCl, followed by 3.0 M NaCl, 2.0 M NaCl, 1.0 M NaCl, and distilled water. The resulting fractions were tested and the results are shown in Table 15, which demonstrates that F-2 contains GAGP which is characterized by having emulsifying activity and emulsion stabilizing activity. Table 15 also demonstrates that F-2 separates into four components which differ in hydrophobicity, with the 2.0M and 1.0M NaCl hydrolysates being good emulsifiers

TABLE 15

Emulsion Properties of F-2 Fractions Separated by Hydrophobic Interaction Column

| Fractions | 4.2M NaCl | | 3.0M NaCl | 2.0M NaCl | 1.0M NaCl | Distilled water |
|---|---|---|---|---|---|---|
| | 1 | 2 | | | | |
| EA | 0.076 | 0.284 | 0.475 | 0.710 | 0.670 | 0.04 |
| ES | 28% | 60.5% | 78.5% | 93.5% | 94.6% | 21.0% |

In order to determine the effect of the size of GAGPs on their emulsion activity and emulsion stabilizing activity, the F-2 fraction containing native GAGP was incubated in 0.2 N NaOH at 50° C. for 0.5 hr, 1.0 hr, 2.0 hr, 4.0 hr, and 8.0 hr and the emulsifying properties of each sample were determined as shown in Table 16.

TABLE 16

Emulsion Properties of Partially-deglycosylated F-2

| Samples | 0 hr | 0.5 hr | 1.0 hr | 2.0 hr | 4.0 hr | 8.0 hr |
|---|---|---|---|---|---|---|
| EA | 0.558 | 0.354 | 0.245 | 0.097 | 0.036 | 0.011 |
| ES | 84.2% | 61.2% | 41.5% | 23.2% | 0 | 0 |

The results in Table 16 demonstrate that both the emulsifying activity and emulsion stabilizing activity of GAGP decrease with decreasing GAGP size.

To determine whether the carbohydrate moiety of GAGPs affects their emulsion activity and emulsion stabilizing activity, the F-2 fraction was partially deglycosylated by anhydrous hydrogen fluoride (HF) as described above, and the emulsifying properties of the deglycosylated sample were determined. Deglycosylated F-2 fraction had an EA of 0.269, and an ES of 46.5%. These results demonstrate that the GAGP in the F-2 fraction lost most of its ability to emulsify, thus indicating the importance of the carbohydrate moiety of the GAGP for emulsification.

From the above, it should be clear that the present invention provides a new approach and solution to the problem of producing plant gums. The approach is not dependent on environmental factors and greatly simplifies production of a variety of naturally-occurring gums, as well as designer gums.

SEQUENCE LISTING

```
<160> NUMBER OF SEQ ID NOS: 236

<210> SEQ ID NO 1
<211> LENGTH: 19
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(5)
<223> OTHER INFORMATION: The Proline at these positions is a
      hydroxyproline.
<221> NAME/KEY: SITE
<222> LOCATION: (8)..(8)
```

```
<223> OTHER INFORMATION: The Proline at this position is a
      hydroxyproline.
<221> NAME/KEY: SITE
<222> LOCATION: (10)..(10)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.
<221> NAME/KEY: SITE
<222> LOCATION: (14)..(16)
<223> OTHER INFORMATION: The Proline at these positions is a
      hydroxyproline.

<400> SEQUENCE: 1

Ser Pro Pro Pro Pro Leu Ser Pro Ser Pro Thr Pro Thr Pro Pro Pro
1               5                   10                  15

Gly Pro His

<210> SEQ ID NO 2
<211> LENGTH: 19
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(4)
<223> OTHER INFORMATION: The Proline at these positions is a
      hydroxyproline.
<221> NAME/KEY: SITE
<222> LOCATION: (8)..(8)
<223> OTHER INFORMATION: The Proline at this position is a
      hydroxyproline.
<221> NAME/KEY: SITE
<222> LOCATION: (10)..(10)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.
<221> NAME/KEY: SITE
<222> LOCATION: (14)..(16)
<223> OTHER INFORMATION: The Proline at these positions is a
      hydroxyproline.

<400> SEQUENCE: 2

Ser Pro Pro Pro Thr Leu Ser Pro Ser Pro Thr Pro Thr Pro Pro Pro
1               5                   10                  15

Gly Pro His

<210> SEQ ID NO 3
<211> LENGTH: 5
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(5)
<223> OTHER INFORMATION: The Proline at these positions is a
      hydroxyproline.

<400> SEQUENCE: 3

Ser Pro Pro Pro Pro
1               5

<210> SEQ ID NO 4
<211> LENGTH: 5
```

```
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(2)
<223> OTHER INFORMATION: The Proline at this position is a
      hydroxyproline.

<400> SEQUENCE: 4

Pro Pro Val Tyr Lys
1               5

<210> SEQ ID NO 5
<211> LENGTH: 5
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (1)..(1)
<223> OTHER INFORMATION: Xaa can be Thr, Glu, hydroxyproline, Pro, His,
      and Ile.
<221> NAME/KEY: SITE
<222> LOCATION: (2)..(2)
<223> OTHER INFORMATION: The Proline at this position is a
      hydroxyproline.

<400> SEQUENCE: 5

Xaa Pro Val Tyr Lys
1               5

<210> SEQ ID NO 6
<211> LENGTH: 5
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(2)
<223> OTHER INFORMATION: The Proline at this position is a
      hydroxyproline.
<221> NAME/KEY: SITE
<222> LOCATION: (4)..(4)
<223> OTHER INFORMATION: Xaa can be Thr, Glu, hydroxyproline, Pro, His
      and Ile.

<400> SEQUENCE: 6

Pro Pro Val Xaa Lys
1               5

<210> SEQ ID NO 7
<211> LENGTH: 5
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (3)..(3)
<223> OTHER INFORMATION: Xaa can be Thr, Glu, hydroxyproline, Pro, His
      and Ile.

<400> SEQUENCE: 7

Pro Pro Xaa Tyr Lys
1               5

<210> SEQ ID NO 8
```

```
<211> LENGTH: 5
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (3)..(3)
<223> OTHER INFORMATION: Xaa can be Thr, Glu, hydroxyproline, Pro, His
      and Ile.
<221> NAME/KEY: SITE
<222> LOCATION: (5)..(5)
<223> OTHER INFORMATION: Xaa can be Thr, Glu, hydroxyproline, Pro, His
      and Ile.

<400> SEQUENCE: 8

Pro Pro Xaa Tyr Xaa
1               5

<210> SEQ ID NO 9
<211> LENGTH: 4
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (1)..(1)
<223> OTHER INFORMATION: Xaa can be Thr, Glu, hydroxyproline, Pro, His
      and Ile.
<221> NAME/KEY: SITE
<222> LOCATION: (3)..(3)
<223> OTHER INFORMATION: Xaa can be Thr, Glu, hydroxyproline, Pro, His
      and Ile.

<400> SEQUENCE: 9

Xaa Pro Xaa Pro
1

<210> SEQ ID NO 10
<211> LENGTH: 30
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 10
ccaccacctt cacctccacc cccatctcca                                    30

<210> SEQ ID NO 11
<211> LENGTH: 30
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 11
tcaccatcac catctccttc gccatcaccc                                    30

<210> SEQ ID NO 12
<211> LENGTH: 123
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 12
```

```
gctggatcct caacccgggc ctcaccacca ccaccttcac ctccaccccc atctccacca      60
ccaccttcac ctccaccccc atctccacca ccaccttcac cggtcgcccg gaattcacca     120
ccc                                                                   123
```

<210> SEQ ID NO 13
<211> LENGTH: 12
<212> TYPE: PRT
<213> ORGANISM: Artificial/Unknown
<220> FEATURE:
<221> NAME/KEY: misc_feature
<223> OTHER INFORMATION: Synthetic

<400> SEQUENCE: 13

```
Ser Pro Ser Pro Thr Pro Thr Pro Pro Pro Gly Pro
1               5                   10
```

<210> SEQ ID NO 14
<211> LENGTH: 34
<212> TYPE: PRT
<213> ORGANISM: Artificial/Unknown
<220> FEATURE:
<221> NAME/KEY: misc_feature
<223> OTHER INFORMATION: Synthetic

<400> SEQUENCE: 14

```
Met Gly Lys Met Ala Ser Leu Phe Ala Thr Phe Leu Val Val Leu Val
1               5                   10                  15

Ser Leu Ser Leu Ala Gln Thr Thr Arg Val Val Pro Val Ala Ser Ser
            20                  25                  30

Ala Pro
```

<210> SEQ ID NO 15
<211> LENGTH: 4
<212> TYPE: PRT
<213> ORGANISM: Artificial/Unknown
<220> FEATURE:
<221> NAME/KEY: misc_feature
<223> OTHER INFORMATION: Synthetic

<400> SEQUENCE: 15

```
Gly Ala Gly Pro
1
```

<210> SEQ ID NO 16
<211> LENGTH: 18
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(5)
<223> OTHER INFORMATION: The Proline at these positions is a
      hydroxyproline.
<221> NAME/KEY: SITE
<222> LOCATION: (8)..(8)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.
<221> NAME/KEY: SITE
<222> LOCATION: (14)..(15)
<223> OTHER INFORMATION: The Proline at these positions is a
      hydroxyproline.

<400> SEQUENCE: 16

```
Ser Pro Pro Pro Leu Ser Pro Ser Leu Thr Thr Pro Thr Pro Pro Leu
1               5                   10                  15

Gly Pro

<210> SEQ ID NO 17
<211> LENGTH: 18
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(5)
<223> OTHER INFORMATION: The Proline at these positions is a
      hydroxyproline.
<221> NAME/KEY: SITE
<222> LOCATION: (8)..(8)
<223> OTHER INFORMATION: The Proline at this position is a
      hydroxyproline.
<221> NAME/KEY: SITE
<222> LOCATION: (10)..(10)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.
<221> NAME/KEY: SITE
<222> LOCATION: (14)..(15)
<223> OTHER INFORMATION: The Proline at these positions is a
      hydroxyproline.

<400> SEQUENCE: 17

Ser Pro Pro Pro Pro Leu Ser Pro Ser Pro Thr Pro Thr Pro Pro Leu
1               5                   10                  15

Gly Pro

<210> SEQ ID NO 18
<211> LENGTH: 23
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(4)
<223> OTHER INFORMATION: The Proline at these positions is a
      hydroxyproline.
<221> NAME/KEY: SITE
<222> LOCATION: (8)..(8)
<223> OTHER INFORMATION: The Proline at this position is a
      hydroxyproline.
<221> NAME/KEY: SITE
<222> LOCATION: (10)..(10)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.
<221> NAME/KEY: SITE
<222> LOCATION: (14)..(16)
<223> OTHER INFORMATION: The Proline at these positions is a
      hydroxyproline.
<221> NAME/KEY: SITE
<222> LOCATION: (21)..(23)
<223> OTHER INFORMATION: The Proline at these positions is a
      hydroxyproline.

<400> SEQUENCE: 18

Ser Pro Pro Pro Thr Leu Ser Pro Ser Pro Thr Pro Thr Pro Pro Pro
1               5                   10                  15
```

```
Gly Pro His Ser Pro Pro Pro
            20

<210> SEQ ID NO 19
<211> LENGTH: 19
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(4)
<223> OTHER INFORMATION: The Proline at these positions is a
      hydroxyproline.
<221> NAME/KEY: SITE
<222> LOCATION: (8)..(8)
<223> OTHER INFORMATION: The Proline at this position is a
      hydroxyproline.
<221> NAME/KEY: SITE
<222> LOCATION: (10)..(10)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.
<221> NAME/KEY: SITE
<222> LOCATION: (14)..(15)
<223> OTHER INFORMATION: The Proline at these positions is a
      hydroxyproline.

<400> SEQUENCE: 19

Ser Pro Pro Pro Ser Leu Ser Pro Ser Pro Thr Pro Thr Pro Pro Thr
1               5                   10                  15

Gly Pro His

<210> SEQ ID NO 20
<211> LENGTH: 13
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(2)
<223> OTHER INFORMATION: The Proline at this position is a
      hydroxyproline.
<221> NAME/KEY: SITE
<222> LOCATION: (4)..(4)
<223> OTHER INFORMATION: The Proline at this position is a
      hydroxyproline.
<221> NAME/KEY: SITE
<222> LOCATION: (6)..(6)
<223> OTHER INFORMATION: The Proline at this position is a
      hydroxyproline.
<221> NAME/KEY: SITE
<222> LOCATION: (8)..(10)
<223> OTHER INFORMATION: The Proline at these positions is a
      hydroxyproline.

<400> SEQUENCE: 20

Ser Pro Ser Pro Thr Pro Thr Pro Pro Pro Gly Pro His
1               5                   10

<210> SEQ ID NO 21
<211> LENGTH: 13
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
```

```
<222> LOCATION: (2)..(2)
<223> OTHER INFORMATION: The Proline at this position is a
      hydroxyproline.
<221> NAME/KEY: SITE
<222> LOCATION: (4)..(4)
<223> OTHER INFORMATION: The Proline at this position is a
      hydroxyproline.
<221> NAME/KEY: SITE
<222> LOCATION: (6)..(6)
<223> OTHER INFORMATION: The Proline at this position is a
      hydroxyproline.
<221> NAME/KEY: SITE
<222> LOCATION: (8)..(9)
<223> OTHER INFORMATION: The Proline at these positions is a
      hydroxyproline.

<400> SEQUENCE: 21

Ser Pro Ser Pro Ala Pro Thr Pro Pro Leu Gly Pro His
1               5                   10

<210> SEQ ID NO 22
<211> LENGTH: 13
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(2)
<223> OTHER INFORMATION: The Proline at this position is a
      hydroxyproline.
<221> NAME/KEY: SITE
<222> LOCATION: (6)..(6)
<223> OTHER INFORMATION: The Proline at this position is a
      hydroxyproline.
<221> NAME/KEY: SITE
<222> LOCATION: (8)..(9)
<223> OTHER INFORMATION: The Proline at these positions is a
      hydroxyproline.

<400> SEQUENCE: 22

Ser Pro Leu Pro Thr Pro Thr Pro Pro Leu Gly Pro His
1               5                   10

<210> SEQ ID NO 23
<211> LENGTH: 13
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(2)
<223> OTHER INFORMATION: The Proline at this position is a
      hydroxyproline.
<221> NAME/KEY: SITE
<222> LOCATION: (4)..(4)
<223> OTHER INFORMATION: The Proline at this position is a
      hydroxyproline.
<221> NAME/KEY: SITE
<222> LOCATION: (6)..(6)
<223> OTHER INFORMATION: The Proline at this position is a
      hydroxyproline.
<221> NAME/KEY: SITE
<222> LOCATION: (8)..(9)
<223> OTHER INFORMATION: The Proline at these positions is a
      hydroxyproline.

<400> SEQUENCE: 23

Ser Pro Ser Pro Thr Pro Thr Pro Pro Leu Gly Pro His
1               5                   10

<210> SEQ ID NO 24
```

```
<211> LENGTH: 13
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(3)
<223> OTHER INFORMATION: The Proline at these positions is a
      hydroxyproline.
<221> NAME/KEY: SITE
<222> LOCATION: (6)..(6)
<223> OTHER INFORMATION: The Proline at this position is a
      hydroxyproline.
<221> NAME/KEY: SITE
<222> LOCATION: (8)..(9)
<223> OTHER INFORMATION: The Proline at these positions is a
      hydroxyproline.

<400> SEQUENCE: 24

Ser Pro Pro Leu Thr Pro Thr Pro Pro Leu Leu Pro His
1               5                   10

<210> SEQ ID NO 25
<211> LENGTH: 19
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(2)
<223> OTHER INFORMATION: The Proline at this position is a
      hydroxyproline.
<221> NAME/KEY: SITE
<222> LOCATION: (8)..(8)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.
<221> NAME/KEY: SITE
<222> LOCATION: (14)..(16)
<223> OTHER INFORMATION: The Proline at these positions is a
      hydroxyproline.

<400> SEQUENCE: 25

Ser Pro Leu Pro Thr Leu Ser Pro Leu Pro Ala Pro Thr Pro Pro Pro
1               5                   10                  15

Gly Pro His

<210> SEQ ID NO 26
<211> LENGTH: 19
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(2)
<223> OTHER INFORMATION: The Proline at this position is a
      hydroxyproline.
<221> NAME/KEY: SITE
<222> LOCATION: (8)..(8)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.
<221> NAME/KEY: SITE
<222> LOCATION: (14)..(16)
<223> OTHER INFORMATION: The Proline at these positions is a
```

```
      hydroxyproline.

<400> SEQUENCE: 26

Ser Pro Leu Pro Thr Leu Ser Pro Leu Pro Thr Pro Thr Pro Pro Pro
1               5                   10                  15

Gly Pro His

<210> SEQ ID NO 27
<211> LENGTH: 19
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(4)
<223> OTHER INFORMATION: The Proline at these positions is a
      hydroxyproline.
<221> NAME/KEY: SITE
<222> LOCATION: (8)..(8)
<223> OTHER INFORMATION: The Proline at this position is a
      hydroxyproline.
<221> NAME/KEY: SITE
<222> LOCATION: (10)..(10)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.
<221> NAME/KEY: SITE
<222> LOCATION: (14)..(15)
<223> OTHER INFORMATION: The Proline at these positions is a
      hydroxyproline.

<400> SEQUENCE: 27

Ser Pro Pro Pro Thr Leu Ser Pro Ser Pro Thr Pro Thr Pro Pro Leu
1               5                   10                  15

Gly Pro His

<210> SEQ ID NO 28
<211> LENGTH: 19
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(5)
<223> OTHER INFORMATION: The Proline at these positions is a
      hydroxyproline.
<221> NAME/KEY: SITE
<222> LOCATION: (8)..(8)
<223> OTHER INFORMATION: The Proline at this position is a
      hydroxyproline.
<221> NAME/KEY: SITE
<222> LOCATION: (10)..(10)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.
<221> NAME/KEY: SITE
<222> LOCATION: (14)..(15)
<223> OTHER INFORMATION: The Proline at these positions is a
      hydroxyproline.

<400> SEQUENCE: 28

Ser Pro Pro Pro Pro Leu Ser Pro Ser Pro Thr Pro Thr Pro Pro Leu
1               5                   10                  15
```

Gly Pro His

```
<210> SEQ ID NO 29
<211> LENGTH: 12
<212> TYPE: PRT
<213> ORGANISM: Artificial/Unknown
<220> FEATURE:
<221> NAME/KEY: misc_feature
<223> OTHER INFORMATION: Synthetic

<400> SEQUENCE: 29

Ala Gly Ser Ser Thr Arg Ala Ser Pro Pro Pro Pro
1               5                   10

<210> SEQ ID NO 30
<211> LENGTH: 27
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 30
gctggatcct caacccgggc ctcacca                                              27

<210> SEQ ID NO 31
<211> LENGTH: 36
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 31
aggtggtggt ggtgagcccc gggttgagga tccagc                                    36

<210> SEQ ID NO 32
<211> LENGTH: 12
<212> TYPE: PRT
<213> ORGANISM: Artificial/Unknown
<220> FEATURE:
<221> NAME/KEY: misc_feature
<223> OTHER INFORMATION: Synthetic

<400> SEQUENCE: 32

Pro Pro Pro Ser Pro Val Ala Arg Asn Ser Pro Pro
1               5                   10

<210> SEQ ID NO 33
<211> LENGTH: 36
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 33
ccaccacctt caccggtcgc ccggaattca ccaccc                                    36

<210> SEQ ID NO 34
<211> LENGTH: 27
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 34
```

```
gggtggtgaa ttccgggcga ccggtga                                          27

<210> SEQ ID NO 35
<211> LENGTH: 24
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 35
ccaccacctt aatagagctc cccc                                             24

<210> SEQ ID NO 36
<211> LENGTH: 15
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 36
gggggagctc tatta                                                       15

<210> SEQ ID NO 37
<211> LENGTH: 10
<212> TYPE: PRT
<213> ORGANISM: Artificial/Unknown
<220> FEATURE:
<221> NAME/KEY: misc_feature
<223> OTHER INFORMATION: Synthetic

<400> SEQUENCE: 37

Pro Pro Pro Ser Pro Pro Pro Pro Ser Pro
1               5                   10

<210> SEQ ID NO 38
<211> LENGTH: 30
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 38
ccaccacctt cacctccacc cccatctcca                                       30

<210> SEQ ID NO 39
<211> LENGTH: 30
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 39
aggtggtggt ggagatgggg gtggaggtga                                       30

<210> SEQ ID NO 40
<211> LENGTH: 11
<212> TYPE: PRT
<213> ORGANISM: Artificial/Unknown
<220> FEATURE:
<221> NAME/KEY: misc_feature
<223> OTHER INFORMATION: Synthetic

<400> SEQUENCE: 40
```

```
Ala Ala Gly Ser Ser Thr Arg Ala Ser Pro Ser
1               5                   10
```

<210> SEQ ID NO 41
<211> LENGTH: 24
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 41
gctgccggat cctcaacccg ggcc                                          24

<210> SEQ ID NO 42
<211> LENGTH: 33
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 42
tgacggtgag gcccggggttg aggatccggc agc                               33

<210> SEQ ID NO 43
<211> LENGTH: 11
<212> TYPE: PRT
<213> ORGANISM: Artificial/Unknown
<220> FEATURE:
<221> NAME/KEY: misc_feature
<223> OTHER INFORMATION: Synthetic

<400> SEQUENCE: 43

```
Ser Pro Ser Pro Val Ala Arg Asn Ser Pro Pro
1               5                   10
```

<210> SEQ ID NO 44
<211> LENGTH: 33
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 44
tcaccctcac cggtcgcccg gaattcacca ccc                                33

<210> SEQ ID NO 45
<211> LENGTH: 24
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 45
gggtggtgaa ttccgggcga ccgg                                          24

<210> SEQ ID NO 46
<211> LENGTH: 24
<212> TYPE: DNA
<213> ORGANISM: Artificial/Unknown
<220> FEATURE:
<221> NAME/KEY: misc_feature
<223> OTHER INFORMATION: Synthetic

```
<400> SEQUENCE: 46
tcaccctcat aatagagctc cccc                                          24

<210> SEQ ID NO 47
<211> LENGTH: 15
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 47
gggggagctc tatta                                                    15

<210> SEQ ID NO 48
<211> LENGTH: 19
<212> TYPE: PRT
<213> ORGANISM: Artificial/Unknown
<220> FEATURE:
<221> NAME/KEY: misc_feature
<223> OTHER INFORMATION: Synthetic

<400> SEQUENCE: 48

Ser Pro Ser Pro Thr Pro Thr Pro Pro Pro Gly Pro His Ser Pro Pro
1               5                   10                  15
Pro Thr Leu

<210> SEQ ID NO 49
<211> LENGTH: 57
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 49
tcaccctcac caactcctac cccaccacct ggtccacact caccaccacc aacattg      57

<210> SEQ ID NO 50
<211> LENGTH: 57
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 50
tgagggtgac aatgttggtg gtggtgagtg tggaccaggt ggtggggtag gagttgg      57

<210> SEQ ID NO 51
<211> LENGTH: 11
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (8)..(8)
<223> OTHER INFORMATION: The Proline at this position is a
      hydroxyproline.

<400> SEQUENCE: 51

Val Lys Pro Tyr His Pro Thr Pro Val Tyr Lys
1               5                   10

<210> SEQ ID NO 52
```

<210> SEQ ID NO 52
<211> LENGTH: 30
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 52
tcaccctcac catctccttc gccatcaccc                                    30

<210> SEQ ID NO 53
<211> LENGTH: 30
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 53
tgagggtgag ggtgatggcg aaggagatgg                                    30

<210> SEQ ID NO 54
<211> LENGTH: 30
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 54
gctccagcac ctgccccagc ccctgcacca                                    30

<210> SEQ ID NO 55
<211> LENGTH: 21
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 55
tggtgcaggg gctggggcag g                                             21

<210> SEQ ID NO 56
<211> LENGTH: 21
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 56
gctgccggat cctcaacccg g                                             21

<210> SEQ ID NO 57
<211> LENGTH: 30
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 57
tgctggagcc cgggttgagg atccggcagc                                    30

<210> SEQ ID NO 58
<211> LENGTH: 33

```
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 58
gctccagcac cggtcgcccg gaattcacca ccc                              33

<210> SEQ ID NO 59
<211> LENGTH: 24
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 59
gggtggtgaa ttccgggcga ccgg                                       24

<210> SEQ ID NO 60
<211> LENGTH: 24
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 60
gctccagcat aatagagctc cccc                                       24

<210> SEQ ID NO 61
<211> LENGTH: 15
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 61
gggggagctc tatta                                                 15

<210> SEQ ID NO 62
<211> LENGTH: 42
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 62
acaccaaccc ctactcccac gccaacacct acacccactc ca                   42

<210> SEQ ID NO 63
<211> LENGTH: 42
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 63
ggttggtgtt ggagtgggtc taggtgttgg cgtgggagta gg                   42

<210> SEQ ID NO 64
<211> LENGTH: 21
<212> TYPE: DNA
```

```
<213> ORGANISM: Artificial/Unknown
<220> FEATURE:
<221> NAME/KEY: misc_feature
<223> OTHER INFORMATION: Synthetic

<400> SEQUENCE: 64
gctgccggat cctcaacccg g                                              21

<210> SEQ ID NO 65
<211> LENGTH: 30
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 65
ggttggtgtc cgggttgagg atccggcagc                                     30

<210> SEQ ID NO 66
<211> LENGTH: 33
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 66
acaccaaccc cggtcgcccg gaattcacca ccc                                 33

<210> SEQ ID NO 67
<211> LENGTH: 24
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 67
gggtggtgaa ttccgggcga ccgg                                           24

<210> SEQ ID NO 68
<211> LENGTH: 24
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 68
acaccaacct aatagagctc cccc                                           24

<210> SEQ ID NO 69
<211> LENGTH: 15
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 69
gggggagctc tatta                                                     15

<210> SEQ ID NO 70
<211> LENGTH: 45
<212> TYPE: DNA
<213> ORGANISM: Artificial/Unknown
```

<220> FEATURE:
<221> NAME/KEY: misc_feature
<223> OTHER INFORMATION: Synthetic

<400> SEQUENCE: 70
ccaccatcac caccctctcc tccatcaccc ccatccccac catca      45

<210> SEQ ID NO 71
<211> LENGTH: 45
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 71
tgatggtggt gatggtgggg atgggggtga tggaggagag ggtgg      45

<210> SEQ ID NO 72
<211> LENGTH: 24
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 72
gctgccggat cctcaacccg ggcc      24

<210> SEQ ID NO 73
<211> LENGTH: 33
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 73
tgatggtggg gcccggggttg aggatccggc agc      33

<210> SEQ ID NO 74
<211> LENGTH: 33
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 74
ccaccatcac cggtcgcccg gaattcacca ccc      33

<210> SEQ ID NO 75
<211> LENGTH: 24
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 75
gggtggtgaa ttccgggcga ccgg      24

<210> SEQ ID NO 76
<211> LENGTH: 24
<212> TYPE: DNA
<213> ORGANISM: Artificial/Unknown
<220> FEATURE:

<221> NAME/KEY: misc_feature
<223> OTHER INFORMATION: Synthetic

<400> SEQUENCE: 76
ccaccatcat aatagagctc cccc                                              24

<210> SEQ ID NO 77
<211> LENGTH: 15
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 77
gggggagctc tatta                                                        15

<210> SEQ ID NO 78
<211> LENGTH: 48
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 78
ccaccacctt caccacctcc atctccccca ccttcccctc caccatca                    48

<210> SEQ ID NO 79
<211> LENGTH: 48
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 79
aggtggtggt gatggtggag gggaaggtgg gggagatgga ggtggtga                    48

<210> SEQ ID NO 80
<211> LENGTH: 24
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 80
gctggatcct caacccgggc ctca                                              24

<210> SEQ ID NO 81
<211> LENGTH: 33
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 81
aggtggtggt gaggcccggg ttgaggatcc agc                                    33

<210> SEQ ID NO 82
<211> LENGTH: 36
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 82
ccaccacctt caccggtcgc ccggaattca ccaccc                      36

<210> SEQ ID NO 83
<211> LENGTH: 27
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 83
gggtggtgaa ttccgggcga ccggtga                                27

<210> SEQ ID NO 84
<211> LENGTH: 24
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 84
ccaccacctt aatagagctc cccc                                   24

<210> SEQ ID NO 85
<211> LENGTH: 15
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 85
gggggagctc tatta                                             15

<210> SEQ ID NO 86
<211> LENGTH: 42
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 86
ccaccacctt caccctctcc acctccacca tctccgtcac ca               42

<210> SEQ ID NO 87
<211> LENGTH: 42
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 87
aggtggtggt ggtgacggag atggtggagg tggagagggt ga               42

<210> SEQ ID NO 88
<211> LENGTH: 48
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 88 ccaccaccttt cacccccatc tccacctcca ccatctccac cgtcacca        48

<210> SEQ ID NO 89
<211> LENGTH: 48
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 89
aggtggtggt ggtgacggtg gagatggtgg aggtggagat gggggtga        48

<210> SEQ ID NO 90
<211> LENGTH: 60
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 90
ccaccaccta ctcccgttta caaatcacca ccaccaccta ctcccgttta caaatcacca    60

<210> SEQ ID NO 91
<211> LENGTH: 60
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 91
aggtggtggt ggtgatttgt aaacgggagt aggtggtggt ggtgatttgt aaacgggagt    60

<210> SEQ ID NO 92
<211> LENGTH: 48
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 92
ccaccacctg tcaagcctta ccaccccact cccgtttttc tttcacca        48

<210> SEQ ID NO 93
<211> LENGTH: 48
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 93
aggtggtggt ggtgaaagaa aaacgggagt ggggtggtaa ggcttgac        48

<210> SEQ ID NO 94
<211> LENGTH: 48
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 94
ccaccacctg tcttaccttt ccaccccact cccgtttaca aatcacca          48

<210> SEQ ID NO 95
<211> LENGTH: 48
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 95
aggtggtggt ggtgatttgt aaacgggagt ggggtggaaa ggtaagac          48

<210> SEQ ID NO 96
<211> LENGTH: 21
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 96
ggccgcgagc tccagcacgg g                                      21

<210> SEQ ID NO 97
<211> LENGTH: 17
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 97
cccgtgctgg agctcgc                                           17

<210> SEQ ID NO 98
<211> LENGTH: 121
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 98
gatccgcaat gggaaaaatg gcttctctat ttgccacatt tttagtggtt ttagtgtcac    60
ttagcttagc acaaacaacc cgggtaccgg tcgccaccat ggtgtaaagc ggccgcgagc   120
t                                                                  121

<210> SEQ ID NO 99
<211> LENGTH: 113
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 99
cgcggccgct ttacaccatg gtggcgaccg gtacccgggt tgtttgtgct aagctaagtg    60
acactaaaac cactaaaaat gtggcaaata gagaagccat ttttcccatt gcg          113

<210> SEQ ID NO 100
<211> LENGTH: 19
<212> TYPE: PRT

<213> ORGANISM: Artificial/Unknown
<220> FEATURE:
<221> NAME/KEY: misc_feature
<223> OTHER INFORMATION: Synthetic

<400> SEQUENCE: 100

Ser Pro Ser Pro Thr Pro Thr Ala Pro Pro Gly Pro His Ser Pro Pro
1               5                   10                  15

Pro Thr Leu

<210> SEQ ID NO 101
<211> LENGTH: 57
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 101
tcaccctcac caactcctac cgcaccacct ggtccacact ctccaccacc aacattg      57

<210> SEQ ID NO 102
<211> LENGTH: 57
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 102
caatgttggt ggtggagagt gtggaccagg tggtgcggta ggagttggtg agggtga      57

<210> SEQ ID NO 103
<211> LENGTH: 19
<212> TYPE: PRT
<213> ORGANISM: Artificial/Unknown
<220> FEATURE:
<221> NAME/KEY: misc_feature
<223> OTHER INFORMATION: Synthetic

<400> SEQUENCE: 103

Ser Pro Ser Pro Thr Pro Thr Ala Pro Pro Gly Pro His Ser Pro Pro
1               5                   10                  15

Pro Ser Leu

<210> SEQ ID NO 104
<211> LENGTH: 57
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 104
tcaccctcac caactcctac cgcaccacct ggtccacact ctccaccacc atcattg      57

<210> SEQ ID NO 105
<211> LENGTH: 57
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 105
caatgatggt ggtggagagt gtggaccagg tggtgcggta ggagttggtg agggtga      57

<210> SEQ ID NO 106
<211> LENGTH: 279
<212> TYPE: DNA
<213> ORGANISM: Artificial/Unknown
<220> FEATURE:
<221> NAME/KEY: misc_feature
<223> OTHER INFORMATION: Synthetic
<221> NAME/KEY: misc_feature
<223> OTHER INFORMATION: The sequence encoding Green Fluorescent Protein
      (GFP) was linked to the 3' end of the polynucleotide sequence

<400> SEQUENCE: 106
ggatccgcaa tgggaaaaat ggcttctcta tttgccacat ttttagtcgt tttagtgtca    60
cttagcttag cacaaacaac ccgggactca ccctcaccaa ctcctaccgc accacctggt   120
ccacactctc caccaccaac attgtcaccc tcaccaactc ctaccgcacc acctggtcca   180
cactcaccac caccaacatt gtcaccctca ccaactccta ccgcaccacc tggtccacac   240
tcaccaccac catcattgtc accctcaccg gtcgccacc                          279

<210> SEQ ID NO 107
<211> LENGTH: 88
<212> TYPE: PRT
<213> ORGANISM: Artificial/Unknown
<220> FEATURE:
<221> NAME/KEY: misc_feature
<223> OTHER INFORMATION: Synthetic

<400> SEQUENCE: 107

Met Gly Lys Met Ala Ser Leu Phe Ala Thr Phe Leu Val Val Leu Val
1               5                   10                  15

Ser Leu Ser Leu Ala Gln Thr Thr Arg Asp Ser Pro Ser Pro Thr Pro
            20                  25                  30

Thr Ala Pro Pro Gly Pro His Ser Pro Pro Thr Leu Ser Pro Ser
        35                  40                  45

Pro Thr Pro Thr Ala Pro Pro Gly Pro His Ser Pro Pro Thr Leu
    50                  55                  60

Ser Pro Ser Pro Thr Pro Thr Ala Pro Pro Gly Pro His Ser Pro Pro
65                  70                  75                  80

Pro Ser Leu Ser Pro Ser Pro Val
                85

<210> SEQ ID NO 108
<211> LENGTH: 13
<212> TYPE: PRT
<213> ORGANISM: Artificial/Unknown
<220> FEATURE:
<221> NAME/KEY: misc_feature
<223> OTHER INFORMATION: Synthetic

<400> SEQUENCE: 108

Ser Pro Ser Pro Ser Pro Ser Pro Ser Pro Ser Pro Ser
1               5                   10

<210> SEQ ID NO 109
<211> LENGTH: 30
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 109
tcaccctcac catctccttc gccatcaccc                                    30

<210> SEQ ID NO 110
<211> LENGTH: 30
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 110
tgagggtgag ggtgatggcg aaggagatgg                                    30

<210> SEQ ID NO 111
<211> LENGTH: 288
<212> TYPE: DNA
<213> ORGANISM: Artificial/Unknown
<220> FEATURE:
<221> NAME/KEY: misc_feature
<223> OTHER INFORMATION: Synthetic
<221> NAME/KEY: misc_feature
<223> OTHER INFORMATION: The sequence encoding Green Fluorescent Protein
      (GFP) was linked to the 3' end of the polynucleotide sequence

<400> SEQUENCE: 111
ggatccgcaa tgggaaaaat ggcttctcta tttgccacat ttttagtggt tttagtgtca    60
cttagcttag cacaaacaac ccgggcctca ccctcaccat ctccttcgcc atcaccctca   120
ccctcaccat ctccttcgcc atcaccctca ccctcaccat ctccttcgcc atcaccctca   180
ccctcaccat ctccttcgcc atcaccctca ccctcaccat ctccttcgcc atcaccctca   240
ccctcaccat ctccttcgcc atcaccctca ccctcaccgg tcgccacc               288

<210> SEQ ID NO 112
<211> LENGTH: 30
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 112
tcaccctcac catctccttc gccatcaccc                                    30

<210> SEQ ID NO 113
<211> LENGTH: 30
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 113
tgagggtgag ggtgatggcg aaggagatgg                                    30

<210> SEQ ID NO 114
<211> LENGTH: 10
<212> TYPE: PRT
<213> ORGANISM: Artificial/Unknown
<220> FEATURE:
<221> NAME/KEY: misc_feature
<223> OTHER INFORMATION: Synthetic

<400> SEQUENCE: 114

Ser Pro Ser Pro Ser Pro Ser Pro Ser Pro
1               5                   10

```
<210> SEQ ID NO 115
<211> LENGTH: 57
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 115
tcaccctcac caactcctac cgcaccacct ggtccacact caccaccacc aacattg        57

<210> SEQ ID NO 116
<211> LENGTH: 57
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 116
tgagggtgac aatgttggtg gtggtgagtg tggaccaggt ggtgcggtag gagttgg        57

<210> SEQ ID NO 117
<211> LENGTH: 19
<212> TYPE: PRT
<213> ORGANISM: Artificial/Unknown
<220> FEATURE:
<221> NAME/KEY: misc_feature
<223> OTHER INFORMATION: Synthetic

<400> SEQUENCE: 117

Ser Pro Ser Pro Thr Pro Thr Ala Pro Pro Gly Pro His Ser Pro Pro
1               5                   10                  15

Pro Thr Leu

<210> SEQ ID NO 118
<211> LENGTH: 87
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 118
gctgccggat ccgcaatggg aaaaatggct tctctatttg ccacattttt agtggtttta    60
gtgtcactta gcttagcaca aacaacc                                        87

<210> SEQ ID NO 119
<211> LENGTH: 66
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 119
cccccgtctc gacgccagcg gtactacccg ggttgtttgt gctaagctaa gtgacactaa    60
aaccac                                                               66

<210> SEQ ID NO 120
<211> LENGTH: 24
<212> TYPE: DNA
<213> ORGANISM: Artificial/Unknown
<220> FEATURE:
<221> NAME/KEY: misc_feature
```

```
<223> OTHER INFORMATION: Synthetic

<400> SEQUENCE: 120
gctgccggat cctcaacccg ggcc                                              24

<210> SEQ ID NO 121
<211> LENGTH: 33
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 121
tgagggtgag gcccggggttg aggatccggc agc                                    33

<210> SEQ ID NO 122
<211> LENGTH: 8
<212> TYPE: PRT
<213> ORGANISM: Artificial/Unknown
<220> FEATURE:
<221> NAME/KEY: misc_feature
<223> OTHER INFORMATION: Synthetic

<400> SEQUENCE: 122

Ala Ala Gly Ser Ser Thr Arg Ala
1               5

<210> SEQ ID NO 123
<211> LENGTH: 33
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 123
tcaccctcac cggtcgcccg gaattcacca ccc                                     33

<210> SEQ ID NO 124
<211> LENGTH: 24
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 124
gggtggtgaa ttccgggcga ccgg                                              24

<210> SEQ ID NO 125
<211> LENGTH: 11
<212> TYPE: PRT
<213> ORGANISM: Artificial/Unknown
<220> FEATURE:
<221> NAME/KEY: misc_feature
<223> OTHER INFORMATION: Synthetic

<400> SEQUENCE: 125

Ser Pro Ser Pro Val Ala Thr Asn Ser Pro Pro
1               5                   10

<210> SEQ ID NO 126
<211> LENGTH: 12
<212> TYPE: PRT
<213> ORGANISM: Artificial/Unknown
<220> FEATURE:
```

<221> NAME/KEY: misc_feature
<223> OTHER INFORMATION: Synthetic
<221> NAME/KEY: SITE
<222> LOCATION: (4)..(4)
<223> OTHER INFORMATION: The Proline at this position is a
      hydroxyproline.
<221> NAME/KEY: SITE
<222> LOCATION: (6)..(6)
<223> OTHER INFORMATION: The Proline at this position is a
      hydroxyproline.
<221> NAME/KEY: SITE
<222> LOCATION: (8)..(8)
<223> OTHER INFORMATION: The Proline at this position is a
      hydroxyproline.
<221> NAME/KEY: SITE
<222> LOCATION: (10)..(10)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.

<400> SEQUENCE: 126

Ser Pro Ser Pro Ser Pro Ser Pro Ser Pro Ser Pro
1               5                   10

<210> SEQ ID NO 127
<211> LENGTH: 22
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(2)
<223> OTHER INFORMATION: The Proline at this position is a
      hydroxyproline.
<221> NAME/KEY: SITE
<222> LOCATION: (4)..(4)
<223> OTHER INFORMATION: The Proline at this position is a
      hydroxyproline.
<221> NAME/KEY: SITE
<222> LOCATION: (6)..(6)
<223> OTHER INFORMATION: The Proline at this position is a
      hydroxyproline.
<221> NAME/KEY: SITE
<222> LOCATION: (8)..(8)
<223> OTHER INFORMATION: The Proline at this position is a
      hydroxyproline.
<221> NAME/KEY: SITE
<222> LOCATION: (10)..(10)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.
<221> NAME/KEY: SITE
<222> LOCATION: (14)..(14)
<223> OTHER INFORMATION: The Proline at this position is a
      hydroxyproline.
<221> NAME/KEY: SITE
<222> LOCATION: (16)..(16)
<223> OTHER INFORMATION: The Proline at this position is a
      hydroxyproline.
<221> NAME/KEY: SITE
<222> LOCATION: (18)..(18)
<223> OTHER INFORMATION: The Proline at this position is a
      hydroxyproline.
<221> NAME/KEY: SITE
<222> LOCATION: (20)..(20)
<223> OTHER INFORMATION: The Proline at this position is a
      hydroxyproline.
<221> NAME/KEY: SITE
<222> LOCATION: (22)..(22)
<223> OTHER INFORMATION: The Proline at this position is a hydroxyproline.

<400> SEQUENCE: 127

Ser Pro Ser Pro Ser Pro Ser Pro Ser Pro Ser Pro Ser Pro Ser Pro
1               5                   10                  15

Ser Pro Ser Pro Ser Pro
            20

<210> SEQ ID NO 128
<211> LENGTH: 18
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (3)..(3)
<223> OTHER INFORMATION: The Proline at this position is a
      hydroxyproline.
<221> NAME/KEY: SITE
<222> LOCATION: (5)..(5)
<223> OTHER INFORMATION: The Proline at this position is a
      hydroxyproline.
<221> NAME/KEY: SITE
<222> LOCATION: (7)..(7)
<223> OTHER INFORMATION: The Proline at this position is a
      hydroxyproline.
<221> NAME/KEY: SITE
<222> LOCATION: (10)..(11)
<223> OTHER INFORMATION: The Proline at these positions is a
      hydroxyproline.
<221> NAME/KEY: SITE
<222> LOCATION: (16)..(18)
<223> OTHER INFORMATION: The Proline at these positions is a
      hydroxyproline.

<400> SEQUENCE: 128

Asp Ser Pro Ser Pro Thr Pro Thr Ala Pro Pro Gly Pro His Ser Pro
1               5                   10                  15

Pro Pro

<210> SEQ ID NO 129
<211> LENGTH: 25
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (3)..(3)
<223> OTHER INFORMATION: The Proline at this position is a
      hydroxyproline.
<221> NAME/KEY: SITE
<222> LOCATION: (5)..(5)
<223> OTHER INFORMATION: The Proline at this position is a
      hydroxyproline.
<221> NAME/KEY: SITE
<222> LOCATION: (7)..(7)
<223> OTHER INFORMATION: The Proline at this position is a
      hydroxyproline.
<221> NAME/KEY: SITE
<222> LOCATION: (10)..(11)
<223> OTHER INFORMATION: The Proline at these positions is a
      hydroxyproline.
<221> NAME/KEY: SITE
<222> LOCATION: (16)..(16)
<223> OTHER INFORMATION: The Proline at this position is a
      hydroxyproline.
<221> NAME/KEY: SITE
<222> LOCATION: (18)..(18)
<223> OTHER INFORMATION: The Proline at this position is a
      hydroxyproline.
<221> NAME/KEY: SITE

```
<222> LOCATION: (22)..(22)
<223> OTHER INFORMATION: The Proline at this position is a
      hydroxyproline.
<221> NAME/KEY: SITE
<222> LOCATION: (24)..(24)
<223> OTHER INFORMATION: The Proline at this position is a
      hydroxyproline.

<400> SEQUENCE: 129

Asp Ser Pro Ser Pro Thr Pro Thr Ala Pro Pro Gly Pro His Ser Pro
1               5                   10                  15

Pro Pro Thr Leu Ser Pro Ser Pro Thr
            20                  25

<210> SEQ ID NO 130
<211> LENGTH: 139
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 130
gccaagcttc cggagtgccg gccctcatag cccacctcca ccattatcac catcacctac     60
tccaactcct cctttgggac cacacagtcc accccctaca ctttcccctt caccaacccc    120
aacaccaccc cccgggtac                                                 139

<210> SEQ ID NO 131
<211> LENGTH: 39
<212> TYPE: PRT
<213> ORGANISM: Artificial/Unknown
<220> FEATURE:
<221> NAME/KEY: misc_feature
<223> OTHER INFORMATION: Synthetic

<400> SEQUENCE: 131

Gly Pro His Ser Pro Pro Pro Leu Ser Pro Ser Pro Thr Pro Thr
1               5                   10                  15

Pro Pro Leu Gly Pro His Ser Pro Pro Pro Thr Leu Ser Pro Ser Pro
            20                  25                  30

Thr Pro Thr Pro Pro Pro Gly
            35

<210> SEQ ID NO 132
<211> LENGTH: 253
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 132
gccaagcttc cggagtgccg gccctcatag cccacctcca ccattatcac catcacctac     60
tccaactcct cctttgggac cacacagtcc accccctaca ctttcccctt caccaacccc    120
aacaccaccc cccggccctc atagcccacc tccaccatta tcaccatcac ctactccaac    180
tcctcctttg ggaccacaca gtccaccccc tacactttcc ccttcaccaa ccccaacacc    240
accccccggg tac                                                       253

<210> SEQ ID NO 133
<211> LENGTH: 74
<212> TYPE: PRT
<213> ORGANISM: Artificial/Unknown
```

<220> FEATURE:
<221> NAME/KEY: misc_feature
<223> OTHER INFORMATION: Synthetic

<400> SEQUENCE: 133

```
Gly Pro His Ser Pro Pro Pro Leu Ser Pro Ser Pro Thr Pro Thr
1               5                   10                  15
Pro Pro Leu Gly Pro His Ser Pro Pro Pro Thr Leu Ser Pro Ser Pro
            20                  25                  30
Thr Pro Thr Pro Pro Pro Gly Pro His Ser Pro Pro Pro Leu Ser
            35                  40                  45
Pro Ser Pro Thr Pro Thr Pro Pro Leu Gly Pro His Ser Pro Pro Pro
    50                  55                  60
Thr Leu Ser Pro Ser Pro Thr Pro Thr Pro
65                  70
```

<210> SEQ ID NO 134
<211> LENGTH: 19
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (1)..(1)
<223> OTHER INFORMATION: The amino acid at this position is selected
      from Ser, Thr, and Ala
<221> NAME/KEY: SITE
<222> LOCATION: (2)..(2)
<223> OTHER INFORMATION: The Proline at this position is a
      hydroxyproline.
<221> NAME/KEY: SITE
<222> LOCATION: (3)..(3)
<223> OTHER INFORMATION: The amino acid at this position is selected
      from Hyp, Pro, Leu, and Ile
<221> NAME/KEY: SITE
<222> LOCATION: (4)..(4)
<223> OTHER INFORMATION: The amino acid at this position is selected
      from Pro and Hyp.
<221> NAME/KEY: SITE
<222> LOCATION: (5)..(5)
<223> OTHER INFORMATION: The amino acid at this position is selected
      from Hyp, Pro, Ser, Thr, and Ala
<221> NAME/KEY: SITE
<222> LOCATION: (6)..(6)
<223> OTHER INFORMATION: The amino acid at this position is selected
      from Leu and Ile.
<221> NAME/KEY: SITE
<222> LOCATION: (7)..(7)
<223> OTHER INFORMATION: The amino acid at this position is selected
      from Ser, Thr, and Ala
<221> NAME/KEY: SITE
<222> LOCATION: (8)..(8)
<223> OTHER INFORMATION: The Proline at this position is a
      hydroxyproline.
<221> NAME/KEY: SITE
<222> LOCATION: (9)..(9)
<223> OTHER INFORMATION: The amino acid at this position is selected
      from Ser, Leu, Hyp, Thr, Ala, and Ile
<221> NAME/KEY: SITE
<222> LOCATION: (10)..(10)
<223> OTHER INFORMATION: The amino acid at this position is selected
      from Hyp, Pro, Leu, a
      nd Ile
<221> NAME/KEY: SITE
<222> LOCATION: (11)..(11)
<223> OTHER INFORMATION: The amino acid at this position is selected
      from Thr, Ala, and Ser
<221> NAME/KEY: SITE
<222> LOCATION: (12)..(12)
<223> OTHER INFORMATION: The Proline at this position is a
      hydroxyproline.
<221> NAME/KEY: SITE

```
<222> LOCATION: (13)..(13)
<223> OTHER INFORMATION: The amino acid at this position is selected
      from Thr, Ser, and Ala
<221> NAME/KEY: SITE
<222> LOCATION: (14)..(15)
<223> OTHER INFORMATION: The Proline at these positions is a
      hydroxyproline.
<221> NAME/KEY: SITE
<222> LOCATION: (16)..(16)
<223> OTHER INFORMATION: The amino acid at this position is selected
      from Thr, Leu, Hyp, Ser, Ala, and Ile
<221> NAME/KEY: SITE
<222> LOCATION: (17)..(17)
<223> OTHER INFORMATION: The amino acid at this position is selected
      from Gly, Leu, Ala, and Ile
<221> NAME/KEY: SITE
<222> LOCATION: (19)..(19)
<223> OTHER INFORMATION: The amino acid at this position is selected
      from His and Pro.

<400> SEQUENCE: 134

Xaa Pro Xaa Xaa Xaa Xaa Xaa Pro Xaa Xaa Xaa Pro Xaa Pro Pro Xaa
1               5                   10                  15

Xaa Pro Xaa

<210> SEQ ID NO 135
<211> LENGTH: 11
<212> TYPE: PRT
<213> ORGANISM: Acacia senegal
<220> FEATURE:
<221> NAME/KEY: SITE
<222> LOCATION: (1)..(4)
<223> OTHER INFORMATION: The Proline at these positions is a
      hydroxyproline.

<400> SEQUENCE: 135

Pro Pro Pro Pro Ser Ser Thr Pro Gly Leu His
1               5                   10

<210> SEQ ID NO 136
<211> LENGTH: 19
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (1)..(1)
<223> OTHER INFORMATION: The amino acid at this position is selected
      from Ser, Thr, and Ala
<221> NAME/KEY: SITE
<222> LOCATION: (3)..(3)
<223> OTHER INFORMATION: The amino acid at this position is selected
      from Hyp, Pro, Leu, and Ile
<221> NAME/KEY: SITE
<222> LOCATION: (4)..(4)
<223> OTHER INFORMATION: The amino acid at this position is selected
      from Pro and Hyp.
<221> NAME/KEY: SITE
<222> LOCATION: (5)..(5)
<223> OTHER INFORMATION: The amino acid at this position is selected
      from Hyp, Pro, Ser, Thr, and Ala
<221> NAME/KEY: SITE
<222> LOCATION: (6)..(6)
<223> OTHER INFORMATION: The amino acid at this position is selected
      from Leu and Ile.
<221> NAME/KEY: SITE
<222> LOCATION: (7)..(7)
<223> OTHER INFORMATION: The amino acid at this position is selected
      from Ser, Thr, and Ala
<221> NAME/KEY: SITE
<222> LOCATION: (9)..(9)
<223> OTHER INFORMATION: The amino acid at this position is selected
      from Ser, Leu, Hyp, Thr, Ala, and Ile
```

```
<221> NAME/KEY: SITE
<222> LOCATION: (10)..(10)
<223> OTHER INFORMATION: The amino acid at this position is selected
      from Hyp, Pro, Leu, and Ile
<221> NAME/KEY: SITE
<222> LOCATION: (11)..(11)
<223> OTHER INFORMATION: The amino acid at this position is selected
      from Thr, Ala, and Ser
<221> NAME/KEY: SITE
<222> LOCATION: (13)..(13)
<223> OTHER INFORMATION: The amino acid at this position is selected
      from Thr, Ser, and Ala
<221> NAME/KEY: SITE
<222> LOCATION: (16)..(16)
<223> OTHER INFORMATION: The amino acid at this position is selected
      from Thr, Leu, Hyp, Ser, Ala, and Ile
<221> NAME/KEY: SITE
<222> LOCATION: (17)..(17)
<223> OTHER INFORMATION: The amino acid at this position is selected
      from Gly, Leu, Ala, and Ile
<221> NAME/KEY: SITE
<222> LOCATION: (19)..(19)
<223> OTHER INFORMATION: The amino acid at this position is selected
      from His and Pro.
<221> NAME/KEY: SITE
<222> LOCATION: (2)..(2)
<223> OTHER INFORMATION: The Proline at this position is a
      hydroxyproline.
<221> NAME/KEY: SITE
<222> LOCATION: (8)..(8)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.
<221> NAME/KEY: SITE
<222> LOCATION: (14)..(15)
<223> OTHER INFORMATION: The Proline at these positions is a
      hydroxyproline.

<400> SEQUENCE: 136

Xaa Pro Xaa Xaa Xaa Xaa Xaa Pro Xaa Xaa Xaa Pro Xaa Pro Pro Xaa
1               5                   10                  15

Xaa Pro Xaa

<210> SEQ ID NO 137
<211> LENGTH: 6
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (1)..(1)
<223> OTHER INFORMATION: The amino acid at this position is selected
      from Ser, Thr, and Ala
<221> NAME/KEY: SITE
<222> LOCATION: (2)..(2)
<223> OTHER INFORMATION: The Proline at this position is a
      hydroxyproline.
<221> NAME/KEY: SITE
<222> LOCATION: (3)..(3)
<223> OTHER INFORMATION: The amino acid at this position is selected
      from Ser, Leu, Hyp, Thr, Ala, and Ile
<221> NAME/KEY: SITE
<222> LOCATION: (4)..(4)
<223> OTHER INFORMATION: The amino acid at this position is selected
      from Hyp, Pro, Leu, and Ile
<221> NAME/KEY: SITE
<222> LOCATION: (5)..(5)
<223> OTHER INFORMATION: The amino acid at this position is selected
      from Thr, Ala, and Ser
<221> NAME/KEY: SITE
<222> LOCATION: (6)..(6)
<223> OTHER INFORMATION: The Proline at this position is a
``` hydroxyproline.

<400> SEQUENCE: 137

Xaa Pro Xaa Xaa Xaa Pro
1               5

<210> SEQ ID NO 138
<211> LENGTH: 6
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(2)
<223> OTHER INFORMATION: The Proline at this position is a
      hydroxyproline.
<221> NAME/KEY: SITE
<222> LOCATION: (4)..(4)
<223> OTHER INFORMATION: The Proline at this position is a
      hydroxyproline.
<221> NAME/KEY: SITE
<222> LOCATION: (6)..(6)
<223> OTHER INFORMATION: The Proline at this position is a
      hydroxyproline.

<400> SEQUENCE: 138

Ser Pro Ser Pro Thr Pro
1               5

<210> SEQ ID NO 139
<211> LENGTH: 6
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (1)..(1)
<223> OTHER INFORMATION: The amino acid at this position is selected
      from Ser, Thr, and Ala
<221> NAME/KEY: SITE
<222> LOCATION: (2)..(2)
<223> OTHER INFORMATION: The Proline at this position is a
      hydroxyproline.
<221> NAME/KEY: SITE
<222> LOCATION: (3)..(3)
<223> OTHER INFORMATION: The amino acid at this position is selected
      from Hyp, Leu, and Ile
<221> NAME/KEY: SITE
<222> LOCATION: (4)..(4)
<223> OTHER INFORMATION: The amino acid at this position is selected
      from Pro and Hyp.
<221> NAME/KEY: SITE
<222> LOCATION: (5)..(5)
<223> OTHER INFORMATION: The amino acid at this position is selected
      from Hyp, Ser, Thr, and Ala
<221> NAME/KEY: SITE
<222> LOCATION: (6)..(6)
<223> OTHER INFORMATION: The amino acid at this position is selected
      from Leu and Ile.

<400> SEQUENCE: 139

Ala Pro Asx Cys Asp Glu
1               5

<210> SEQ ID NO 140
<211> LENGTH: 6
<212> TYPE: PRT
<213> ORGANISM: Artificial/Unknown
<220> FEATURE:
<221> NAME/KEY: misc_feature
<223> OTHER INFORMATION: Synthetic

```
<221> NAME/KEY: SITE
<222> LOCATION: (2)..(4)
<223> OTHER INFORMATION: The Proline at these positions is a
      hydroxyproline.
<221> NAME/KEY: SITE
<222> LOCATION: (5)..(5)
<223> OTHER INFORMATION: The amino acid at this position is selected
      from Hyp, Thr, and Ser

<400> SEQUENCE: 140

Ser Pro Pro Pro Xaa Leu
1               5

<210> SEQ ID NO 141
<211> LENGTH: 7
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (1)..(1)
<223> OTHER INFORMATION: The amino acid at this position is selected
      from Thr, Ser, and Ala
<221> NAME/KEY: SITE
<222> LOCATION: (2)..(3)
<223> OTHER INFORMATION: The Proline at these positions is a
      hydroxyproline.
<221> NAME/KEY: SITE
<222> LOCATION: (4)..(4)
<223> OTHER INFORMATION: The amino acid at this position is selected
      from Thr, Leu, Hyp, Ser, Ala, and Ile
<221> NAME/KEY: SITE
<222> LOCATION: (5)..(5)
<223> OTHER INFORMATION: The amino acid at this position is selected
      from Gly, Leu, Ala, a
      nd Ile
<221> NAME/KEY: SITE
<222> LOCATION: (7)..(7)
<223> OTHER INFORMATION: The amino acid at this position is selected
      from His and Pro.

<400> SEQUENCE: 141

Xaa Pro Pro Xaa Xaa Pro Xaa
1               5

<210> SEQ ID NO 142
<211> LENGTH: 12
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (1)..(1)
<223> OTHER INFORMATION: The Proline at this position is a
      hydroxyproline.
<221> NAME/KEY: SITE
<222> LOCATION: (3)..(3)
<223> OTHER INFORMATION: The Proline at this position is a
      hydroxyproline.
<221> NAME/KEY: SITE
<222> LOCATION: (5)..(5)
<223> OTHER INFORMATION: The Proline at this position is a
      hydroxyproline.
<221> NAME/KEY: SITE
<222> LOCATION: (7)..(8)
<223> OTHER INFORMATION: The Proline at these positions is a
      hydroxyproline.
<221> NAME/KEY: SITE
<222> LOCATION: (9)..(9)
<223> OTHER INFORMATION: The amino acid at this position is selected
      from Hyp and Leu.

<400> SEQUENCE: 142
```

Pro Ser Pro Thr Pro Thr Pro Pro Xaa Gly Pro His
1               5                   10

<210> SEQ ID NO 143
<211> LENGTH: 19
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(5)
<223> OTHER INFORMATION: The Proline at these positions is a
      hydroxyproline.
<221> NAME/KEY: SITE
<222> LOCATION: (8)..(8)
<223> OTHER INFORMATION: The Proline at this position is a
      hydroxyproline.
<221> NAME/KEY: SITE
<222> LOCATION: (10)..(10)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.
<221> NAME/KEY: SITE
<222> LOCATION: (14)..(15)
<223> OTHER INFORMATION: The Proline at these positions is a
      hydroxyproline.

<400> SEQUENCE: 143

Ser Pro Pro Pro Pro Leu Ser Pro Ser Pro Thr Pro Thr Pro Pro Leu
1               5                   10                  15

Gly Pro His

<210> SEQ ID NO 144
<211> LENGTH: 19
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(4)
<223> OTHER INFORMATION: The Proline at these positions is a
      hydroxyproline.
<221> NAME/KEY: SITE
<222> LOCATION: (8)..(8)
<223> OTHER INFORMATION: The Proline at this position is a
      hydroxyproline.
<221> NAME/KEY: SITE
<222> LOCATION: (10)..(10)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.
<221> NAME/KEY: SITE
<222> LOCATION: (14)..(16)
<223> OTHER INFORMATION: The Proline at these positions is a
      hydroxyproline.

<400> SEQUENCE: 144

Ser Pro Pro Pro Thr Leu Ser Pro Ser Pro Thr Pro Thr Pro Pro Pro
1               5                   10                  15

Gly Pro His

<210> SEQ ID NO 145
<211> LENGTH: 19

```
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(4)
<223> OTHER INFORMATION: The Proline at these positions is a
      hydroxyproline.
<221> NAME/KEY: SITE
<222> LOCATION: (8)..(8)
<223> OTHER INFORMATION: The Proline at this position is a
      hydroxyproline.
<221> NAME/KEY: SITE
<222> LOCATION: (10)..(10)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.
<221> NAME/KEY: SITE
<222> LOCATION: (14)..(15)
<223> OTHER INFORMATION: The Proline at these positions is a
      hydroxyproline.

<400> SEQUENCE: 145

Ser Pro Pro Pro Ser Leu Ser Pro Ser Pro Thr Pro Thr Pro Pro Thr
1               5                   10                  15

Gly Pro His

<210> SEQ ID NO 146
<211> LENGTH: 19
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(5)
<223> OTHER INFORMATION: The Proline at these positions is a
      hydroxyproline.
<221> NAME/KEY: SITE
<222> LOCATION: (8)..(8)
<223> OTHER INFORMATION: The Proline at this position is a
      hydroxyproline.
<221> NAME/KEY: SITE
<222> LOCATION: (10)..(10)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.
<221> NAME/KEY: SITE
<222> LOCATION: (14)..(16)
<223> OTHER INFORMATION: The Proline at these positions is a
      hydroxyproline.
<221> NAME/KEY: SITE
<222> LOCATION: (19)..(19)
<223> OTHER INFORMATION: The Proline at this position is a
      hydroxyproline.

<400> SEQUENCE: 146

Ser Pro Pro Pro Pro Leu Ser Pro Ser Pro Thr Pro Thr Pro Pro Pro
1               5                   10                  15

Gly Pro Pro

<210> SEQ ID NO 147
<211> LENGTH: 19
<212> TYPE: PRT
<213> ORGANISM: Artificial/Unknown
<220> FEATURE:
```

```
<221> NAME/KEY: misc_feature
<223> OTHER INFORMATION: Synthetic
<221> NAME/KEY: SITE
<222> LOCATION: (2)..(2)
<223> OTHER INFORMATION: The Proline at this position is a
      hydroxyproline.
<221> NAME/KEY: SITE
<222> LOCATION: (6)..(6)
<223> OTHER INFORMATION: The Proline at this position is a
      hydroxyproline.
<221> NAME/KEY: SITE
<222> LOCATION: (8)..(8)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.
<221> NAME/KEY: SITE
<222> LOCATION: (14)..(16)
<223> OTHER INFORMATION: The Proline at these positions is a
      hydroxyproline.

<400> SEQUENCE: 147

Ser Pro Leu Pro Thr Leu Ser Pro Leu Pro Thr Pro Thr Pro Pro Pro
1               5                   10                  15

Gly Pro His

<210> SEQ ID NO 148
<211> LENGTH: 19
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(2)
<223> OTHER INFORMATION: The Proline at this position is a
      hydroxyproline.
<221> NAME/KEY: SITE
<222> LOCATION: (8)..(8)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.
<221> NAME/KEY: SITE
<222> LOCATION: (14)..(16)
<223> OTHER INFORMATION: The Proline at these positions is a
      hydroxyproline.

<400> SEQUENCE: 148

Ser Pro Leu Pro Thr Leu Ser Pro Leu Pro Ala Pro Thr Pro Pro Pro
1               5                   10                  15

Gly Pro His

<210> SEQ ID NO 149
<211> LENGTH: 19
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(5)
<223> OTHER INFORMATION: The Proline at these positions is a
      hydroxyproline.
<221> NAME/KEY: SITE
<222> LOCATION: (8)..(8)
<223> OTHER INFORMATION: The Proline at this position is a
      hydroxyproline.
<221> NAME/KEY: SITE
```

```
<222> LOCATION: (12)..(12)
<223> OTHER INFORMATION: The Proline at this position is a
      hydroxyproline.
<221> NAME/KEY: SITE
<222> LOCATION: (14)..(15)
<223> OTHER INFORMATION: The Proline at these positions is a
      hydroxyproline.
<221> NAME/KEY: SITE
<222> LOCATION: (19)..(19)
<223> OTHER INFORMATION: The Proline at this position is a
      hydroxyproline.

<400> SEQUENCE: 149

Ser Pro Pro Pro Pro Leu Ser Pro Ser Leu Thr Pro Thr Pro Pro Leu
1               5                   10                  15

Gly Pro Pro

<210> SEQ ID NO 150
<211> LENGTH: 19
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(5)
<223> OTHER INFORMATION: The Proline at these positions is a
      hydroxyproline.
<221> NAME/KEY: SITE
<222> LOCATION: (8)..(8)
<223> OTHER INFORMATION: The Proline at this position is a
      hydroxyproline.
<221> NAME/KEY: SITE
<222> LOCATION: (10)..(10)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.
<221> NAME/KEY: SITE
<222> LOCATION: (14)..(16)
<223> OTHER INFORMATION: The Proline at these positions is a
      hydroxyproline.

<400> SEQUENCE: 150

Ser Pro Pro Pro Pro Leu Ser Pro Ser Pro Thr Pro Thr Pro Pro Pro
1               5                   10                  15

Gly Pro His

<210> SEQ ID NO 151
<211> LENGTH: 19
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(4)
<223> OTHER INFORMATION: The Proline at these positions is a
      hydroxyproline.
<221> NAME/KEY: SITE
<222> LOCATION: (8)..(8)
<223> OTHER INFORMATION: The Proline at this position is a
      hydroxyproline.
<221> NAME/KEY: SITE
<222> LOCATION: (10)..(10)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.
```

```
<221> NAME/KEY: SITE
<222> LOCATION: (14)..(16)
<223> OTHER INFORMATION: The Proline at these positions is a
      hydroxyproline.

<400> SEQUENCE: 151

Ser Pro Pro Pro Thr Leu Ser Pro Ser Pro Thr Pro Thr Pro Pro
1               5                   10                  15

Gly Pro His

<210> SEQ ID NO 152
<211> LENGTH: 19
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(5)
<223> OTHER INFORMATION: The Proline at these positions is a
      hydroxyproline.
<221> NAME/KEY: SITE
<222> LOCATION: (8)..(8)
<223> OTHER INFORMATION: The Proline at this position is a
      hydroxyproline.
<221> NAME/KEY: SITE
<222> LOCATION: (10)..(10)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.
<221> NAME/KEY: SITE
<222> LOCATION: (14)..(16)
<223> OTHER INFORMATION: The Proline at these positions is a
      hydroxyproline.

<400> SEQUENCE: 152

Ser Pro Pro Pro Pro Leu Ser Pro Ser Pro Ala Pro Thr Pro Pro
1               5                   10                  15

Gly Pro His

<210> SEQ ID NO 153
<211> LENGTH: 19
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(5)
<223> OTHER INFORMATION: The Proline at these positions is a
      hydroxyproline.
<221> NAME/KEY: SITE
<222> LOCATION: (8)..(8)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.
<221> NAME/KEY: SITE
<222> LOCATION: (14)..(15)
<223> OTHER INFORMATION: The Proline at these positions is a
      hydroxyproline.

<400> SEQUENCE: 153

Ser Pro Pro Pro Pro Leu Ser Pro Leu Pro Thr Pro Thr Pro Leu
1               5                   10                  15

Gly Pro His
```

```
<210> SEQ ID NO 154
<211> LENGTH: 19
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(4)
<223> OTHER INFORMATION: The Proline at these positions is a
      hydroxyproline.
<221> NAME/KEY: SITE
<222> LOCATION: (8)..(8)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.
<221> NAME/KEY: SITE
<222> LOCATION: (14)..(15)
<223> OTHER INFORMATION: The Proline at these positions is a
      hydroxyproline.

<400> SEQUENCE: 154

Ser Pro Pro Pro Ser Leu Ser Pro Leu Pro Thr Pro Thr Pro Pro Leu
1               5                   10                  15

Gly Pro His

<210> SEQ ID NO 155
<211> LENGTH: 19
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(4)
<223> OTHER INFORMATION: The Proline at these positions is a
      hydroxyproline.
<221> NAME/KEY: SITE
<222> LOCATION: (8)..(9)
<223> OTHER INFORMATION: The Proline at these positions is a
      hydroxyproline.
<221> NAME/KEY: SITE
<222> LOCATION: (12)..(12)
<223> OTHER INFORMATION: The Proline at this position is a
      hydroxyproline.
<221> NAME/KEY: SITE
<222> LOCATION: (14)..(15)
<223> OTHER INFORMATION: The Proline at these positions is a
      hydroxyproline.

<400> SEQUENCE: 155

Ser Pro Pro Pro Thr Leu Ser Pro Pro Leu Thr Pro Thr Pro Pro Leu
1               5                   10                  15

Leu Pro His

<210> SEQ ID NO 156
<211> LENGTH: 16
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (1)..(2)
<223> OTHER INFORMATION: The Proline at these positions is a
      hydroxyproline.
<221> NAME/KEY: SITE
<222> LOCATION: (6)..(7)
```

```
<223> OTHER INFORMATION: The Proline at these positions is a
      hydroxyproline.
<221> NAME/KEY: SITE
<222> LOCATION: (10)..(10)
<223> OTHER INFORMATION: The Proline at this position is a
      hydroxyproline.
<221> NAME/KEY: SITE
<222> LOCATION: (12)..(13)
<223> OTHER INFORMATION: The Proline at these positions is a
      hydroxyproline.

<400> SEQUENCE: 156

Pro Pro Thr Leu Ser Pro Pro Leu Thr Pro Thr Pro Pro Leu Leu Pro
1               5                   10                  15

<210> SEQ ID NO 157
<211> LENGTH: 16
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(4)
<223> OTHER INFORMATION: The Proline at these positions is a
      hydroxyproline.
<221> NAME/KEY: SITE
<222> LOCATION: (8)..(8)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.
<221> NAME/KEY: SITE
<222> LOCATION: (14)..(15)
<223> OTHER INFORMATION: The Proline at these positions is a
      hydroxyproline.

<400> SEQUENCE: 157

Ser Pro Pro Pro Ser Leu Ser Pro Leu Pro Thr Pro Thr Pro Pro Leu
1               5                   10                  15

<210> SEQ ID NO 158
<211> LENGTH: 16
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (1)..(2)
<223> OTHER INFORMATION: The Proline at these positions is a
      hydroxyproline.
<221> NAME/KEY: SITE
<222> LOCATION: (5)..(5)
<223> OTHER INFORMATION: The Proline at this position is a
      hydroxyproline.
<221> NAME/KEY: SITE
<222> LOCATION: (9)..(9)
<223> OTHER INFORMATION: The Proline at this position is a
      hydroxyproline.
<221> NAME/KEY: SITE
<222> LOCATION: (11)..(12)
<223> OTHER INFORMATION: The Proline at these positions is a
      hydroxyproline.

<400> SEQUENCE: 158

Pro Pro Leu Ser Pro Leu Pro Thr Pro Thr Pro Pro Leu Gly Pro His
1               5                   10                  15

<210> SEQ ID NO 159
<211> LENGTH: 14
```

```
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(4)
<223> OTHER INFORMATION: The Proline at these positions is a
      hydroxyproline.
<221> NAME/KEY: SITE
<222> LOCATION: (8)..(8)
<223> OTHER INFORMATION: The Proline at this position is a
      hydroxyproline.
<221> NAME/KEY: SITE
<222> LOCATION: (10)..(10)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.
<221> NAME/KEY: SITE
<222> LOCATION: (14)..(14)
<223> OTHER INFORMATION: The Proline at this position is a
      hydroxyproline.

<400> SEQUENCE: 159

Ser Pro Pro Pro Thr Leu Ser Pro Ser Pro Thr Pro Thr Pro
1               5                   10

<210> SEQ ID NO 160
<211> LENGTH: 14
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (3)..(3)
<223> OTHER INFORMATION: The Proline at this position is a
      hydroxyproline.
<221> NAME/KEY: SITE
<222> LOCATION: (7)..(7)
<223> OTHER INFORMATION: The Proline at this position is a
      hydroxyproline.
<221> NAME/KEY: SITE
<222> LOCATION: (9)..(10)
<223> OTHER INFORMATION: The Proline at these positions is a
      hydroxyproline.
<221> NAME/KEY: SITE
<222> LOCATION: (14)..(14)
<223> OTHER INFORMATION: The Proline at this position is a
      hydroxyproline.

<400> SEQUENCE: 160

Leu Ser Pro Ser Leu Thr Pro Thr Pro Pro Leu Gly Pro Pro
1               5                   10

<210> SEQ ID NO 161
<211> LENGTH: 14
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (1)..(1)
<223> OTHER INFORMATION: The Proline at this position is a
      hydroxyproline.
<221> NAME/KEY: SITE
<222> LOCATION: (5)..(5)
<223> OTHER INFORMATION: The Proline at this position is a
      hydroxyproline.
<221> NAME/KEY: SITE
<222> LOCATION: (9)..(9)
```

<223> OTHER INFORMATION: The Proline at this position is a
     hydroxyproline.
<221> NAME/KEY: SITE
<222> LOCATION: (11)..(13)
<223> OTHER INFORMATION: The Proline at these positions is a
     hydroxyproline.

<400> SEQUENCE: 161

Pro Thr Leu Ser Pro Leu Pro Ala Pro Thr Pro Pro Pro Gly
1               5                   10

<210> SEQ ID NO 162
<211> LENGTH: 12
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(5)
<223> OTHER INFORMATION: The Proline at these positions is a
     hydroxyproline.
<221> NAME/KEY: SITE
<222> LOCATION: (8)..(8)
<223> OTHER INFORMATION: The Proline at this position is a
     hydroxyproline.
<221> NAME/KEY: SITE
<222> LOCATION: (10)..(10)
<223> OTHER INFORMATION: The Proline at this position is a
     hydroxyproline.
<221> NAME/KEY: SITE
<222> LOCATION: (12)..(12)
<223> OTHER INFORMATION: The Proline at this position is a
     hydroxyproline.

<400> SEQUENCE: 162

Ser Pro Pro Pro Pro Leu Ser Pro Ser Pro Thr Pro
1               5                   10

<210> SEQ ID NO 163
<211> LENGTH: 12
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (4)..(4)
<223> OTHER INFORMATION: The Proline at this position is a
     hydroxyproline.
<221> NAME/KEY: SITE
<222> LOCATION: (6)..(6)
<223> OTHER INFORMATION: The Proline at this position is a
     hydroxyproline.
<221> NAME/KEY: SITE
<222> LOCATION: (8)..(8)
<223> OTHER INFORMATION: The Proline at this position is a
     hydroxyproline.
<221> NAME/KEY: SITE
<222> LOCATION: (10)..(11)
<223> OTHER INFORMATION: The Proline at these positions is a
     hydroxyproline.

<400> SEQUENCE: 163

Ser Leu Ser Pro Ser Pro Thr Pro Thr Pro Pro Thr
1               5                   10

<210> SEQ ID NO 164
<211> LENGTH: 12
<212> TYPE: PRT
<213> ORGANISM: Artificial/Unknown
<220> FEATURE:
<221> NAME/KEY: misc_feature

```
<223> OTHER INFORMATION: Synthetic
<221> NAME/KEY: SITE
<222> LOCATION: (1)..(2)
<223> OTHER INFORMATION: The Proline at these positions is a
      hydroxyproline.
<221> NAME/KEY: SITE
<222> LOCATION: (6)..(6)
<223> OTHER INFORMATION: The Proline at this position is a
      hydroxyproline.
<221> NAME/KEY: SITE
<222> LOCATION: (8)..(8)
<223> OTHER INFORMATION: The Proline at this position is a
      hydroxyproline.
<221> NAME/KEY: SITE
<222> LOCATION: (10)..(10)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.

<400> SEQUENCE: 164

Pro Pro Thr Leu Ser Pro Ser Pro Thr Pro Thr Pro
1               5                   10

<210> SEQ ID NO 165
<211> LENGTH: 10
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (1)..(1)
<223> OTHER INFORMATION: The Proline at this position is a
      hydroxyproline.
<221> NAME/KEY: SITE
<222> LOCATION: (3)..(3)
<223> OTHER INFORMATION: The Proline at this position is a
      hydroxyproline.
<221> NAME/KEY: SITE
<222> LOCATION: (5)..(6)
<223> OTHER INFORMATION: The Proline at these positions is a
      hydroxyproline.

<400> SEQUENCE: 165

Pro Thr Pro Thr Pro Pro Leu Gly Pro His
1               5                   10

<210> SEQ ID NO 166
<211> LENGTH: 10
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (1)..(2)
<223> OTHER INFORMATION: The Proline at these positions is a
      hydroxyproline.
<221> NAME/KEY: SITE
<222> LOCATION: (6)..(7)
<223> OTHER INFORMATION: The Proline at these positions is a
      hydroxyproline.
<221> NAME/KEY: SITE
<222> LOCATION: (10)..(10)
<223> OTHER INFORMATION: The Proline at this position is a
      hydroxyproline.

<400> SEQUENCE: 166

Pro Pro Thr Leu Ser Pro Pro Leu Thr Pro
1               5                   10
```

```
<210> SEQ ID NO 167
<211> LENGTH: 10
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(4)
<223> OTHER INFORMATION: The Proline at these positions is a
      hydroxyproline.
<221> NAME/KEY: SITE
<222> LOCATION: (8)..(8)
<223> OTHER INFORMATION: The Proline at this position is a
      hydroxyproline.

<400> SEQUENCE: 167

Ser Pro Pro Pro Ser Leu Ser Pro Leu Pro
1               5                   10

<210> SEQ ID NO 168
<211> LENGTH: 8
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (1)..(1)
<223> OTHER INFORMATION: The Proline at this position is a
      hydroxyproline.
<221> NAME/KEY: SITE
<222> LOCATION: (3)..(4)
<223> OTHER INFORMATION: The Proline at these positions is a
      hydroxyproline.

<400> SEQUENCE: 168

Pro Thr Pro Pro Leu Gly Pro His
1               5

<210> SEQ ID NO 169
<211> LENGTH: 8
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (1)..(1)
<223> OTHER INFORMATION: The Proline at this position is a
      hydroxyproline.
<221> NAME/KEY: SITE
<222> LOCATION: (4)..(4)
<223> OTHER INFORMATION: The Proline at this position is a
      hydroxyproline.
<221> NAME/KEY: SITE
<222> LOCATION: (6)..(6)
<223> OTHER INFORMATION: The Proline at this position is a
      hydroxyproline.
<221> NAME/KEY: SITE
<222> LOCATION: (8)..(8)
<223> OTHER INFORMATION: The Proline at this position is a
      hydroxyproline.

<400> SEQUENCE: 169

Pro Leu Ser Pro Ser Pro Ala Pro
1               5

<210> SEQ ID NO 170
<211> LENGTH: 8
<212> TYPE: PRT
<213> ORGANISM: Artificial/Unknown
```

```
<220> FEATURE:
<221> NAME/KEY: misc_feature
<223> OTHER INFORMATION: Synthetic
<221> NAME/KEY: SITE
<222> LOCATION: (1)..(3)
<223> OTHER INFORMATION: The Proline at these positions is a
      hydroxyproline.
<221> NAME/KEY: SITE
<222> LOCATION: (7)..(7)
<223> OTHER INFORMATION: The Proline at this position is a
      hydroxyproline.

<400> SEQUENCE: 170

Pro Pro Pro Thr Leu Ser Pro Ser
1               5

<210> SEQ ID NO 171
<211> LENGTH: 6
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(4)
<223> OTHER INFORMATION: The Proline at these positions is a
      hydroxyproline.

<400> SEQUENCE: 171

Thr Pro Pro Pro Gly Pro
1               5

<210> SEQ ID NO 172
<211> LENGTH: 6
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (1)..(2)
<223> OTHER INFORMATION: The Proline at these positions is a
      hydroxyproline.
<221> NAME/KEY: SITE
<222> LOCATION: (5)..(5)
<223> OTHER INFORMATION: The Proline at this position is a
      hydroxyproline.

<400> SEQUENCE: 172

Pro Pro Leu Ser Pro Ser
1               5

<210> SEQ ID NO 173
<211> LENGTH: 6
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(2)
<223> OTHER INFORMATION: The Proline at this position is a
      hydroxyproline.
<221> NAME/KEY: SITE
<222> LOCATION: (6)..(6)
<223> OTHER INFORMATION: The Proline at this position is a
      hydroxyproline.

<400> SEQUENCE: 173

Ser Pro Leu Pro Ala Pro
1               5
```

```
<210> SEQ ID NO 174
<211> LENGTH: 6
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (6)..(6)
<223> OTHER INFORMATION: The Proline at this position is a
      hydroxyproline.

<400> SEQUENCE: 174

Leu Pro Thr Leu Ser Pro
1               5

<210> SEQ ID NO 175
<211> LENGTH: 4
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(2)
<223> OTHER INFORMATION: The Proline at this position is a
      hydroxyproline.
<221> NAME/KEY: SITE
<222> LOCATION: (4)..(4)
<223> OTHER INFORMATION: The Proline at this position is a
      hydroxyproline.

<400> SEQUENCE: 175

Ser Pro Ser Pro
1

<210> SEQ ID NO 176
<211> LENGTH: 4
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(2)
<223> OTHER INFORMATION: The proline at this position is a
      hydroxyproline.
<221> NAME/KEY: SITE
<222> LOCATION: (4)..(4)
<223> OTHER INFORMATION: The proline at this position is a
      hydroxyproline.

<400> SEQUENCE: 176

Ser Pro Thr Pro
1

<210> SEQ ID NO 177
<211> LENGTH: 4
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(2)
<223> OTHER INFORMATION: The Proline at this position is a
      hydroxyproline.
<221> NAME/KEY: SITE
<222> LOCATION: (4)..(4)
<223> OTHER INFORMATION: The Proline at this position is a
      hydroxyproline.
```

```
<400> SEQUENCE: 177

Thr Pro Thr Pro
1

<210> SEQ ID NO 178
<211> LENGTH: 4
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(4)
<223> OTHER INFORMATION: The Proline at these positions is a
      hydroxyproline.

<400> SEQUENCE: 178

Thr Pro Pro Pro
1

<210> SEQ ID NO 179
<211> LENGTH: 19
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(4)
<223> OTHER INFORMATION: The Proline at these positions is a
      hydroxyproline.
<221> NAME/KEY: SITE
<222> LOCATION: (5)..(5)
<223> OTHER INFORMATION: The amino acid at this position is selected
      from Hyp, Thr, and Ser
<221> NAME/KEY: SITE
<222> LOCATION: (8)..(8)
<223> OTHER INFORMATION: The Proline at this position is a
      hydroxyproline.
<221> NAME/KEY: SITE
<222> LOCATION: (10)..(10)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.
<221> NAME/KEY: SITE
<222> LOCATION: (14)..(15)
<223> OTHER INFORMATION: The Proline at these positions is a
      hydroxyproline.
<221> NAME/KEY: SITE
<222> LOCATION: (16)..(16)
<223> OTHER INFORMATION: The amino acid at this position is selected
      from Hyp and Leu.

<400> SEQUENCE: 179

Ser Pro Pro Pro Xaa Leu Ser Pro Ser Pro Thr Pro Thr Pro Pro Xaa
1               5                   10                  15

Gly Pro His

<210> SEQ ID NO 180
<211> LENGTH: 38
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (3)..(3)
<223> OTHER INFORMATION: The Proline at this position is a
      hydroxyproline.
```

```
<221> NAME/KEY: SITE
<222> LOCATION: (5)..(7)
<223> OTHER INFORMATION: The Proline at these positions is a
      hydroxyproline.
<221> NAME/KEY: SITE
<222> LOCATION: (11)..(12)
<223> OTHER INFORMATION: The Proline at these positions is a
      hydroxyproline.
<221> NAME/KEY: SITE
<222> LOCATION: (15)..(15)
<223> OTHER INFORMATION: The Proline at this position is a
      hydroxyproline.
<221> NAME/KEY: SITE
<222> LOCATION: (17)..(18)
<223> OTHER INFORMATION: The Proline at these positions is a
      hydroxyproline.
<221> NAME/KEY: SITE
<222> LOCATION: (24)..(27)
<223> OTHER INFORMATION: The Proline at these positions is a
      hydroxyproline.
<221> NAME/KEY: SITE
<222> LOCATION: (30)..(30)
<223> OTHER INFORMATION: The Proline at this position is a
      hydroxyproline.
<221> NAME/KEY: SITE
<222> LOCATION: (34)..(34)
<223> OTHER INFORMATION: The Proline at this position is a
      hydroxyproline.
<221> NAME/KEY: SITE
<222> LOCATION: (36)..(37)
<223> OTHER INFORMATION: The Proline at these positions is a
      hydroxyproline.

<400> SEQUENCE: 180

Gly Pro Pro Ser Pro Pro Pro Thr Leu Ser Pro Pro Leu Thr Pro Thr
1               5                   10                  15

Pro Pro Leu Leu Pro His Ser Pro Pro Pro Leu Ser Pro Ser Leu
            20                  25                  30

Thr Pro Thr Pro Pro Leu
        35

<210> SEQ ID NO 181
<211> LENGTH: 38
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (5)..(8)
<223> OTHER INFORMATION: The Proline at these positions is a
      hydroxyproline.
<221> NAME/KEY: SITE
<222> LOCATION: (11)..(11)
<223> OTHER INFORMATION: The Proline at this position is a
      hydroxyproline.
<221> NAME/KEY: SITE
<222> LOCATION: (13)..(13)
<223> OTHER INFORMATION: The Proline at this position is a
      hydroxyproline.
<221> NAME/KEY: SITE
<222> LOCATION: (15)..(15)
<223> OTHER INFORMATION: The Proline at this position is a
      hydroxyproline.
<221> NAME/KEY: SITE
<222> LOCATION: (17)..(19)
<223> OTHER INFORMATION: The Proline at these positions is a
      hydroxyproline.
<221> NAME/KEY: SITE
<222> LOCATION: (24)..(26)
<223> OTHER INFORMATION: The Proline at these positions is a
      hydroxyproline.
<221> NAME/KEY: SITE
<222> LOCATION: (30)..(34)
<223> OTHER INFORMATION: The Proline at these positions is a
```

```
        hydroxyproline.
<221> NAME/KEY: SITE
<222> LOCATION: (36)..(37)
<223> OTHER INFORMATION: The Proline at these positions is a
      hydroxyproline.

<400> SEQUENCE: 181

Gly Pro His Ser Pro Pro Pro Pro Leu Ser Pro Ser Pro Ala Pro Thr
1               5                   10                  15

Pro Pro Pro Gly Pro His Ser Pro Pro Pro Ser Leu Ser Pro Leu Pro
            20                  25                  30

Thr Pro Thr Pro Pro Leu
            35

<210> SEQ ID NO 182
<211> LENGTH: 2
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (1)..(2)
<223> OTHER INFORMATION: The seq  Xaa-Pro is repeated x times, x being
      an integer from 1 to 1000.  Xaa is any amino acid other than
      hydroxyproline.  Each of the Proline residues is a hydroxyproline

<400> SEQUENCE: 182

Xaa Pro
1

<210> SEQ ID NO 183
<211> LENGTH: 6
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (1)..(1)
<223> OTHER INFORMATION: Xaa is any amino acid other than
      hydroxyproline.
<221> NAME/KEY: SITE
<222> LOCATION: (2)..(2)
<223> OTHER INFORMATION: The Proline at this position is
      hydroxyproline.
<221> NAME/KEY: SITE
<222> LOCATION: (3)..(4)
<223> OTHER INFORMATION: Xaa at these positions is any amino acid other
      than hydroxyproline
<221> NAME/KEY: SITE
<222> LOCATION: (5)..(5)
<223> OTHER INFORMATION: The Proline at this position is
      hydroxyproline.
<221> NAME/KEY: SITE
<222> LOCATION: (6)..(6)
<223> OTHER INFORMATION: Xaa is any amino acid other than
      hydroxyproline.

<400> SEQUENCE: 183

Xaa Pro Xaa Xaa Pro Xaa
1               5

<210> SEQ ID NO 184
<211> LENGTH: 23
<212> TYPE: PRT
<213> ORGANISM: Acacia senegal
<220> FEATURE:
<221> NAME/KEY: SITE
<222> LOCATION: (2)..(4)
<223> OTHER INFORMATION: The Proline at these positions is a
```

```
      hydroxyproline.
<221> NAME/KEY: SITE
<222> LOCATION: (8)..(8)
<223> OTHER INFORMATION: The Proline at this position is a
      hydroxyproline.
<221> NAME/KEY: SITE
<222> LOCATION: (10)..(10)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.
<221> NAME/KEY: SITE
<222> LOCATION: (14)..(16)
<223> OTHER INFORMATION: The Proline at these positions is a
      hydroxyproline.
<221> NAME/KEY: SITE
<222> LOCATION: (21)..(23)
<223> OTHER INFORMATION: The Proline at these positions is a
      hydroxyproline.

<400> SEQUENCE: 184

Ser Pro Pro Pro Thr Leu Ser Pro Ser Pro Thr Pro Thr Pro Pro Pro
1               5                   10                  15

Gly Pro His Ser Pro Pro Pro
            20

<210> SEQ ID NO 185
<211> LENGTH: 24
<212> TYPE: PRT
<213> ORGANISM: Acacia senegal
<220> FEATURE:
<221> NAME/KEY: SITE
<222> LOCATION: (2)..(4)
<223> OTHER INFORMATION: The Proline at these positions is a
      hydroxyproline.
<221> NAME/KEY: SITE
<222> LOCATION: (8)..(8)
<223> OTHER INFORMATION: The Proline at this position is a
      hydroxyproline.
<221> NAME/KEY: SITE
<222> LOCATION: (10)..(10)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.
<221> NAME/KEY: SITE
<222> LOCATION: (14)..(16)
<223> OTHER INFORMATION: The Proline at these positions is a
      hydroxyproline.
<221> NAME/KEY: SITE
<222> LOCATION: (21)..(24)
<223> OTHER INFORMATION: The Proline at these positions is a
      hydroxyproline.

<400> SEQUENCE: 185

Ser Pro Pro Pro Thr Leu Ser Pro Ser Pro Thr Pro Thr Pro Pro Pro
1               5                   10                  15

Gly Pro His Ser Pro Pro Pro Pro
            20

<210> SEQ ID NO 186
<211> LENGTH: 16
<212> TYPE: PRT
<213> ORGANISM: Acacia senegal
<220> FEATURE:
<221> NAME/KEY: SITE
<222> LOCATION: (2)..(4)
<223> OTHER INFORMATION: The Proline at these positions is a
      hydroxyproline.
```

```
<221> NAME/KEY: SITE
<222> LOCATION: (8)..(8)
<223> OTHER INFORMATION: The Proline at this position is a
      hydroxyproline.
<221> NAME/KEY: SITE
<222> LOCATION: (10)..(10)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.
<221> NAME/KEY: SITE
<222> LOCATION: (15)..(16)
<223> OTHER INFORMATION: The Proline at these positions is a
      hydroxyproline.

<400> SEQUENCE: 186

Ser Pro Pro Pro Thr Leu Ser Pro Ser Pro Thr Pro Thr Xaa Pro Pro
1               5                   10                  15

<210> SEQ ID NO 187
<211> LENGTH: 16
<212> TYPE: PRT
<213> ORGANISM: Acacia senegal
<220> FEATURE:
<221> NAME/KEY: SITE
<222> LOCATION: (2)..(4)
<223> OTHER INFORMATION: The Proline at these positions is a
      hydroxyproline.
<221> NAME/KEY: SITE
<222> LOCATION: (8)..(8)
<223> OTHER INFORMATION: The Proline at this position is a
      hydroxyproline.
<221> NAME/KEY: SITE
<222> LOCATION: (10)..(10)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.
<221> NAME/KEY: SITE
<222> LOCATION: (15)..(16)
<223> OTHER INFORMATION: The Proline at these positions is a
      hydroxyproline.

<400> SEQUENCE: 187

Ser Pro Pro Pro Ser Leu Ser Pro Ser Pro Thr Pro Thr Xaa Pro Pro
1               5                   10                  15

<210> SEQ ID NO 188
<211> LENGTH: 12
<212> TYPE: PRT
<213> ORGANISM: Acacia senegal
<220> FEATURE:
<221> NAME/KEY: SITE
<222> LOCATION: (2)..(2)
<223> OTHER INFORMATION: The Proline at this position is a
      hydroxyproline.
<221> NAME/KEY: SITE
<222> LOCATION: (4)..(4)
<223> OTHER INFORMATION: The Proline at this position is a
      hydroxyproline.
<221> NAME/KEY: SITE
<222> LOCATION: (6)..(6)
<223> OTHER INFORMATION: The Proline at this position is a
      hydroxyproline.
<221> NAME/KEY: SITE
<222> LOCATION: (8)..(10)
<223> OTHER INFORMATION: The Proline at these positions is a
      hydroxyproline.

<400> SEQUENCE: 188
```

```
Ser Pro Ser Pro Thr Pro Thr Pro Pro Gly Pro
1               5                   10
```

<210> SEQ ID NO 189
<211> LENGTH: 19
<212> TYPE: PRT
<213> ORGANISM: Acacia senegal
<220> FEATURE:
<221> NAME/KEY: SITE
<222> LOCATION: (2)..(4)
<223> OTHER INFORMATION: The Proline at these positions is a
      hydroxyproline.
<221> NAME/KEY: SITE
<222> LOCATION: (10)..(10)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.
<221> NAME/KEY: SITE
<222> LOCATION: (14)..(15)
<223> OTHER INFORMATION: The Proline at these positions is a
      hydroxyproline.

<400> SEQUENCE: 189

```
Ser Pro Pro Pro Ser Leu Ser Pro Ser Pro Thr Pro Thr Pro Thr
1               5                   10                  15

Gly Pro His
```

<210> SEQ ID NO 190
<211> LENGTH: 18
<212> TYPE: PRT
<213> ORGANISM: Acacia senegal
<220> FEATURE:
<221> NAME/KEY: SITE
<222> LOCATION: (2)..(5)
<223> OTHER INFORMATION: The Proline at these positions is a
      hydroxyproline.
<221> NAME/KEY: SITE
<222> LOCATION: (8)..(8)
<223> OTHER INFORMATION: The Proline at this position is a
      hydroxyproline.
<221> NAME/KEY: SITE
<222> LOCATION: (10)..(10)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.
<221> NAME/KEY: SITE
<222> LOCATION: (14)..(16)
<223> OTHER INFORMATION: The Proline at these positions is a
      hydroxyproline.

<400> SEQUENCE: 190

```
Ser Pro Pro Pro Pro Leu Ser Pro Ser Pro Thr Pro Thr Pro Pro
1               5                   10                  15

Gly Pro
```

<210> SEQ ID NO 191
<211> LENGTH: 19
<212> TYPE: PRT
<213> ORGANISM: Acacia senegal
<220> FEATURE:
<221> NAME/KEY: SITE
<222> LOCATION: (2)..(2)
<223> OTHER INFORMATION: The proline at this position is a
      hydroxyproline.
<221> NAME/KEY: SITE
<222> LOCATION: (8)..(8)

```
<223> OTHER INFORMATION: The proline at this position is a
      hydroxyproline.
<221> NAME/KEY: SITE
<222> LOCATION: (12)..(12)
<223> OTHER INFORMATION: The proline at this position is a
      hydroxyproline.
<221> NAME/KEY: SITE
<222> LOCATION: (14)..(16)
<223> OTHER INFORMATION: The proline at these positions is a
      hydroxyproline.

<400> SEQUENCE: 191

Ser Pro Leu Pro Thr Leu Ser Pro Leu Pro Ala Pro Thr Pro Pro Pro
1               5                   10                  15

Gly Pro His

<210> SEQ ID NO 192
<211> LENGTH: 19
<212> TYPE: PRT
<213> ORGANISM: Acacia senegal
<220> FEATURE:
<221> NAME/KEY: SITE
<222> LOCATION: (2)..(2)
<223> OTHER INFORMATION: The Proline at this position is a
      hydroxyproline.
<221> NAME/KEY: SITE
<222> LOCATION: (8)..(8)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.
<221> NAME/KEY: SITE
<222> LOCATION: (14)..(16)
<223> OTHER INFORMATION: The Proline at these positions is a
      hydroxyproline.

<400> SEQUENCE: 192

Ser Pro Leu Pro Thr Leu Ser Pro Leu Pro Thr Pro Thr Pro Pro Pro
1               5                   10                  15

Gly Pro His

<210> SEQ ID NO 193
<211> LENGTH: 18
<212> TYPE: PRT
<213> ORGANISM: Acacia senegal
<220> FEATURE:
<221> NAME/KEY: SITE
<222> LOCATION: (2)..(5)
<223> OTHER INFORMATION: The Proline at these positions is a
      hydroxyproline.
<221> NAME/KEY: SITE
<222> LOCATION: (8)..(8)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.
<221> NAME/KEY: SITE
<222> LOCATION: (14)..(15)
<223> OTHER INFORMATION: The Proline at these positions is a
      hydroxyproline.

<400> SEQUENCE: 193

Ser Pro Pro Pro Pro Leu Ser Pro Ser Leu Thr Pro Thr Pro Pro Leu
1               5                   10                  15

Gly Pro
```

```
<210> SEQ ID NO 194
<211> LENGTH: 13
<212> TYPE: PRT
<213> ORGANISM: Acacia senegal
<220> FEATURE:
<221> NAME/KEY: SITE
<222> LOCATION: (2)..(2)
<223> OTHER INFORMATION: The Proline at this position is a
      hydroxyproline.
<221> NAME/KEY: SITE
<222> LOCATION: (4)..(4)
<223> OTHER INFORMATION: The Proline at this position is a
      hydroxyproline.
<221> NAME/KEY: SITE
<222> LOCATION: (6)..(6)
<223> OTHER INFORMATION: The Proline at this position is a
      hydroxyproline.
<221> NAME/KEY: SITE
<222> LOCATION: (8)..(10)
<223> OTHER INFORMATION: The Proline at these positions is a
      hydroxyproline.

<400> SEQUENCE: 194

Ser Pro Ser Pro Thr Pro Thr Pro Pro Pro Gly Pro His
1               5                   10

<210> SEQ ID NO 195
<211> LENGTH: 13
<212> TYPE: PRT
<213> ORGANISM: Acacia senegal
<220> FEATURE:
<221> NAME/KEY: SITE
<222> LOCATION: (2)..(2)
<223> OTHER INFORMATION: The Proline at this position is a
      hydroxyproline.
<221> NAME/KEY: SITE
<222> LOCATION: (4)..(4)
<223> OTHER INFORMATION: The Proline at this position is a
      hydroxyproline.
<221> NAME/KEY: SITE
<222> LOCATION: (6)..(6)
<223> OTHER INFORMATION: The Proline at this position is a
      hydroxyproline.
<221> NAME/KEY: SITE
<222> LOCATION: (8)..(9)
<223> OTHER INFORMATION: The Proline at these positions is a
      hydroxyproline.

<400> SEQUENCE: 195

Ser Pro Ser Pro Ala Pro Thr Pro Pro Leu Gly Pro His
1               5                   10

<210> SEQ ID NO 196
<211> LENGTH: 14
<212> TYPE: PRT
<213> ORGANISM: Acacia senegal
<220> FEATURE:
<221> NAME/KEY: SITE
<222> LOCATION: (2)..(2)
<223> OTHER INFORMATION: The Proline at this position is a
      hydroxyproline.
<221> NAME/KEY: SITE
<222> LOCATION: (6)..(6)
<223> OTHER INFORMATION: The Proline at this position is a
      hydroxyproline.
<221> NAME/KEY: SITE
<222> LOCATION: (8)..(9)
<223> OTHER INFORMATION: The Proline at these positions is a
      hydroxyproline.

<400> SEQUENCE: 196

Ser Pro Leu Pro Thr Pro Thr Pro Pro Leu Gly Pro His Ser
1               5                   10
```

```
<210> SEQ ID NO 197
<211> LENGTH: 13
<212> TYPE: PRT
<213> ORGANISM: Acacia senegal
<220> FEATURE:
<221> NAME/KEY: SITE
<222> LOCATION: (2)..(2)
<223> OTHER INFORMATION: The Proline at this position is a
      hydroxyproline.
<221> NAME/KEY: SITE
<222> LOCATION: (4)..(4)
<223> OTHER INFORMATION: The Proline at this position is a
      hydroxyproline.
<221> NAME/KEY: SITE
<222> LOCATION: (6)..(6)
<223> OTHER INFORMATION: The Proline at this position is a
      hydroxyproline.
<221> NAME/KEY: SITE
<222> LOCATION: (8)..(9)
<223> OTHER INFORMATION: The Proline at these positions is a
      hydroxyproline.

<400> SEQUENCE: 197

Ser Pro Ser Pro Thr Pro Thr Pro Pro Leu Gly Pro His
1               5                   10

<210> SEQ ID NO 198
<211> LENGTH: 13
<212> TYPE: PRT
<213> ORGANISM: Acacia senegal
<220> FEATURE:
<221> NAME/KEY: SITE
<222> LOCATION: (2)..(3)
<223> OTHER INFORMATION: The Proline at these positions is a
      hydroxyproline.
<221> NAME/KEY: SITE
<222> LOCATION: (6)..(6)
<223> OTHER INFORMATION: The Proline at this position is a
      hydroxyproline.
<221> NAME/KEY: SITE
<222> LOCATION: (8)..(9)
<223> OTHER INFORMATION: The Proline at these positions is a
      hydroxyproline.

<400> SEQUENCE: 198

Ser Pro Pro Leu Thr Pro Thr Pro Pro Leu Leu Pro His
1               5                   10

<210> SEQ ID NO 199
<211> LENGTH: 11
<212> TYPE: PRT
<213> ORGANISM: Acacia senegal
<220> FEATURE:
<221> NAME/KEY: SITE
<222> LOCATION: (1)..(4)
<223> OTHER INFORMATION: The Proline at these positions is a
      hydroxyproline.

<400> SEQUENCE: 199

Pro Pro Pro Pro Ser Ser Thr Pro Gly Leu His
1               5                   10

<210> SEQ ID NO 200
<211> LENGTH: 1
<212> TYPE: PRT
<213> ORGANISM: Acacia senegal
<220> FEATURE:
<221> NAME/KEY: SITE
<222> LOCATION: (1)..(1)
<223> OTHER INFORMATION: The Proline is hydroxyproline linked to Ara Ara
      Ara Ara.
```

<400> SEQUENCE: 200

Pro
1

<210> SEQ ID NO 201
<211> LENGTH: 1
<212> TYPE: PRT
<213> ORGANISM: Acacia senegal
<220> FEATURE:
<221> NAME/KEY: SITE
<222> LOCATION: (1)..(1)
<223> OTHER INFORMATION: The Proline is hydroxyproline linked to Ara Ara
      Ara.

<400> SEQUENCE: 201

Pro
1

<210> SEQ ID NO 202
<211> LENGTH: 1
<212> TYPE: PRT
<213> ORGANISM: Acacia senegal
<220> FEATURE:
<221> NAME/KEY: SITE
<222> LOCATION: (1)..(1)
<223> OTHER INFORMATION: The Proline is hydroxyproline linked to Ara
      Ara.

<400> SEQUENCE: 202

Pro
1

<210> SEQ ID NO 203
<211> LENGTH: 1
<212> TYPE: PRT
<213> ORGANISM: Acacia senegal
<220> FEATURE:
<221> NAME/KEY: SITE
<222> LOCATION: (1)..(1)
<223> OTHER INFORMATION: The Proline is hydroxyproline linked to Ara.

<400> SEQUENCE: 203

Pro
1

<210> SEQ ID NO 204
<211> LENGTH: 30
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 204
gataccgcga gacccacgct caccagctcc                                      30

<210> SEQ ID NO 205
<211> LENGTH: 21
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 205
ctcggtcgcc gcatacacta t                                               21

```
<210> SEQ ID NO 206
<211> LENGTH: 87
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 206
ggcaagcttc cggagtgccg gccctcatag cccacctcca ccattatcac catcacctac      60
tccaactcct cctttgggac cacacag                                         87

<210> SEQ ID NO 207
<211> LENGTH: 72
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 207
ggtcccgggg ggtggtgttg gggttggtga agggggaaagt gtaggggggtg gactgtgtgg      60 tcccaaagga gg                                                         72

<210> SEQ ID NO 208
<211> LENGTH: 19
<212> TYPE: PRT
<213> ORGANISM: Artificial/Unknown
<220> FEATURE:
<221> NAME/KEY: misc_feature
<223> OTHER INFORMATION: Synthetic

<400> SEQUENCE: 208

Ser Pro Ser Pro Thr Pro Thr Pro Pro Gly Pro His Ser Pro Pro
1               5                   10                  15

Pro Thr Leu

<210> SEQ ID NO 209
<211> LENGTH: 3
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (1)..(1)
<223> OTHER INFORMATION: Xaa is any amino acid other than
      hydroxyproline.
<221> NAME/KEY: SITE
<222> LOCATION: (2)..(2)
<223> OTHER INFORMATION: The Proline at this position is a
      hydroxyproline.
<221> NAME/KEY: SITE
<222> LOCATION: (3)..(3)
<223> OTHER INFORMATION: The hydroxyproline at this position is repeated
      n times, n being an integer from 1 to 100.  Each of the proline
      residues at positions 3 - 102 is hydroxyproline

<400> SEQUENCE: 209

Xaa Pro Pro
1

<210> SEQ ID NO 210
<211> LENGTH: 3
<212> TYPE: PRT
<213> ORGANISM: Artificial/Unknown
<220> FEATURE:
<221> NAME/KEY: misc_feature
```

```
<223> OTHER INFORMATION: Synthetic
<221> NAME/KEY: SITE
<222> LOCATION: (1)..(1)
<223> OTHER INFORMATION: Xaa at this position is any amino acid other
      than hydroxyproline.
<221> NAME/KEY: SITE
<222> LOCATION: (3)..(3)
<223> OTHER INFORMATION: The hydroxyproline at this position is repeated
      n times, n being an integer from 1 to 100.  Each of the proline
      residues at positions 3 - 102 is hydroxyproline

<400> SEQUENCE: 210

Xaa Pro Pro
1

<210> SEQ ID NO 211
<211> LENGTH: 3
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(3)
<223> OTHER INFORMATION: The Proline at these positions is a
      hydroxyproline.

<400> SEQUENCE: 211

Ser Pro Pro
1

<210> SEQ ID NO 212
<211> LENGTH: 4
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(4)
<223> OTHER INFORMATION: The Proline at these positions is a
      hydroxyproline.

<400> SEQUENCE: 212

Ser Pro Pro Pro
1

<210> SEQ ID NO 213
<211> LENGTH: 3
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(3)
<223> OTHER INFORMATION: The Proline at these positions is a
      hydroxyproline.

<400> SEQUENCE: 213

Thr Pro Pro
1

<210> SEQ ID NO 214
<211> LENGTH: 4
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
```

```
<222> LOCATION: (2)..(4)
<223> OTHER INFORMATION: The Proline at these positions is a
      hydroxyproline.

<400> SEQUENCE: 214

Thr Pro Pro Pro
1

<210> SEQ ID NO 215
<211> LENGTH: 4
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(3)
<223> OTHER INFORMATION: The Proline at these positions is a
      hydroxyproline.

<400> SEQUENCE: 215

Ser Pro Pro Pro
1

<210> SEQ ID NO 216
<211> LENGTH: 5
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(3)
<223> OTHER INFORMATION: The Proline at these positions is a
      hydroxyproline.
<221> NAME/KEY: SITE
<222> LOCATION: (5)..(5)
<223> OTHER INFORMATION: The Proline at this position is a
      hydroxyproline.

<400> SEQUENCE: 216

Ser Pro Pro Pro Pro
1               5

<210> SEQ ID NO 217
<211> LENGTH: 19
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(2)
<223> OTHER INFORMATION: The Proline at this position is a
      hydroxyproline.
<221> NAME/KEY: SITE
<222> LOCATION: (8)..(8)
<223> OTHER INFORMATION: The Proline at this position is a
      hydroxyproline.
<221> NAME/KEY: SITE
<222> LOCATION: (10)..(10)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.
<221> NAME/KEY: SITE
<222> LOCATION: (14)..(15)
<223> OTHER INFORMATION: The Proline at these positions is a
      hydroxyproline.

<400> SEQUENCE: 217
```

Ser Pro Pro Pro Pro Leu Ser Pro Ser Pro Thr Pro Thr Pro Pro Leu
1               5                   10                  15

Gly Pro His

<210> SEQ ID NO 218
<211> LENGTH: 19
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(3)
<223> OTHER INFORMATION: The Proline at these positions is a
      hydroxyproline.
<221> NAME/KEY: SITE
<222> LOCATION: (8)..(8)
<223> OTHER INFORMATION: The Proline at this position is a
      hydroxyproline.
<221> NAME/KEY: SITE
<222> LOCATION: (10)..(10)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.
<221> NAME/KEY: SITE
<222> LOCATION: (14)..(15)
<223> OTHER INFORMATION: The Proline at these positions is a
      hydroxyproline.

<400> SEQUENCE: 218

Ser Pro Pro Pro Pro Leu Ser Pro Ser Pro Thr Pro Thr Pro Pro Leu
1               5                   10                  15

Gly Pro His

<210> SEQ ID NO 219
<211> LENGTH: 19
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(2)
<223> OTHER INFORMATION: The Proline at this position is a
      hydroxyproline.
<221> NAME/KEY: SITE
<222> LOCATION: (4)..(4)
<223> OTHER INFORMATION: The Proline at this position is a
      hydroxyproline.
<221> NAME/KEY: SITE
<222> LOCATION: (8)..(8)
<223> OTHER INFORMATION: The Proline at this position is a
      hydroxyproline.
<221> NAME/KEY: SITE
<222> LOCATION: (10)..(10)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.
<221> NAME/KEY: SITE
<222> LOCATION: (14)..(15)
<223> OTHER INFORMATION: The Proline at these positions is a
      hydroxyproline.

<400> SEQUENCE: 219

Ser Pro Pro Pro Pro Leu Ser Pro Ser Pro Thr Pro Thr Pro Pro Leu
1               5                   10                  15

Gly Pro His

<210> SEQ ID NO 220
<211> LENGTH: 19
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(2)
<223> OTHER INFORMATION: The Proline at this position is a
      hydroxyproline.
<221> NAME/KEY: SITE
<222> LOCATION: (8)..(8)
<223> OTHER INFORMATION: The Proline at this position is a
      hydroxyproline.
<221> NAME/KEY: SITE
<222> LOCATION: (10)..(10)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.
<221> NAME/KEY: SITE
<222> LOCATION: (14)..(15)
<223> OTHER INFORMATION: The Proline at these positions is a
      hydroxyproline.

<400> SEQUENCE: 220

Ser Pro Pro Pro Pro Leu Ser Pro Ser Pro Thr Pro Thr Pro Pro Leu
1               5                   10                  15

Gly Pro His

<210> SEQ ID NO 221
<211> LENGTH: 19
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(4)
<223> OTHER INFORMATION: The Proline at these positions is a
      hydroxyproline.
<221> NAME/KEY: SITE
<222> LOCATION: (8)..(8)
<223> OTHER INFORMATION: The Proline at this position is a
      hydroxyproline.
<221> NAME/KEY: SITE
<222> LOCATION: (10)..(10)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.
<221> NAME/KEY: SITE
<222> LOCATION: (14)..(15)
<223> OTHER INFORMATION: The Proline at these positions is a
      hydroxyproline.

<400> SEQUENCE: 221

Ser Pro Pro Pro Pro Leu Ser Pro Ser Pro Thr Pro Thr Pro Pro Leu
1               5                   10                  15

Gly Pro His

<210> SEQ ID NO 222
<211> LENGTH: 19
<212> TYPE: PRT

```
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(3)
<223> OTHER INFORMATION: The Proline at these positions is a
      hydroxyproline.
<221> NAME/KEY: SITE
<222> LOCATION: (8)..(8)
<223> OTHER INFORMATION: The Proline at this position is a
      hydroxyproline.
<221> NAME/KEY: SITE
<222> LOCATION: (10)..(10)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.
<221> NAME/KEY: SITE
<222> LOCATION: (14)..(15)
<223> OTHER INFORMATION: The Proline at these positions is a
      hydroxyproline.

<400> SEQUENCE: 222

Ser Pro Pro Pro Pro Leu Ser Pro Ser Pro Thr Pro Thr Pro Pro Leu
1               5                   10                  15

Gly Pro His

<210> SEQ ID NO 223
<211> LENGTH: 19
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(2)
<223> OTHER INFORMATION: The Proline at this position is a
      hydroxyproline.
<221> NAME/KEY: SITE
<222> LOCATION: (4)..(4)
<223> OTHER INFORMATION: The Proline at this position is a
      hydroxyproline.
<221> NAME/KEY: SITE
<222> LOCATION: (8)..(8)
<223> OTHER INFORMATION: The Proline at this position is a
      hydroxyproline.
<221> NAME/KEY: SITE
<222> LOCATION: (10)..(10)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.
<221> NAME/KEY: SITE
<222> LOCATION: (14)..(15)
<223> OTHER INFORMATION: The Proline at these positions is a
      hydroxyproline.

<400> SEQUENCE: 223

Ser Pro Pro Pro Pro Leu Ser Pro Ser Pro Thr Pro Thr Pro Pro Leu
1               5                   10                  15

Gly Pro His

<210> SEQ ID NO 224
<211> LENGTH: 19
<212> TYPE: PRT
<213> ORGANISM: Artificial/Unknown
<220> FEATURE:
<221> NAME/KEY: misc_feature
```

```
<223> OTHER INFORMATION: Synthetic
<221> NAME/KEY: SITE
<222> LOCATION: (2)..(4)
<223> OTHER INFORMATION: The Proline at these positions is a
      hydroxyproline.
<221> NAME/KEY: SITE
<222> LOCATION: (8)..(8)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.
<221> NAME/KEY: SITE
<222> LOCATION: (14)..(15)
<223> OTHER INFORMATION: The Proline at these positions is a
      hydroxyproline.

<400> SEQUENCE: 224

Ser Pro Pro Pro Pro Leu Ser Pro Ser Pro Thr Pro Thr Pro Pro Leu
1               5                   10                  15

Gly Pro His

<210> SEQ ID NO 225
<211> LENGTH: 19
<212> TYPE: PRT
<213> ORGANISM: Artificial/Unknown
<220> FEATURE:
<221> NAME/KEY: misc_feature
<223> OTHER INFORMATION: Synthetic
<221> NAME/KEY: SITE
<222> LOCATION: (2)..(5)
<223> OTHER INFORMATION: The Proline at these positions is a
      hydroxyproline.
<221> NAME/KEY: SITE
<222> LOCATION: (8)..(8)
<223> OTHER INFORMATION: The Proline at this position is a
      hydroxyproline.
<221> NAME/KEY: SITE
<222> LOCATION: (12)..(12)
<223> OTHER INFORMATION: The Proline at this position is a
      hydroxyproline.
<221> NAME/KEY: SITE
<222> LOCATION: (14)..(15)
<223> OTHER INFORMATION: The Proline at these positions is a
      hydroxyproline.

<400> SEQUENCE: 225

Ser Pro Pro Pro Pro Leu Ser Pro Ser Leu Thr Pro Thr Pro Pro Leu
1               5                   10                  15

Gly Pro His

<210> SEQ ID NO 226
<211> LENGTH: 23
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 226
gaagatggtg cgctcctgga cgt                                         23

<210> SEQ ID NO 227
<211> LENGTH: 38
<212> TYPE: DNA
<213> ORGANISM: Artificial/Unknown
<220> FEATURE:
<221> NAME/KEY: misc_feature
<223> OTHER INFORMATION: Synthetic
```

<400> SEQUENCE: 227
ctctttttct ctggatccgg tctatatttt cttttagc                            38

<210> SEQ ID NO 228
<211> LENGTH: 37
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 228
cgggtgctgc ccgggttgtc tgacccgtga cacttgc                             37

<210> SEQ ID NO 229
<211> LENGTH: 334
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 229
ggatccgcaa tgggaaaaat ggcttctcta tttgccacat ttttagtggt tttaggtgtc     60
acttagctta gcacaaacaa cccgggcccc accttcaccc ccatctccac cgagtccacc    120
atccccacct tcaccccat ctccaccgag tccaccatcc ccaccttcac ccccatctcc    180
accgagtcca ccatccccac cttcaccccc atctccaccg agtccaccat cccaccttc    240 accccatct ccaccgagtc caccatcccc accttcaccc ccatctccac cgagtccacc    300
atccccacct tcatccatgg cataatagag ctcg                                334

<210> SEQ ID NO 230
<211> LENGTH: 105
<212> TYPE: PRT
<213> ORGANISM: Artificial/Unknown
<220> FEATURE:
<221> NAME/KEY: misc_feature
<223> OTHER INFORMATION: Synthetic

<400> SEQUENCE: 230

Ser Ala Met Gly Lys Met Ala Ser Leu Phe Ala Thr Phe Leu Val Val
1               5                   10                  15

Leu Val Ser Leu Val Leu Ala Gln Thr Thr Arg Ala Pro Pro Ser Pro
                20                  25                  30

Pro Ser Pro Pro Ser Pro Pro Ser Pro Pro Ser Pro Pro Ser Pro Pro
            35                  40                  45

Ser Pro Pro Ser Pro Pro Ser Pro Pro Ser Pro Pro Ser Pro Pro Ser
        50                  55                  60

Pro Pro Ser Pro Pro Ser Pro Pro Ser Pro Pro Ser Pro Pro Ser Pro
65                  70                  75                  80

Pro Ser Pro Pro Ser Pro Pro Ser Pro Pro Ser Pro Pro Ser Pro Pro
                85                  90                  95

Ser Pro Pro Ser Pro Ser Ser Met Ala
            100                 105

<210> SEQ ID NO 231
<211> LENGTH: 72
<212> TYPE: PRT
<213> ORGANISM: Artificial/Unknown
<220> FEATURE:
<221> NAME/KEY: misc_feature -continued

```
<223> OTHER INFORMATION: Synthetic
<221> NAME/KEY: SITE
<222> LOCATION: (2)..(2)
<223> OTHER INFORMATION: The Proline at this position is a
      hydroxyproline.
<221> NAME/KEY: SITE
<222> LOCATION: (4)..(5)
<223> OTHER INFORMATION: The Proline at these positions is a
      hydroxyproline.
<221> NAME/KEY: SITE
<222> LOCATION: (7)..(8)
<223> OTHER INFORMATION: The Proline at these positions is a
      hydroxyproline.
<221> NAME/KEY: SITE
<222> LOCATION: (10)..(11)
<223> OTHER INFORMATION: The Proline at these positions is a
      hydroxyproline.
<221> NAME/KEY: SITE
<222> LOCATION: (14)..(14)
<223> OTHER INFORMATION: The Proline at this position is a
      hydroxyproline.
<221> NAME/KEY: SITE
<222> LOCATION: (16)..(17)
<223> OTHER INFORMATION: The Proline at these positions is a
      hydroxyproline.
<221> NAME/KEY: SITE
<222> LOCATION: (19)..(20)
<223> OTHER INFORMATION: The Proline at these positions is a
      hydroxyproline.
<221> NAME/KEY: SITE
<222> LOCATION: (22)..(23)
<223> OTHER INFORMATION: The Proline at these positions is a
      hydroxyproline.
<221> NAME/KEY: SITE
<222> LOCATION: (26)..(26)
<223> OTHER INFORMATION: The Proline at this position is a
      hydroxyproline.
<221> NAME/KEY: SITE
<222> LOCATION: (28)..(29)
<223> OTHER INFORMATION: The Proline at these positions is a
      hydroxyproline.
<221> NAME/KEY: SITE
<222> LOCATION: (31)..(32)
<223> OTHER INFORMATION: The Proline at these positions is a
      hydroxyproline.
<221> NAME/KEY: SITE
<222> LOCATION: (34)..(35)
<223> OTHER INFORMATION: The Proline at these positions is a
      hydroxyproline.
<221> NAME/KEY: SITE
<222> LOCATION: (38)..(38)
<223> OTHER INFORMATION: The Proline at this position is a
      hydroxyproline.
<221> NAME/KEY: SITE
<222> LOCATION: (40)..(41)
<223> OTHER INFORMATION: The Proline at these positions is a
      hydroxyproline.
<221> NAME/KEY: SITE
<222> LOCATION: (43)..(44)
<223> OTHER INFORMATION: The Proline at these positions is a
      hydroxyproline.
<221> NAME/KEY: SITE
<222> LOCATION: (46)..(47)
<223> OTHER INFORMATION: The Proline at these positions is a
      hydroxyproline.
<221> NAME/KEY: SITE
<222> LOCATION: (50)..(50)
<223> OTHER INFORMATION: The Proline at this position is a
      hydroxyproline.
<221> NAME/KEY: SITE
<222> LOCATION: (52)..(53)
<223> OTHER INFORMATION: The Proline at these positions is a
      hydroxyproline.
<221> NAME/KEY: SITE
<222> LOCATION: (55)..(56)
<223> OTHER INFORMATION: The Proline at these positions is a
      hydroxyproline.
<221> NAME/KEY: SITE
<222> LOCATION: (58)..(59)
```

<223> OTHER INFORMATION: The Proline at these positions is a
      hydroxyproline.
<221> NAME/KEY: SITE
<222> LOCATION: (62)..(62)
<223> OTHER INFORMATION: The Proline at this position is a
      hydroxyproline.
<221> NAME/KEY: SITE
<222> LOCATION: (64)..(65)
<223> OTHER INFORMATION: The Proline at these positions is a
      hydroxyproline.
<221> NAME/KEY: SITE
<222> LOCATION: (67)..(68)
<223> OTHER INFORMATION: The Proline at these positions is a
      hydroxyproline.
<221> NAME/KEY: SITE
<222> LOCATION: (70)..(71)
<223> OTHER INFORMATION: The Proline at these positions is a
      hydroxyproline.

<400> SEQUENCE: 231

Pro Pro Ser Pro Pro Ser Pro Pro Ser Pro Pro Ser Pro Pro Ser Pro
1               5                   10                  15

Pro Ser Pro Pro Ser Pro Pro Ser Pro Pro Ser Pro Pro Ser Pro Pro
            20                  25                  30

Ser Pro Pro Ser Pro Pro Ser Pro Pro Ser Pro Pro Ser Pro Pro Ser
        35                  40                  45

Pro Pro Ser Pro Pro Ser Pro Pro Ser Pro Pro Ser Pro Pro Ser Pro
50                  55                  60

Pro Ser Pro Pro Ser Pro Pro Ser
65                  70

<210> SEQ ID NO 232
<211> LENGTH: 246
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 232
ggatcctcaa cccgggcctc accaccacca ccttctccac ctccatcacc cccaccttcg     60
cctccaccat ccccaccacc ttctccacct ccatcacccc caccttcgcc tccaccatcc   120
ccaccacctt ctccacctcc atcaccccca ccttcgcctc caccatcccc accaccttct   180
ccacctccat caccccacc ttcgcctcca ccatcccctt ccatggcata atagagctcg    240
aattcg                                                              246

<210> SEQ ID NO 233
<211> LENGTH: 76
<212> TYPE: PRT
<213> ORGANISM: Artificial/Unknown
<220> FEATURE:
<221> NAME/KEY: misc_feature
<223> OTHER INFORMATION: Synthetic

<400> SEQUENCE: 233

Gly Ser Ser Thr Arg Ala Ser Pro Pro Pro Ser Pro Pro Pro Ser
1               5                   10                  15

Pro Pro Pro Ser Pro Pro Pro Ser Pro Pro Pro Ser Pro Pro Pro Ser
            20                  25                  30

Pro Pro Pro Ser Pro Pro Pro Ser Pro Pro Pro Ser Pro Pro Pro Ser
        35                  40                  45

Pro Pro Pro Ser Pro Pro Pro Ser Pro Pro Pro Ser Pro Pro Pro Ser
50                  55                  60

Pro Pro Pro Ser Pro Pro Ser Pro Ser Met Ala
65                  70              75

<210> SEQ ID NO 234
<211> LENGTH: 324
<212> TYPE: DNA
<213> ORGANISM: Artificial/Unknown
<220> FEATURE:
<221> NAME/KEY: misc_feature
<223> OTHER INFORMATION: Synthetic

<400> SEQUENCE: 234

```
ggatcctcaa cccgggcctc accaccacca ccttcacctc accccccatc tccaccacca      60
ccttcacctc accccccatc tccaccacca ccttcacctc accccccatc tccaccacca     120
ccttcacctc accccccatc tccaccacca ccttcacctc accccccatc tccaccacca     180
ccttcacctc accccccatc tccaccacca ccttcacctc accccccatc tccaccacca     240
ccttcacctc accccccatc tccaccacca ccttcacctc accccccatc tccaccacca     300
ccttccatgg cattatagag ctcg                                            324
```

<210> SEQ ID NO 235
<211> LENGTH: 104
<212> TYPE: PRT
<213> ORGANISM: Artificial/Unknown
<220> FEATURE:
<221> NAME/KEY: misc_feature
<223> OTHER INFORMATION: Synthetic

<400> SEQUENCE: 235

Gly Ser Ser Thr Arg Ala Ser Pro Pro Pro Ser Pro Pro Pro Pro
1               5                   10                  15

Ser Pro Pro Pro Pro Ser Pro Pro Pro Ser Pro Pro Pro Pro Ser
            20                  25                  30

Pro Pro Pro Ser Pro Pro Pro Ser Pro Pro Pro Pro Ser Pro Pro
        35                  40                  45

Pro Pro Ser Pro Pro Pro Pro Ser Pro Pro Pro Ser Pro Pro Pro
    50                  55                  60

Pro Ser Pro Pro Pro Ser Pro Pro Pro Pro Ser Pro Pro Pro Pro
65                  70                  75                  80

Pro Ser Pro Pro Pro Ser Pro Pro Pro Ser Pro Pro Pro Pro
            85                  90                  95

Ser Pro Pro Pro Pro Ser Met Ala
            100

<210> SEQ ID NO 236
<211> LENGTH: 96
<212> TYPE: PRT
<213> ORGANISM: Artificial/Unknown
<220> FEATURE:
<221> NAME/KEY: misc_feature
<223> OTHER INFORMATION: Synthetic

<400> SEQUENCE: 236

Gly Ser Ala Met Gly Lys Met Ala Ser Leu Phe Ala Thr Phe Leu Val
1               5                   10                  15

Val Leu Val Ser Leu Ser Leu Ala Gln Thr Thr Arg Ala Ser Pro Ser
            20                  25                  30

Pro Ser Pro Ser Pro Ser Pro Ser Pro Ser Pro Ser Pro Ser Pro Ser
        35                  40                  45

-continued

```
Pro Ser Pro Ser Pro Ser Pro Ser Pro Ser Pro Ser Pro Ser
         50              55              60

Pro Ser Pro Ser Pro Ser Pro Ser Pro Ser Pro Ser Pro Ser
65              70              75              80

Pro Ser Pro Ser Pro Ser Pro Ser Pro Ser Pro Ser Pro Val Ala Thr
              85              90              95
```

I claim:

1. An emulsion system, comprising:
   (A) a plant-expressed fusion protein in aqueous solution, said protein having emulsifying activity and comprising (i) a first glycomodule of Xaa-Hyp-Xaa-Hyp (SEQ ID NO:9) and (ii) a second glycomodule selected from Xaa-Hyp-Hyp$_n$ (SEQ ID NO:209) and Xaa-Pro-Hyp$_n$ (SEQ ID NO: 210);
   wherein n is selected from 2 to 100 and Xaa is selected from Ser, Thr, and Ala;
   wherein the first glycomodule is hydroxyproline O-glycosylated with at least one arabinogalactan polysaccharide; and
   (B) an oil.

2. The emulsion system according to claim 1, wherein the second glycomodule is hydroxyproline O-arabinosylated with at least one arabinoside.

3. The emulsion system according to claim 1, wherein the fusion protein has emulsion stabilizing activity.

4. The emulsion system according to claim 1, wherein the fusion protein comprises at least a portion of a non-gum arabic glycoprotein.

5. The emulsion system according to claim 1, wherein said fusion protein is suitable for use in food.

6. The emulsion system according to claim 1, wherein said system is a water-in-oil emulsion.

7. The emulsion system according to claim 1, wherein said system is an oil-in-water emulsion.

8. A method of preparing an emulsion, comprising:
   (A) providing a plant-expressed fusion protein in aqueous solution, said protein having emulsifying activity and comprising (i) a first glycomodule of Xaa-Hyp-Xaa-Hyp (SEQ ID NO:9) and (ii) a second glycomodule selected from Xaa-Hyp-Hyp$_n$ (SEQ ID NO:209) and Xaa-Pro-Hyp$_n$ (SEQ ID NO: 210);
   wherein n is selected from 2 to 100 and Xaa is selected from Ser, Thr, and Ala;
   wherein the first glycomodule is hydroxyproline O-glycosylated with at least one arabinogalactan polysaccharide; and
   (B) combining the provided aqueous solution with an oil; and
   (C) forming an emulsion.

9. The method according to claim 8, wherein the second glycomodule is hydroxyproline O-arabinosylated with at least one arabinoside.

10. The method according to claim 8, wherein the aqueous solution comprises a buffer.

11. The method according to claim 8, wherein the fusion protein comprises at least a portion of a non-gum arabic glycoprotein.

12. The method according to claim 8, wherein the fusion protein has emulsion stabilizing activity.

13. The method according to claim 8, wherein said formed emulsion is a water-in-oil emulsion.

14. The method according to claim 8, wherein said formed emulsion is an oil-in-water emulsion.

* * * * *

UNITED STATES PATENT AND TRADEMARK OFFICE
CERTIFICATE OF CORRECTION

| | | |
|---|---|---|
| PATENT NO. | : 8,871,468 B2 | Page 1 of 1 |
| APPLICATION NO. | : 13/149016 | |
| DATED | : October 28, 2014 | |
| INVENTOR(S) | : Marcia J. Kieliszewski | |

It is certified that error appears in the above-identified patent and that said Letters Patent is hereby corrected as shown below:

Please insert the following section header and paragraph at column 1, line 20 of the specification, immediately following the section CROSS-REFERENCE TO RELATED APPLICATIONS:

--STATEMENT REGARDING FEDERALLY SPONSORED RESEARCH OR DEVELOPMENT

"This invention was made with government support under MCB9805960 awarded by the National Science Foundation. The government has certain rights in the invention."--

Signed and Sealed this
Eleventh Day of October, 2016

Michelle K. Lee
*Director of the United States Patent and Trademark Office*